US009287511B2

(12) United States Patent
Egawa et al.

(10) Patent No.: US 9,287,511 B2
(45) Date of Patent: Mar. 15, 2016

(54) ANTHRACENE DERIVATIVE, AND LIGHT-EMITTING ELEMENT, LIGHT-EMITTING DEVICE, ELECTRONIC DEVICE USING ANTHRACENE DERIVATIVE

(71) Applicant: Semiconductor Energy Laboratory Co., Ltd., Kanagawa-ken (JP)

(72) Inventors: Masakazu Egawa, Tochigi-ken (JP); Harue Nakashima, Kanagawa (JP); Sachiko Kawakami, Kanagawa (JP); Tsunenori Suzuki, Kanagawa (JP); Ryoji Nomura, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 438 days.

(21) Appl. No.: 13/836,986

(22) Filed: Mar. 15, 2013

(65) Prior Publication Data
US 2013/0306941 A1 Nov. 21, 2013

Related U.S. Application Data

(63) Continuation of application No. 13/359,810, filed on Jan. 27, 2012, now Pat. No. 8,431,252, which is a continuation of application No. 12/952,874, filed on Nov. 23, 2010, now Pat. No. 8,106,392, which is a continuation of application No. 11/789,407, filed on Apr. 24, 2007, now Pat. No. 7,842,945.

(30) Foreign Application Priority Data

Apr. 28, 2006 (JP) .................. 2006-127118
Aug. 30, 2006 (JP) .................. 2006-233244

(51) Int. Cl.
*C07D 209/00* (2006.01)
*H01L 51/00* (2006.01)
*C07C 211/61* (2006.01)
*C07D 209/86* (2006.01)
*C07D 209/88* (2006.01)
*C09K 11/06* (2006.01)
*H05B 33/14* (2006.01)
*H01L 51/50* (2006.01)

(52) U.S. Cl.
CPC .......... *H01L 51/0072* (2013.01); *C07C 211/61* (2013.01); *C07D 209/86* (2013.01); *C07D 209/88* (2013.01); *C09K 11/06* (2013.01); *H01L 51/006* (2013.01); *H01L 51/0052* (2013.01); *H01L 51/0058* (2013.01); *H01L 51/0059* (2013.01); *H05B 33/14* (2013.01); *C07C 2103/24* (2013.01); *C09K 2211/1007* (2013.01); *C09K 2211/1011* (2013.01); *C09K 2211/1014* (2013.01); *C09K 2211/1029* (2013.01); *H01L 51/0081* (2013.01); *H01L 51/5012* (2013.01)

(58) Field of Classification Search
CPC .... C07C 211/61; C07C 25/00; C07C 2103/06
See application file for complete search history.

(56) References Cited

U.S. PATENT DOCUMENTS

| 7,227,027 | B2 | 6/2007 | Qiu et al. |
| 7,252,894 | B2 | 8/2007 | Yu et al. |
| 7,351,999 | B2 | 4/2008 | Li |
| 7,431,997 | B2 | 10/2008 | Hwang et al. |
| 7,442,803 | B2 | 10/2008 | Nakashima et al. |
| 7,476,745 | B2 | 1/2009 | Egawa et al. |
| 7,674,914 | B2 | 3/2010 | Egawa et al. |
| 7,737,627 | B2 | 6/2010 | Hwang et al. |
| 7,795,449 | B2 | 9/2010 | Nakashima et al. |
| 7,842,945 | B2 | 11/2010 | Egawa et al. |
| 7,898,171 | B2 | 3/2011 | Egawa et al. |
| 7,965,032 | B2 | 6/2011 | Bae et al. |
| 8,021,764 | B2 | 9/2011 | Hwang et al. |
| 8,021,765 | B2 | 9/2011 | Hwang et al. |
| 8,030,646 | B2 | 10/2011 | Suzuki et al. |
| 8,084,146 | B2 | 12/2011 | Murase et al. |
| 8,106,392 | B2 | 1/2012 | Egawa et al. |
| 8,110,980 | B2 | 2/2012 | Egawa et al. |
| 8,178,885 | B2 | 5/2012 | Nakashima et al. |
| 8,188,315 | B2 | 5/2012 | Hwang et al. |
| 8,193,701 | B2 | 6/2012 | Egawa et al. |
| 8,389,735 | B2 | 3/2013 | Murata et al. |
| 8,686,159 | B2 | 4/2014 | Murata et al. |

(Continued)

FOREIGN PATENT DOCUMENTS

CN 101395105 A 3/2009
EP 1 863 105 A2 12/2007

(Continued)

OTHER PUBLICATIONS

Gomez-Lor (Organic Letters, 6(17) (2004) 2993-2996).*

(Continued)

*Primary Examiner* — Kuo-Liang Peng
(74) *Attorney, Agent, or Firm* — Husch Blackwell LLP

(57) ABSTRACT

An object is to provide a novel anthracene derivative. Another object is to provide a light-emitting element with high luminous efficiency. Yet another object is to provide a light-emitting element with a long lifetime. Still another object is to provide a light-emitting device and an electronic device having a long lifetime by using the light-emitting elements of the present invention. The anthracene derivative represented by General Formula (1) is provided. The ability of the anthracene derivative represented by General Formula (1) to exhibit high luminous efficiency allows the production of a light-emitting element with high luminous efficiency and a long lifetime.

10 Claims, 105 Drawing Sheets

(56) References Cited

U.S. PATENT DOCUMENTS

| | | |
|---|---|---|
| 8,704,242 B2 | 4/2014 | Nakashima et al. |
| 8,901,542 B2 | 12/2014 | Egawa et al. |
| 9,048,436 B2 | 6/2015 | Murata et al. |
| 2003/0189401 A1 | 10/2003 | Kido et al. |
| 2005/0260442 A1 | 11/2005 | Yu et al. |
| 2006/0043859 A1 | 3/2006 | Fukuoda et al. |
| 2006/0158102 A1 | 7/2006 | Kawamura et al. |
| 2006/0240278 A1 | 10/2006 | Hatwar et al. |
| 2007/0205412 A1 | 9/2007 | Bae et al. |
| 2008/0006821 A1 | 1/2008 | Suzuki et al. |
| 2008/0103315 A1 | 5/2008 | Egawa et al. |
| 2008/0130278 A1 | 6/2008 | Ushikubo et al. |
| 2009/0004506 A1 | 1/2009 | Nomura et al. |
| 2010/0164376 A1 | 7/2010 | Egawa et al. |
| 2012/0138907 A1 | 6/2012 | Murase et al. |
| 2012/0211733 A1 | 8/2012 | Hwang et al. |

FOREIGN PATENT DOCUMENTS

| | | |
|---|---|---|
| EP | 1 918 350 A2 | 5/2008 |
| EP | 2 364 964 A1 | 9/2011 |
| JP | 2000-68057 | 3/2000 |
| JP | 2003-146951 | 5/2003 |
| JP | 2003-267973 | 9/2003 |
| JP | 2003-313156 | 11/2003 |
| JP | 2004-91334 | 3/2004 |
| JP | 2004-95850 | 3/2004 |
| JP | 2004-273163 | 9/2004 |
| JP | 2005-104971 | 4/2005 |
| JP | 2005-290000 | 10/2005 |
| KR | 10-2007-0091540 A | 9/2007 |
| WO | WO 2005/113531 A1 | 12/2005 |
| WO | WO 2007/102683 A1 | 9/2007 |

OTHER PUBLICATIONS

Korean Office Action re Application No. KR 10-2008-7029301, dated Oct. 24, 2013.

Chemical Abstract of Japanese Patent Application No. JP 2004-91334, published Mar. 25, 2004.

International Search Report re application No. PCT/JP2007/058896, dated Aug. 14, 2007.

Written Opinion re application No. PCT/JP2007/058896, dated Aug. 14, 2007.

Search Report re European application No. EP 07742331.7, dated Feb. 14, 2012.

Chinese Office Action re Application No. CN 201310332965.6, dated May 13, 2014.

* cited by examiner

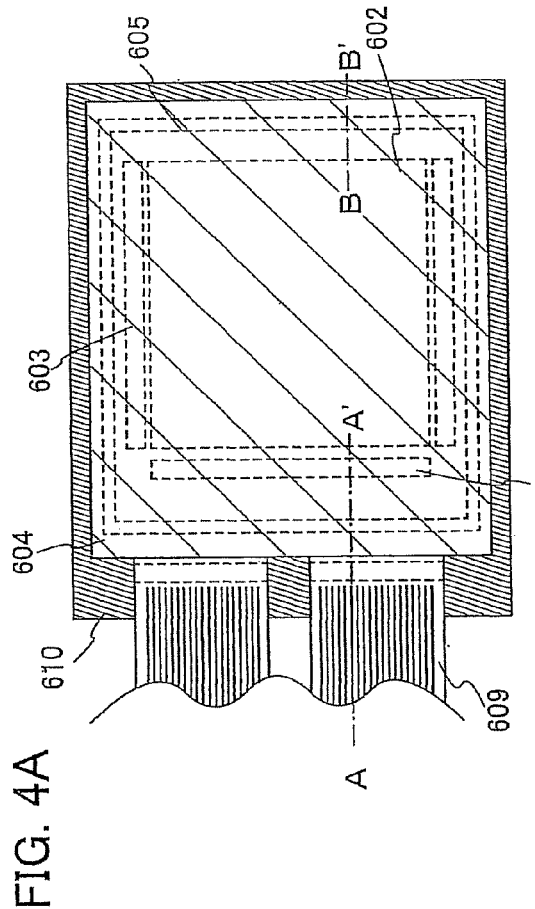
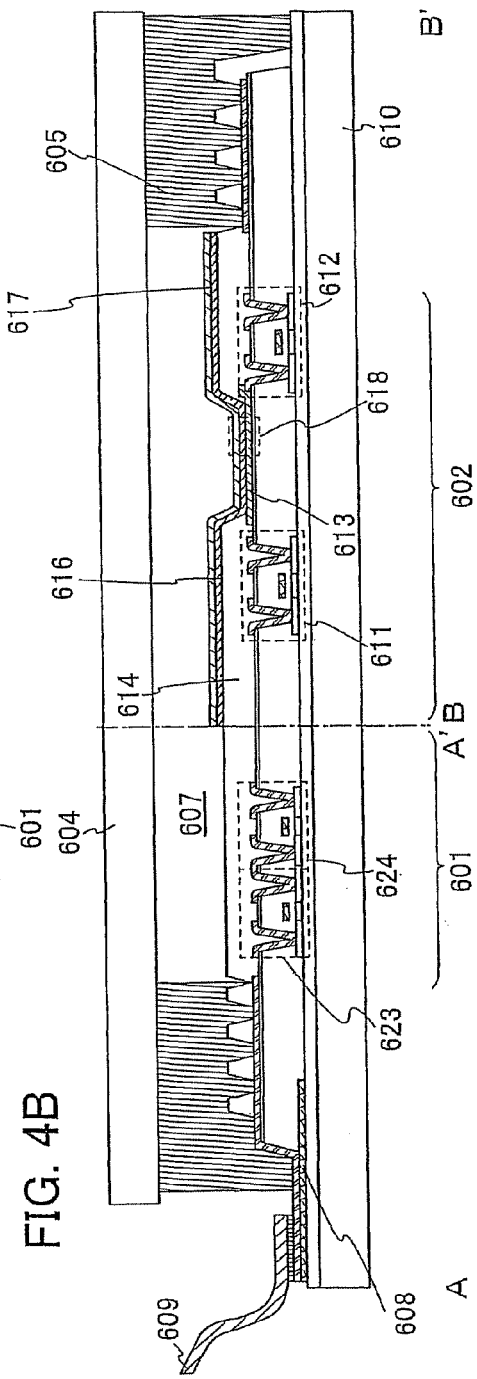
FIG. 4A
FIG. 4B

ANTHRACENE DERIVATIVE, AND LIGHT-EMITTING ELEMENT, LIGHT-EMITTING DEVICE, ELECTRONIC DEVICE USING ANTHRACENE DERIVATIVE

This application is a continuation of copending application Ser. No. 13/359,810 filed on Jan. 27, 2012 which is a continuation of application Ser. No. 12/952,874 filed on Nov. 23, 2010 (now U.S. Pat. No. 8,106,392 issued Jan. 31, 2012) which is a continuation of application Ser. No. 11/789,407 filed on Apr. 24, 2007 (U.S. Pat. No. 7,842,945 issued Nov. 30, 2010).

TECHNICAL FIELD

The present invention relates to an anthracene derivative, and a light-emitting element, a light-emitting device, and an electronic device each using an anthracene derivative.

BACKGROUND ART

An organic compound can take various structures compared with an inorganic compound, and it is possible to synthesize a material having various functions by appropriate molecular-design of an organic compound. Owing to these advantages, photo electronics and electronics, which employ a functional organic material, have been attracting attention in recent years.

A solar cell, a light-emitting element, an organic transistor, and the like can be exemplified as an electronic device using an organic compound as a functional organic material. These devices take advantage of electrical properties and optical properties of the organic compound. Among them, in particular, a light-emitting element has been making remarkable progress.

It is considered that the light emission mechanism of a light-emitting element is as follows: when a voltage is applied between a pair of electrodes which interpose a light-emitting layer, electrons injected from a cathode and holes injected from an anode are recombined in the light-emitting layer to form a molecular exciton, and energy is released to emit light when the molecular exciton relaxes to the ground state. As excited states, a singlet excited state and a triplet excited state are known, and light emission is considered to be possible through either of these excited states.

In an attempt to improve the performances of such a light-emitting element, there are many problems which depend on the material, and in order to solve these problems, improvement of the element structure and development of a material have been carried out.

For example, in Patent Document 1: United States Patent Application Laid-Open No. 2005-0260442, an anthracene derivative exhibiting green light emission is disclosed. However, in Patent Document 1, only the PL spectrum of the anthracene derivative is described, and the device performance is not disclosed when the anthracene derivative was applied to a light-emitting element.

Also, in Patent Document 2: Japanese Published Patent Application No. 2004-91334, a light-emitting element using an anthracene derivative as a charge transporting layer is mentioned. However, in Patent Document 2, there is no description on the lifetime of the light-emitting element.

If commercialization is considered, extending the lifetime is an important issue. Further, the development of light-emitting elements with much higher performances is desired.

DISCLOSURE OF INVENTION

In view of the foregoing problems, an object of the present invention is to provide a novel anthracene derivative.

In addition, an object is to provide a light-emitting element with high luminous efficiency as well as a light-emitting element with a long lifetime. Another object is to provide a light-emitting, device and an electronic device each having a long lifetime by using these light-emitting elements.

One feature of the present invention is an anthracene derivative represented by General Formula (1).

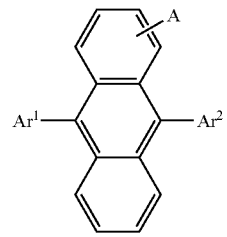

(1)

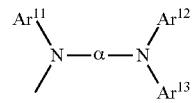

(1-1)

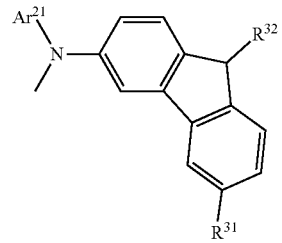

(1-2)

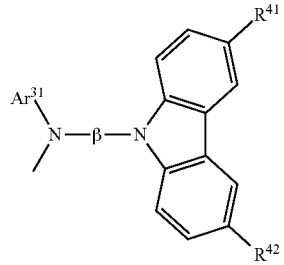

(1-3)

(In the formula, each of $Ar^1$ and $Ar^2$ represents an aryl group having 6 to 25 carbon atoms, and A represents a substituent represented by any of General Formulae (1-1) to (1-3). In General Formulae (1-1) to (1-3), each of $Ar^{11}$ to $Ar^{13}$ represents an aryl group having 6 to 25 carbon atoms; α represents an arylene group having 6 to 25 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents any of hydrogen, an alkyl group having 1 to 4 carbon atoms, and an aryl group having 6 to 25 carbon atoms.)

Another feature of the present invention is an anthracene derivative represented by General Formula (2).

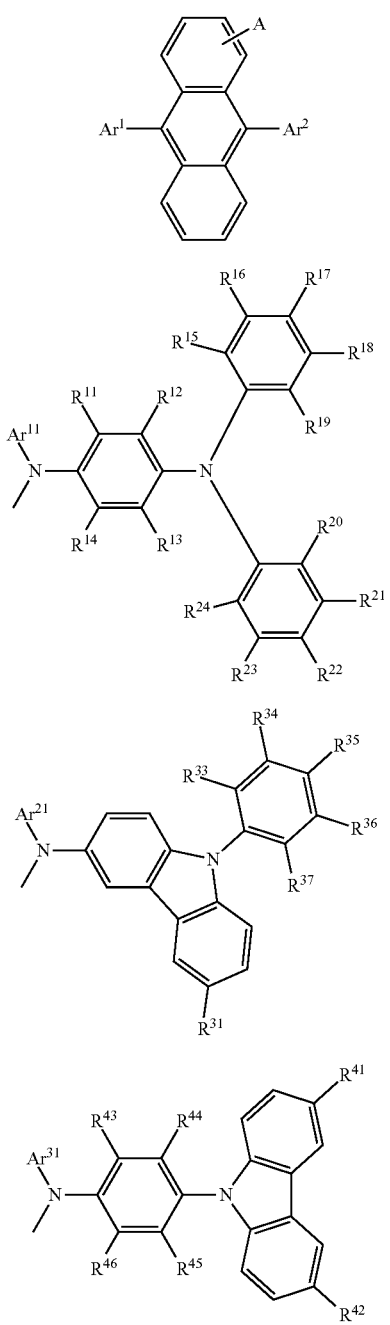

(In the formula, each of Ar$^1$ and Ar$^2$ represents an aryl group having 6 to 25 carbon atoms, and A represents a substituent represented by any of General Formulae (2-1) to (2-3). In General Formulae (2-1) to (2-3), Ar$^{11}$ represents an aryl group having 6 to 25 carbon atoms; each of R$^{11}$ to R$^{24}$ represents any of hydrogen, an alkyl group having 1 to 4 carbon atoms, and an aryl group having 6 to 15 carbon atoms; Ar$^{21}$ represents an aryl group having 6 to 25 carbon atoms; R$^{31}$ represents any of hydrogen, an alkyl group having 1 to 4 carbon atoms, and an aryl group having 6 to 25 carbon atoms; each of R$^{33}$ to R$^{37}$ represents any of hydrogen, an alkyl group having 1 to 4 carbon atoms, and an aryl group having 6 to 15 carbon atoms; Ar$^{31}$ represents an aryl group having 6 to 25 carbon atoms; each of R$^{41}$ and R$^{42}$ represents any of hydrogen, an alkyl group having 1 to 4 carbon atoms, and an aryl group having 6 to 25 carbon atoms; and each of R$^{43}$ to R$^{46}$ represents any of hydrogen, an alkyl group having 1 to 4 carbon atoms, and an aryl group having 6 to 15 carbon atoms.)

Yet another feature of the present invention is an anthracene derivative represented by General Formula (3).

(In the formula, each of Ar$^1$ and Ar$^2$ represents an aryl group having 6 to 25 carbon atoms, and A represents any substituent represented by General Formulae (3-1) to (3-3). In General Formulae (3-1) to (3-3), Ar$^{11}$ represents an aryl group having 6 to 25 carbon atoms; each of R$^{25}$ and R$^{26}$ represents any of hydrogen, an alkyl group having 1 to 4 carbon atoms, and an aryl group having 6 to 15 carbon atoms; Ar$^{21}$ represents an aryl group having 6 to 25 carbon atoms; R$^{31}$ represents any of hydrogen, an alkyl group having 1 to 4 carbon atoms, and an aryl group having 6 to 25 carbon atoms; Ar$^{31}$ represents an aryl group having 6 to 25 carbon atoms; and each of R$^{41}$ and R$^{42}$ represents any of hydrogen, an alkyl group having 1 to 4 carbon atoms, and an aryl group having 6 to 25 carbon atoms.)

Still another feature of the present invention is an anthracene derivative represented by General Formula (4).

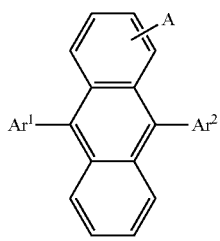
(4)

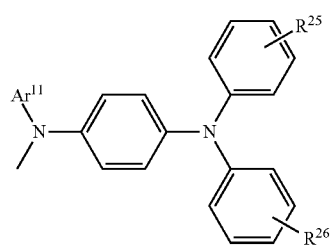
(4-1)

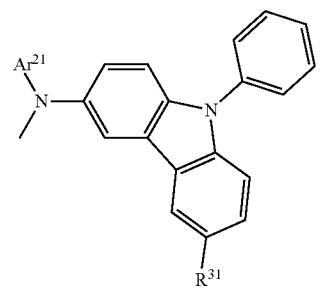
(4-2)

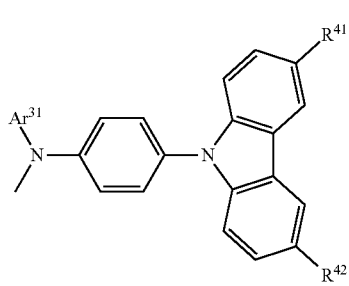
(4-3)

(In the formula, each of Ar$^1$ and Ar$^2$ represents an aryl group having 6 to 25 carbon atoms, and A represents any substituent represented by General Formulae (4-1) to (4-3). In General Formulae (4-1) to (4-3), Ar$^{11}$ represents any of phenyl group, 1-naphthyl group, and 2-naphthyl group; each of R$^{25}$ and R$^{26}$ represents any of hydrogen, an alkyl group having 1 to 4 carbon atoms, and an aryl group having 6 to 15 carbon atoms; Ar$^{21}$ represents any of phenyl group, 1-naphthyl group, and 2-naphthyl group; R$^{31}$ represents any of hydrogen, an alkyl group having 1 to 4 carbon atoms, and an aryl group having 6 to 25 carbon atoms; Ar$^{31}$ represents any of a phenyl group, 1-naphthyl group, and 2-naphthyl group; and each of R$^{41}$ and R$^{42}$ represents any of hydrogen, an alkyl group having 1 to 4 carbon atoms, and an aryl group having 6 to 25 carbon atoms.)

In the above structure, each of Ar$^1$ and Ar$^2$ is preferably a substituent represented by General Formula (11-1).

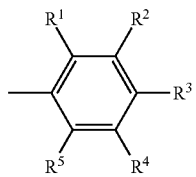
(11-1)

(In the formula, each of R$^1$ to R$^5$ represents any of hydrogen, an alkyl group having 1 to 4 carbon atoms, a haloalkyl group having 1 to 4 carbon atoms, and an aryl group having 6 to 15 carbon atoms.)

In the above structure, each of Ar$^1$ and Ar$^2$ is preferably a substituent represented by Structural Formula (11-2) or (11-3).

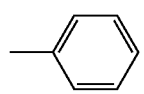
(11-2)

(11-3)

In the above structure, each of Ar1 and Ar2 is preferably a substituent represented by General Formula (11-4).

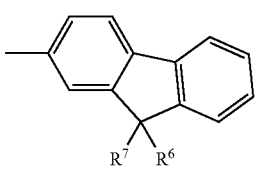
(11-4)

(In the formula, each of R$^6$ and R$^7$ represents any of an alkyl group having 1 to 4 carbon atoms and an aryl group having 6 to 15 carbon atoms.)

In the above structure, each of Ar$^1$ and Ar$^2$ is preferably a substituent represented by Structural Formula (11-5) or (11-6).

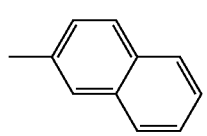
(11-5)

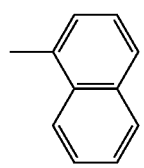
(11-6)

In the above structure, Ar$^1$ and Ar$^2$ are preferably substituents having the same structure.

Another feature of the present invention is an anthracene derivative represented by General Formula (5).

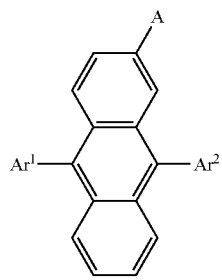

(5)

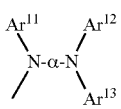

(5-1)

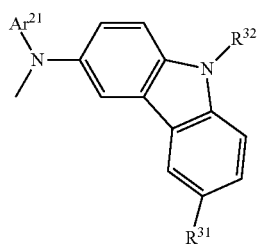

(5-2)

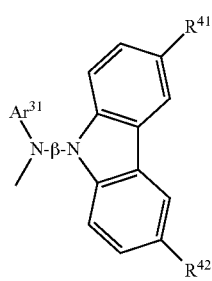

(5-3)

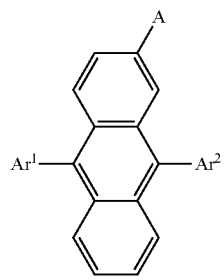

(6)

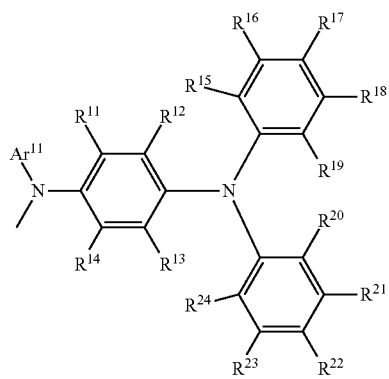

(6-1)

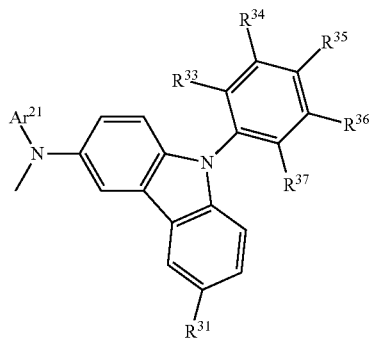

(6-2)

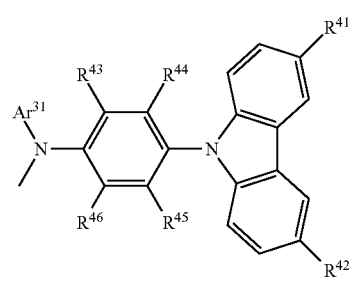

(6-3)

(In the formula, each of $Ar^1$ and $Ar^2$ represents an aryl group having 6 to 25 carbon atoms, and A represents a substituent represented by any of General Formulae (5-1) to (5-3). In General Formulae (5-1) to (5-3), each of $Ar^{11}$ to $Ar^{13}$ represents an aryl group having 6 to 25 carbon atoms; a represents an arylene group having 6 to 25 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents any of hydrogen, an alkyl group having 1 to 4 carbon atoms, and an aryl group having 6 to 25 carbon atoms.)

Further, one feature of the present invention is an anthracene derivative represented by General Formula (6).

(In the formula, each of $Ar^1$ and $Ar^2$ represents an aryl group having 6 to 25 carbon atoms, and A represents a substituent represented by any of General Formulae (6-1) to (6-3). In General Formulae (6-1) to (6-3), $Ar^{11}$ represents an aryl group having 6 to 25 carbon atoms; each of $R^{11}$ to $R^{24}$ represents any of hydrogen, an 1 alkyl group having 1 to 4 carbon atoms, and an aryl group having 6 to 15 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; each of $R^{33}$ to $R^{37}$ represents any of hydrogen, an alkyl group having 1 to 4 carbon atoms, and an aryl group having 6 to 15 carbon atoms; $Ar^{31}$ represents an aryl group having 6 to 25 carbon atoms; each of $R^{41}$ and $R^{42}$ represents any of hydrogen, an alkyl group having 1 to 4 carbon atoms, and an aryl group having 6 to 25 carbon atoms; and each of $R^{43}$ to $R^{46}$ represents any of hydrogen, an alkyl group having 1 to 4 carbon atoms, and an aryl group having 6 to 15 carbon atoms.)

Also, one feature of the present invention is an anthracene derivative represented by General Formula (7).

each of $R^{41}$ and $R^{42}$ represents any of hydrogen, an alkyl group having 1 to 4 carbon atoms, and an aryl group having 6 to 25 carbon atoms.)

Yet another feature of the present invention is an anthracene derivative represented by General Formula (8).

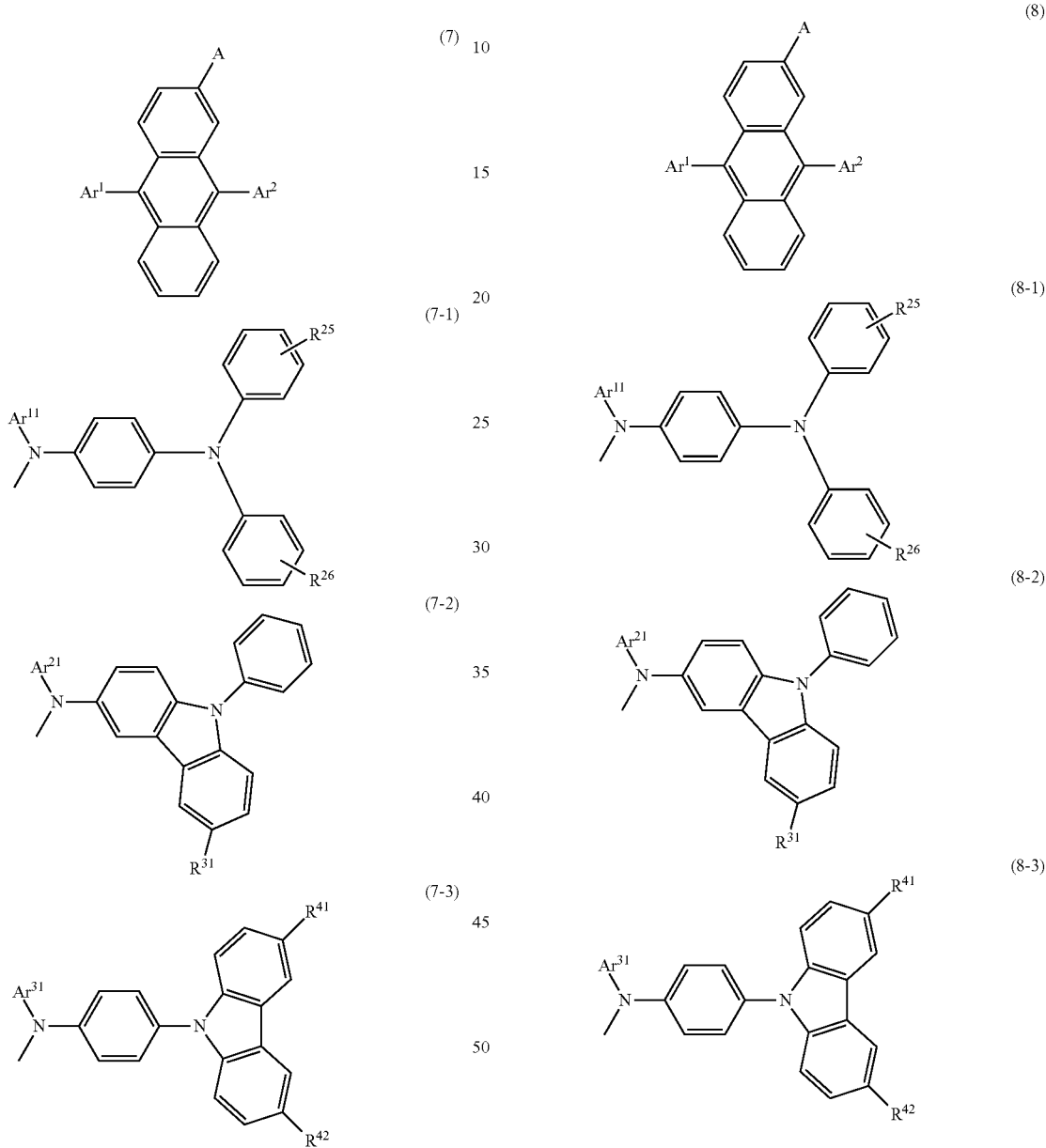

(In the formula, each of $Ar^1$ and $Ar^2$ represents an aryl group having 6 to 25 carbon atoms, and A represents any substituent represented by General Formulae (7-1) to (7-3). In General Formulae (7-1) to (7-3), $Ar^{11}$ represents an aryl group having 6 to 25 carbon atoms; each of $R^{25}$ and $R^{26}$ represents any of hydrogen, an alkyl group having 1 to 4 carbon atoms, and an aryl group having 6 to 15 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; $Ar^{31}$ represents an aryl group having 6 to 25 carbon atoms; and (In the formula, each of $Ar^1$ and $Ar^2$ represents an aryl group having 6 to 25 carbon atoms, and A represents any substituent represented by General Formulae (8-1) to (8-3). In General Formulae (8-1) to (8-3), $Ar^{11}$ represents any of phenyl group, 1-naphthyl group, and 2-naphthyl group; each of $R^{25}$ and $R^{26}$ represents any of hydrogen, an alkyl group having 1 to 4 carbon atoms, and an aryl group having 6 to 15 carbon atoms; $Ar^{21}$ represents any of phenyl group, 1-naphthyl group, and 2-naphthyl group; $R^{31}$ represents any of hydrogen, an alkyl group having 1 to 4 carbon atoms, and an aryl group having 6 to 25 carbon atoms; $Ar^{31}$ represents any of a phenyl group, 1-naphthyl group, and 2-naphthyl group; and each of $R^{41}$ and $R^{42}$ represents any of hydrogen, an alkyl group having 1 to 4 carbon atoms, and an aryl group having 6 to 25 carbon atoms.)

In the above structure, each of $Ar^1$ and $Ar^2$ is preferably a substituent represented by General Formula (11-1).

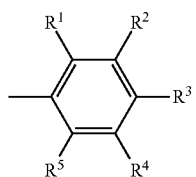

(11-1)

(In the formula, each of $R^1$ to $R^5$ represents any of hydrogen, an alkyl group having 1 to 4 carbon atoms, a haloalkyl group having 1 to 4 carbon atoms, and an aryl group having 6 to 15 carbon atoms.)

In the above structure, each of $Ar^1$ and $Ar^2$ is preferably a substituent represented by Structural Formula (11-2) or (11-3).

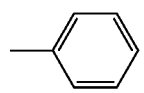

(11-2)

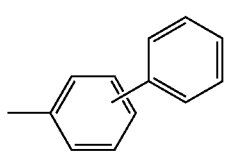

(11-3)

Also, in the above structure, each of $Ar^1$ and $Ar^2$ is preferably a substituent represented by General Formula (11-4).

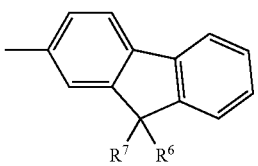

(11-4)

(In the formula, each of $R^6$ and $R^7$ represents any of an alkyl group having 1 to 4 carbon atoms and an aryl group having 6 to 15 carbon atoms.)

Further, in the above structure, each of $Ar^1$ and $Ar^2$ is preferably a substituent represented by Structural Formula (11-5) or (11-6).

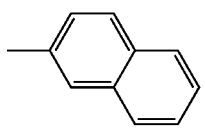

(11-5)

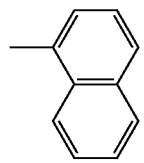

(11-6)

Also, in the foregoing structure, $Ar^1$ and $Ar^2$ are preferably substituents having the same structure.

Further, one feature of the present invention is a light-emitting element using the foregoing anthracene derivative. Specifically, the feature of the present invention is a light-emitting element having the anthracene derivative between a pair of electrodes.

Another feature of the present invention is a light-emitting element having a light-emitting layer between a pair of electrodes, in which the light-emitting layer includes the above-mentioned anthracene derivative. It is particularly preferable to use the abovementioned anthracene derivative as a light-emitting substance. That is, it is preferable to have a structure in which the anthracene derivative emits light.

The light-emitting device of the present invention has the above-mentioned light-emitting element. The light-emitting element comprises a layer including a light-emitting substance between a pair of electrodes, and said layer including a light-emitting substance comprises the foregoing anthracene derivative. The light-emitting device of the present invention also possesses a controller for controlling light emission of the light-emitting element. The light-emitting device in this specification includes an image display device, a light-emitting device, and a light source (including a lighting device). Further, the light-emitting device also includes a module in which a connector such as an FPC (Flexible Printed Circuit), a TAB (Tape Automated Bonding) tape, or a TCP (Tape Carrier Package) is attached to a panel, a module in which a printed wiring board is provided at an end of a TAB tape or a TCP, and a module in which an IC (Integrated Circuit) is directly mounted on the light-emitting device by a COG (Chip On Glass) method.

Further, an electronic device using the light-emitting element of the present invention in its display portion is also included in the category of the present invention. Therefore, the electronic device of the present invention has a display portion, and the display portion is equipped with the above-described light-emitting element and a controller for controlling light emission of the light-emitting element.

An anthracene derivative of the present invention has high luminous efficiency. Therefore, by using the anthracene derivative of the present invention in a light-emitting element, a light-emitting element with high luminous efficiency can be obtained. Also, by using the anthracene derivative of the present invention in a light-emitting element, a light-emitting element with a long lifetime can be obtained.

Further, by using an anthracene derivative of the present invention, a light-emitting device and an electronic device each with a long lifetime can be obtained.

BRIEF DESCRIPTION OF DRAWINGS

In the drawings.

FIGS. 4A and 4B describe a light-emitting device of the present invention;

FIG. 121 shows the absorption spectrum of a toluene solution of 9,10-diphenyl-2-[N-(4'-diphenylamino-1,1'-biphenyl-4-yl)-N-phenylamino]anthracene (abbreviation: 2DPBAPA);

FIG. 122 shows the emission spectrum of a toluene solution of 9,10-diphenyl-2-[N-(4'-diphenylamino-1,1'-biphenyl-4-yl)-N-phenylamino]anthracene (abbreviation: 2DPBAPA);

Figure 123A:
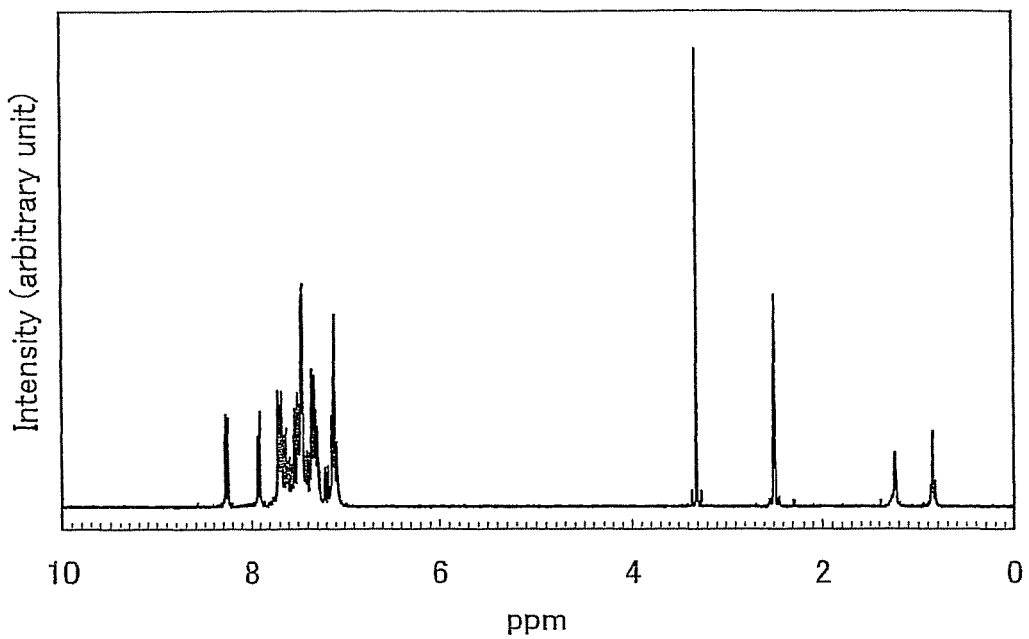
Figure 123B:
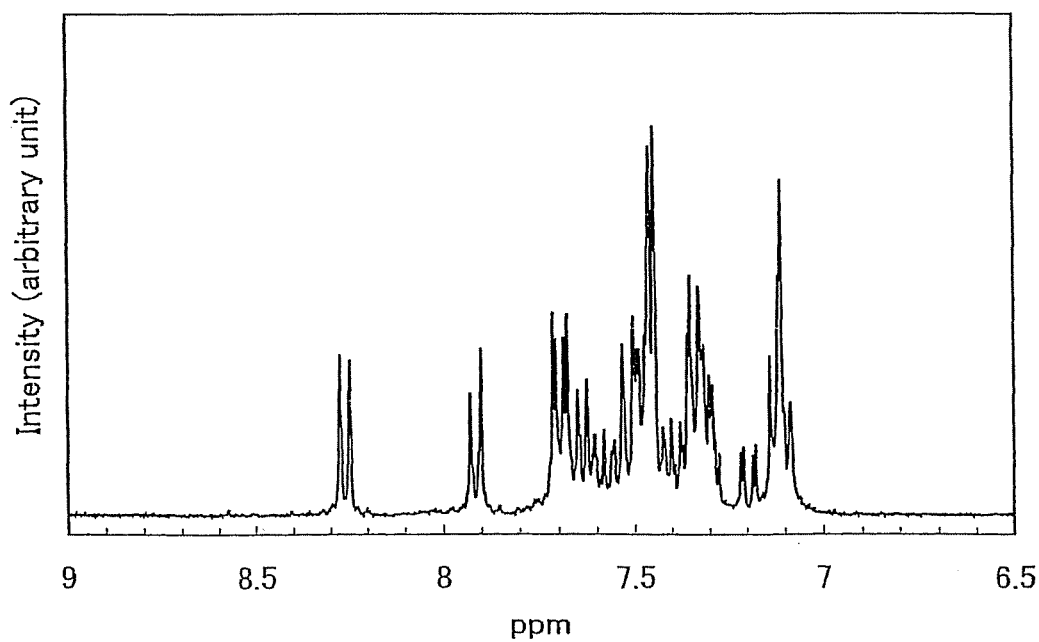
Figure 124:
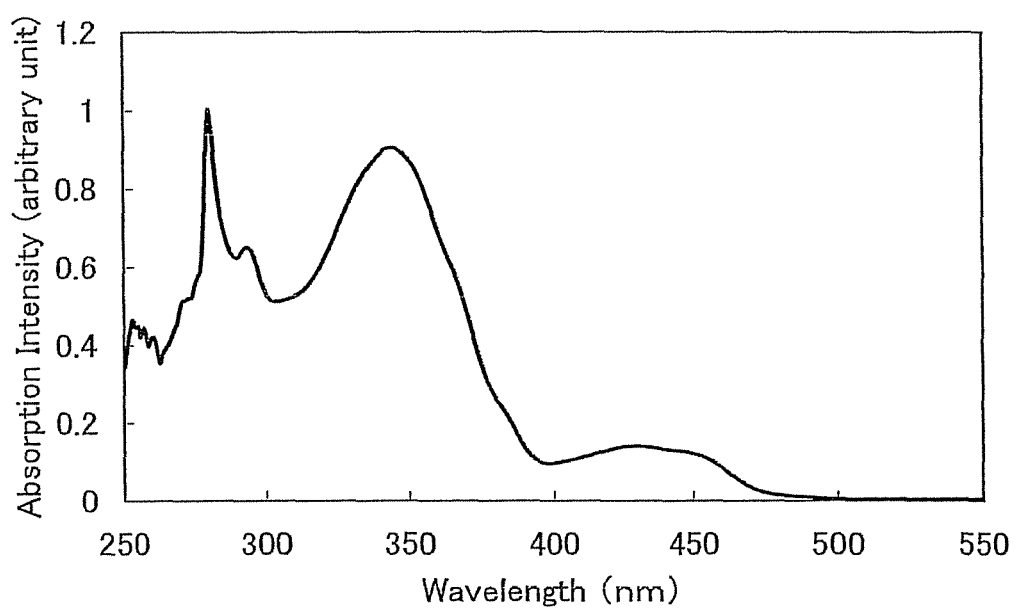
Figure 125:
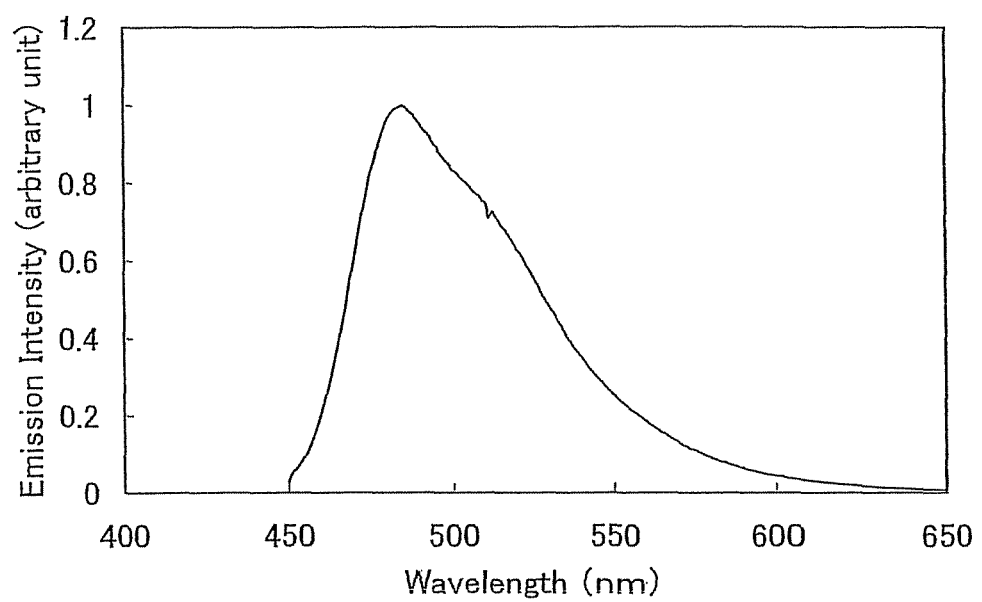
Figure 126:
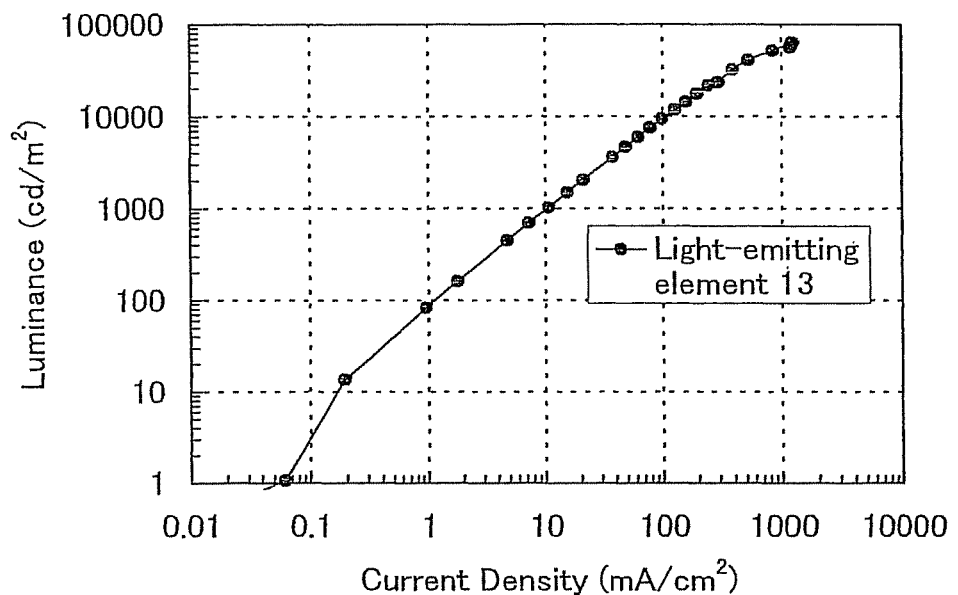
Figure 127:
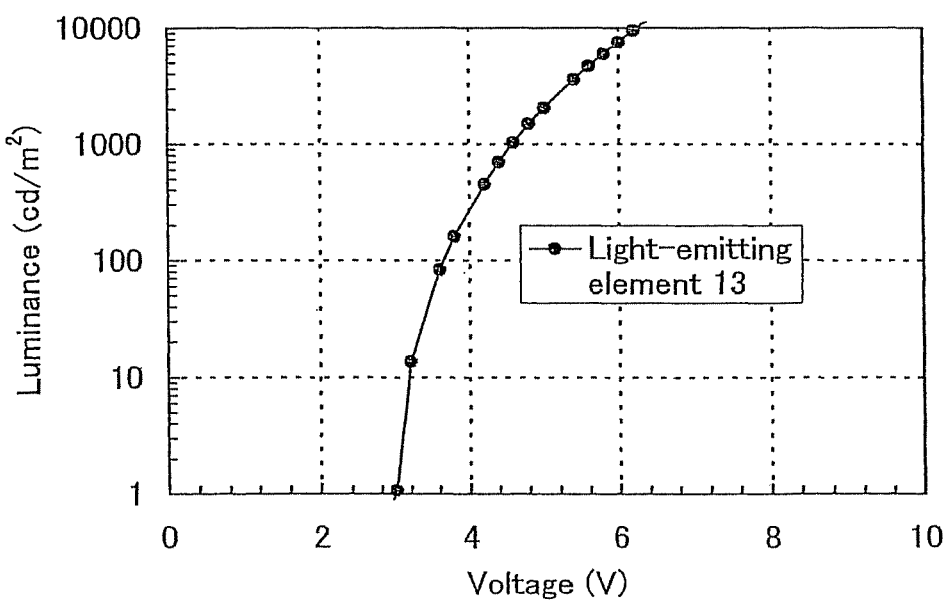
Figure 128:
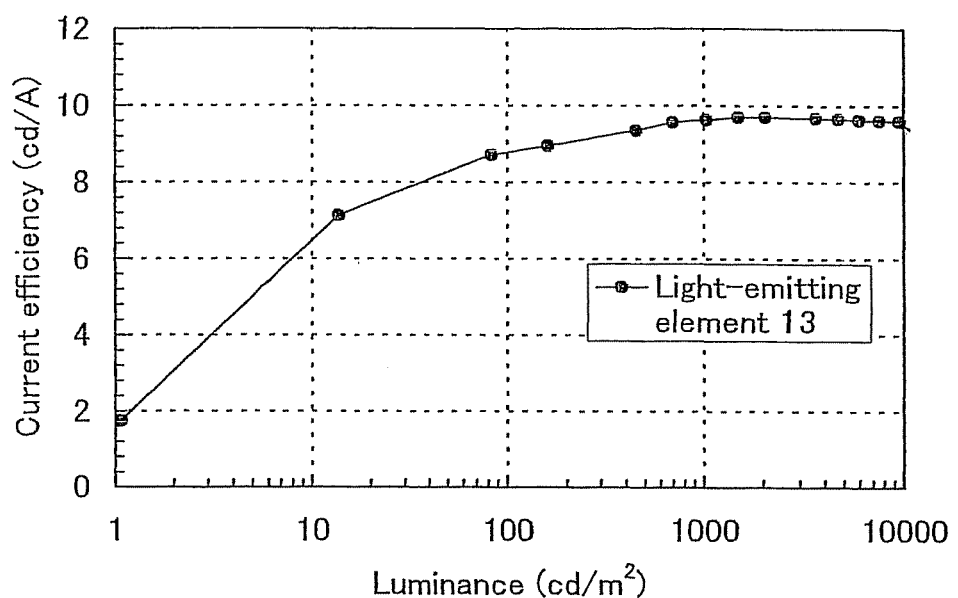
Figure 129:
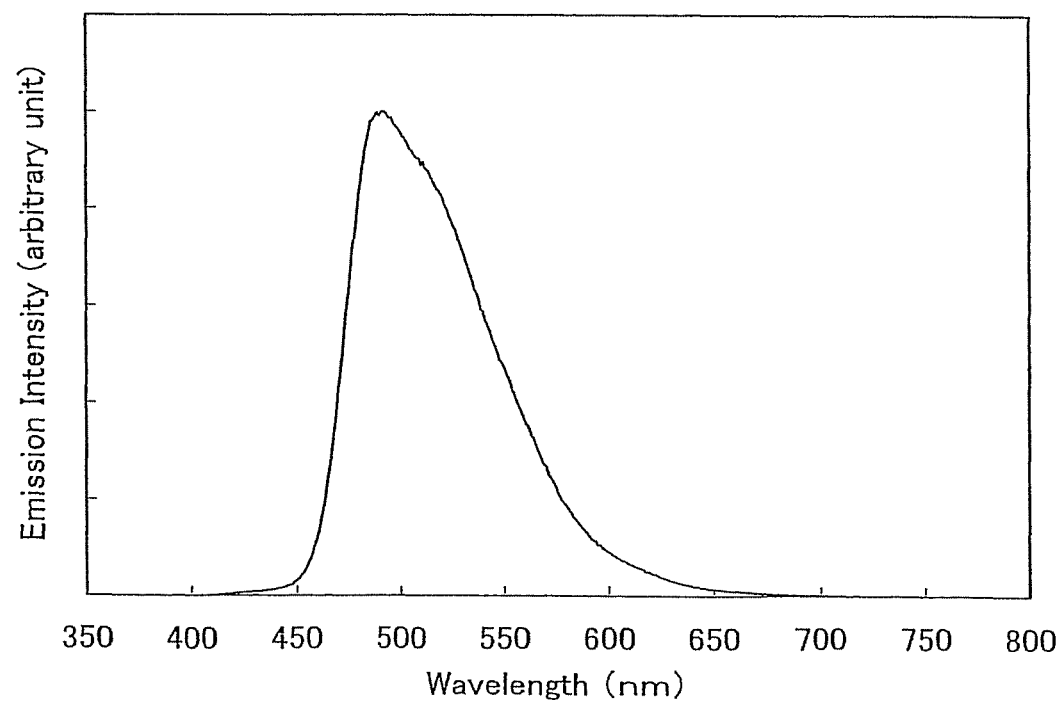
Figure 130:
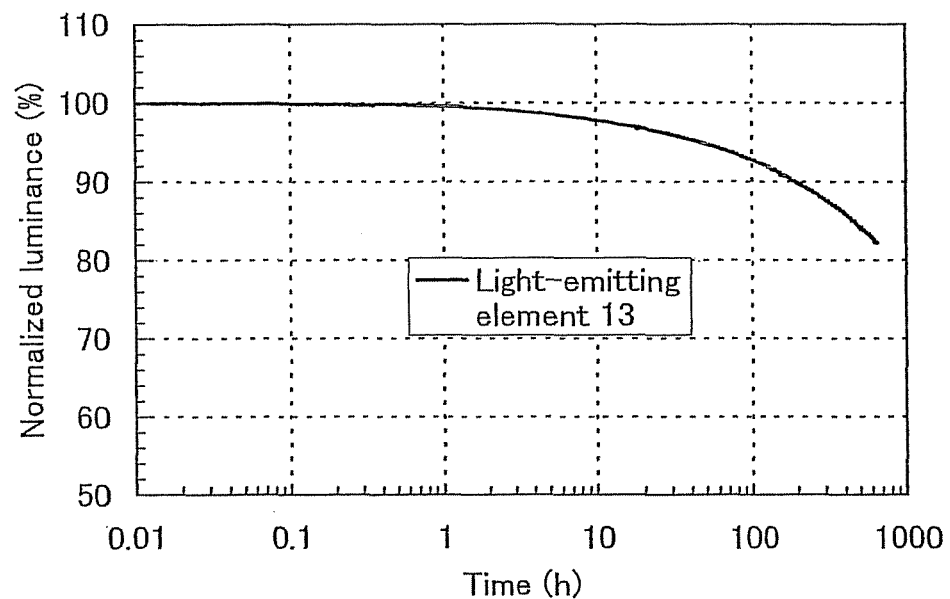
Figure 131:
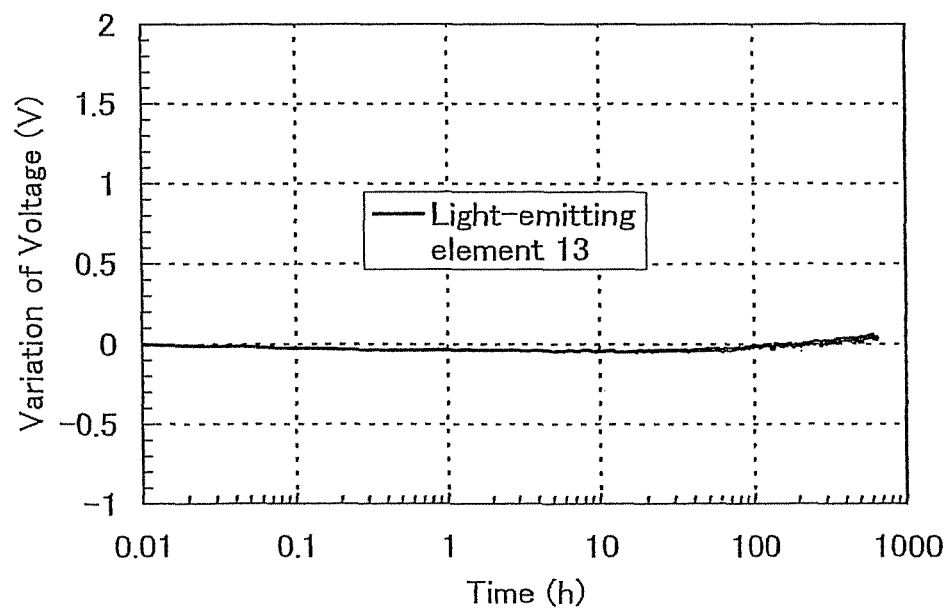
Figure 132:
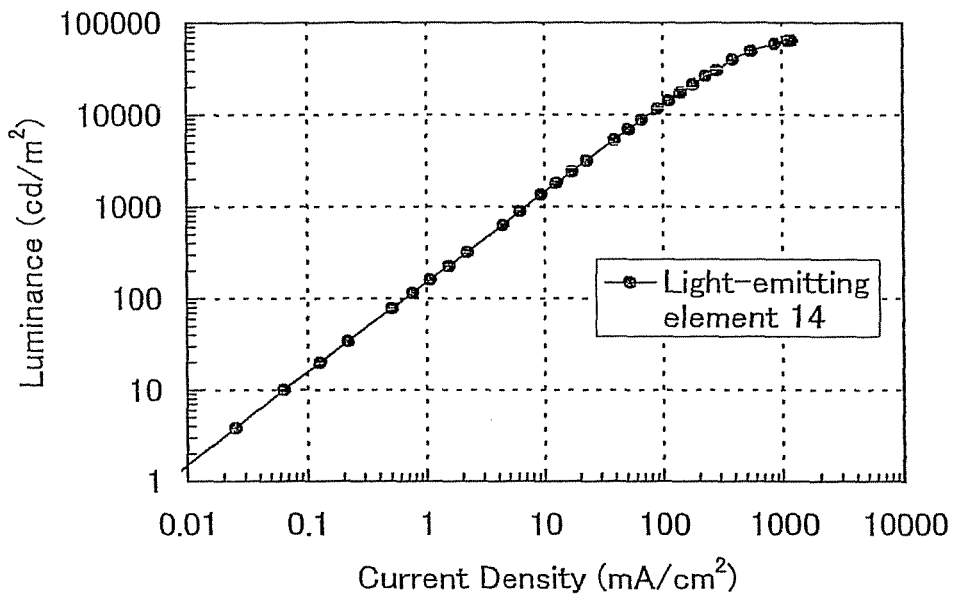
Figure 133:
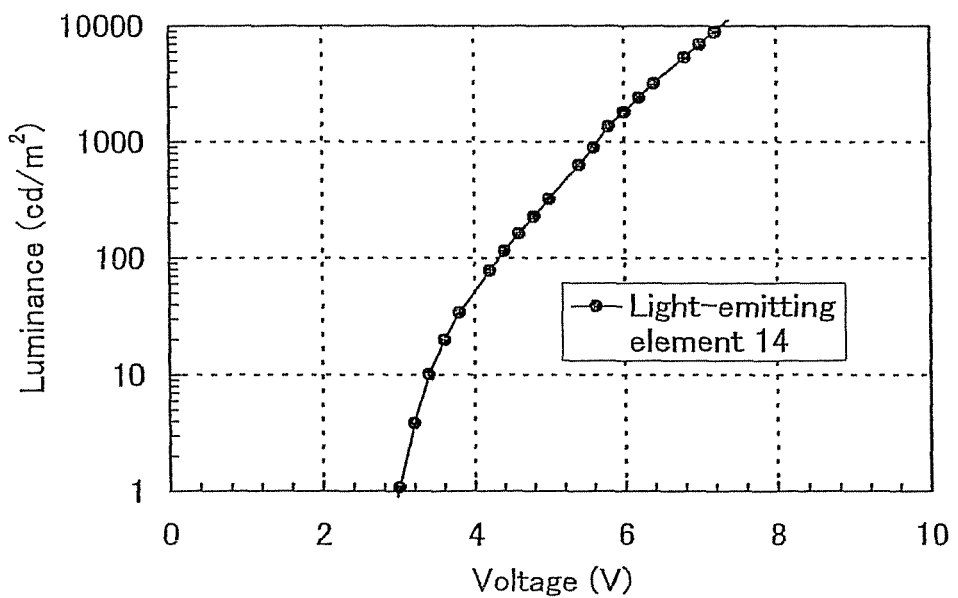
Figure 134:
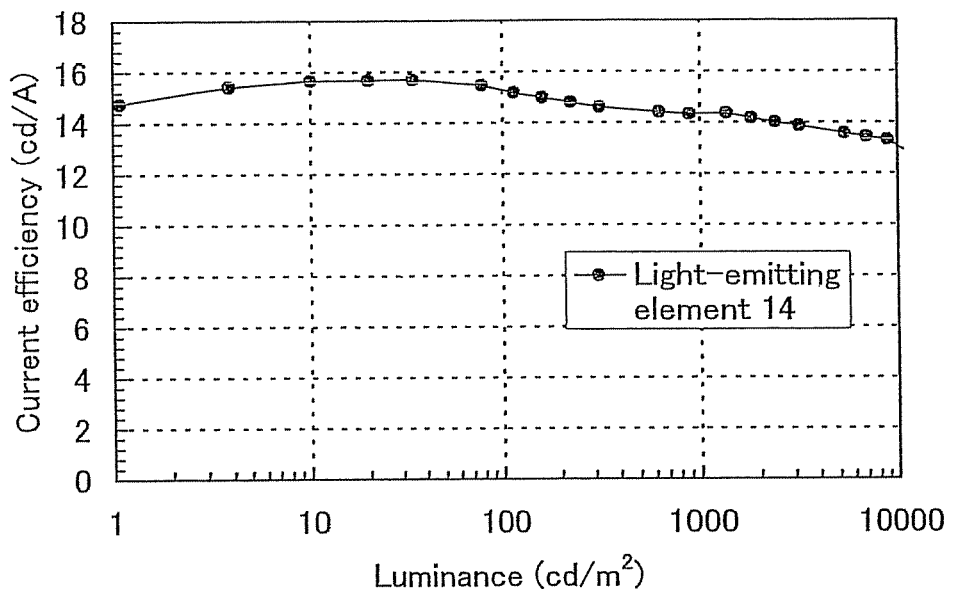
Figure 135:
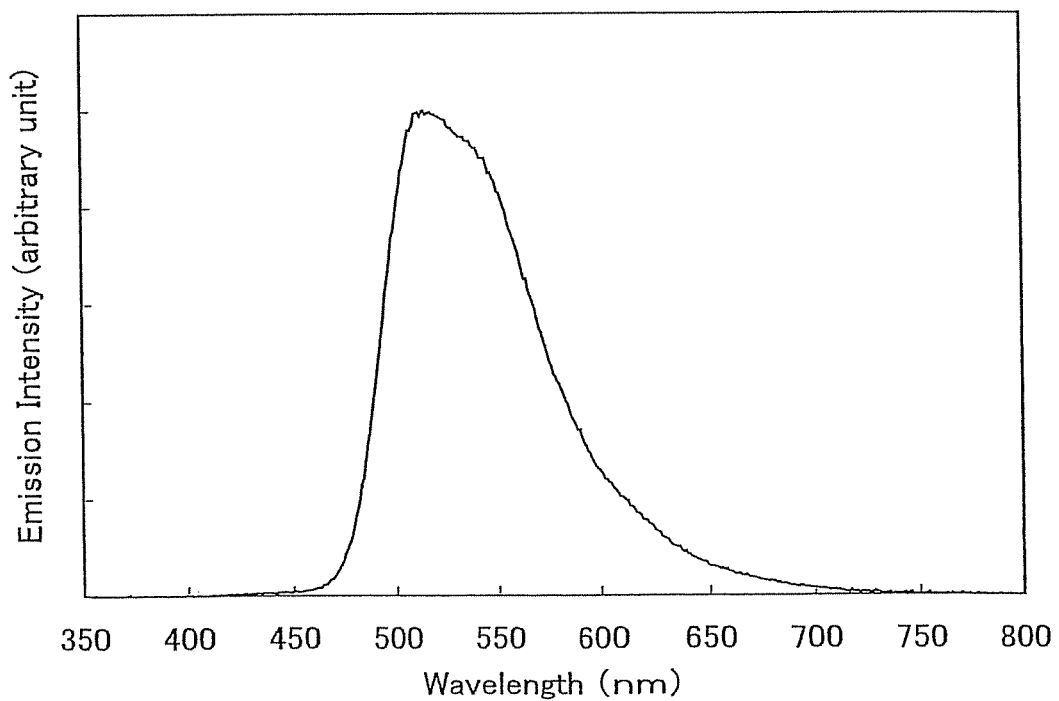
Figure 136:
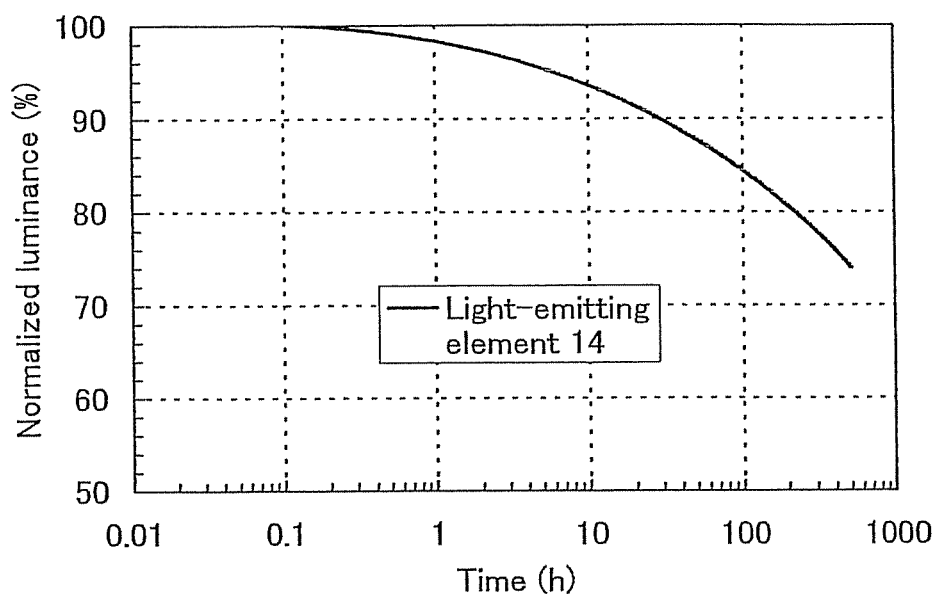
Figure 137:
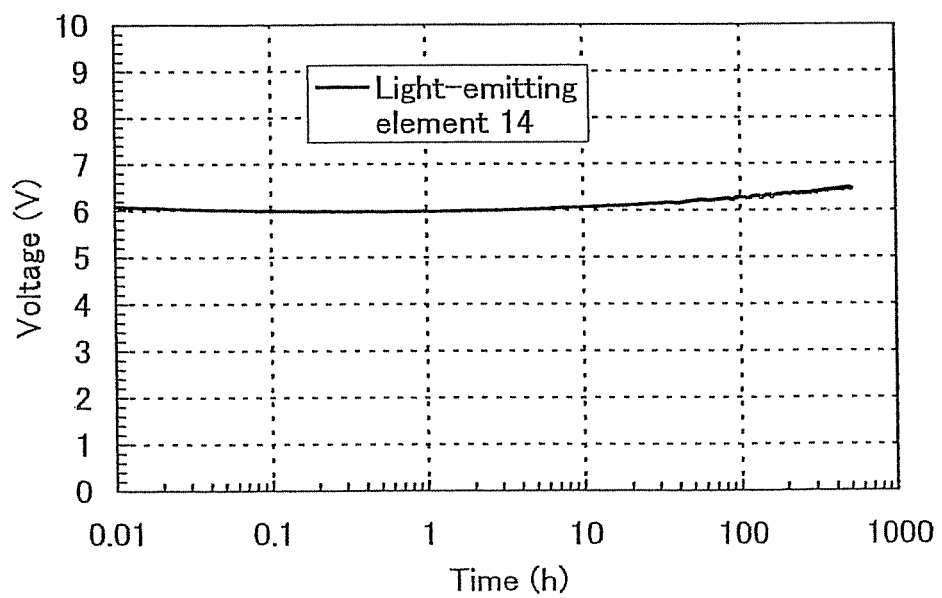
Figure 138:
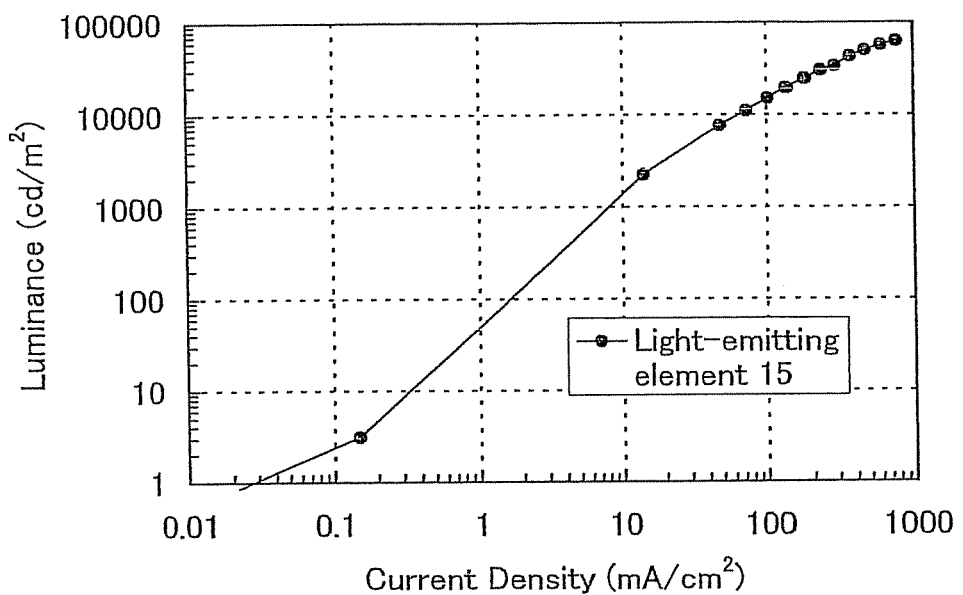
Figure 139:
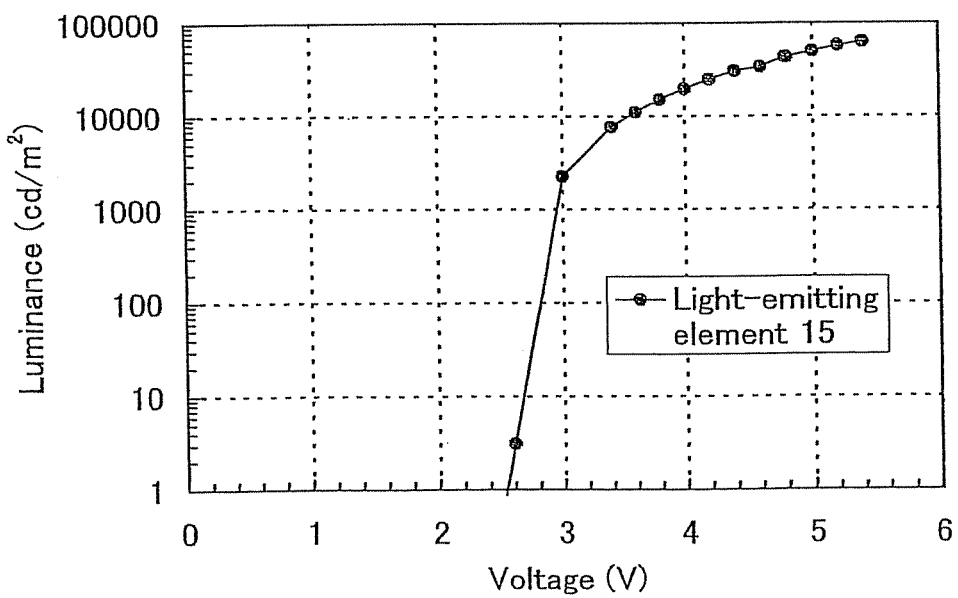
Figure 140:
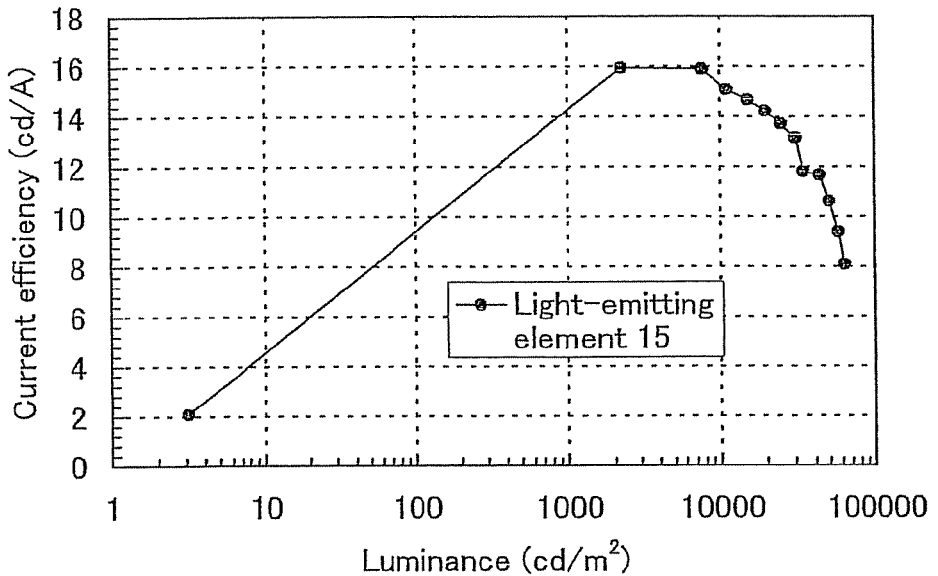
Figure 141:
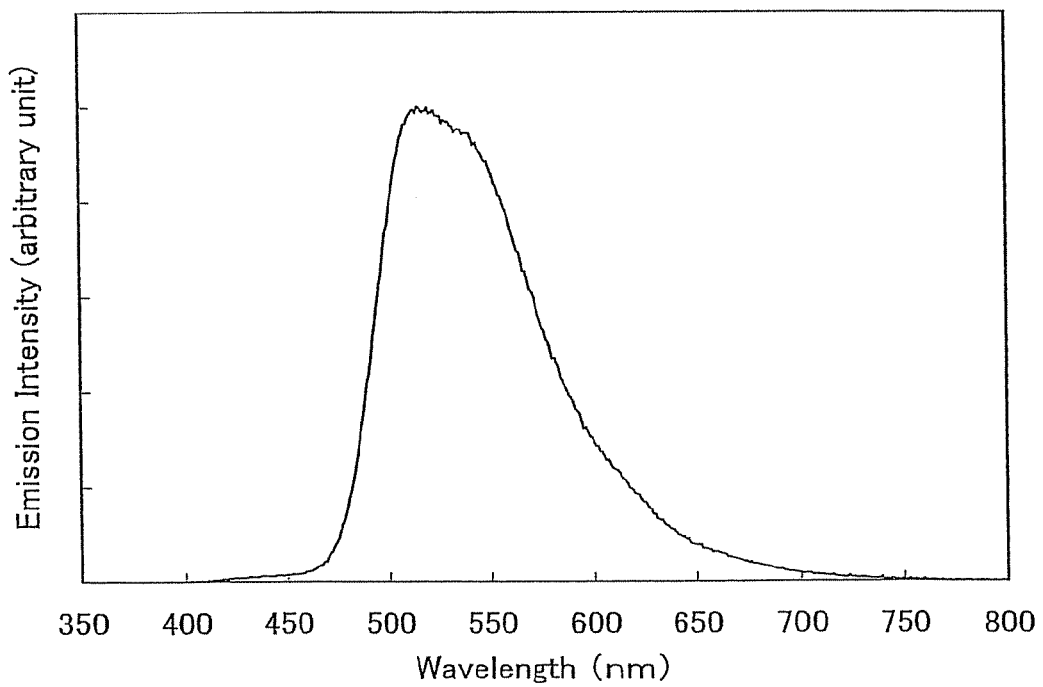

FIGS. 123A and 123B each show the $^1$H NMR chart of 2-{N-[4'-(9H-carbazol-9-yl)-1,1'-biphenyl-4-yl]-N-phenylamino}-9,10-diphenylanthracene (abbreviation: 2YGBAPA);

FIG. 124 shows the absorption spectrum of a toluene solution of 2-{N-[4'-(9H-carbazol-9-yl)-1,1'-biphenyl-4-yl]-N-phenylamino}-9,10-diphenylanthracene (abbreviation: 2YGBAPA);

FIG. 125 shows the emission spectrum of a toluene solution of 2-{N-[4'-(9H-carbazol-9-yl)-1,1'-biphenyl-4-yl]-N-phenylamino}-9,10-diphenylanthracene (abbreviation: 2YGBAPA);

FIG. 126 shows the current density-luminance characteristic of light-emitting element 13;

FIG. 127 shows the voltage-luminance characteristic of light-emitting element 13;

FIG. 128 shows the luminance-current efficiency characteristic of light-emitting element 13;

FIG. 129 shows the emission spectrum of light-emitting element 13;

FIG. 130 shows time dependence of normalized luminance of light-emitting element 13;

FIG. 131 shows time dependence of operation voltage of light-emitting element 13;

FIG. 132 shows the current density-luminance characteristic of light-emitting element 14;

FIG. 133 shows the voltage-luminance characteristic of light-emitting element 14;

FIG. 134 shows the luminance-current efficiency characteristic of light-emitting element 14;

FIG. 135 shows the emission spectrum of light-emitting element 14;

FIG. 136 shows time dependence of normalized luminance of light-emitting element 14;

FIG. 137 shows time dependence of operation voltage of light-emitting element 14;

FIG. 138 shows the current density-luminance characteristic of light-emitting element 15;

FIG. 139 shows the voltage-luminance characteristic of light-emitting element 15;

FIG. 140 shows the luminance-current efficiency characteristic of light-emitting element 15; and FIG. 141 shows the emission spectrum of light-emitting element 15.

BEST MODE FOR CARRYING OUT THE INVENTION

Hereinafter, embodiment modes and embodiments of the present invention will be explained with reference to the accompanied drawings. However, the present invention is not limited to the following description, and it is easily understood by those skilled in the art that the modes and details thereof can be changed in various ways without departing from the concept and scope of the present invention. Therefore, the present invention is not interpreted limited to the following description of embodiment modes and embodiments.

Embodiment Mode 1

In this embodiment mode, an anthracene derivative of the present invention is described.

The anthracene derivative of the present invention is the anthracene derivative represented by General Formula (1).

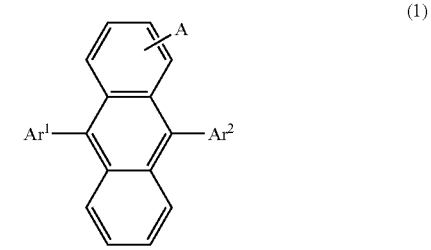

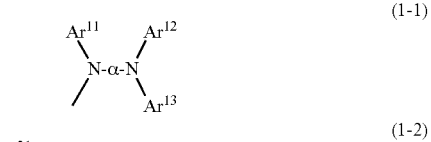

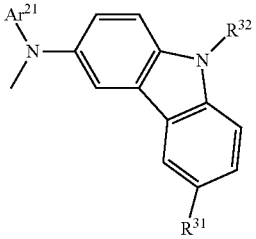

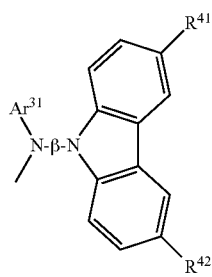
(1-3)

(In the formula, each of $Ar^1$ and $Ar^2$ represents an aryl group having 6 to 25 carbon atoms, and A represents a substituent represented by any of General Formulae (1-1) to (1-3). In General Formulae (1-1) to (1-3), each of $Ar^{11}$ to $Ar^{13}$ represents an aryl group having 6 to 25 carbon atoms; a represents an arylene group having 6 to 25 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents any of hydrogen, an alkyl group having 1 to 4 carbon atoms, and an aryl group having 6 to 25 carbon atoms.)

In General Formula (1), a substituent represented by Structural Formulae (20-1) to (20-9) can be given as a substituent represented by each of $Ar^1$ and $Ar^2$, for example.

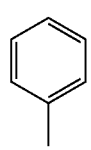
(20-1)

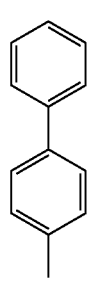
(20-2)

(20-3)

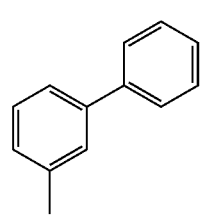

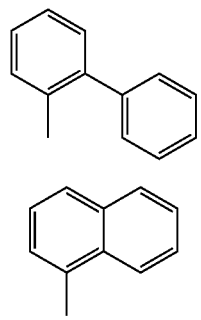
(20-4)

(20-5)

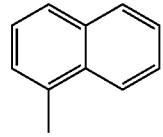

(20-6)

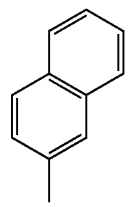

(20-7)

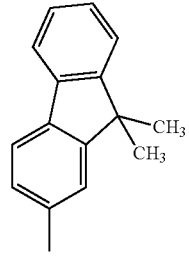

(20-8)

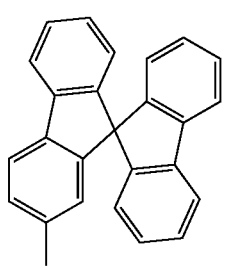

(20-9)

In General Formula (14), a substituent represented by Structural Formulae (21-1) to (21-9) can be given as a substituent represented by each of $Ar^{11}$ to $Ar^{13}$, for example.

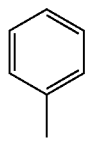
(21-1)

(21-2)
(21-3)
(21-4)
(21-5)
(21-6)
(21-7)
(21-8)
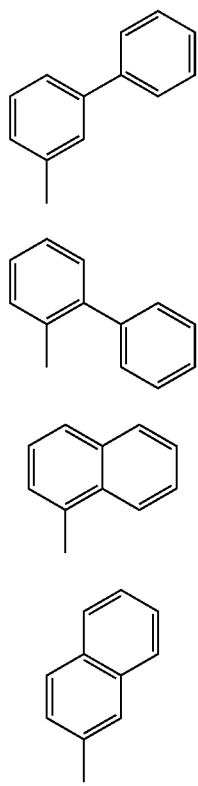
(21-9)
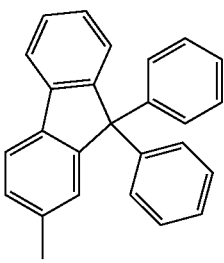
Also, in General Formula (1-1), a substituent represented by Structural Formulae (22-1) to (22-9) can be given as a substituent represented by α, for example.
(22-1)
(22-2)
(22-3)
(22-4)
(22-5)
(22-6)
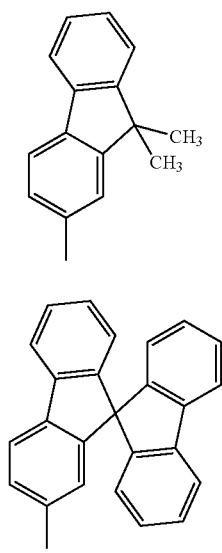

(22-7)
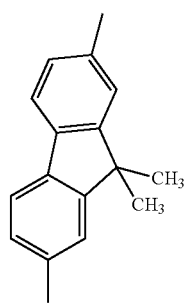
(22-8)
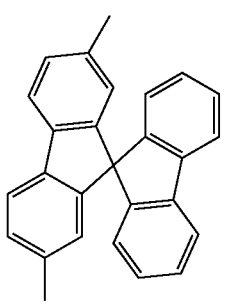
(22-9)
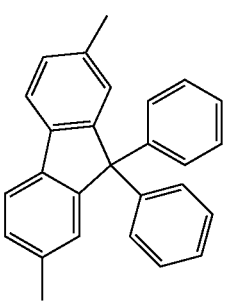
Consequently, a substituent represented by Structural Formulae (31-1) to (31-23) can be given as a substituent represented by General Formula (1-1), for example.
(31-1)
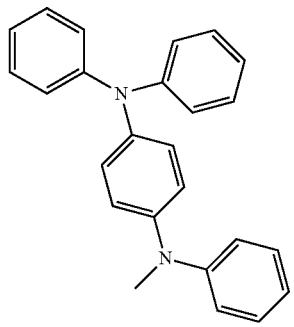
(31-2)
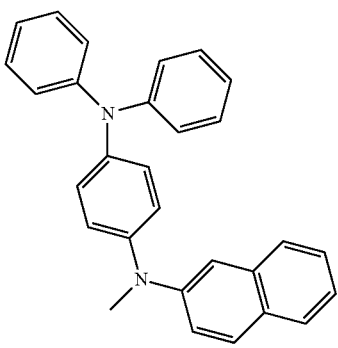
(31-3)
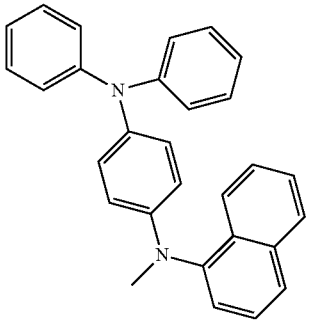
(31-4)
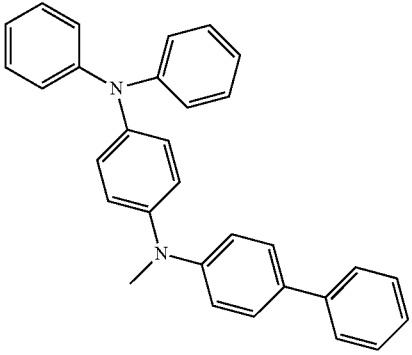
(31-5)
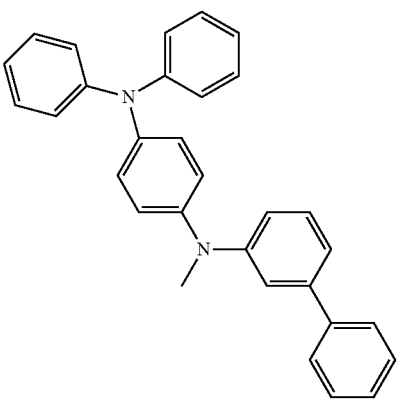

(31-6)
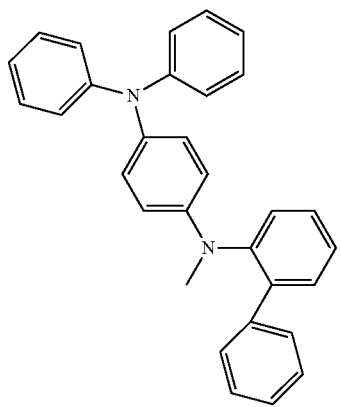
(31-7)
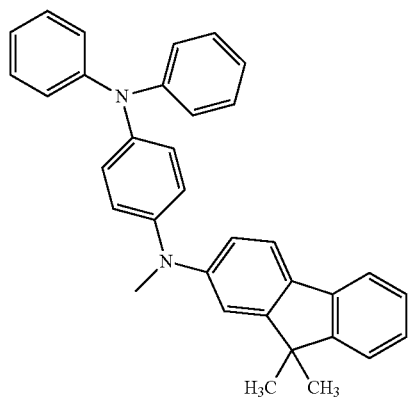
(31-8)
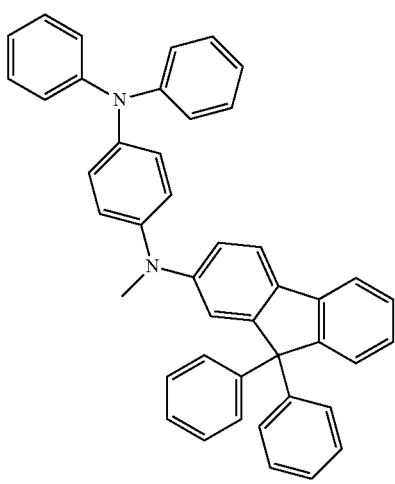
(31-9)
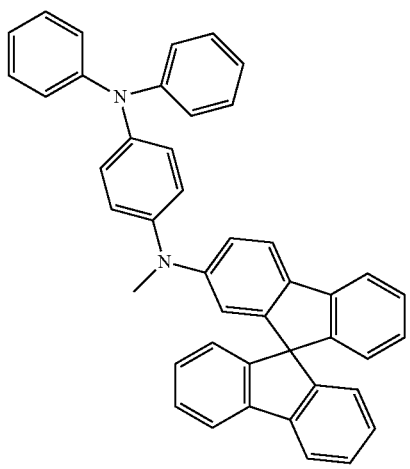
(31-10)
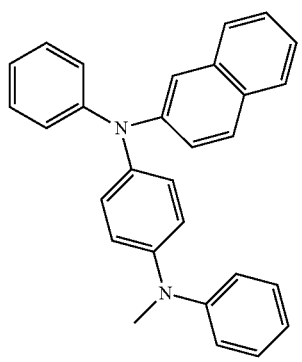
(31-11)
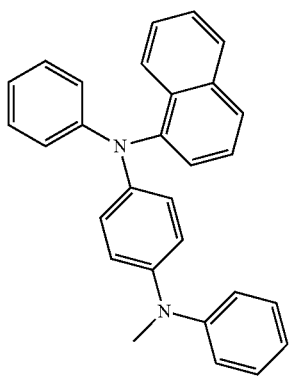
(31-12)
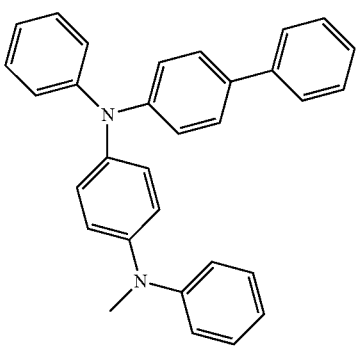

(31-13) 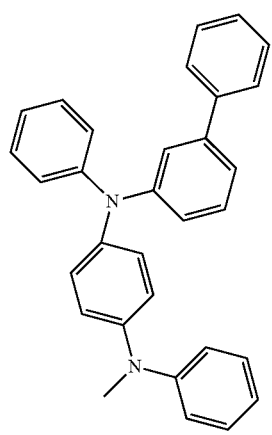
(31-14) 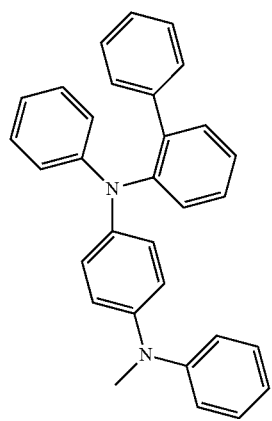
(31-15) 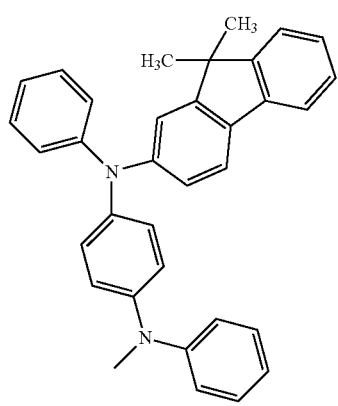
(31-16) 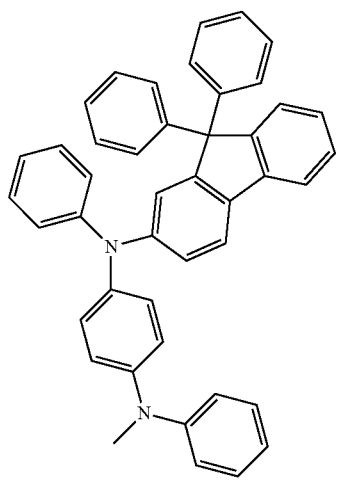
(31-17) 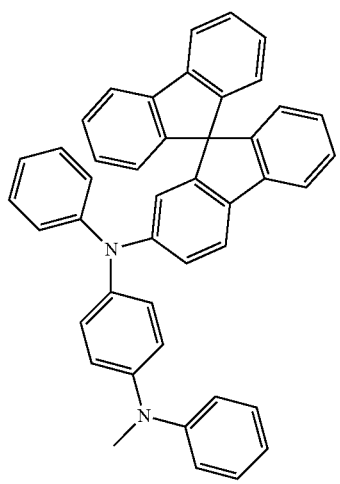
(31-18) 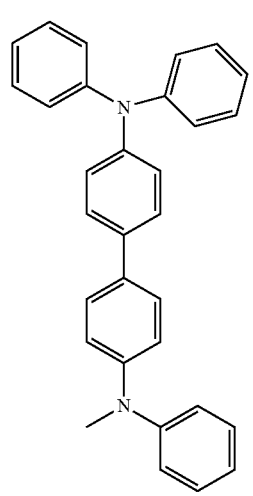

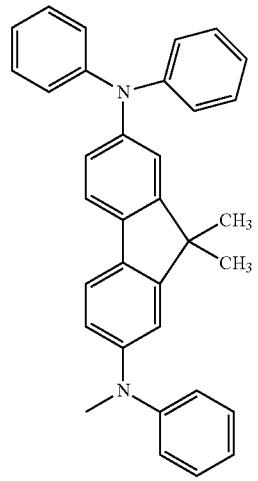
(31-19)
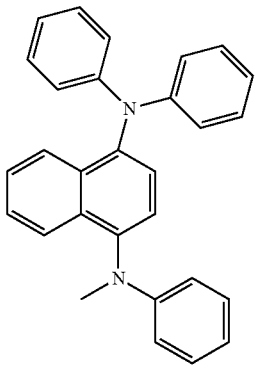
(31-22)
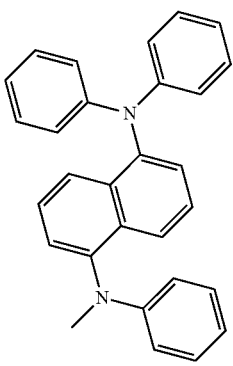
(31-20)
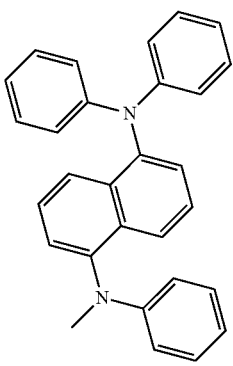
(31-23)
Further, in General Formula (1-2), a substituent represented by Structural Formulae (23-1) to (23-9) can be given as a substituent represented by $Ar^{21}$, for example.
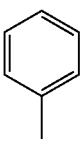
(23-1)
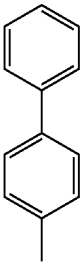
(23-2)
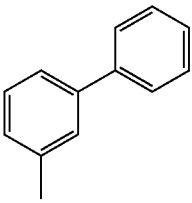
(31-21)
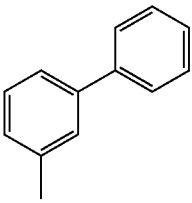
(23-3)

-continued
(23-4)
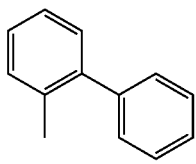
(23-5)
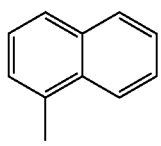
(23-6)
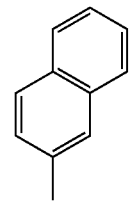
(23-7)
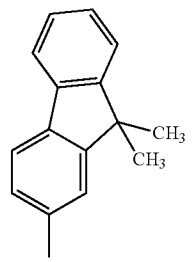
(23-8)
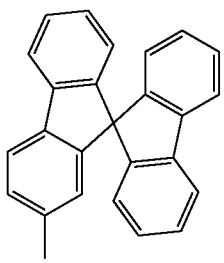
(23-9)
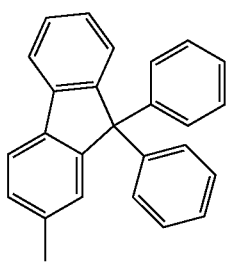
Furthermore, in General Formula (1-2), Structural Formulae (24-1) to (24-18) can be given as specific examples of $R^{31}$, for example.
(24-1)
H
(24-2)
CH₃
-continued
(24-3)
(24-4)
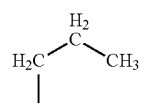
(24-5)
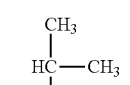
(24-6)
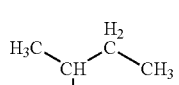
(24-7)
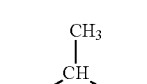
(24-8)
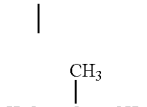
(24-9)
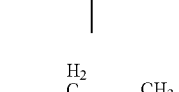
(24-10)
(24-11)
(24-12)
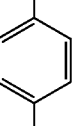
(24-12)
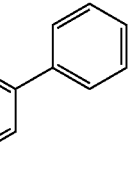
(24-13)
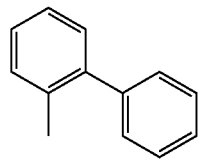

(24-14)
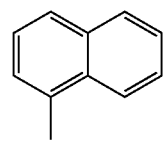
(24-15)
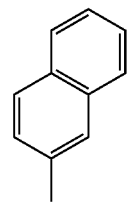
(24-16)
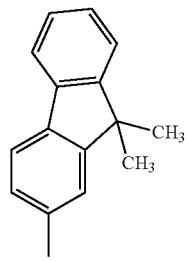
(24-17)
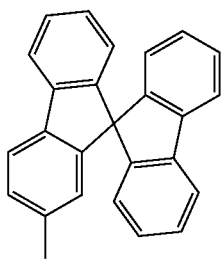
(24-18)
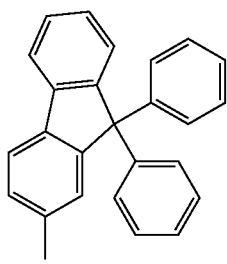
Also, in General Formula (1-2), Structural Formulae (25-1) to (25-17) can be given as specific examples of $R^{32}$, for example.
(25-1)
CH₃—
(25-2)
CH₃—CH₂—
(25-3)
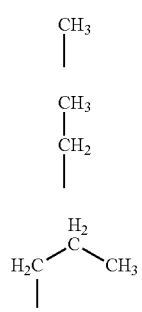
(25-4)
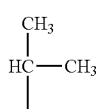
(25-5)
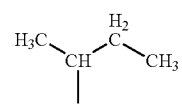
(25-6)
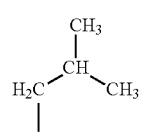
(25-7)
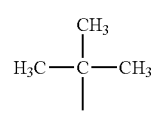
(25-8)
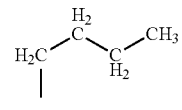
(25-9)
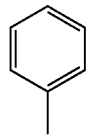
(25-10)
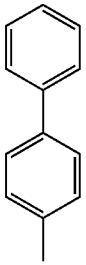
(25-11)
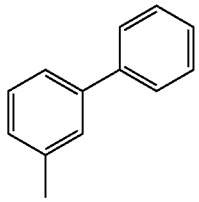
(25-12)
(25-13)

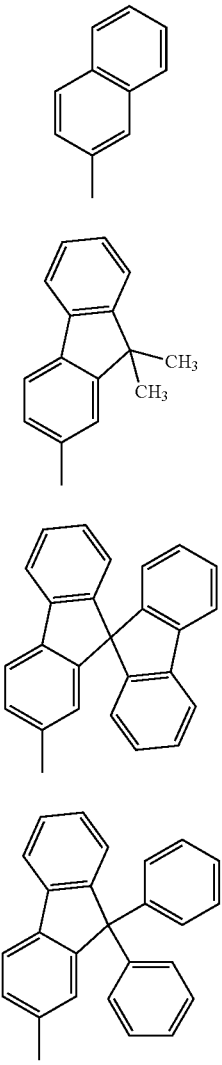
Consequently, Structural Formulae (32-1) to (32-42) can be given as specific examples of General Formula (1-2), for example.
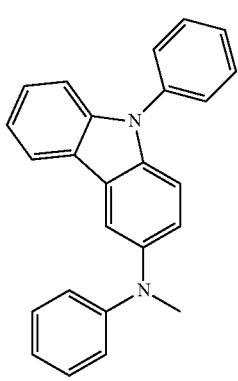
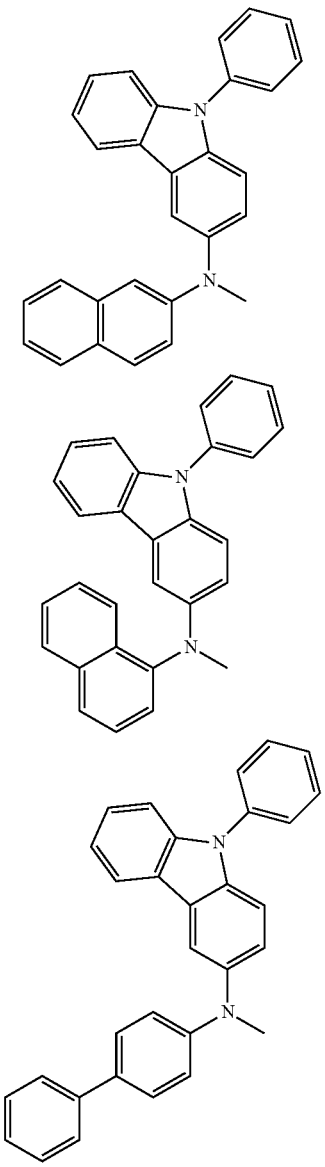

-continued
(32-6)
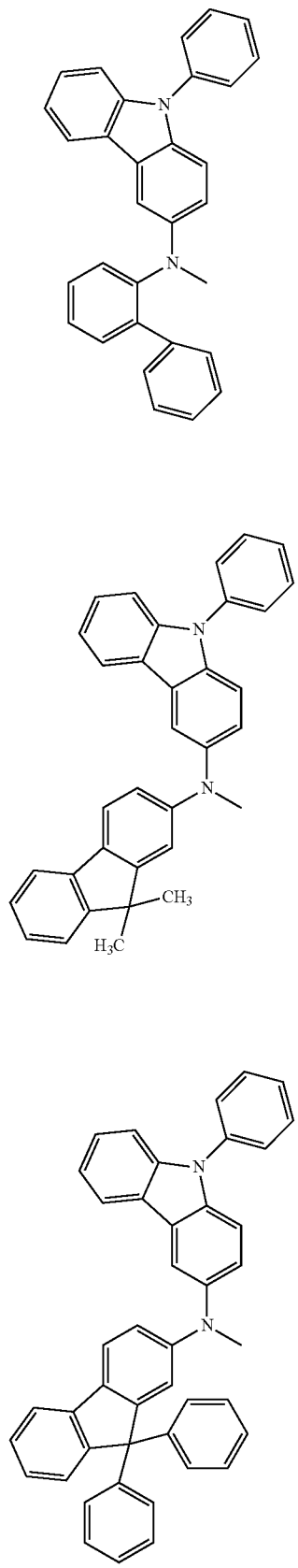
(32-7)
(32-8)
(32-9)
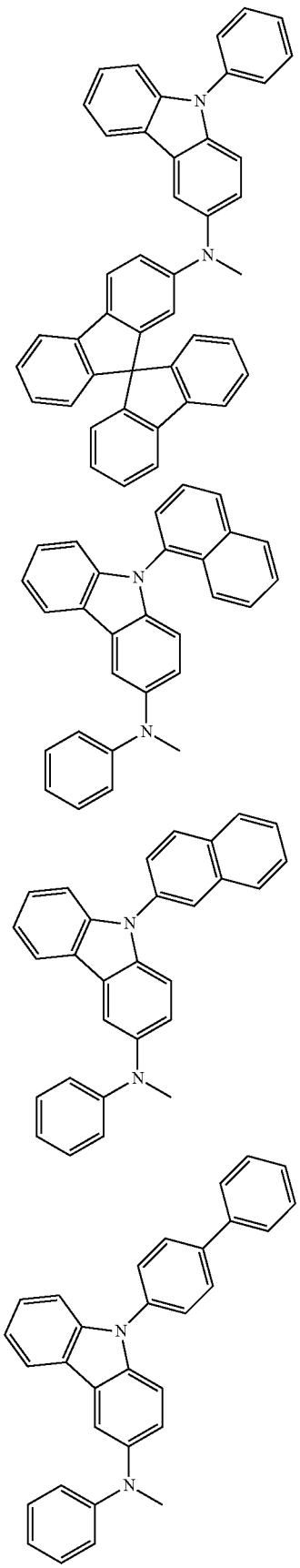
(32-10)
(32-11)
(32-12)

(32-13)
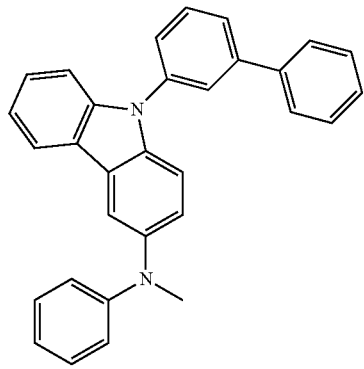
(32-14)
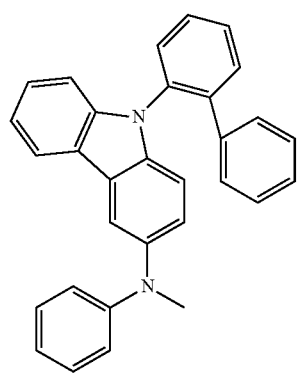
(32-15)
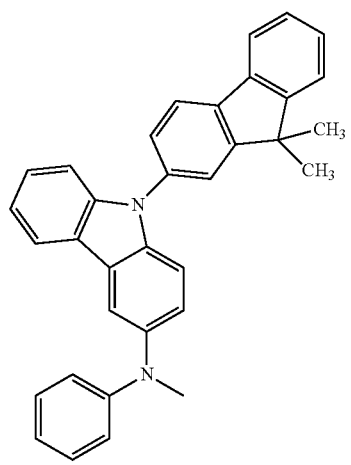
(32-16)
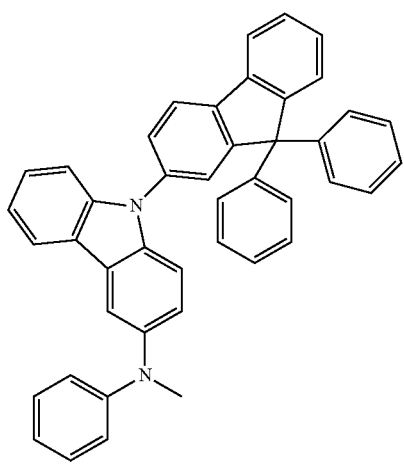
(32-17)
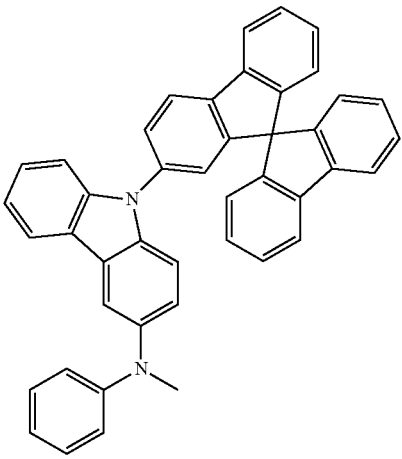
(32-18)
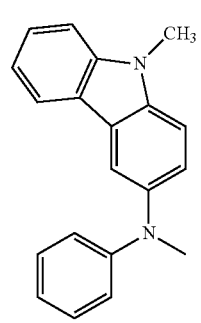
(32-19)
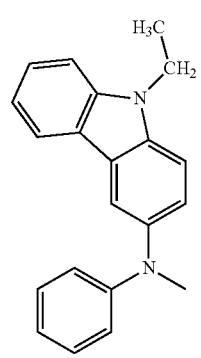
(32-20)
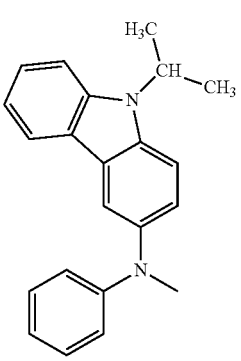

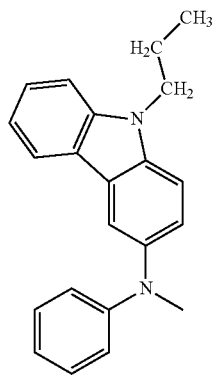 (32-21)
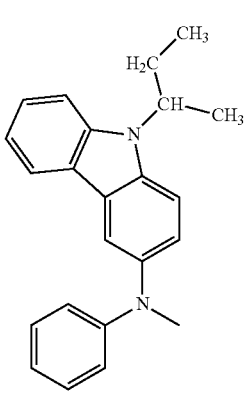 (32-22)
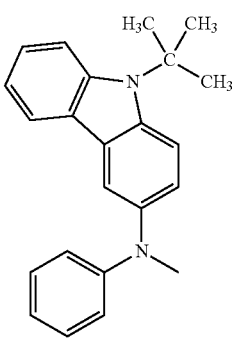 (32-23)
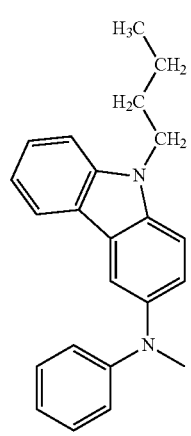 (32-24)
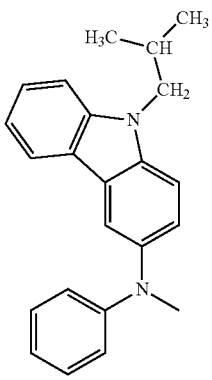 (32-25)
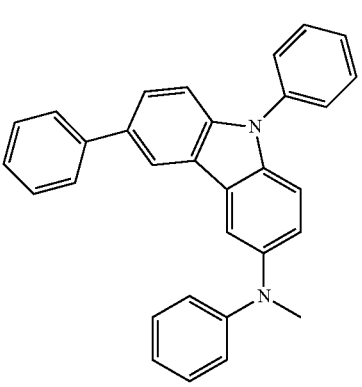 (32-26)
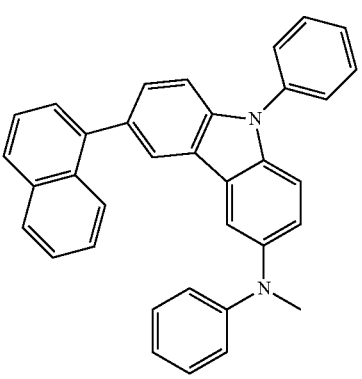 (32-27)
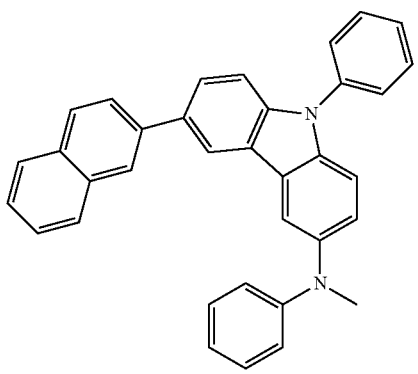 (32-28)

(32-29)
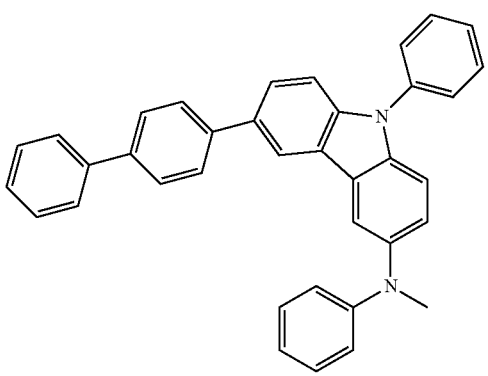
(32-30)
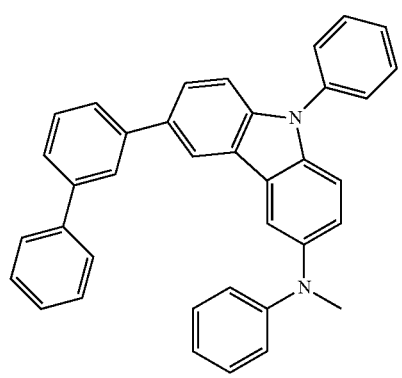
(32-31)
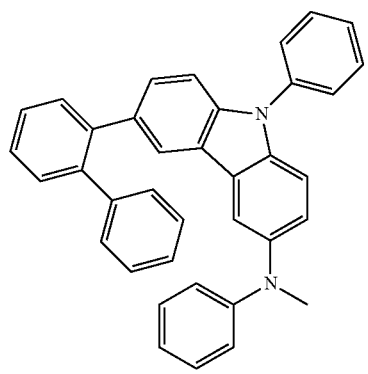
(32-32)
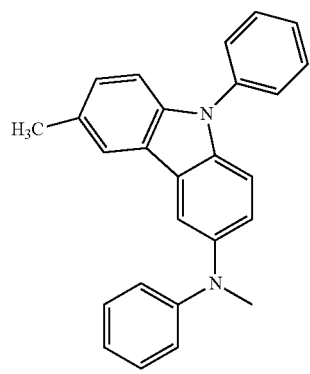
(32-33)
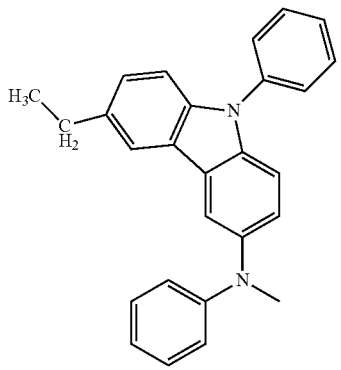
(32-34)
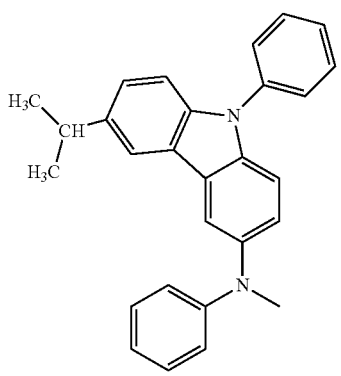
(32-35)
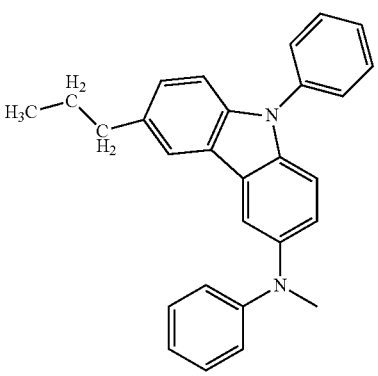
(32-36)
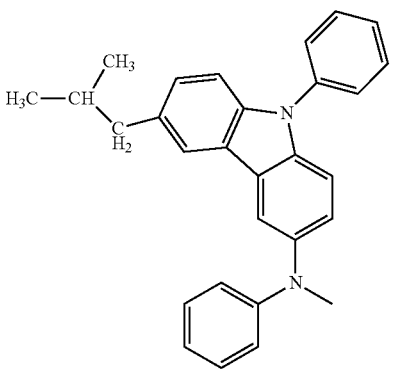

(32-37)
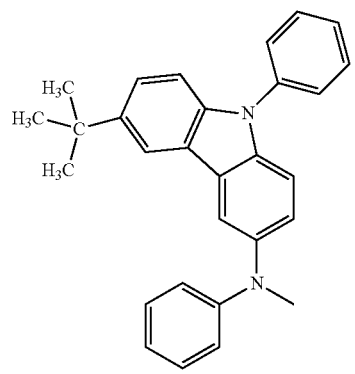
(32-38)
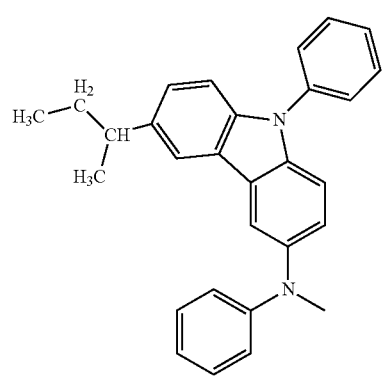
(32-39)
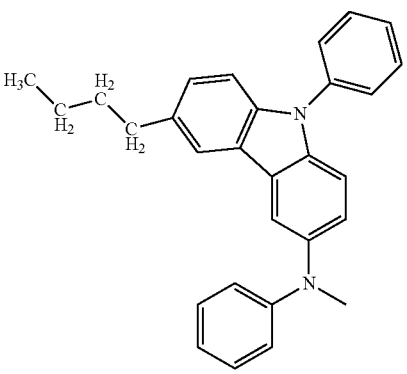
(32-40)
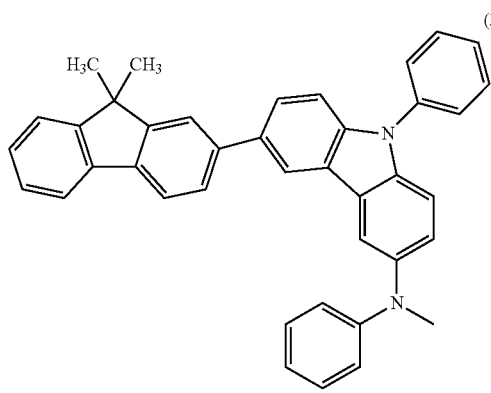
(32-41)
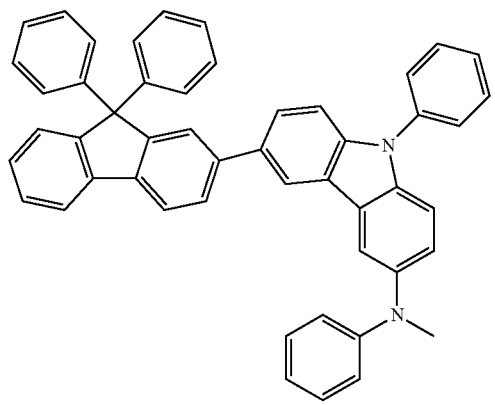
(32-42)
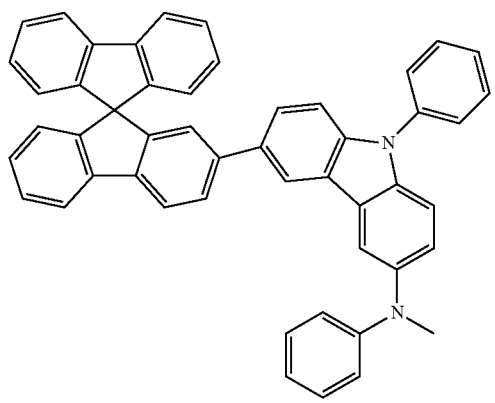
Also, in General Formula (1-3), Structural Formulae (26-1) to (26-9) can be given as specific examples of $Ar^{31}$, for example.
(26-1)
(26-2)
(26-3)
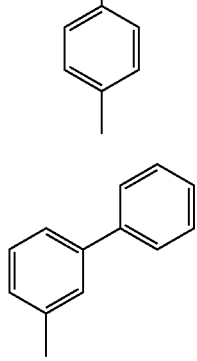

(26-4) 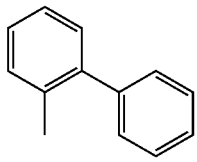
(26-5) 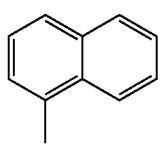
(26-6) 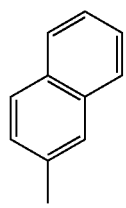
(26-7) 
(26-8) 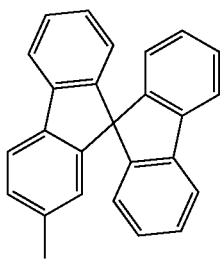
(26-9) 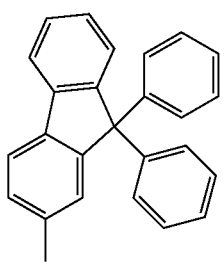
Also, in General Formula (1-3), Structural Formulae (27-1) to (27-9) can be given as specific examples of β, for example.
(27-1) 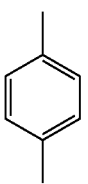
(27-2) 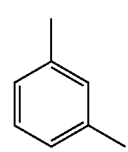
(27-3) 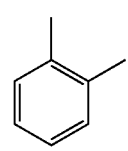
(27-4) 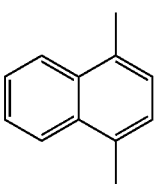
(27-5) 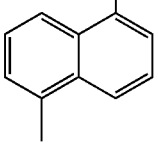
(27-6) 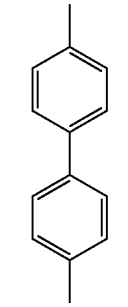
(27-7) 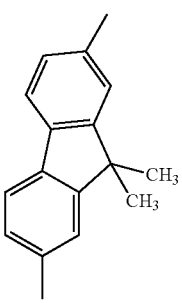

(27-8)
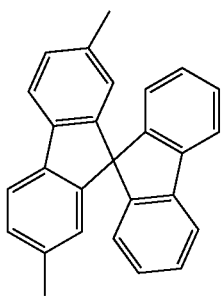
(27-9)
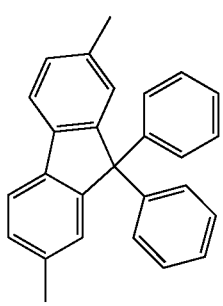
Further, in General Formula (1-3), Structural Formulae (28-1) to (28-18) can be given as specific examples of each of $R^{41}$ and $R^{42}$, for example.
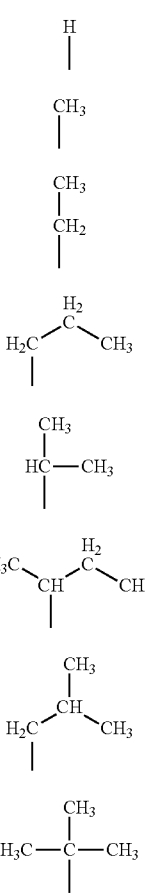
(28-1)
(28-2)
(28-3)
(28-4)
(28-5)
(28-6)
(28-7)
(28-8)
(28-9)
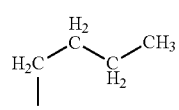
(28-10)
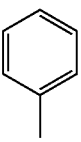
(28-11)
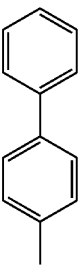
(28-12)
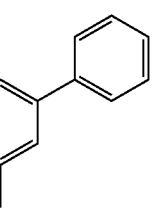
(28-13)
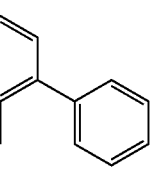
(28-14)
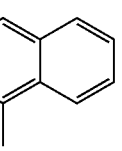
(28-15)
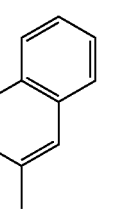
(28-16)
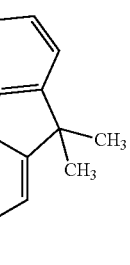

(28-17)
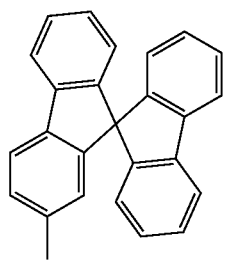
(28-18)
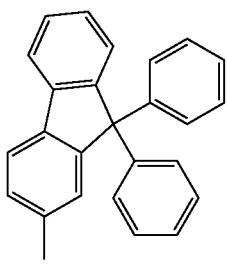
Consequently, Structural Formulae (33-1) to (33-34) can be given as specific examples of General Formula (1-3), for example.
(33-1)
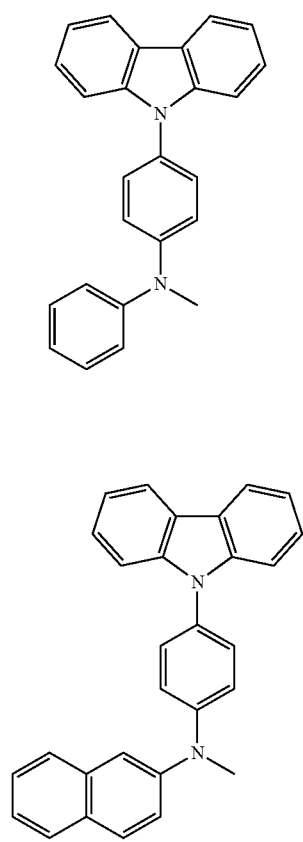
(33-2)
(33-3)
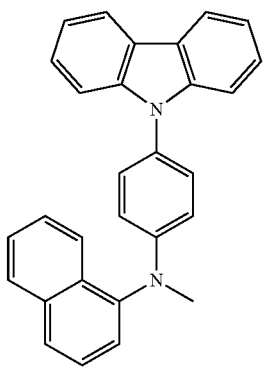
(33-4)
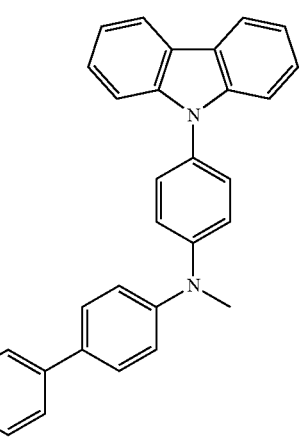
(33-5)
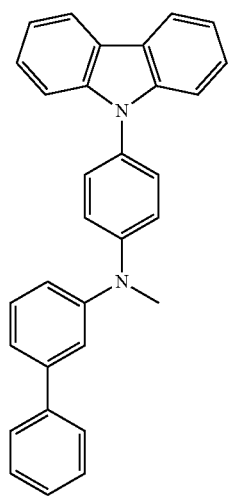

(33-6)
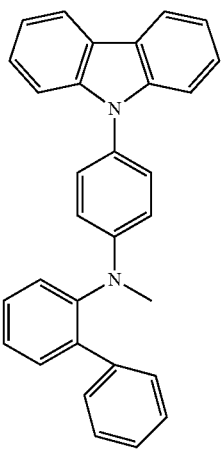
(33-7)
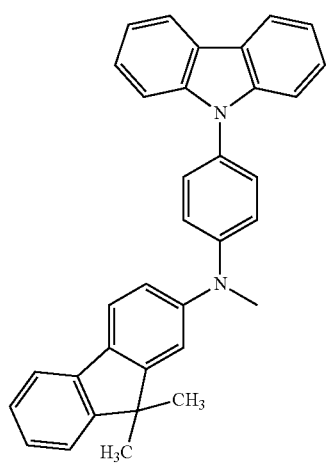
(33-8)
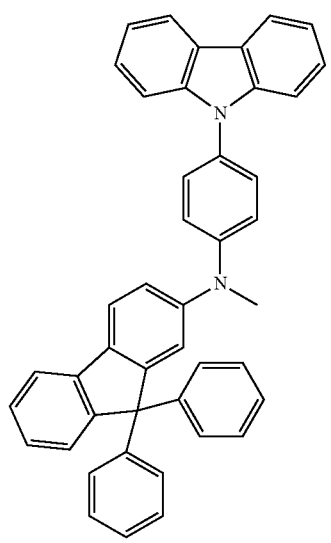
(33-9)
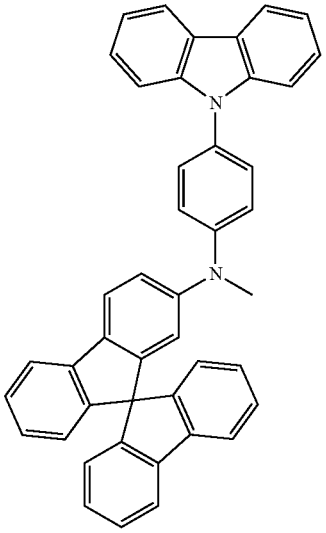
(33-10)
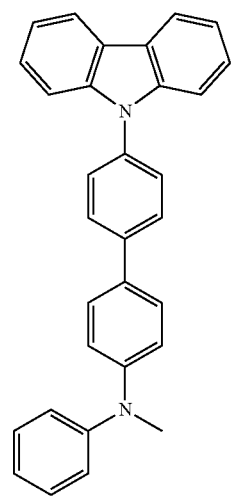
(33-11)
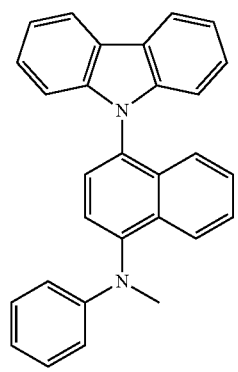

(33-12)
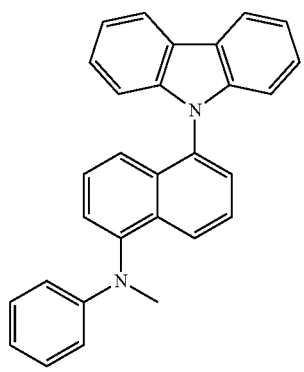
(33-13)
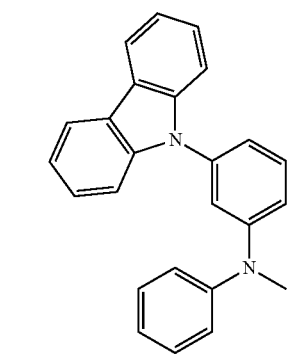
(33-14)
(33-15)
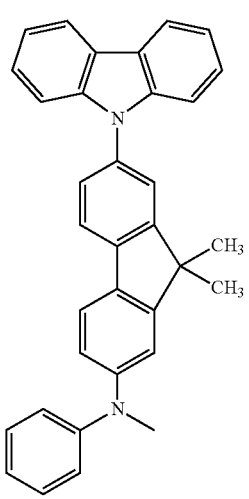
(33-16)
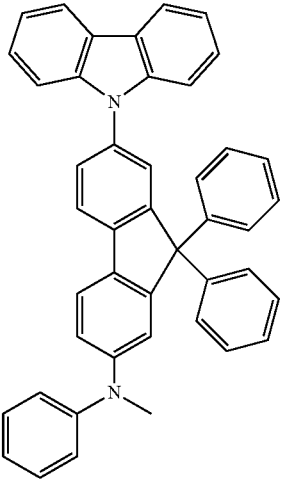
(33-17)
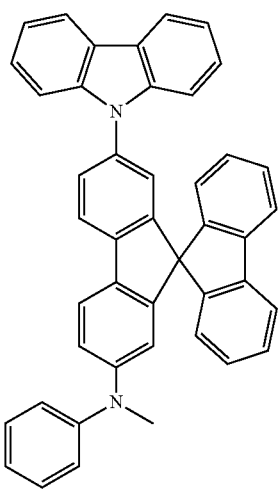
(33-18)
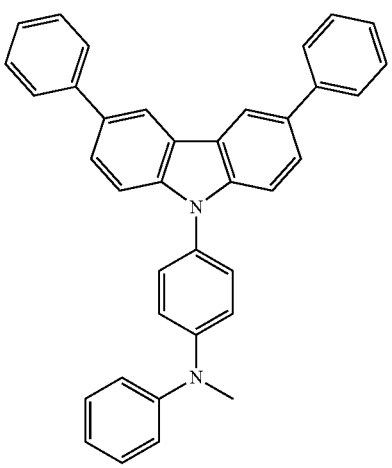

(33-19)
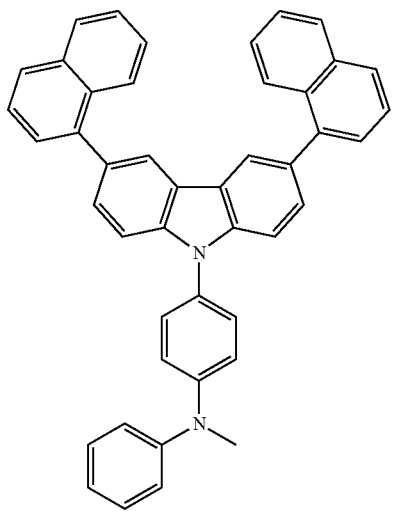
(33-22)
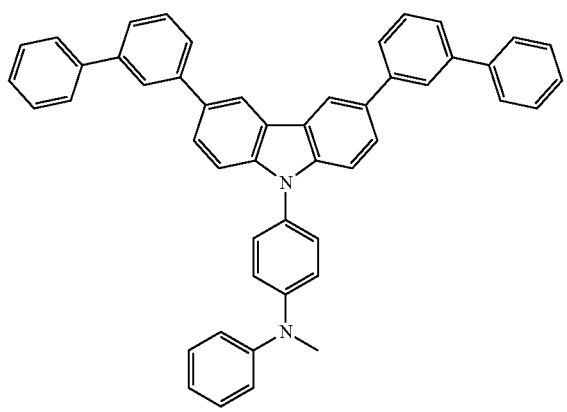
(33-20)
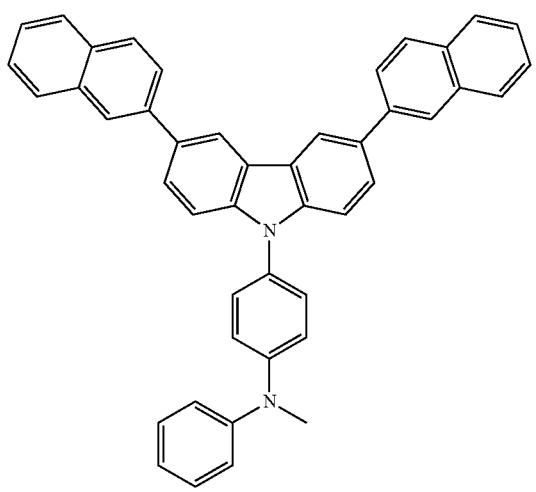
(33-23)
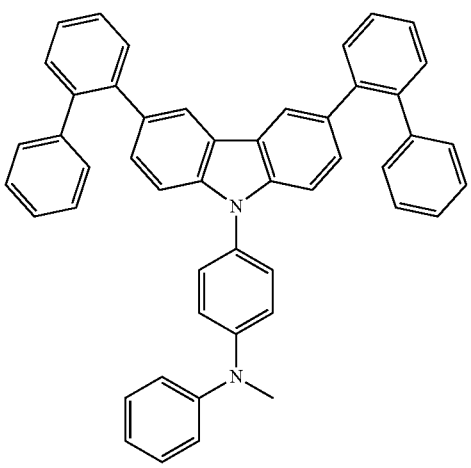
(33-21)
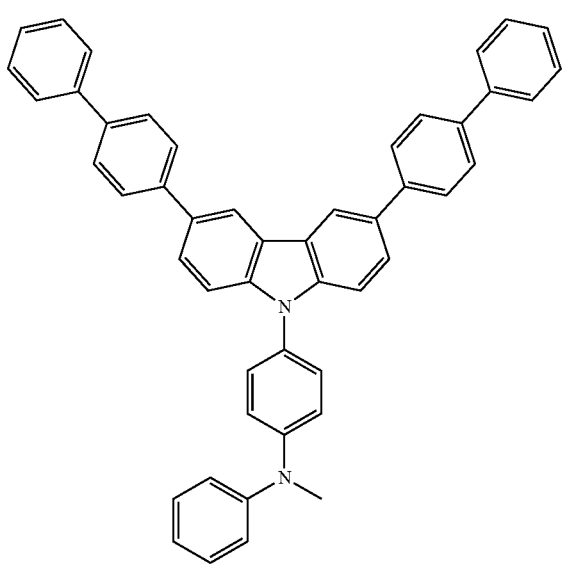
(33-24)
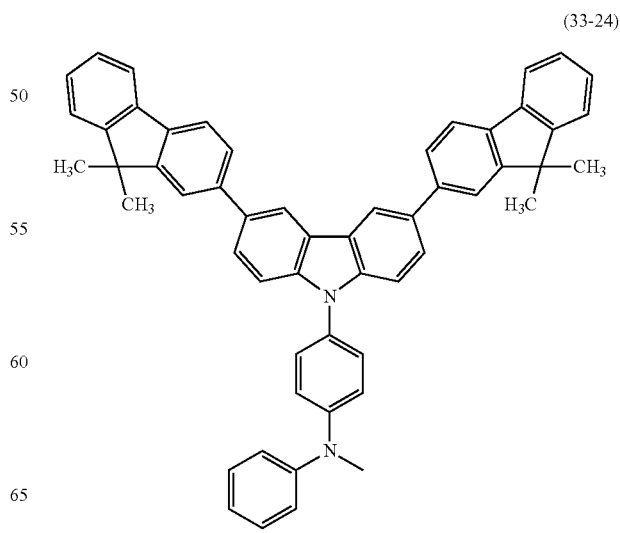

(33-25) 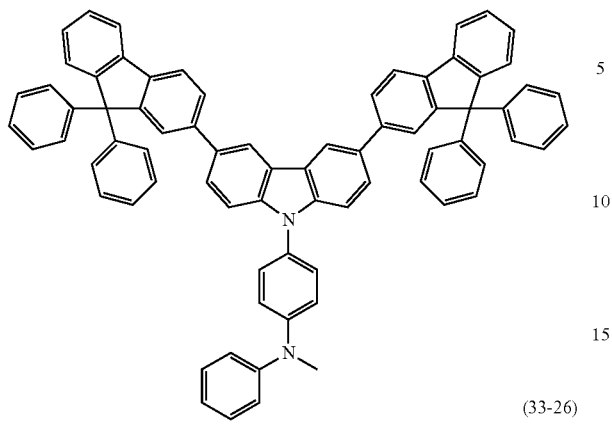
(33-26) 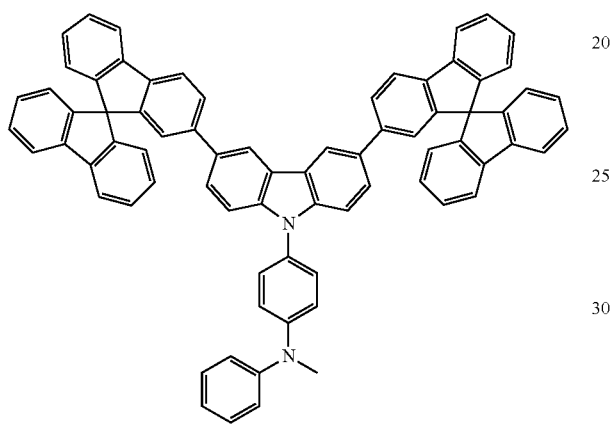
(33-27) 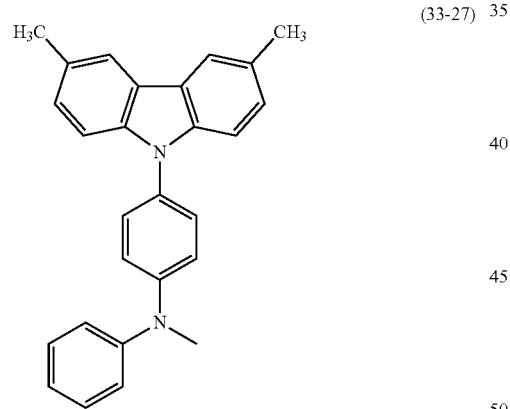
(33-28) 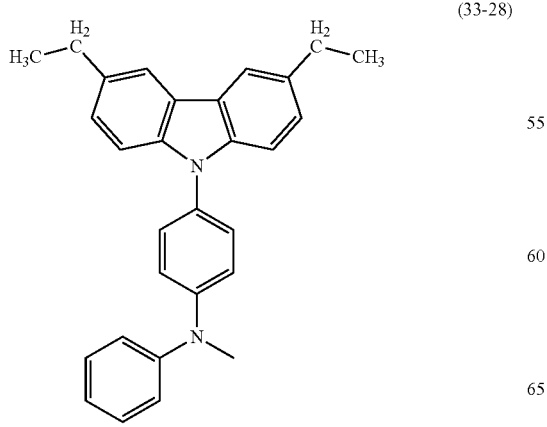
(33-29) 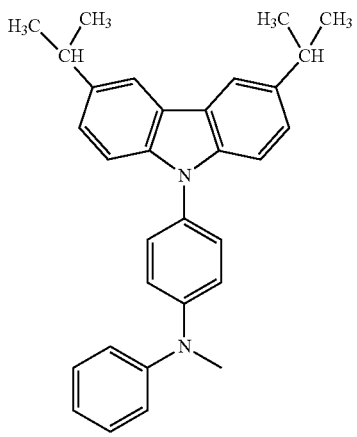
(33-30) 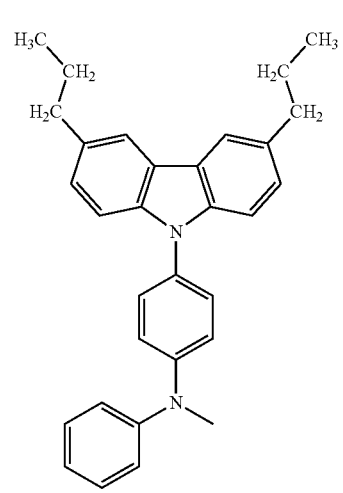
(33-31) 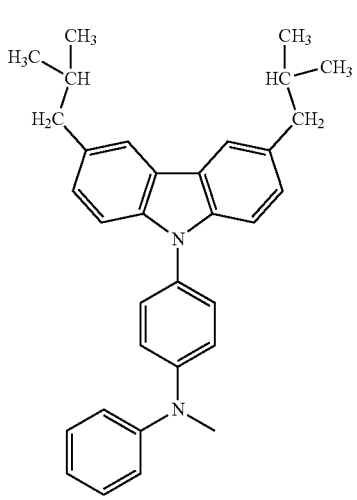

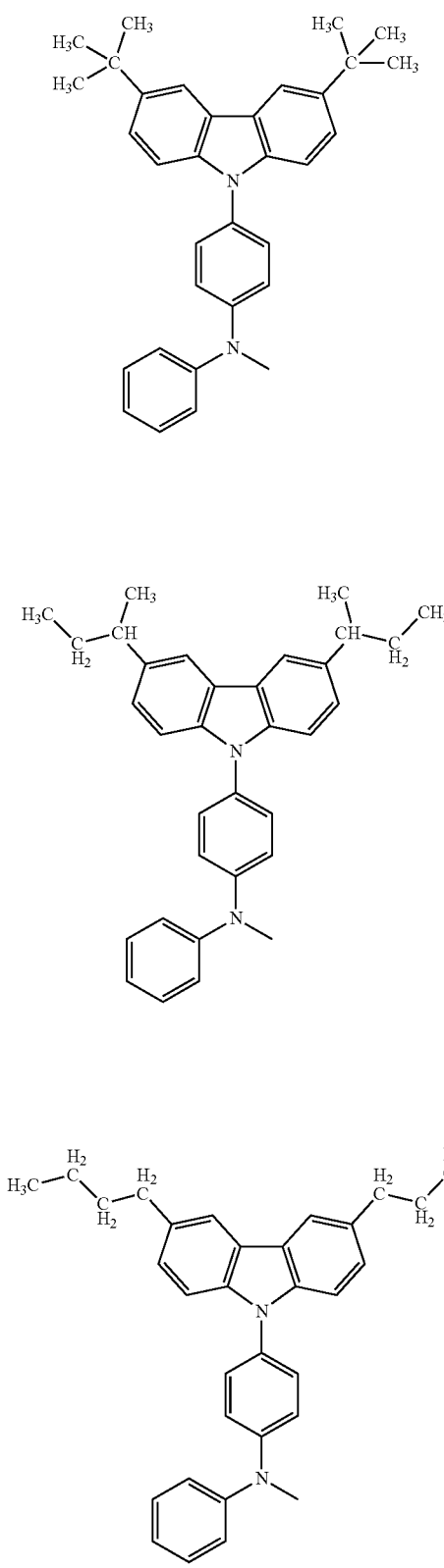

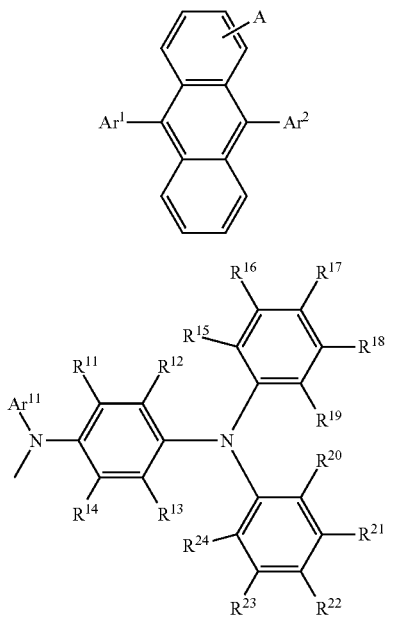

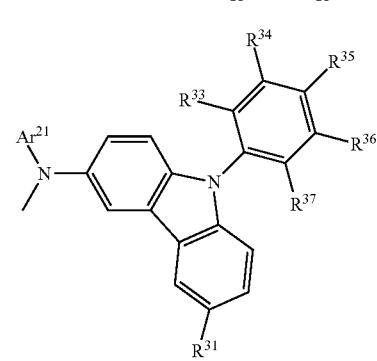

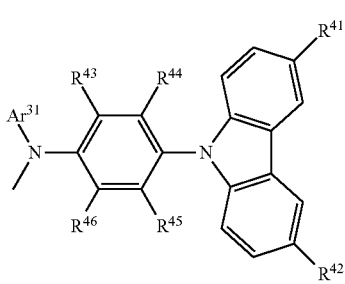

Also, among anthracene derivatives represented by General Formula (1), the anthracene derivative represented by General Formula (2) is preferable.

(In the formula, each of $Ar^1$ and $Ar^2$ represents an aryl group having 6 to 25 carbon atoms, and A represents a substituent represented by any of General Formulae (2-1) to (2-3). In General Formulae (2-1) to (2-3), $Ar^{11}$ represents an aryl group having 6 to 25 carbon atoms; each of $R^{11}$ to $R^{24}$ represents any of hydrogen, an alkyl group having 1 to 4 carbon atoms, and an aryl group having 6 to 15 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; each of $R^{33}$ to $R^{37}$ represents any of hydrogen, an alkyl group having 1 to 4 carbon atoms, and an aryl group having 6 to 15 carbon atoms; $Ar^{31}$ represents an aryl group having 6 to 25 carbon atoms; each of $R^{41}$ and $R^{42}$ represents any of hydrogen, an alkyl group having 1 to 4 carbon atoms, and an aryl group having 6 to 25 carbon atoms; and each of $R^{43}$ to $R^{46}$ represents any of hydrogen, an alkyl group having 1 to 4 carbon atoms, and an aryl group having 6 to 15 carbon atoms.)

Also, among anthracene derivatives represented by General Formula (1), the anthracene derivative represented by General Formula (3) is preferable.

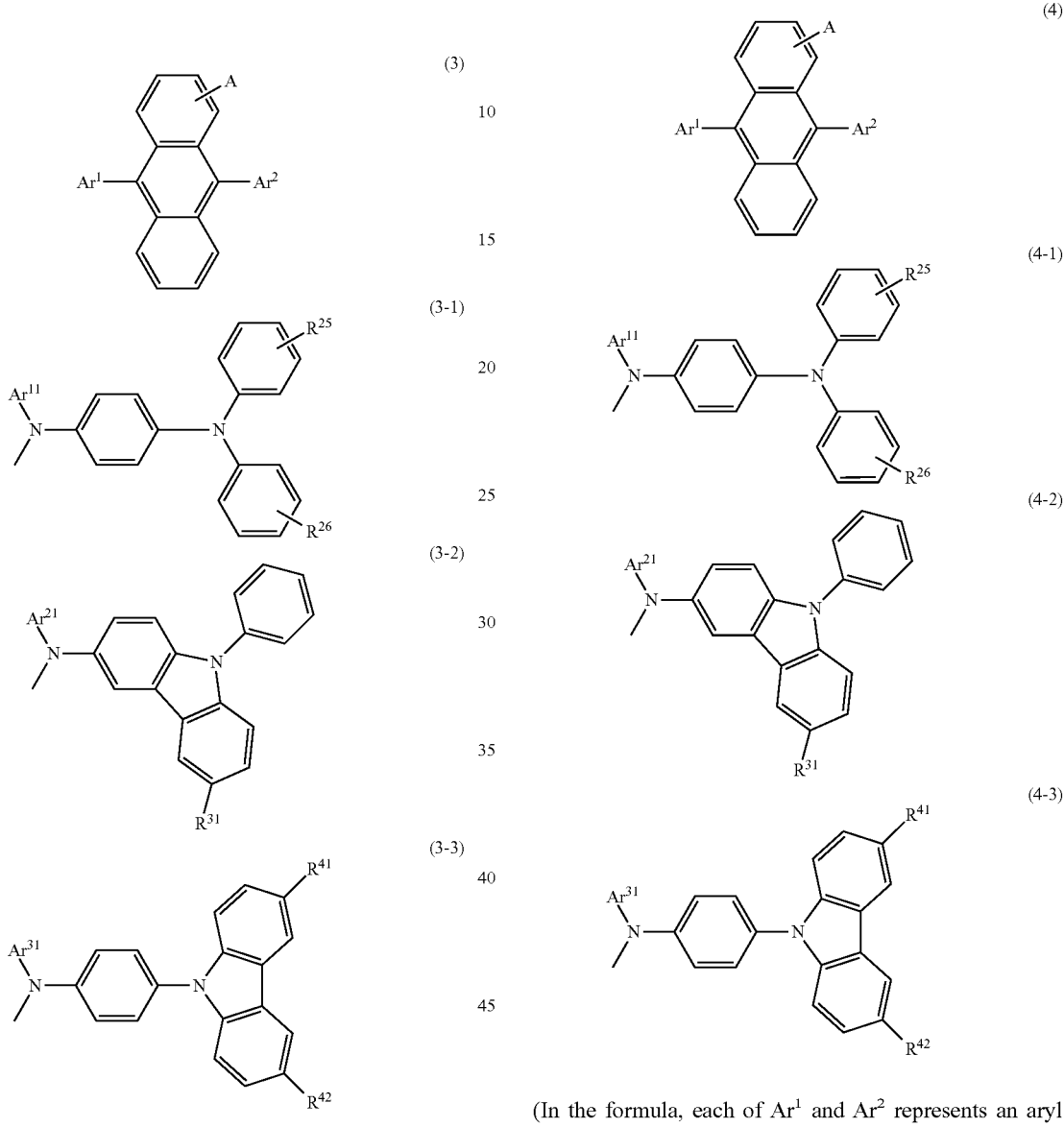

(In the formula, each of $Ar^1$ and $Ar^2$ represents an aryl group having 6 to 25 carbon atoms, and A represents any substituent represented by General Formulae (3-1) to (3-3). In General Formulae (3-1) to (3-3), $Ar^{11}$ represents an aryl group having 6 to 25 carbon atoms; each of $R^{25}$ and $R^{26}$ represents any of hydrogen, an alkyl group having 1 to 4 carbon atoms, and an aryl group having 6 to 15 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; $Ar^{31}$ represents an aryl group having 6 to 25 carbon atoms; and each of $R^{41}$ and $R^{42}$ represents any of hydrogen, an alkyl group having 1 to 4 carbon atoms, and an aryl group having 6 to 25 carbon atoms.)

Also, among anthracene derivatives represented by General Formula (1), the anthracene derivative represented by General Formula (4) is preferable.

(In the formula, each of $Ar^1$ and $Ar^2$ represents an aryl group having 6 to 25 carbon atoms, and A represents any substituent represented by General Formulae (4-1) to (4-3). In General Formulae (4-1) to (4-3), $Ar^{11}$ represents any of a phenyl group, a 1-naphthyl group, and a 2-naphthyl group; each of $R^{25}$ and $R^{26}$ represents any of hydrogen, an alkyl group having 1 to 4 carbon atoms, and an aryl group having 6 to 15 carbon atoms; $Ar^{21}$ represents any of phenyl group, 1-naphthyl group, and 2-naphthyl group; $R^{31}$ represents any of hydrogen, an alkyl group having 1 to 4 carbon atoms, and an aryl group having 6 to 25 carbon atoms; $Ar^{31}$ represents any of a phenyl group, a 1-naphthyl group, and a 2-naphthyl group; and each of $R^{41}$ and $R^{42}$ represents any of hydrogen, an alkyl group having 1 to 4 carbon atoms, and an aryl group having 6 to 25 carbon atoms.)

In foregoing General Formulae (1) to (4), each of $Ar^1$ and $Ar^2$ is preferably a substituent represented by General Formula (11-1).

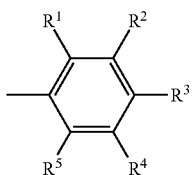

(11-1)

(In the formula, each of $R^1$ to $R^5$ represents any of hydrogen, an alkyl group having 1 to 4 carbon atoms, a haloalkyl group having 1 to 4 carbon atoms, and an aryl group having 6 to 15 carbon atoms.)

Also, in foregoing General Formulae (1) to (4), each of $Ar^1$ and $Ar^2$ is preferably a substituent represented by Structural Formula (11-2) or (11-3).

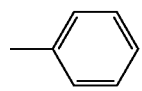

(11-2)

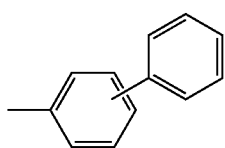

(11-3)

Further, in foregoing General Formulae (1) to (4), each of $Ar^1$ and $Ar^2$ is preferably a substituent represented by General Formula (11-4).

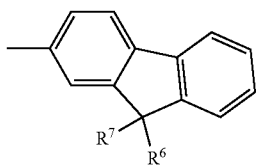

(11-4)

(In the formula, each of $R^6$ and $R^7$ represents an alkyl group having 1 to 4 carbon atoms.)

Also, in foregoing General Formulae (1) to (4), each of $Ar^1$ and $Ar^2$ is preferably a substituent represented by Structural Formula (11-5) or (11-6).

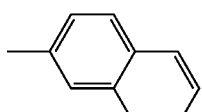

(11-5)

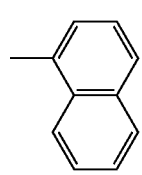

(11-6)

Further, in foregoing General Formulae (1) to (4), $Ar^1$ and $Ar^2$ are preferably substituents having the same structure.

Furthermore, in foregoing General Formulae (1) to (4), A preferably bonds at the 2-position of the anthracene skeleton. By bonding at the 2-position, steric hindrance with each of $Ar^1$ and $Ar^2$ is reduced.

That is, a preferable anthracene derivative is represented by General Formula (5).

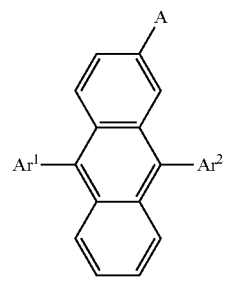

(5)

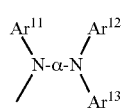

(5-1)

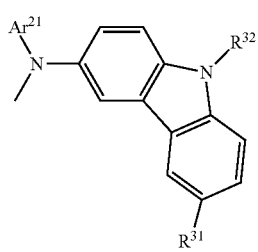

(5-2)

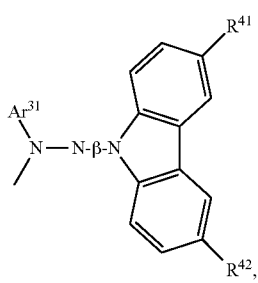

(5-3)

(In the formula, each of $Ar^1$ and $Ar^2$ represents an aryl group having 6 to 25 carbon atoms, and A represents any substituent represented by General Formulae (5-1) to (5-3). In General Formulae (5-1) to (5-3), each of $Ar^{11}$ to $Ar^{13}$ represents an aryl group having 6 to 25 carbon atoms; α represents an arylene group having 6 to 25 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents any of hydrogen, an alkyl group having 1 to 4 carbon atoms, and an aryl group having 6 to 25 carbon atoms.)

Also, a preferable anthracene derivative is exemplified by General Formula (6).

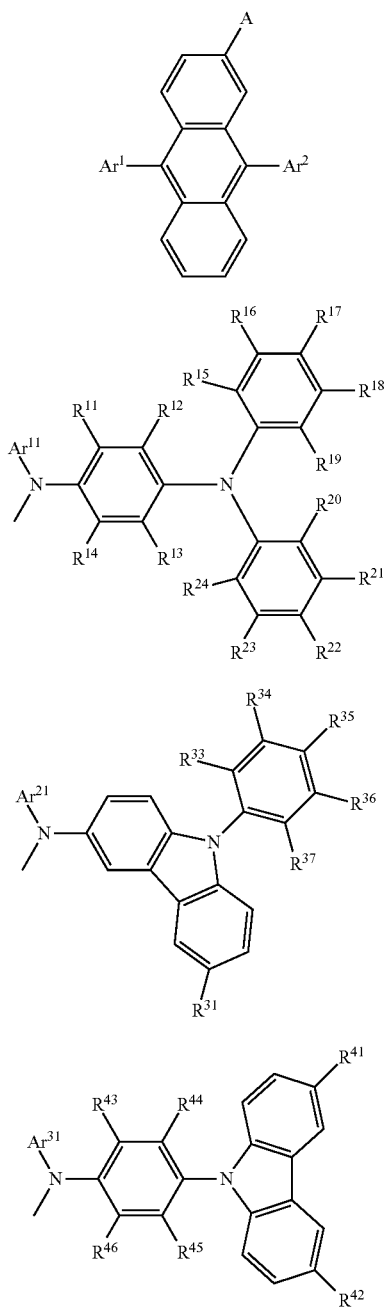

(In the formula, each of Ar¹ and Ar² represents an aryl group having 6 to 25 carbon atoms, and A represents a substituent represented by any of General Formulae (6-1) to (6-3). In General Formulae (6-1) to (6-3), $Ar^{11}$ represents an aryl group having 6 to 25 carbon atoms; each of $R^{11}$ to $R^{24}$ represents any of hydrogen, an alkyl group having 1 to 4 carbon atoms, and an aryl group having 6 to 15 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; each of $R^{33}$ to $R^{37}$ represents any of hydrogen, an alkyl group having 1 to 4 carbon atoms, and an aryl group having 6 to 15 carbon atoms; $Ar^{31}$ represents an aryl group having 6 to 25 carbon atoms; each of $R^{41}$ and $R^{42}$ represents any of hydrogen, an alkyl group having 1 to 4 carbon atoms, and an aryl group having 6 to 25 carbon atoms; and each of $R^{43}$ to $R^{46}$ represents any of hydrogen, an alkyl group having 1 to 4 carbon atoms, and an aryl group having 6 to 15 carbon atoms.)

Further, the anthracene derivative represented by General Formula (7) is preferable.

(In the formula, each of Ar¹ and Ar² represents an aryl group having 6 to 25 carbon atoms, and A represents any substituent represented by General Formulae (7-1) to (7-3). In General Formulae (7-1) to (7-3), $Ar^{11}$ represents an aryl group having 6 to 25 carbon atoms; each of $R^{25}$ and $R^{26}$ represents any of hydrogen, an alkyl group having 1 to 4 carbon atoms, and an aryl group having 6 to 15 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; $Ar^{31}$ represents an aryl group having 6 to 25 carbon atoms; and each of $R^{41}$ and $R^{42}$ represents any of hydrogen, an alkyl group having 1 to 4 carbon atoms, and an aryl group having 6 to 25 carbon atoms.)

Furthermore, preferable example for the anthracene derivative is represented by General Formula (8).

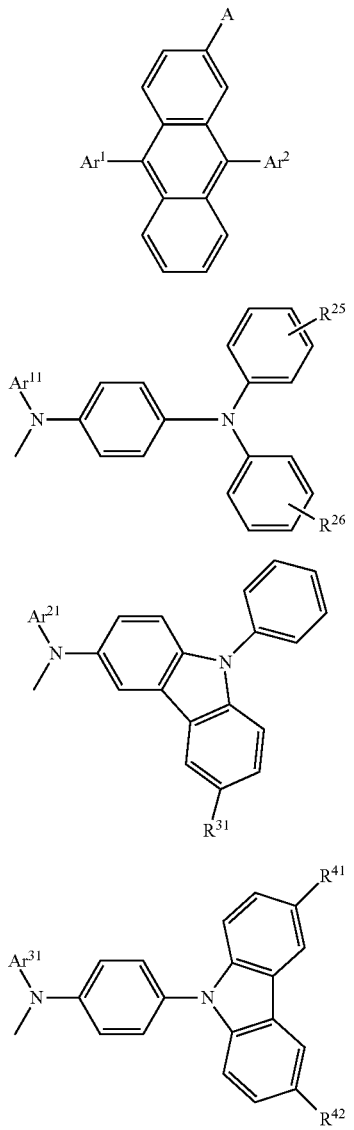

(In the formula, each of $Ar^1$ and $Ar^2$ represents an aryl group having 6 to 25 carbon atoms, and A represents any substituent represented by General Formulae (8-1) to (8-3). In General Formulae (8-1) to (8-3), $Ar^{11}$ represents any of phenyl group, 1-naphthyl group, and 2-naphthyl group; each of $R^{25}$ and $R^{26}$ represents any of hydrogen, an alkyl group having 1 to 4 carbon atoms, and an aryl group having 6 to 15 carbon atoms; $Ar^{21}$ represents any of phenyl group, 1-naphthyl group, and 2-naphthyl group; $R^{31}$ represents any of hydrogen, an alkyl group having 1 to 4 carbon atoms, and an aryl group having 6 to 25 carbon atoms; $Ar^{31}$ represents any of a phenyl group, a 1-naphthyl group, and a 2-naphthyl group; and each of $R^{41}$ and $R^{42}$ represents any of hydrogen, an alkyl group having 1 to 4 carbon atoms, and an aryl group having 6 to 25 carbon atoms.)

In foregoing General Formulae (5) to (8), each of $Ar^1$ and $Ar^2$ is preferably a substituent represented by General Formula (11-1).

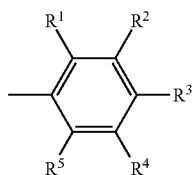

(In the formula, each of $R^1$ to $R^5$ represents any of hydrogen, an alkyl group having 1 to 4 carbon atoms, a haloalkyl group having 1 to 4 carbon atoms, and an aryl group having 6 to 15 carbon atoms.)

Also, in foregoing General Formulae (5) to (8), each of $Ar^1$ and $Ar^2$ is preferably a substituent represented by Structural Formula (11-2) or (11-3).

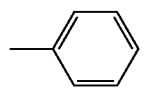

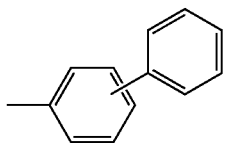

Further, in foregoing General Formulae (5) to (8), each of $Ar^1$ and $Ar^2$ is preferably a substituent represented by General Formula (11-4).

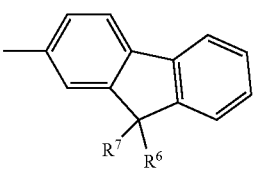

(In the formula, each of $R^6$ and $R^7$ represents an alkyl group having 1 to 4 carbon atoms.)

Also, in foregoing General Formulae (5) to (8), each of $Ar^1$ and $Ar^2$ is preferably a substituent represented by General Formula (11-5) or (11-6).

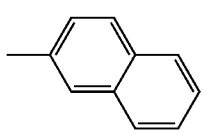

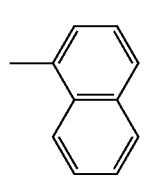

Further, in foregoing General Formulae (5) to (8), $Ar^1$ and $Ar^2$ are preferably substituents having the same structure.

As specific examples of the anthracene derivative represented by General Formula (1), the anthracene derivatives represented by Structural Formulae (101) to (118), Structural Formulae (201) to (218), and Structural Formulae (301) to (318) can be given. However, the present invention is not limited thereto.
(101)
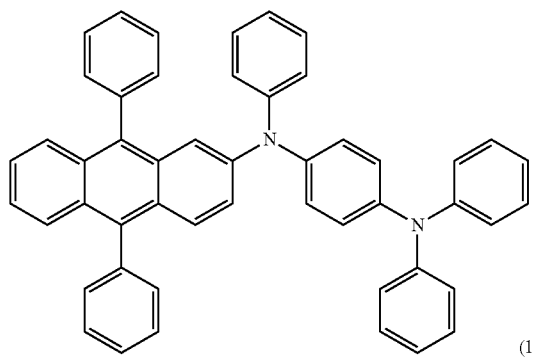
(102)
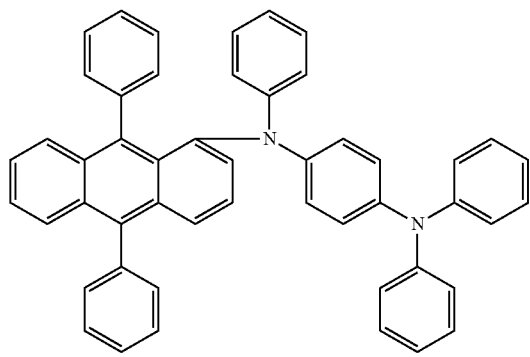
(103)
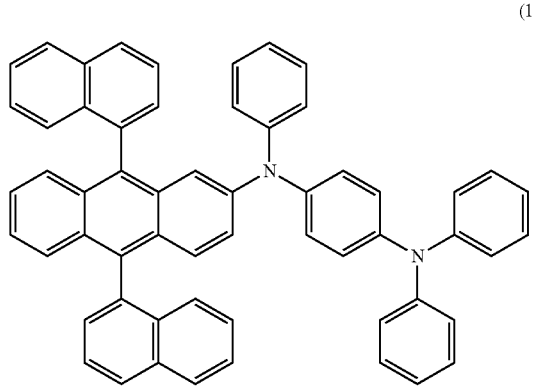
(104)
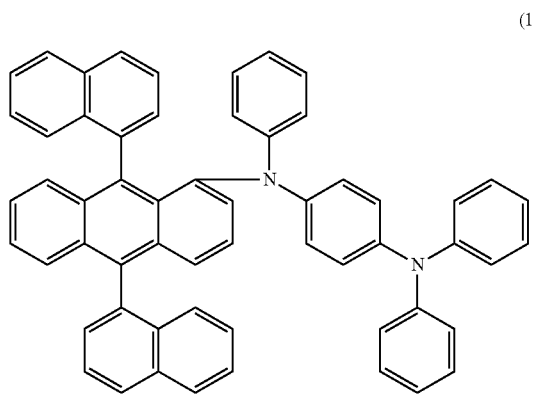
(105)
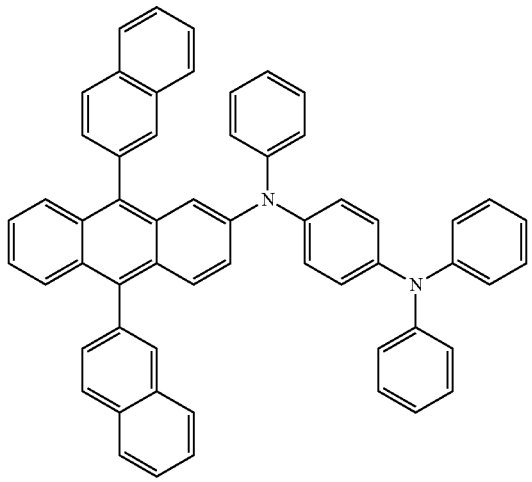
(106)
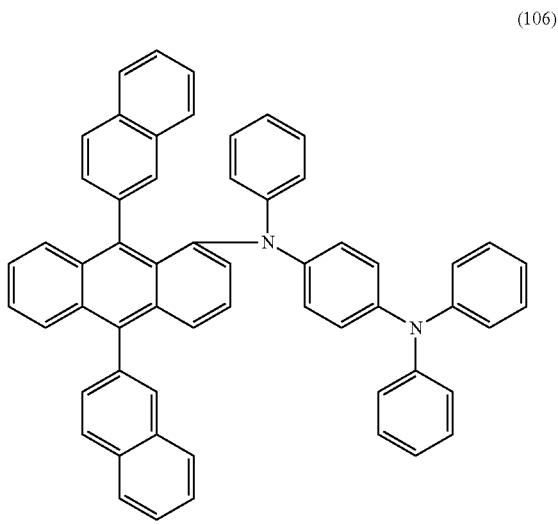
(107)
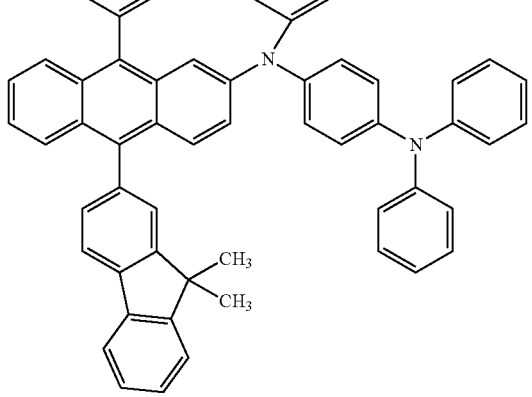

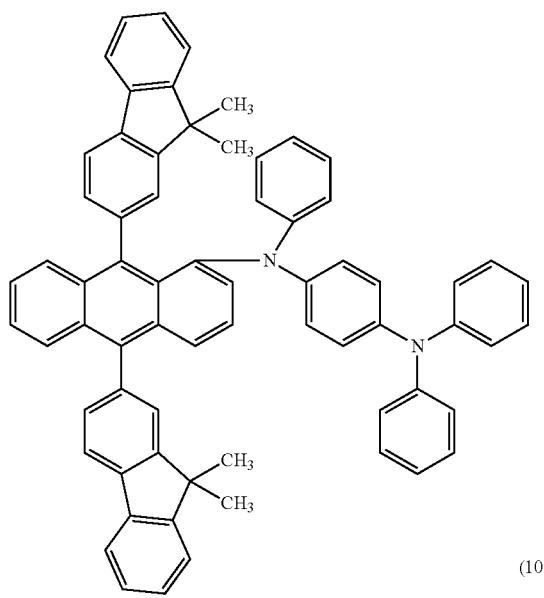
(108)
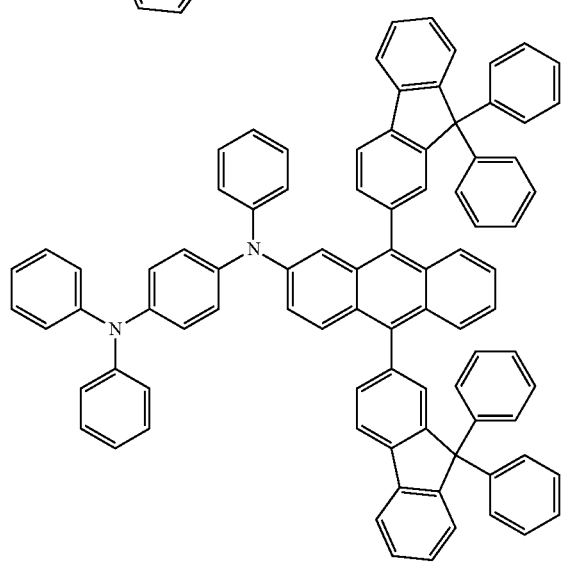
(109)
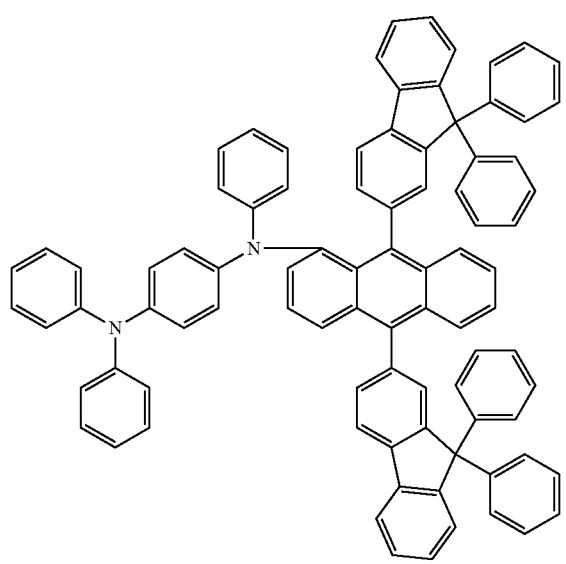
(110)
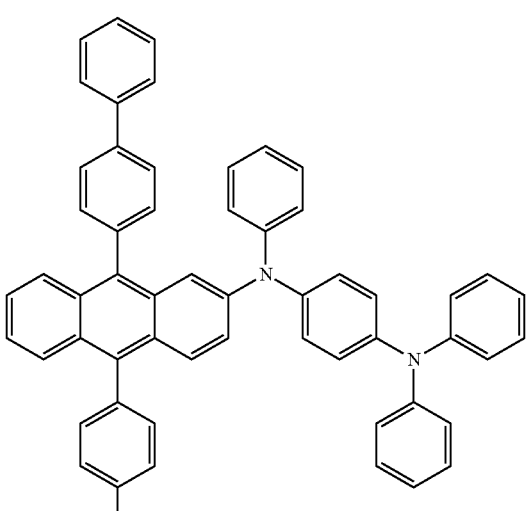
(111)
(112)
(113)

-continued
(114)
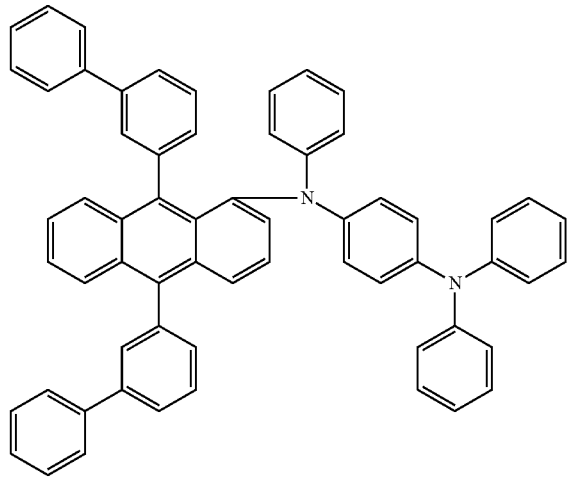
(115)
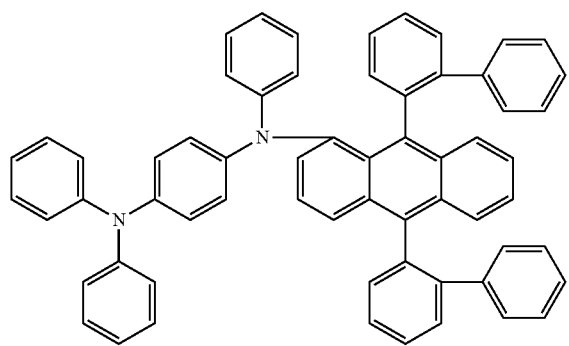
(116)
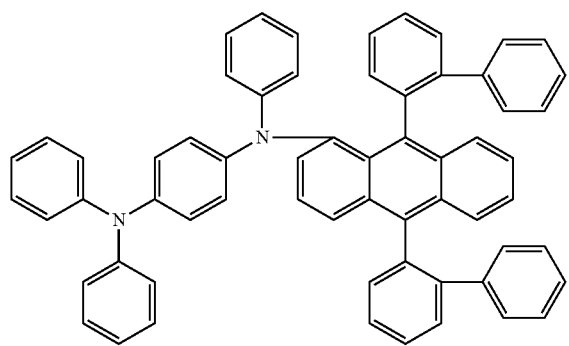
-continued
(117)
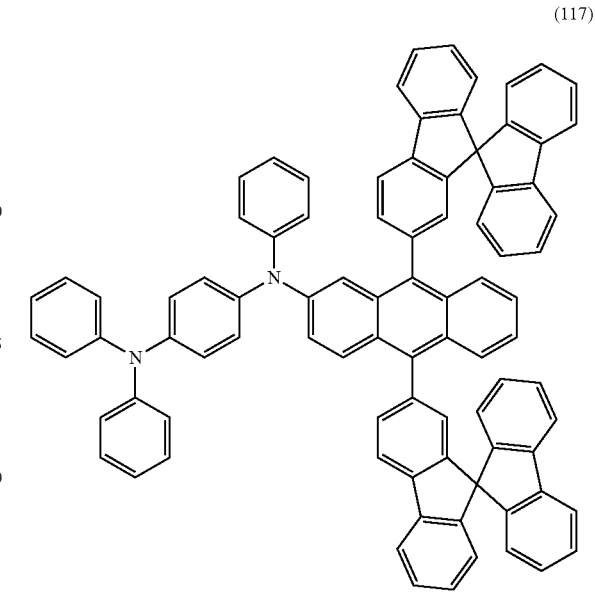
(118)
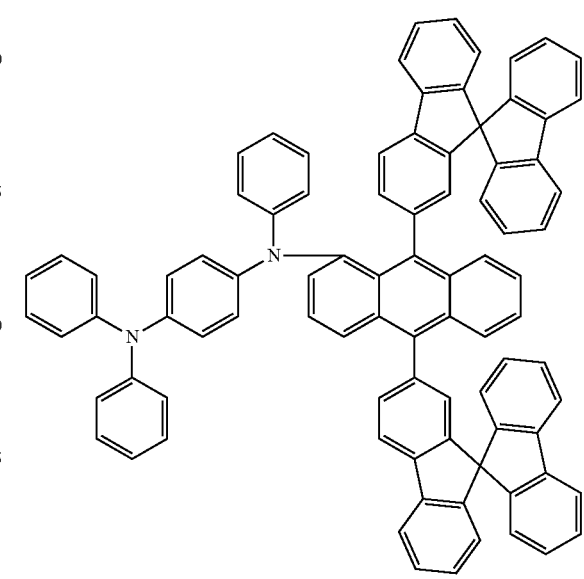
(201)
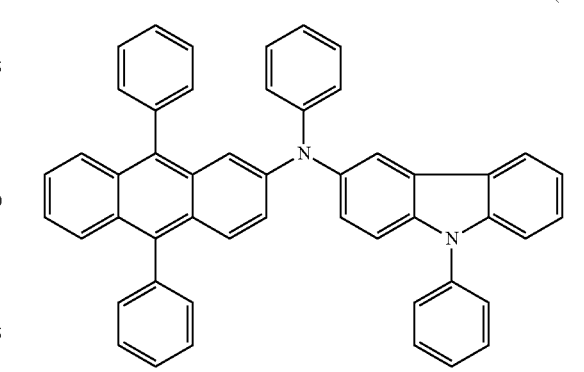

(202)
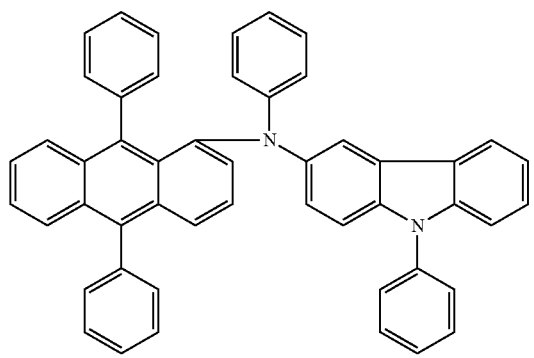
(203)
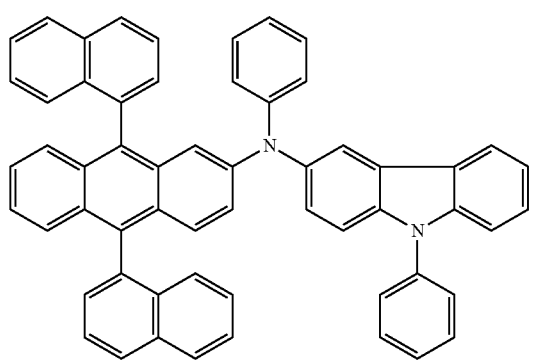
(204)
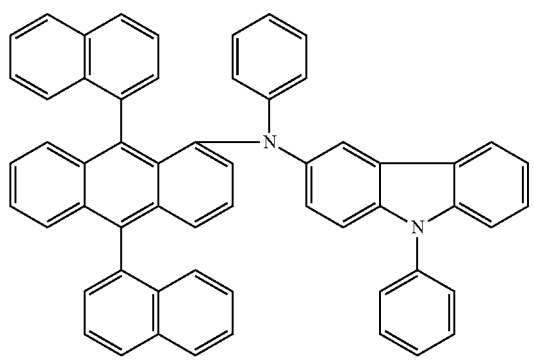
(205)
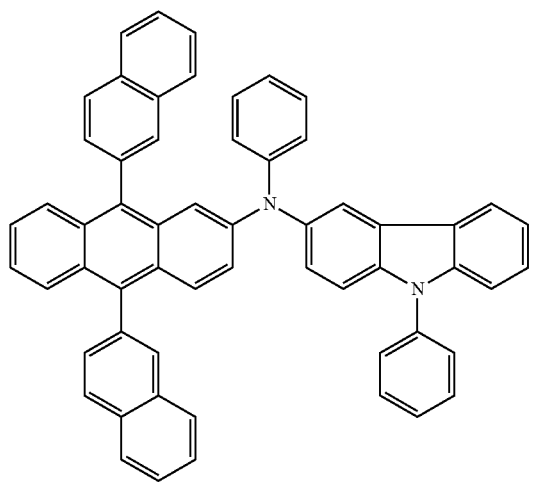
(206)
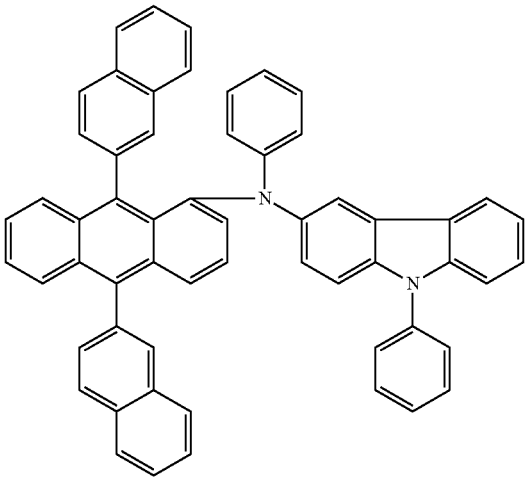
(207)
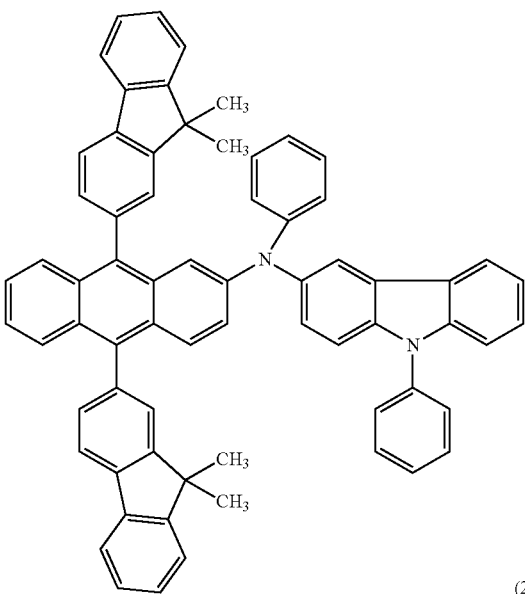
(208)
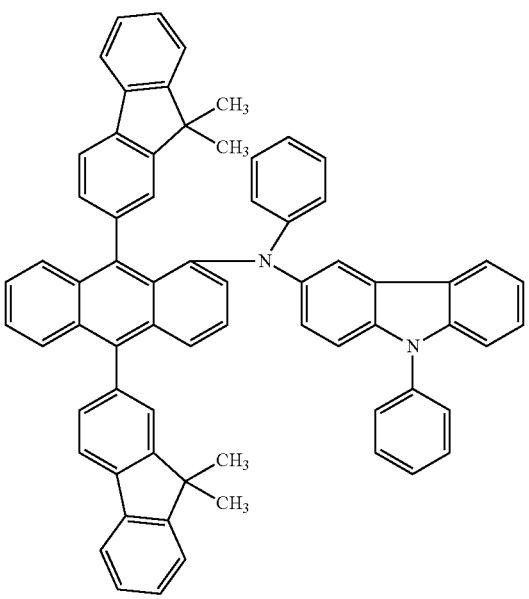

(209)
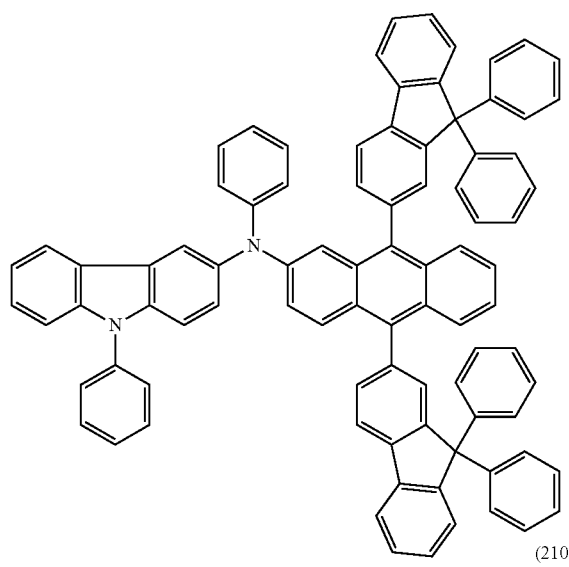
(210)
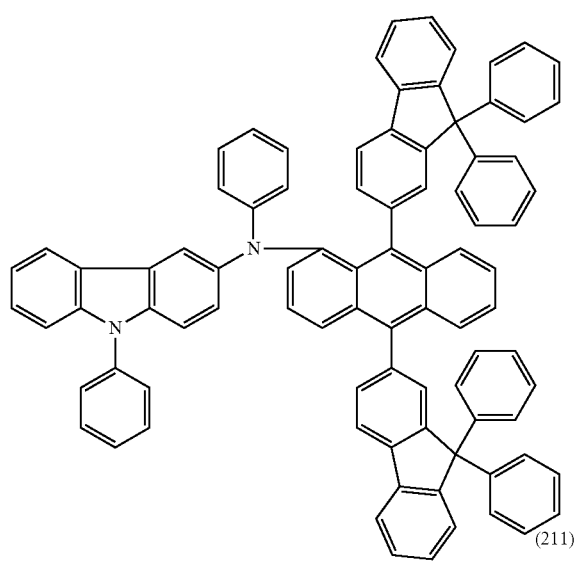
(211)
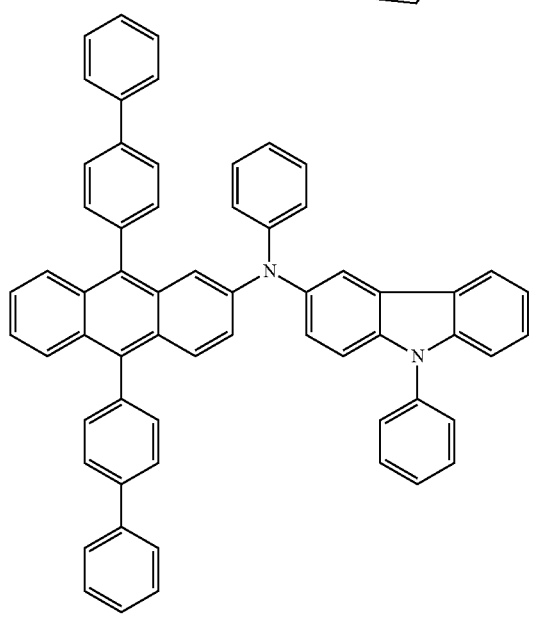
(212)
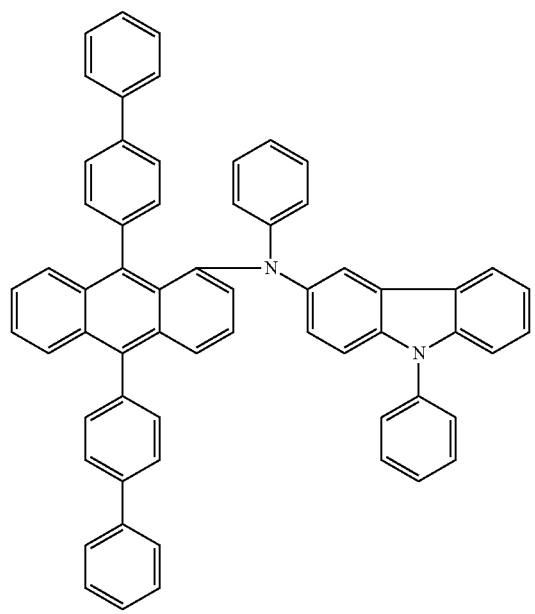
(213)
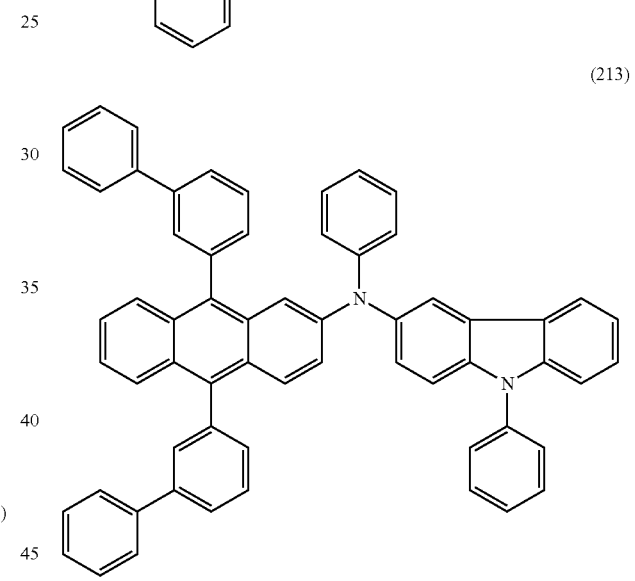
(214)
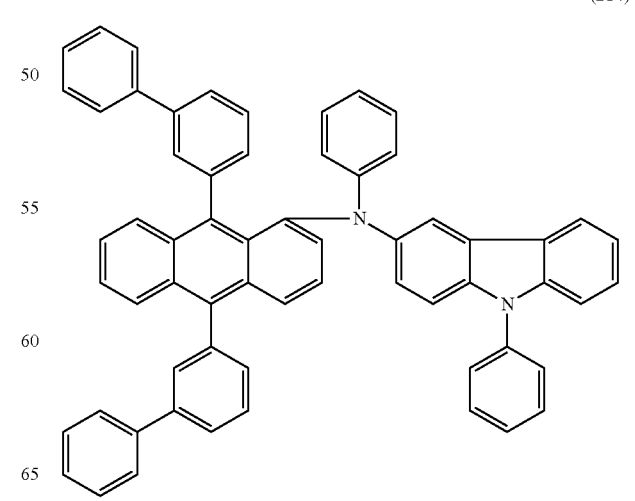

(215)
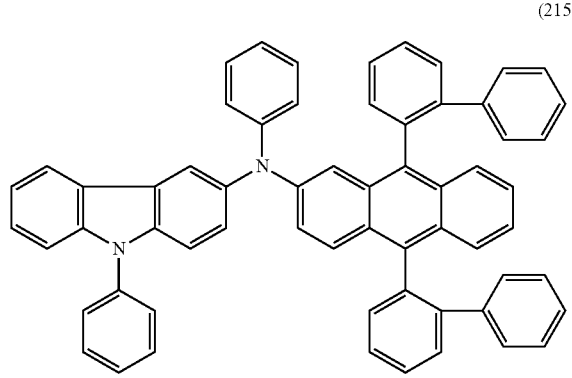
(216)
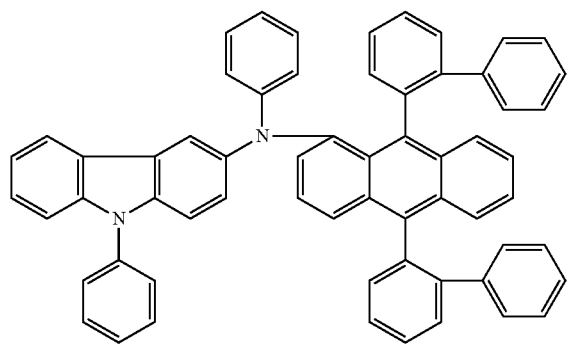
(217)
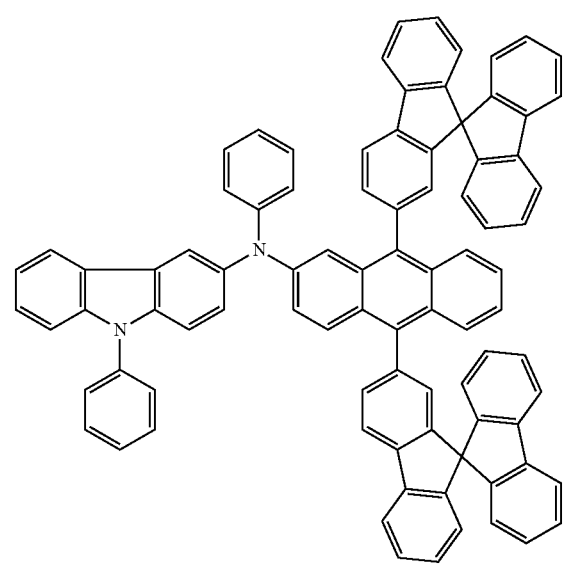
(218)
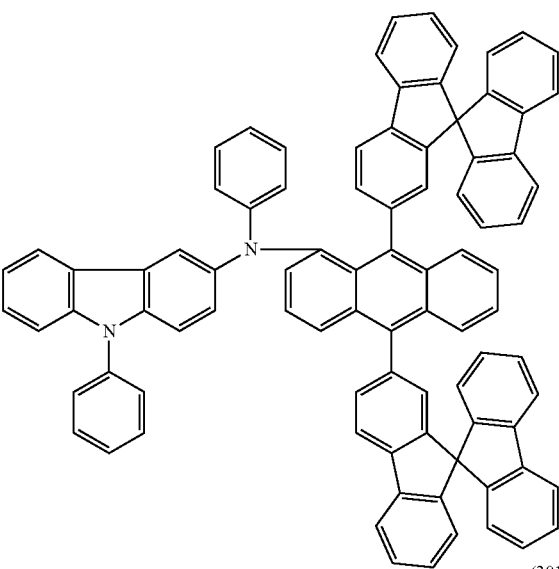
(301)
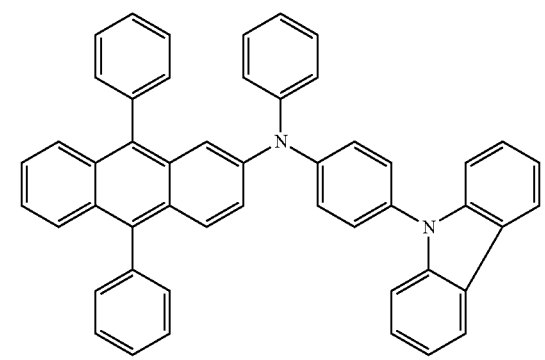
(302)
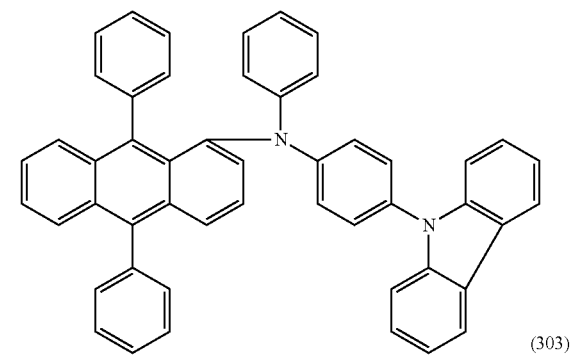
(303)

(304)
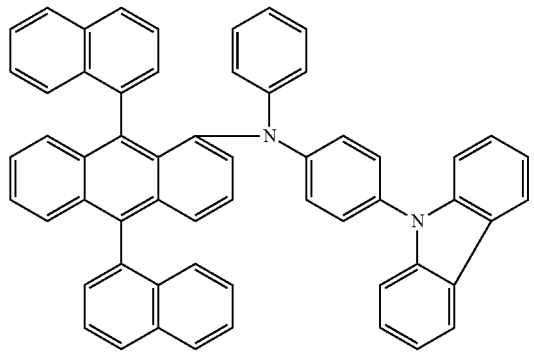
(305)
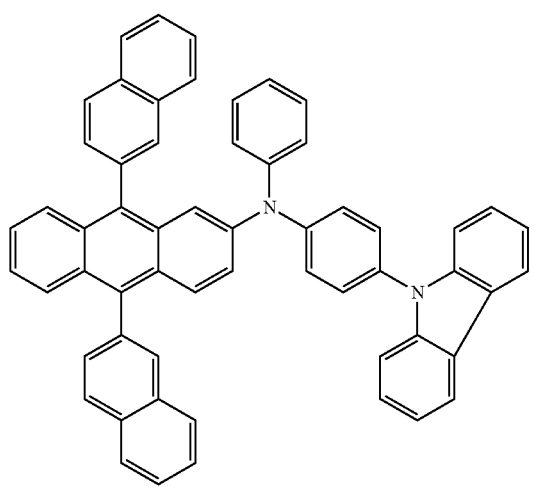
(306)
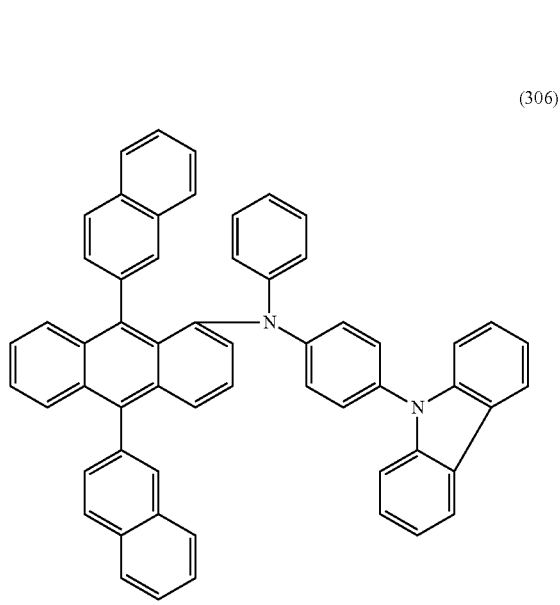
(307)
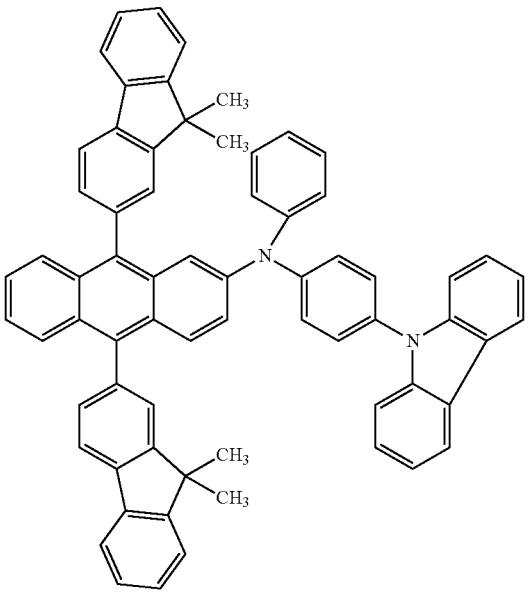
(308)
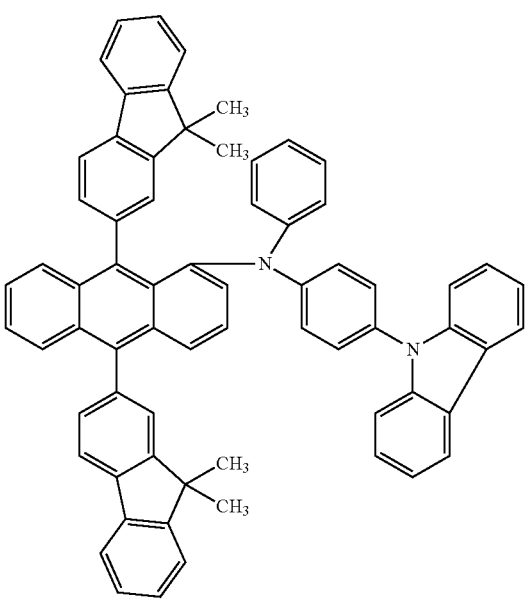

-continued
(309)
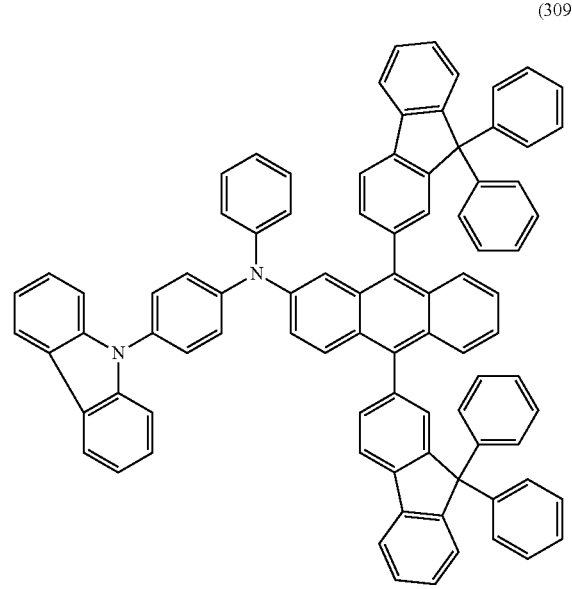 [SMILES: c1ccc(N(c2ccc(-n3c4ccccc4c4ccccc43)cc2)c2cccc3c(-c4ccc5c(c4)C4(c6ccccc6-c6ccccc64)c4ccccc4-5)c4ccccc4c(-c4ccc5c(c4)C4(c6ccccc6-c6ccccc64)c4ccccc4-5)c23)cc1]
(310)
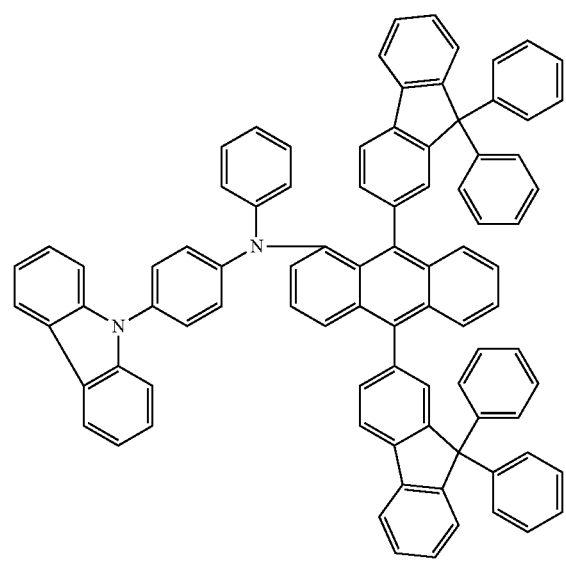
(311)
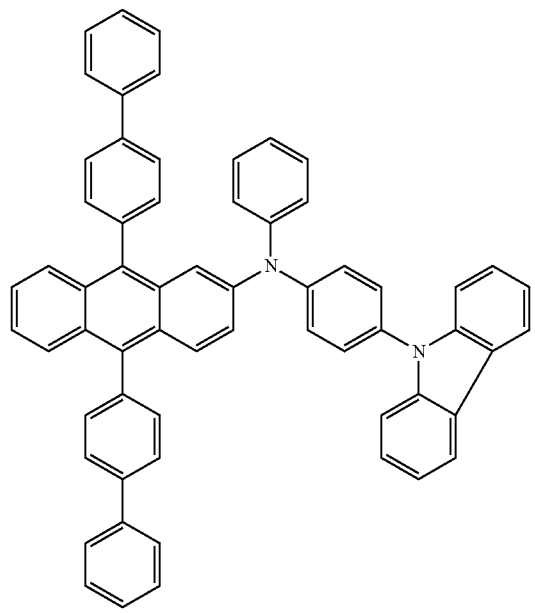
(312)
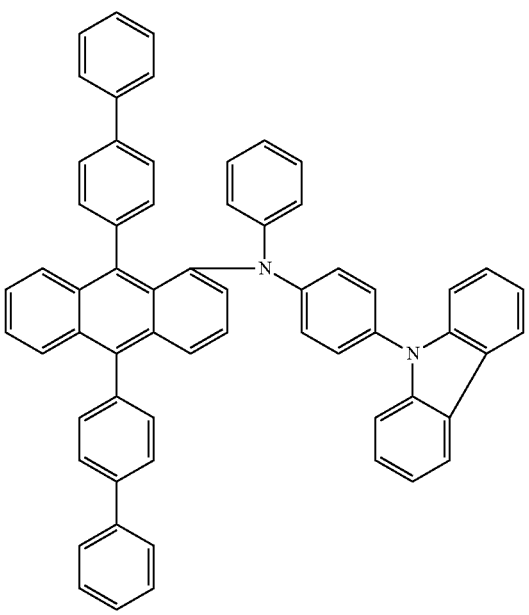

(313)
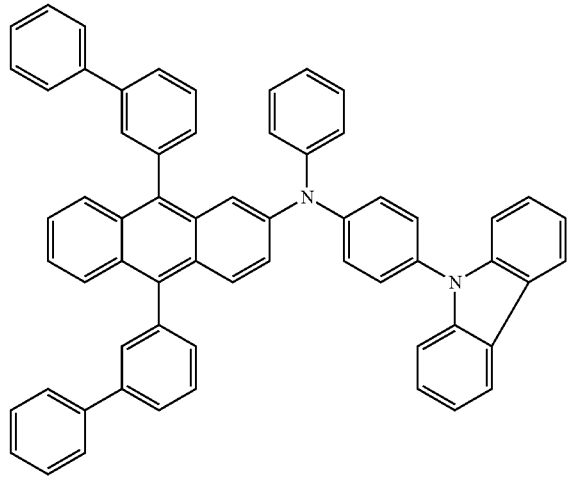
(314)
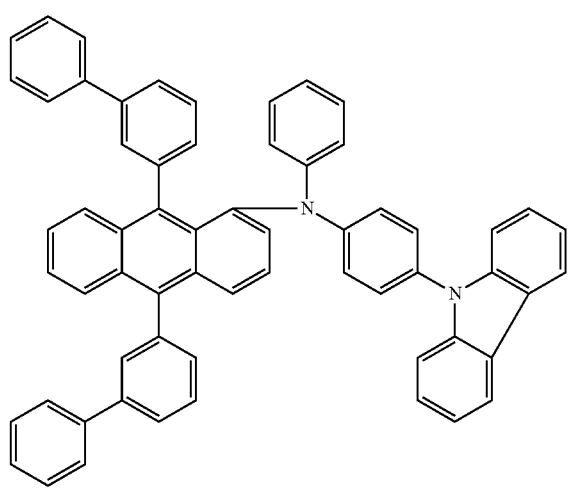
(315)
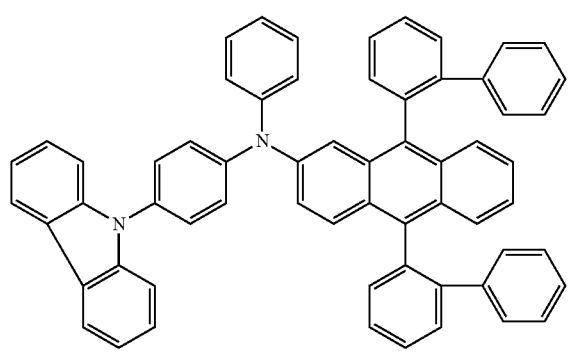
(316)
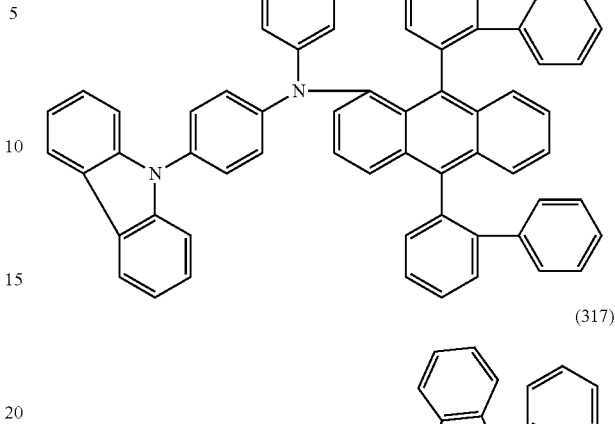
(317)
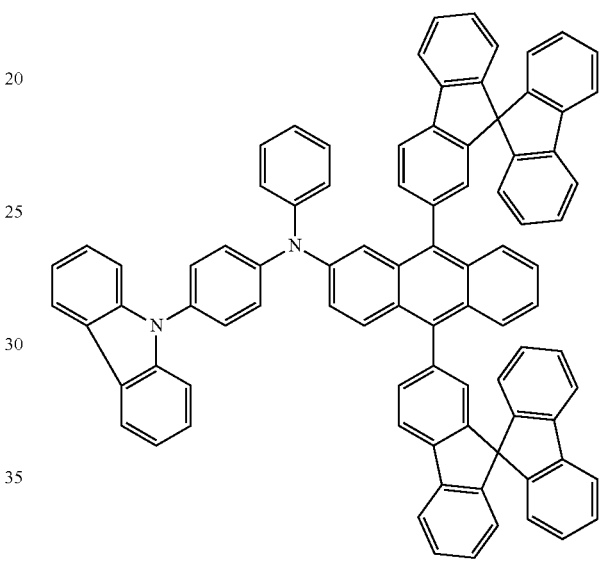
(318)
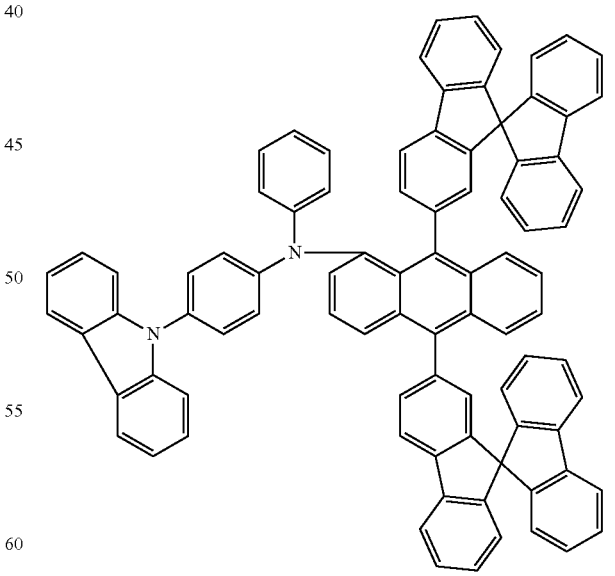
The anthracene derivatives represented by Structural Formulae (101) to (118) are specific examples of General Formula (1) in the case where A is General Formula (1-1), and the anthracene derivatives represented by Structural Formulae (201) to (218) are specific examples of General Formula (1) in the case where A is General Formula (1-2). Also, the anthracene derivatives represented by Structural Formulae (301) to (318) are specific examples of General Formula (1) in the case where A is General Formula (1-3).

A variety of reactions can be applied as a synthetic method of an anthracene derivative of the present invention. For example, the anthracene derivative of the present invention can be synthesized by conducting the synthesis reactions shown in following Reaction Schemes (A-1) to (A-5) and (B-1) to (B-3).

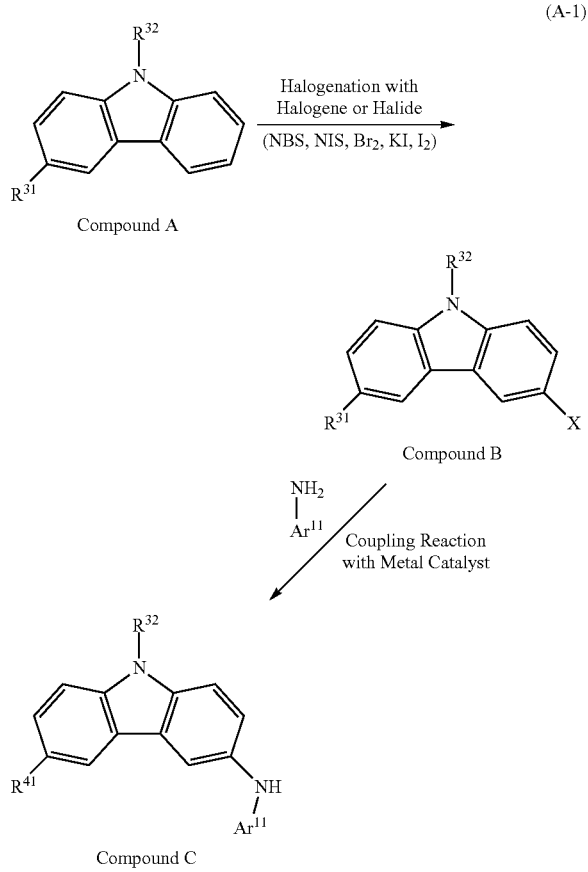

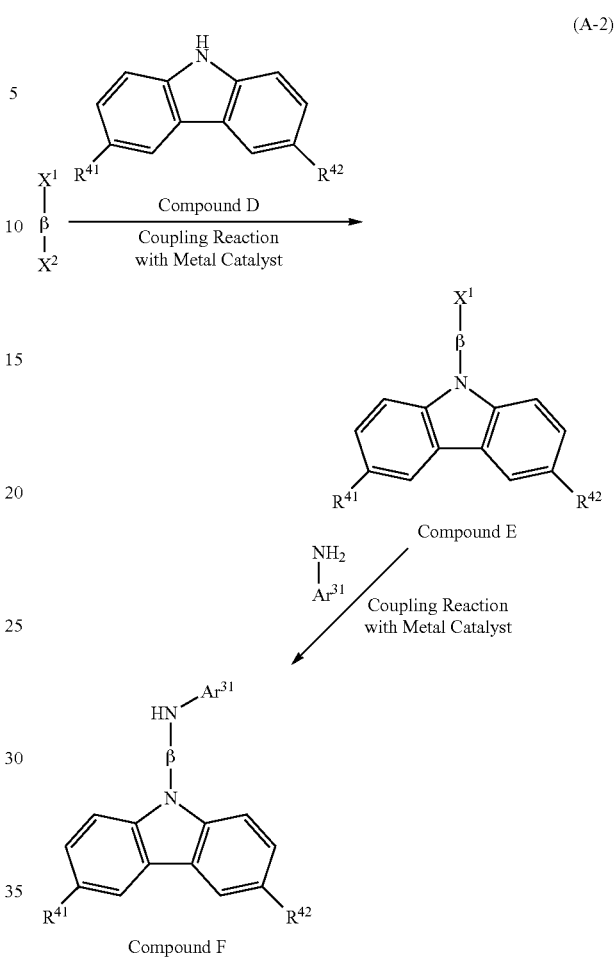

A compound including carbazole in a skeleton (Compound A) is reacted with a halogen or halide such as N-bromosuccinimide (NBS), N-iodosuccinimide (NIS), bromine ($Br_2$), potassium iodide (KI), or iodine ($I_2$) to synthesize a compound including 3-halogenated carbazole in a skeleton (Compound B), and then subjected to a coupling reaction with arylamine using a metal catalyst such as a palladium catalyst (Pd catalyst), thereby obtaining a compound C. In the synthetic scheme (A-1), a halogen, element (X) is preferably iodine or bromine $R^{31}$ represents any of hydrogen, an alkyl group having 1 to 4 carbon atoms, and an aryl group having 6 to 25 carbon atoms. $R^{32}$ represents an alkyl group having 1 to 4 carbon atoms, or an aryl group having 6 to 25 carbon atoms. Further, $Ar^{11}$ represents an aryl group having 6 to 25 carbon atoms.

A compound including carbazole in a skeleton (Compound D) is reacted with a dihalide of an aromatic compound to synthesize a compound including N-(aryl halide)carbazole in a skeleton (Compound E), and Compound E is subjected to a coupling reaction with arylamine using a metal catalyst such as palladium, thereby obtaining Compound F. In the synthetic scheme (A-2), a halogen element ($X_1$ and $X_2$) of the dihalide of an aromatic compound is preferably iodine or bromine. $X_1$ and $X_2$ may be the same or different from each other. Each of $R^{41}$ and $R^{42}$ represents any of hydrogen, an alkyl group having 1 to 4 carbon atoms, and an aryl group having 6 to 25 carbon atoms. β represents an arylene group having 6 to 25 carbon atoms. $Ar^{31}$ represents an aryl group having 6 to 25 carbon atoms.

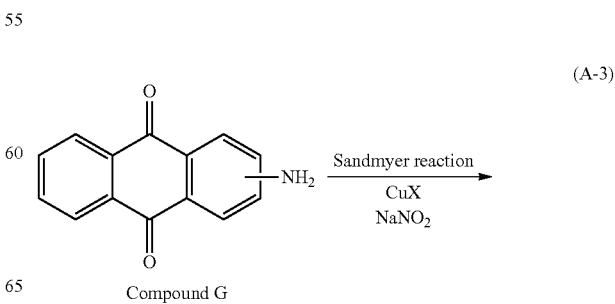

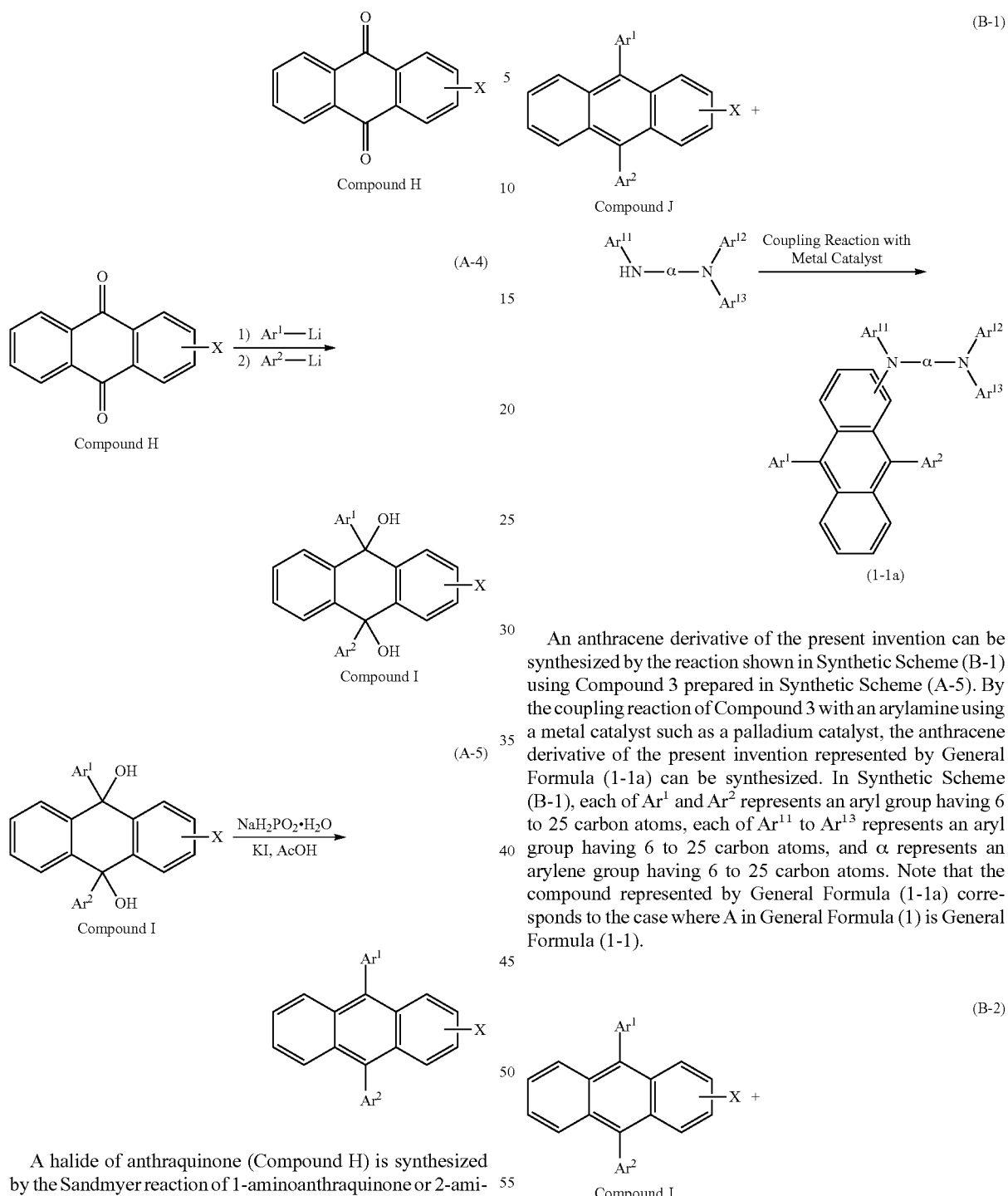

A halide of anthraquinone (Compound H) is synthesized by the Sandmyer reaction of 1-aminoanthraquinone or 2-aminoanthraquinone (Compound G). The halide of anthraquinone (Compound H) is reacted with aryllithium to synthesize a diol of a 9,10-dihydroanthracene derivative (Compound I). Then, the diol of the 9,10-dihydroanthracene derivative (Compound I) is subjected to dehydroxylation using sodium phosphinate monohydrate, potassium iodide in acetic acid, which allows the formation of 9,10-diarylanthracene halide (Compound J).

Note that in each of Synthetic Schemes (A-3) to (A-5), X represents a halogen element. Also, each of $Ar^1$ and $Ar^2$ represents an aryl group having 6 to 25 carbon atoms.

An anthracene derivative of the present invention can be synthesized by the reaction shown in Synthetic Scheme (B-1) using Compound 3 prepared in Synthetic Scheme (A-5). By the coupling reaction of Compound 3 with an arylamine using a metal catalyst such as a palladium catalyst, the anthracene derivative of the present invention represented by General Formula (1-1a) can be synthesized. In Synthetic Scheme (B-1), each of $Ar^1$ and $Ar^2$ represents an aryl group having 6 to 25 carbon atoms, each of $Ar^{11}$ to $Ar^{13}$ represents an aryl group having 6 to 25 carbon atoms, and α represents an arylene group having 6 to 25 carbon atoms. Note that the compound represented by General Formula (1-1a) corresponds to the case where A in General Formula (1) is General Formula (1-1).

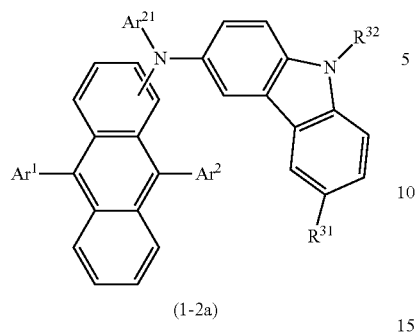

(1-2a)

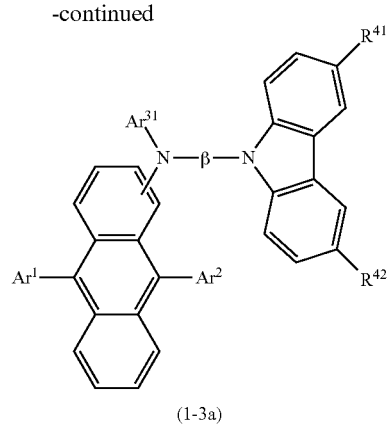

(1-3a)

An anthracene derivative of the present invention can be synthesized by a reaction shown in Synthetic Scheme (B-2), using Compound C prepared according to Synthetic Scheme (A-1) and Compound J provided by Synthetic Scheme (A-5). The coupling reaction between Compound C and Compound J using a metal catalyst such as a palladium catalyst gives the anthracene derivative of the present invention represented by General Formula (1-2a). In Synthetic Scheme (B-2), each of $Ar^1$ and $Ar^2$ represents an aryl group having 6 to 25 carbon atoms; $Ar^{21}$ represents an aryl group having 6 to 25 carbon atoms; $R^{31}$ represents any of hydrogen, an alkyl group having 1 to 4 carbon atoms, and an aryl group having 6 to 25 carbon atoms; and $R^{32}$ represents either of an alkyl group having 1 to 4 carbon atoms and an aryl group having 6 to 25 carbon atoms. Note that the compound represented by General Formula (1-2a) corresponds to the case where A in foregoing General Formula (1) is General Formula (1-2).

(B-3)

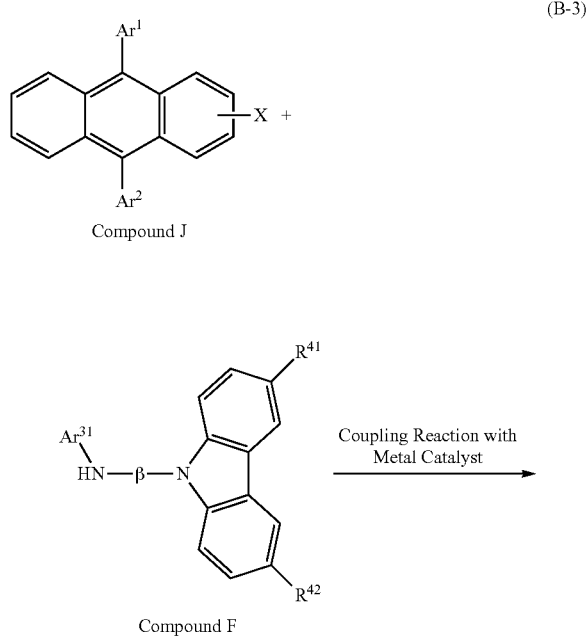

Compound J

Coupling Reaction with Metal Catalyst

Compound F

An anthracene derivative of the present invention can be synthesized by a reaction shown in Synthetic Scheme (B-3), using Compound F formed in Synthetic Scheme (A-2) and Compound 3 prepared by Synthetic Scheme (A-5). The coupling reaction between Compound F and Compound J using a metal catalyst such as a palladium catalyst leads to the formation of the anthracene derivative of the present invention represented by General Formula (1-3a). In Synthetic Scheme (B-3), each of $Ar^1$ and $Ar^2$ represents an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents hydrogen, an alkyl group having 1 to 4 carbon atoms, and an aryl group having 6 to 25 carbon atoms. Note that the compound represented by General Formula (1-3a) corresponds to the case where A in foregoing General Formula (1) is General Formula (1-3).

An anthracene derivative of the present invention has high luminous quantum yield, and emits blue green to yellow green light. Therefore, the anthracene derivative of the present invention can be favorably used for a light-emitting element.

Also, since the anthracene derivatives of the present invention are capable of green light emission with high efficiency, they can be favorably used for a full-color display. Further, the ability of the anthracene derivative of the present invention to achieve green light emission with a long lifetime allows their application in a full-color display.

Furthermore, since the anthracene derivative of the present invention can provide green light emission with high efficiency, white light emission can be obtained by combining with another light emissive material. For example, in an attempt to realize white light emission using red (R), green (G), and blue (B) emissions which exhibit the corresponding NTSC chromaticity coordinates, white color cannot be obtained unless light emissions of these colors are mixed with a proportion of approximately red (R):green (G):blue (B)=1: 6:3. That is, green light emission with high luminance is necessary, and, therefore, the anthracene derivative of the present invention by which green light emission with high efficiency can be obtained is favorable for a light-emitting device.

Also, in the anthracene derivative of the present invention, only one substituent A is bonded to an anthracene skeleton as represented by General Formula (1). Consequently, compared with a disubstituted compound in which two A units are bonded to the anthrace skeleton, the anthracene derivative of the present invention is possible to exhibit light emission with a short wavelength. Further, since the molecular weight of the disubstituted compound is very high, film formation by an evapolariton method is difficult; however, film formation by an evaporation method is possible with the anthracene derivative of the present invention. In addition, synthesis of a disubstituted compound requires higher cost than that of the anthracene derivative of the present invention which is monosubstituted.

Further, the inventors found that, when the anthracene derivatives are applied to a light-emitting element, the use of the monosubstituted anthracene derivative provides a longer lifetime than that of the disubstituted one. Consequently, by applying the anthracene derivative of the present invention to a light-emitting element, a light-emitting element with a long lifetime can be obtained.

Furthermore, the anthracene derivative of the present invention is stable even if they are subjected to the oxidation-reduction cycle repeatedly. Consequently, by using the anthracene derivative of the present invention in a light-emitting element, a light-emitting element with a long lifetime can be obtained.

Embodiment Mode 2

One mode of a light-emitting element using an anthracene derivative of the present invention is described below with reference to FIG. 1A.

A light-emitting element of the present invention has a plurality of layers between a pair of electrodes. The plurality of layers are a combination of layers formed of a substance having a high carrier injecting property and a substance having a high carrier transporting property which are stacked so that a light-emitting region is formed in a region away from the electrodes, that is, recombination of carriers is performed in an area away from the electrodes.

In this embodiment mode, a light-emitting element includes a first electrode 102, a first layer 103, a second layer 104, a third layer 105, and a fourth layer 106 which are sequentially stacked over the first electrode 102, and a second electrode 107 provided thereover. It is to be noted that description will be made below in this embodiment mode with an assumption that the first electrode 102 functions as an anode and the second electrode 107 functions as a cathode.

A substrate 101 is used as a support of the light-emitting element. For the substrate 101, glass, plastic, or the like can be used, for example. It is to be noted that another material may be used as long as it functions as a support in a manufacturing process of the light-emitting element.

As the first electrode 102, a metal, an alloy, an electrically conductive compound, a mixture thereof, or the like having a high work function (specifically, 4.0 eV or more) is preferably used. Specifically, indium oxide-tin oxide (ITO: Indium Tin Oxide), indium oxide-tin oxide including silicon or silicon oxide, indium oxide-zinc oxide (IZO: Indium Zinc Oxide), indium oxide including tungsten oxide and zinc oxide (IWZO), or the like is represented. Although these conductive metal oxide films are generally formed by sputtering, they may be formed by applying a sol-gel method or the like. For example, a film of indium oxide-zinc oxide (IZO) can be formed by a sputtering method using a target in which 1 to 20 wt % of zinc oxide is added to indium oxide. A film of indium oxide including tungsten oxide and zinc oxide (IWZO) can be formed by a sputtering method using a target in which 0.5 to 5 wt % of tungsten oxide and 0.1 to 1 wt % of zinc oxide are included in indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal (such as titanium nitride: TiN), or the like is exemplified.

The first layer 103 is a layer including a substance having a high hole injecting property. Molybdenum oxide (MoOx), vanadium oxide (VOx), ruthenium oxide (RuOx), tungsten oxide (WOx), manganese oxide (MnOx), or the like can be used. Alternatively, the first layer 103 can be formed using phthalocyanine (abbreviation: $H_2Pc$); a phthalocyanine-based compound such as copper phthalocyanine (CuPc); an aromatic amine compound such as 4,4'-bis[N-(4-diphenylaminophenyl)-N-phenylamino]biphenyl (abbreviation: DPAB) or 4,4'-bis(N-{4-[N-(3-methylphenyl)-N-phenylamino]phenyl}-N-phenylamino)biphenyl (abbreviation: DNTPD); or a high molecular weight material such as poly(ethylene dioxythiophene)/poly(styrenesulfonic acid) (PEDOT/PSS), or the like.

Alternatively, a composite material formed by composing an organic compound and an inorganic compound can be used for the first layer 103. In particular, a composite material including an organic compound and an inorganic compound having an electron accepting property with respect to the organic compound has an excellent hole injecting property and hole transporting property because the electron transfer takes place between the organic compound and the inorganic compound, increasing, the carrier density.

In a case of using a composite material formed by mixing an organic compound and an inorganic compound for the first layer 103, the first layer 103 can achieve an ohmic contact with the first electrode 102; therefore, a material of the first electrode can be selected regardless of work function.

As the inorganic compound used for the composite material, an oxide of a transition metal is preferably used. For example, oxides of metals belonging to Groups 4 to 8 in the periodic table can be given. Specifically, it is preferable to use vanadium oxide, niobium oxide, tantalum oxide, chromium oxide, molybdenum oxide, tungsten oxide, manganese oxide, and rhenium oxide because of their high electron accepting properties. Among them, molybdenum oxide is particularly preferable because it is stable under air, has a low moisture absorption property, and is easily handled.

As the organic compound used for the composite material, various compounds such as an aromatic amine compound, a carbazole derivative, an aromatic hydrocarbon, and a high molecular weight compound (such as oligomer, dendrimer, or polymer) can be used. The organic compound used for the composite material is preferably an organic compound having a high hole transporting property. Specifically, a substance having a hole mobility of greater than or equal to $10^{-6}$ $cm^2/Vs$ is preferably used. However, other materials than these materials may also be used as long as the hole transporting properties thereof are higher than the electron transporting properties thereof. The organic compounds which can be used for the composite material will be specifically shown below.

For example, the following can be represented as the aromatic amine compound: N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N'-(3-methylphenyl)-N'-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); and the like.

As the carbazole derivatives which can be used for the composite material, the following can be provided specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphtyl)-N-(9-phenylcarbazol-3-yl)amino]-9-phenylcarbazole (abbreviation: PCzPCN1); and the like.

Moreover, as the carbazole derivative which can be used for the composite material, the following can be given: 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; or the like.

As the aromatic hydrocarbon which can be used for the composite material, the following can be given for example: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides these compounds, pentacene, coronene, or the like can also be used. In particular, an aromatic hydrocarbon which has a hole mobility of greater than or equal to $1 \times 10^{-6}$ cm$^2$/Vs and which has 14 to 42 carbon, atoms is more preferable.

The aromatic hydrocarbon which can be used for the composite material may have a vinyl moiety. As the aromatic hydrocarbon having a vinyl group, the following are given for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, a high molecular weight compound such as poly(N-vinylcarbazole) (abbreviation: PVK) or poly(4-vinyltriphenylamine) (abbreviation: PVTPA) can also be used.

As a substance forming the second layer 104, a substance having a high hole transporting property, specifically, an aromatic amine compound (that is, a compound having a benzene ring-nitrogen bond) is preferable. As a material that is widely used, 4,4'-bis[N-(3-methylphenyl)-N-phenylamino] biphenyl, derivatives thereof such as 4,4'-bis[N-(1-napthyl)-N-phenylamino]biphenyl (hereinafter referred to as NPB), and star burst aromatic amine compounds such as 4,4',4''-tris (N,N-diphenyl-amino)triphenylamine, and 4,4',4''-tris[N-(3-methylphenyl)-N-phenylamino]triphenylamine can be given. These materials described here mainly are substances each having a hole mobility of greater than or equal to $10^{-6}$ cm$^2$/Vs. However, other materials than these compounds may also be used as long as the hole transporting properties thereof are higher than the electron transporting properties. The second layer 104 is not limited to a single layer, and a mixed layer of the aforementioned substances, or a stacked layer which comprises two or more layers each including the aforementioned substance may be used.

The third layer 105 is a layer including a light-emitting substance. In this embodiment mode, the third layer 105 includes the anthracene derivative of the present invention described in Embodiment Mode 1. The anthracene derivative of the present invention can favorably be applied to a light-emitting element as a light-emitting substance since the anthracene derivative of the present invention exhibits light emission of blue green to yellow green.

As the fourth layer 106, a substance having a high electron transporting property can be used. For example, a layer including a metal complex or the like having a quinoline or benzoquinoline moiety, such as tris(8-quinolinolato)aluminum (abbreviation: Alq), tris(4-methyl-8-quinolinolato)aluminum (abbreviation: Almq$_3$), bis(10-hydroxybenzo[h] quinolinato)beryllium (abbreviation: BeBq$_2$), or bis(2-methyl-8-quinolinolato)(4-phenylphenolato)aluminum (abbreviation: BAlq) can be used. Alternatively, a metal complex or the like having an oxazole-based or thiazole-based ligand, such as bis[2-(2-hydroxyphenyl)benzoxazolato]zinc (abbreviation: Zn(BOX)$_2$) or bis[2-(2-hydroxyphenyl)-benzothiazolato]zinc (abbreviation: Zn(BTZ)$_2$) can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here mainly are substances each having an electron mobility of greater than or equal to $10^{-6}$ cm$^2$/Vs. The electron transporting layer may be formed using other materials than those described above as long as the materials have higher electron transporting properties than hole transporting properties. Furthermore, the electron transporting layer is not limited to a single layer, and two or more layers in which each layer is made of the aforementioned material may be stacked.

As a substance forming the second electrode 107, a metal, an alloy, an electrically conductive compound, a mixture thereof, or the like having a low work function (specifically, 3.8 eV or less) is preferably used. As a specific example of such a cathode material, an element belonging to Group 1 or Group 2 in the periodic table, that is, an alkali metal such as lithium (Li) or cesium (Cs), an alkaline earth metal such as magnesium (Mg), calcium (Ca), or strontium (Sr), an alloy including these metals (MgAg, AlLi) can be employed. A rare earth metal such as europium (Eu) or ytterbium (Yb), an alloy including these rare earth metals, or the like is also suitable. However, by providing a layer having a function to promote electron injection from the second electrode 107 to the fourth layer 106, various conductive materials such as Al, Ag, ITO, or ITO including silicon or silicon oxide can be used for the second electrode 107 regardless of the magnitude of the work function.

As the layer having a function of promoting electron injection, an alkali metal, an alkaline earth metal, or a compound thereof such as lithium fluoride (LiF), cesium fluoride (CsF), or calcium fluoride (CaF$_2$) can be used. Alternatively, a layer which contains substance having an electron transporting property and an alkali metal, an alkaline earth metal, or a compound thereof (Alq including magnesium (Mg) for example) can be used. It is preferable to use such a layer since electron injection from the second electrode 107 proceeds efficiently.

Various methods can be used for forming the first layer 103, the second layer 104, the third layer 105, and the fourth layer 106. For example, an evaporation method, an ink-jet method, a spin coating method, or the like may be used. Furthermore, each electrode or each layer may be formed by a different film formation method.

By applying voltage between the first electrode 102 and the second electrode 107, holes and electrons are recombined in the third layer 105 including a substance with a high light-emitting property, which results in a light-emission from the light-emitting element of the present invention. That is, the light-emitting element of the present invention has a structure in which a light-emitting region is formed in the third layer 105.

Light emission is extracted outside through one or both of the first electrode 102 and the second electrode 107. Therefore, one or both of the first electrode 102 and the second electrode 107 is/are formed using an electrode having a light transmitting property. In a case where only the first electrode 102 has a light transmitting property, light emission is extracted from a substrate side through the first electrode 102 as shown in FIG. 1A. Alternatively, in a case where only the second electrode 107 is formed using the electrode having a light transmitting property, light emission is extracted from the side opposite to the substrate through the second electrode 107 as shown in FIG. 1B. In a case where each of the first electrode 102 and the second electrode 107 is the electrode having a light transmitting property, light emission is extracted from both of the substrate side and the side opposite to the substrate through the first electrode 102 and the second electrode 107, as shown in FIG. 1C.

A structure of layers provided between the first electrode 102 and the second electrode 107 is not limited to the above-described structure. A structure other than the above-described structure may be used as long as the light-emitting region, in which holes and electrons are recombined, is located away from the first electrode 102 and the second electrode 107, which permits preventing the quenching phenomenon promoted by the electrodes.

In other words, a stacked structure of the layer is not strictly limited to the abovementioned structure, and a layer formed using a substance having a high electron transporting property, a substance having a high hole transporting property, a substance having a high electron injecting property, a substance having a high hole injecting property, a bipolar substance (substance having a high electron transporting property and a high hole transporting property), a hole blocking material, or the like may be freely combined with the anthracene derivative of the present invention.

Figure 2:
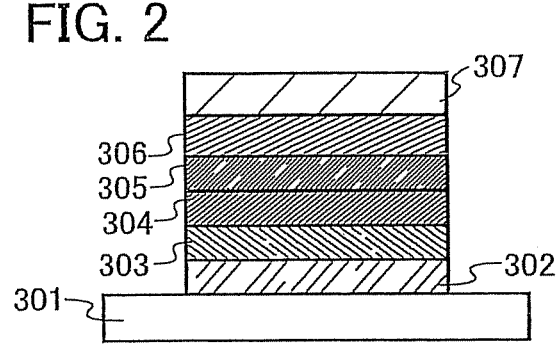
FIG. 2 describes a light-emitting element of the present invention.

A light-emitting element shown in FIG. 2 has a structure in which a first electrode 302 serving as a cathode, a first layer 303 formed using a substance having a high electron transporting property, a second layer 304 including a light-emitting substance, a third layer 305 formed using a substance having a high hole transporting property, a fourth layer 306 formed using a substance having a high hole injecting property, and a second electrode 307 serving as an anode are sequentially stacked over a substrate 301.

In this embodiment mode, a light-emitting element is fabricated over a substrate made of glass, plastic, or the like. By fabricating a plurality of the light-emitting elements described above over one substrate, a passive-type light-emitting device can be manufactured. Alternatively, for example, a thin film transistor (TFT) may be formed over a substrate made of glass, plastic, or the like, and the light-emitting elements may be manufactured over an electrode electrically connected to the TFT. Accordingly, an active matrix light-emitting device can be manufactured, in which driving of the light-emitting element is controlled by the TFT. The structure of the TFT is not strictly limited, and the TFT may be a staggered TFT or an inverted staggered TFT. Crystallinity of a semiconductor used for the TFT is also not limited, and an amorphous semiconductor or a crystalline semiconductor may be used. In addition, a driving circuit formed over a TFT substrate may be formed using an N-type TFT and a P-type TFT, or may be formed using any one of an N-type TFT and a P-type TFT.

As shown in this embodiment mode, an anthracene derivative of the present invention can be used for a light-emitting layer without adding any other light-emitting substance, since said anthracene derivative exhibits light emission of blue green to yellow green.

Since the anthracene derivative of the present invention has high luminous efficiency, a light-emitting element with high luminous efficiency can be obtained by using the anthracene derivative of the present invention in a light-emitting element. Also, by using the anthracene derivative of the present invention in a light-emitting element, a light-emitting element with a long lifetime can be obtained.

Because anthracene derivatives of the present invention are capable of green light emission with high efficiency, they can be favorably used for a full-color display. Further, the ability of the anthracene derivative of the present invention to achieve green light emission with a long lifetime allows their application in a full-color display.

Furthermore, since the light-emitting element using the anthracene derivative of the present invention is capable of green light emission with high efficiency, white light emission can be obtained by combining with another light emission material. For example, in an attempt to realize white light emission using red (R), green (G), and blue (B) emissions which exhibit the corresponding NTSC chromaticity coordinates, white color cannot be obtained unless light emissions of these colors are mixed with a proportion of approximately red (R):green (G):blue (B)=1:6:3. That is, green light emission with high luminance is necessary, and, therefore, the anthracene derivative of the present invention by which green light emission with high efficiency can be obtained is favorable for a light-emitting device.

Embodiment Mode 3

In this embodiment mode, a light-emitting element having a different structure from that described in Embodiment Mode 2 will be explained.

Figure 1A:
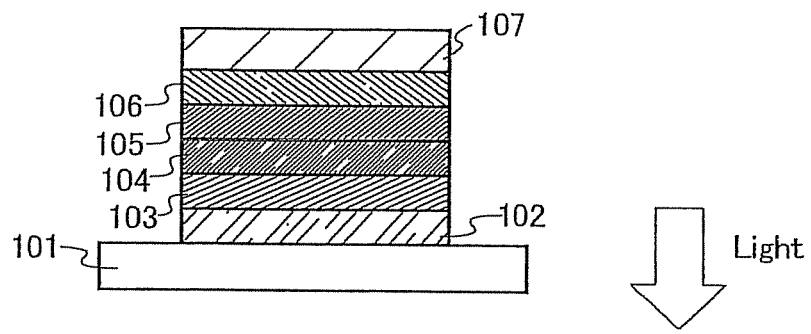
FIGS. 1A to 1C each describe a light-emitting element of the present invention.
Figure 1B:
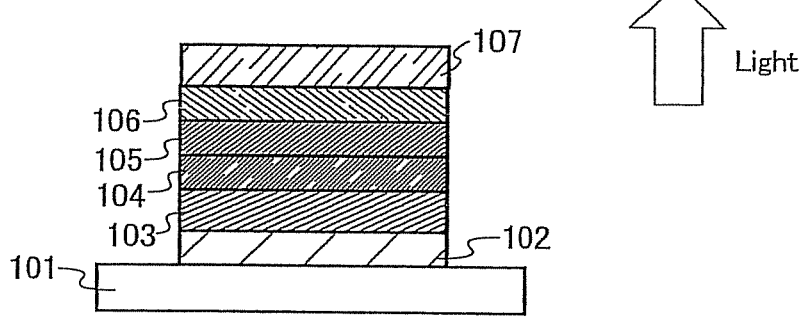
Figure 1C:
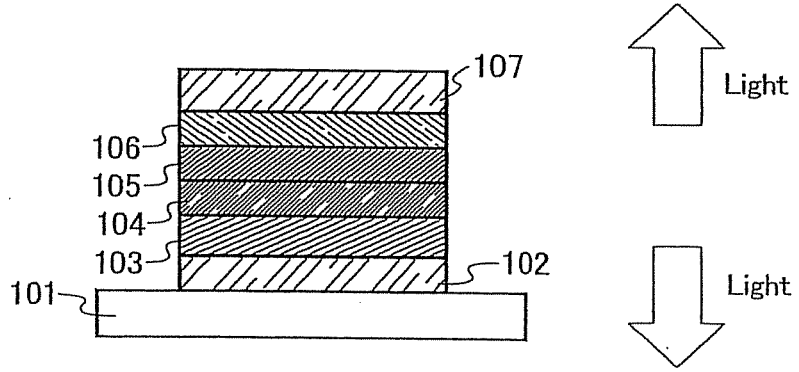

In this embodiment mode, the third layer 105 shown in FIGS. 1A to 1C is formed by dispersing an anthracene derivative of the present invention into another substance, whereby light emission can be obtained from the anthracene derivative of the present invention. Since the anthracene derivative of the present invention exhibits light emission of blue green to yellow green, a light-emitting element exhibiting light emission of blue green to yellow green can be obtained.

Here, various materials can be used as a substance in which the anthracene derivative of the present invention is dispersed. In addition to the substance having a high hole transporting property and the substance having a high electron transporting property, which are described in Embodiment Mode 2,4,4'-bis(N-carbazolyl)-biphenyl (abbreviation: CBP), 2,2',2''-(1,3,5-benzenetri-yl)-tris[1-phenyl-1H-benzimidazole] (abbreviation: TPBI), 9,10-di(2-naphthyl)anthracene (abbreviation: DNA), 2-tert-butyl-9,10-di(2-naphthyl)anthracene (abbreviation: t-BuDNA), 9-[4-(N-carbazolyl)]phenyl-10-phenylanthracene (abbreviation: CzPA), and the like are exemplified.

Since the anthracene derivative of the present invention has high luminous efficiency, a light-emitting element with high luminous efficiency can be obtained by using the anthracene derivative of the present invention in a light-emitting element. Also, by using the anthracene derivative of the present invention in a light-emitting element, a light-emitting element with a long lifetime can be obtained.

Further, since a light-emitting element using the anthracene derivative of the present invention is capable of green light emission with high efficiency, the light-emitting element can be favorably used for a full-color display. In addition, since the light-emitting element using the anthracene derivative of the present invention is capable of green light emission with a long lifetime, it can be favorably used for a full-color display.

Furthermore, since the anthracene derivative of the present invention can provide green light emission with high efficiency, white light emission can be obtained by combining with another light emissive material. For example, in an attempt to realize white light emission using red (R), green (G), and blue (B) emissions which exhibit the corresponding NTSC chromaticity coordinates, white color cannot be obtained unless light emissions of these colors are mixed with a proportion of approximately red (R):green (G):blue (B)=1: 6:3. That is, green light emission with high luminance is necessary, and, therefore, the anthracene derivative of the present invention by which green light emission with high efficiency can be obtained is favorable for a light-emitting device.

Note that, regarding the layers other than the third layer 105, the structure shown in Embodiment Mode 2 can be appropriately used.

Embodiment Mode 4

In this embodiment mode, a light-emitting element with a structure different from the structures described in Embodiment Modes 2 and 3 is described.

In this embodiment mode, the third layer 105 shown in FIGS. 1A to 1C is formed by dispersing a light-emitting substance in the anthracene derivative of the present invention, whereby light emission from the light-emitting substance can be obtained.

In a case where the anthracene derivative of the present invention is used as a material in which another light-emitting substance is dispersed, a light emission color derived from the light-emitting substance can be obtained. Further, a mixed color resulted from the anthracene derivative of the present invention and the light-emitting substance dispersed in the anthracene derivative can also be obtained.

Here, various materials can be used as a light-emitting substance dispersed in the anthracene derivative of the present invention. Specifically, a fluorescence emitting substance that emits fluorescence such as 4-(dicyanomethylene)-2-methyl-6-(p-dimethylaminostyryl)-4H-pyran (abbreviation: DCM1), 4-(dicyanomethylene)-2-methyl-6-(julolidine-4-yl-vinyl)-4H-pyran (abbreviation: DCM2), N,N-dimethylquinacridone (abbreviation: DMQd), or rubrene can be used. Further, a phosphorescence emitting substance that emits phosphorescence such as (acetylacetonato)bis[2,3-bis (4-fluorophenyl)quinoxalinato] (abbreviation: Ir(Fdpq)$_2$ (acac)), 2,3,7,8,12,13,17,18-octaethyl-21H,23H-porphyrin-platinum(II) (abbreviation: PtOEP), or the like can be used.

Note that, regarding the layers other than the third layer 105, the structure shown in Embodiment Mode 2 can be appropriately used.

Embodiment Mode 5

In this embodiment mode, a light-emitting element with a structure different from those of Embodiment Modes 2 and 3 is described.

An anthracene derivative of the present invention has a hole transporting property. Therefore, the layer including the anthracene derivative of the present invention can be used between the anode and the light-emitting layer. Specifically, the anthracene derivative of the present invention can be used in the first layer 103 and the second layer 104 described in Embodiment Mode 1.

Also, in a case of applying the anthracene derivative of the present invention as the first layer 103, it is preferable to compose the anthracene derivative of the present invention and an inorganic compound having an electron accepting property with respect to the anthracene derivative of the present invention. By using such a composite layer, carrier density of the first layer increases, which contributes to improvement of the hole injecting property and hole transporting property. Also, in a case of using the composite in the first layer 103, the first layer 103 can achieve an ohmic contact with the first electrode 102; therefore, a material of the first electrode can be selected regardless of work function.

As the inorganic compound used for the composite material, an oxide of a transition metal is preferably used. Moreover, oxides of metals belonging to Groups 4 to 8 in the periodic table can be represented. Specifically, it is preferable to use vanadium oxide, niobium oxide, tantalum oxide, chromium oxide, molybdenum oxide, tungsten oxide, manganese oxide, and rhenium oxide, because of their high electron accepting properties. Among them, molybdenum oxide is particularly preferable because it is stable under air, has a low moisture absorption property, and is easily handled.

Note that this embodiment mode can be appropriately combined with another embodiment mode.

Embodiment Mode 6

In this embodiment mode, a light-emitting element in which a plurality of light-emitting units according to the present invention is stacked (hereinafter, referred to as a stacked type element) will be explained with reference to FIG. 3. This light-emitting element is a stacked type light-emitting element that has a plurality of light-emitting units between a first electrode and a second electrode. A structure similar to that described in Embodiment Modes 2 to 5 can be used for each light-emitting unit. In other words, the light-emitting element described in Embodiment Mode 2 is a light-emitting element having one light-emitting unit. In this embodiment mode, a light-emitting element having a plurality of light-emitting units will be explained.

Figure 3:
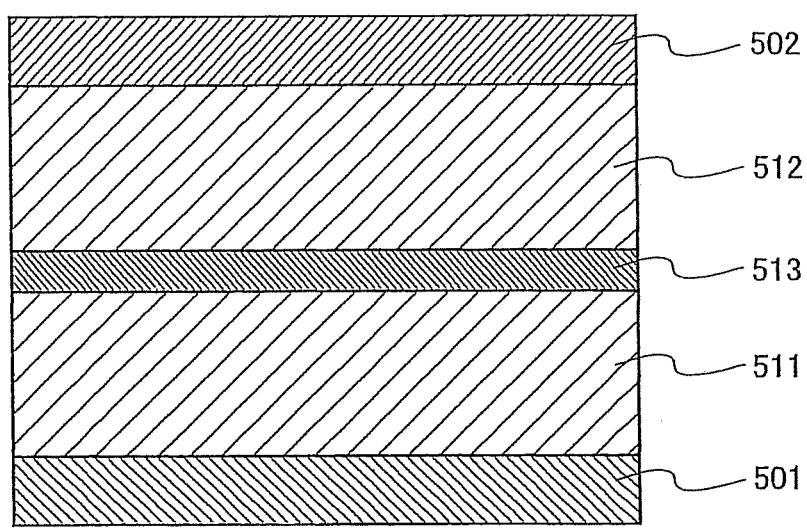
FIG. 3 describes a light-emitting element of the present invention.

In FIG. 3, a first light-emitting unit 511 and a second light-emitting unit 512 are stacked between a first electrode 501 and a second electrode 502. An electrode similar to that described in Embodiment Mode 2 can be applied to the first electrode 501 and the second electrode 502. The first light-emitting unit 511 and the second light-emitting unit 512 may have the same structure or different structures, and a structure similar to those described in Embodiment Modes 2 to 5 can be applied.

A charge generation layer 513 includes a composite material of an organic compound and metal oxide. The composite material of an organic compound and metal oxide is described in Embodiment Mode 2 or 5, and includes an organic compound and metal oxide such as vanadium oxide, molybdenum oxide, or tungsten oxide. As the organic compound, various compounds such as an aromatic amine compound, a carbazole derivative, a aromatic hydrocarbon, and a high molecular weight compound (oligomer, dendrimer, polymer, or the like) can be used. An organic compound having a hole mobility of greater than or equal to $1 \times 10^{-6}$ cm$^2$/Vs is preferably applied as the organic compound. However, other substances than these compounds may also be used as long as the hole transporting properties thereof are higher than the electron transporting properties thereof. The composite material of an organic compound and metal oxide is superior in carrier injecting property and carrier transporting property, and accordingly, low-voltage driving and low-current driving can be realized.

It is to be noted that the charge generation layer 513 may be formed with a combination of a composite material of an organic compound and metal oxide and other materials. For example, the charge generation layer 513 may be formed with a combination of a layer including the composite material of an organic compound and metal oxide and a layer including one compound selected from electron donating substances and a compound having a high electron transporting property. Further, the charge generation layer 513 may be formed with a combination of a layer including the composite material of an organic compound and metal oxide and a transparent conductive film.

In any case, the charge generation layer 513 is acceptable as long as electrons are injected to one light-emitting unit and holes are injected to the other light-emitting unit when a voltage is applied between the first electrode 501 and the second electrode 502. For example, in a case of applying a voltage so that a potential of the first electrode is higher than a potential of the second electrode, any structure is acceptable for the charge generation layer 513 as long as the layer 513 injects electrons and holes into the first light-emitting unit 511 and the second light-emitting unit 512, respectively.

In this embodiment mode, the light-emitting element having two light-emitting units is explained; however, the present invention can be applied to a light-emitting element in which three or more light-emitting units are stacked. By arranging a plurality of light-emitting units between a pair of electrodes in such a manner that the plurality of light-emitting units is partitioned with a charge generation layer, high luminance emission can be realized at a low current density, which contributes to enhancement of the lifetime of the light-emitting element. In other words, a light-emitting device capable of low-voltage driving and low-power consuming can be realized.

This embodiment mode can be appropriately combined with another embodiment mode.

Embodiment Mode 7

In this embodiment mode, a light-emitting device manufactured using an anthracene derivative of the present invention will be described.

In this embodiment mode, a light-emitting device manufactured using the anthracene derivative of the present invention will be explained with reference to FIGS. 4A and 4B. FIG. 4A is a top view showing a light-emitting device, and FIG. 4B is a cross-sectional view of FIG. 4A taken along lines A-A' and B-B'. A driver circuit portion (source side driver circuit), a pixel portion, and a driver circuit portion (gate side driver circuit) are denoted by reference numerals 601, 602, and 603, respectively, and are indicated by dotted lines. Also, a sealing substrate and a sealing material are denoted by reference numerals 604 and 605, respectively, and a portion surrounded by the sealing material 605 corresponds to a space 607.

A leading wiring 608 is a wiring for transmitting a signal to be inputted to the source side driver circuit 601 and the gate side driver circuit 603, and this wiring 608 receives a video signal, a clock signal, a start signal, a reset signal, and the like from an ITC (flexible printed circuit) 609 that is an external input terminal. It is to be noted that only the FPC is shown here; however, the FPC may be provided with a printed wiring board (PWB). The light-emitting device in this specification includes not only a light-emitting device itself but also a light-emitting device attached with an FPC or a PWB.

Subsequently, a cross-sectional structure will be explained with reference to FIG. 4B. The driver circuit portion and the pixel portion are formed over a substrate 610. Here, the source side driver circuit 601, which is the driver circuit portion, and one pixel in the pixel portion 602 are shown.

A CMOS circuit, which is a combination of an n-channel TFT 623 and a p-channel TFT 624, is formed as the source side driver circuit 601. The driver circuit may be formed using various CMOS circuits, PMOS circuits, or NMOS circuits. Although a driver-integration type device, in which a driver circuit is formed over a substrate, is described in this embodiment mode, a driver circuit is not necessarily formed over a substrate and can be formed outside a substrate.

The pixel portion 602 has a plurality of pixels, each of which includes a switching TFT 611, a current control TFT 612, and a first electrode 613 which is electrically connected to a drain of the current control TFT 612. It is to be noted that an insulator 614 is formed so as to cover an edge portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in a case of using positive photosensitive acrylic resin as a material for the insulator 614, the insulator 614 is preferably formed so as to have a curved surface with a curvature radius (0.2 μm to 3 μm) only at the upper end portion thereof. Either a negative type resin which becomes insoluble in an etchant by photo-irradiation or a positive type resin which becomes soluble in an etchant by photo-irradiation can be used for the insulator 614.

A layer 616 including a light-emitting substance and a second electrode 617 are formed over the first electrode 613. Here, a material having a high work function is preferably used as a material for the first electrode 613 serving as an anode. For example, the first electrode 613 can be formed by using stacked layers of a titanium nitride film and a film including aluminum as its main component; a three-layer structure of a titanium nitride film, a film including aluminum as its main component, and a titanium nitride film; or the like as well as a single-layer film such as an ITO film, an indium tin oxide film including silicon, an indium oxide film including 2 to 20 wt % of zinc oxide, a titanium nitride film, a chromium film, a tungsten film, a Zn film, or a Pt film. When the first electrode 613 has a stacked structure, the electrode 613 shows low resistance enough to serve as a wiring, giving an good ohmic contact.

In addition, the layer 616 including a light-emitting substance is formed by various methods such as an evaporation method using an evaporation mask, an ink-jet method, and a spin coating method. The layer 616 including a light-emitting substance has the anthracene derivative of the present invention described in Embodiment Mode 1. Further, the layer 616 including a light-emitting substance may be formed using another material including a low molecular weight compound or a high molecular weight compound (including oligomer and dendrimer).

As a material used for the second electrode 617, which is formed over the layer 616 including a light-emitting substance and serves as a cathode, a material having a low work function (Al, Mg, Li, Ca, or an alloy or a compound thereof such as MgAg, MgIn, AlLi, LiF, or $CaF_2$) is preferably used. In a case where light generated in the layer 616 including a light-emitting substance is transmitted through the second electrode 617, stacked layers of a metal thin film and a transparent conductive film (ITO, indium oxide including 2 to 20 wt % of zinc oxide, indium oxide-tin oxide including silicon or silicon oxide, zinc oxide (ZnO), or the like) are preferably used as the second electrode 617.

By attachment of the sealing substrate 604 to the element substrate 610 with the sealing material 605, a light-emitting element 618 is provided in the space 607 surrounded by the element substrate 610, the sealing substrate 604, and the sealing material 605. It is to be noted that the space 607 is filled with a an inert gas (nitrogen, argon, or the like. There is also a case where the space 607 is filled with the sealing material 605.

It is to be noted that an epoxy-based resin is preferably used as the sealing material 605. It is desired that the material allows as little moisture and oxygen as possible to penetrate. As the sealing substrate 604, a plastic substrate formed using FRP (Fiberglass-Reinforced Plastics), PVF (polyvinyl fluoride), polyester, acrylic resin, or the like can be used as well as a glass substrate or a quartz substrate.

By the abovementioned processes, a light-emitting device having the anthracene derivative of the present invention can be obtained.

Since the anthracene derivative described in Embodiment Mode 1 is used for the light-emitting device of the present invention, a light-emitting device having high performance can be obtained. Specifically, a light-emitting device having a long lifetime can be obtained.

Also, since the anthracene derivative of the present invention has high luminous efficiency, a light-emitting device with low power consumption can be obtained.

Further, since an anthracene derivative of the present invention is capable of green light emission with high efficiency, the anthracene derivative can be favorably used for a full-color display. Further, since the anthracene derivative of the present invention is capable of green light emission with a long lifetime, it can be favorably used for a full-color display.

Furthermore, since the anthracene derivative of the present invention is capable of green light emission with high efficiency, white light emission can be obtained by combining with another light emission material. For example, in an attempt to realize white light emission using red (R), green (G), and blue (B) emissions which exhibit the corresponding NTSC chromaticity coordinates, white color cannot be obtained unless light emissions of these colors are mixed with a proportion of approximately red (R):green (G):blue (B)=1: 6:3. That is, green light emission with high luminance is necessary, and, therefore, the anthracene derivative of the present invention by which green light emission with high efficiency can be obtained is favorable for a light-emitting device.

Figure 5:
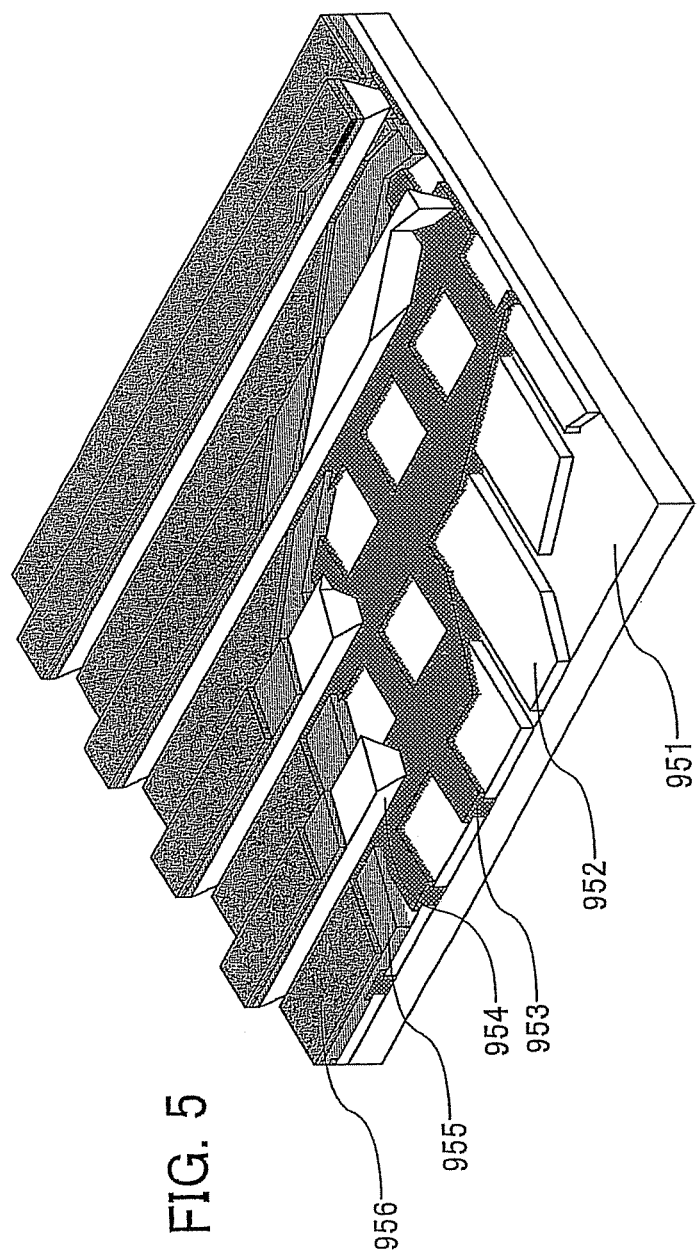
FIG. 5 describes a light-emitting device of the present invention.

As described above, in this embodiment mode, an active type light-emitting device in which driving of a light-emitting element is controlled by a transistor is explained. Alternatively, a passive type light-emitting device in which a light-emitting element is driven without an element for driving such as a transistor may also be used. FIG. 5 shows a perspective view of a passive type light-emitting device which is manufactured by applying the present invention. In FIG. 5, a layer 955 including a light-emitting substance is provided between an electrode 952 and an electrode 956 over a substrate 951. An edge of the electrode 952 is covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a short side is trapezoidal, and a base (a side expanding in a similar direction as a plane direction of the insulating layer 953 and in contact with the insulating layer 953) is shorter than an upper side (a side expanding in a similar direction as the plane direction of the insulating layer 953 and not in contact with the insulating layer 953). The partition layer 954 provided in this manner allows patterning the electrode 956. A light-emitting device with a long lifetime can be also obtained in the case of the passive type light-emitting device by using the light-emitting element of the present invention. Further, a light-emitting device with low power consumption can be obtained.

Embodiment Mode 8

In this embodiment mode, an electronic device of the present invention including the light-emitting device described in Embodiment Mode 7 will be explained. The electronic device of the present invention includes the anthracene derivative described in Embodiment Mode 1, and has a display portion with a long lifetime. Also, the electronic device of the present invention possesses a display portion with reduced power consumption.

As an electronic device including a light-emitting element fabricated using the anthracene derivative of the present invention, a camera such as a video camera or a digital camera, a goggle type display, a navigation system, an audio reproducing device (car audio component stereo, audio component stereo, or the like), a computer, a game machine, a portable information terminal (mobile computer, mobile phone, portable game machine, electronic book, or the like), and an image reproducing device provided with a recording medium (specifically, a device capable of reproducing a recording medium such as a Digital Versatile Disc (DVD) and provided with a display device that can display the image), and the like are given. Specific examples of these electronic devices are shown in FIGS. 6A to 6D.

Figure 6A:
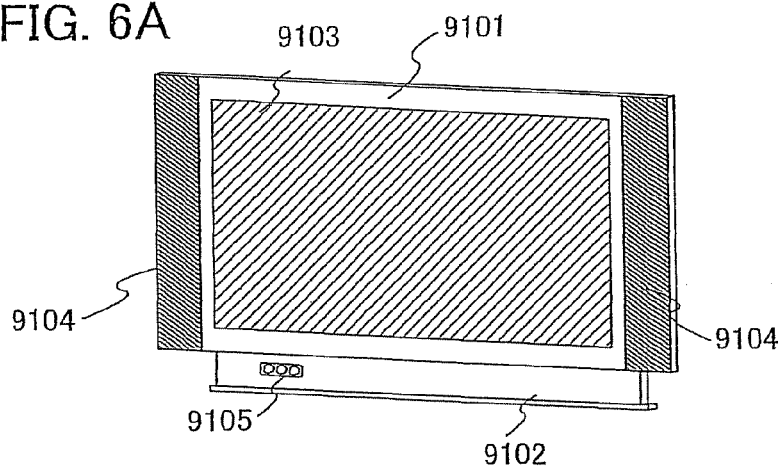
FIGS. 6A to 6D each describe an electronic device of the present invention.

FIG. 6A shows a television device according to the present invention, which includes a housing 9101, a supporting base 9102, a display portion 9103, a speaker portion 9104, a video input terminal 9105, and the like. In the television device, the display portion 9103 has light-emitting elements similar to those described in Embodiment Modes 2 to 5, and the light-emitting elements are arranged in matrix. The features of the light-emitting element are exemplified by the luminous efficiency and long lifetime. The display portion 9103 which includes the light-emitting elements has similar features. Therefore, in the television device, image quality is scarcely deteriorated and low power consumption is achieved. Therefore, deterioration compensation function circuits and power supply circuits can be significantly reduced or downsized in the television device, which enables reduction of the size and weight of the housing 9101 and supporting base 9102. In the television device according to the present invention, low power consumption, high image quality, and small size and lightweight are achieved; therefore, a product which is suitable for living environment can be provided. Also, since the anthracene derivative described in Embodiment Mode 1 is capable of green light emission, a full-color display is possible, and a television device having a display portion with a long life can be obtained.

Figure 6B:
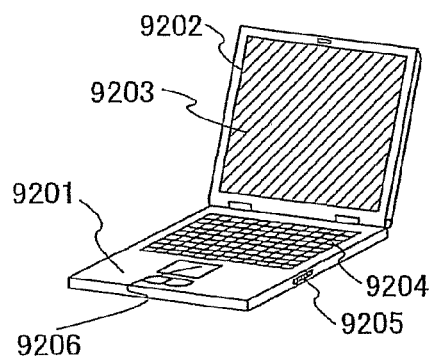

FIG. 6B shows a computer according to the present invention, which includes a main body 9201, a housing 9202, a display portion 9203, a keyboard 9204, an external connection port 9205, a pointing device 9206, and the like. In the computer, the display portion 9203 has light-emitting elements similar to those described in Embodiment Modes 2 to 5, and the light-emitting elements are arranged in matrix. The features of the light-emitting element are given by high luminous efficiency and long lifetime. The display portion 9203 which includes the light-emitting elements has similar features. Therefore, in the computer, image quality is scarcely deteriorated and lower power consumption is achieved. Due to these features, deterioration compensation function circuits and power supply circuits can be significantly reduced or downsized in the computer; therefore, small sized and lightweight main body 9201 and housing 9202 can be achieved. In the computer according to the present invention, low power consumption, high image quality, and small size and lightweight are achieved; therefore, a product which is suitable for an environment can be supplied. Further, since the anthracene derivative described in Embodiment Mode 1 is capable of green light emission, a full-color display is possible, and a computer having a display portion with a long lifetime can be obtained.

Figure 6C:
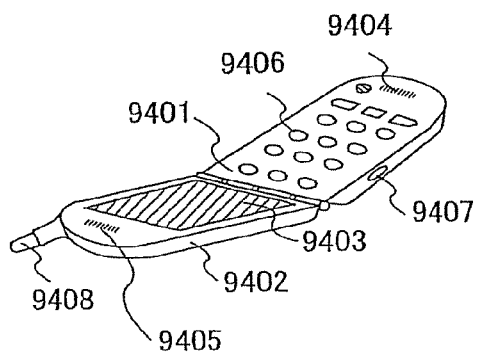

FIG. 6C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, the display portion 9403 has light-emitting elements similar to those described in Embodiment Modes 2 to 5, and the light-emitting elements are arranged in matrix. The features of the light-emitting element are exemplified by high luminous efficiency and long lifetime. The display portion 9403 which includes the light-emitting elements has similar features. Therefore, in the mobile phone, image quality is scarcely deteriorated and lower power consumption is achieved. Owing to these features, deterioration compensation function circuits and power supply circuits can be significantly reduced or downsized in the mobile phone; therefore, small sized and lightweight main body 9401 and housing 9402 can be supplied. In the mobile phone according to the present invention, low power consumption, high image quality, and a small size and lightweight are achieved; therefore, a product which is suitable for carrying can be provided. Further, since the anthracene derivative described in Embodiment Mode 1 is capable of green light emission, a full-color display is possible, and a mobile phone having a display portion with a long lifetime can be obtained.

Figure 6D:
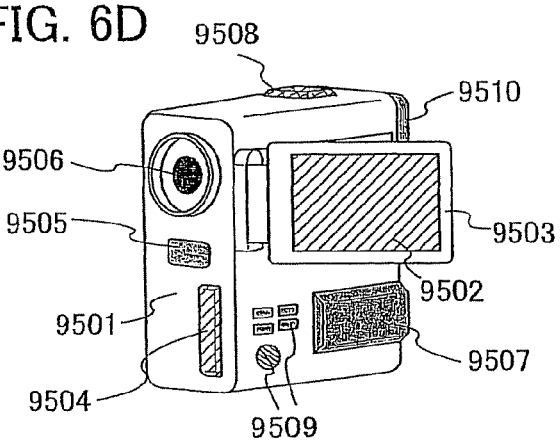

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light-emitting elements similar to those described in Embodiment Modes 2 to 5, and the light-emitting elements are arranged in matrix. Some features of the light-emitting element are its high luminous efficiency long lifetime. The display portion 9502 which includes the light-emitting elements has similar features. Therefore, in the camera, image quality is hardly deteriorated and lower power consumption can be achieved. Such features contribute to significant reduction and downsizing of the deterioration compensation function circuits and power supply circuits in the camera; therefore, a small sized and lightweight main body 9501 can be supplied. In the camera according to the present invention, low power consumption, high image quality, and small size and lightweight are achieved; therefore, a product which is suitable for carrying can be provided. Further, the anthracene derivative described in Embodiment Mode 1 is capable of green light emission, full-color display is possible, and a camera having a display portion with a long lifetime can be obtained.

As described above, the applicable range of the light-emitting device of the present invention is so wide that the light-emitting device can be applied to electronic devices in various fields. By using the anthracene derivative of the present invention, electronic devices which have display portions with a long lifetime can be provided.

The light-emitting device of the present invention can also be used as a lighting device. One mode using the light-emitting element of the present invention as the lighting device will be explained with reference to FIG. 7.

Figure 7:
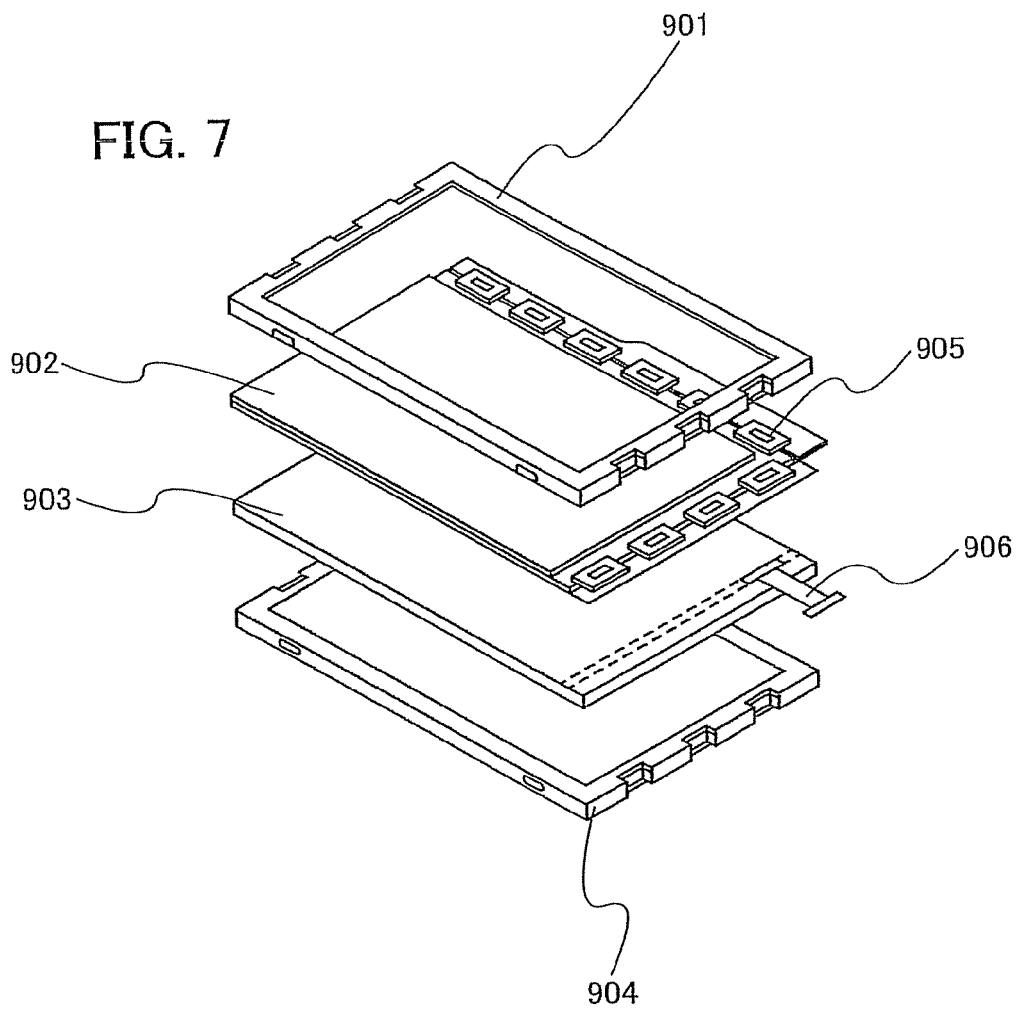
FIG. 7 describes an electronic device of the present invention.

FIG. 7 shows an example of a liquid crystal display device using the light-emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By using the light-emitting device of the present invention as the backlight of the liquid crystal display device, a backlight with reduced power consumption and high luminous efficiency can be obtained. The light-emitting device of the present invention is a lighting device with plane light emission, and can have a large area. Therefore, the backlight can have a large area, and a liquid crystal display device having a large area can be obtained. Furthermore, the light-emitting device of the present invention has a thin shape and has low power consumption; therefore, a thin shape and low power consumption of a display device can also be achieved. Since the light-emitting device of the present invention has a long lifetime, a liquid crystal display device using the light-emitting device of the present invention also has a long lifetime.

Figure 8:
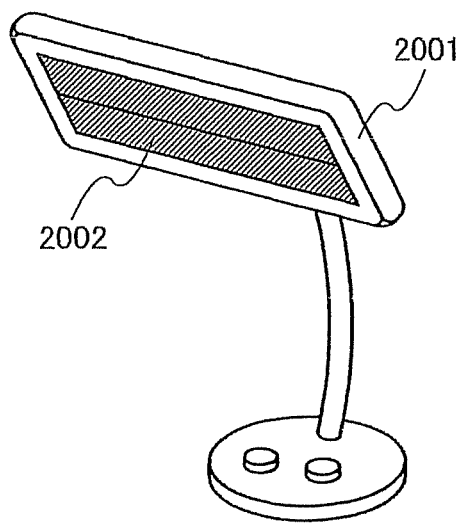
FIG. 8 describes a lighting device of the present invention.

FIG. 8 shows an example of the light-emitting device to which the present invention is applied. In this Figure, an example for the application to a table lamp as a lighting device is illustrated. A table lamp shown in FIG. 8 has a housing 2001 and a light source 2002, and the light-emitting device of the present invention is used as the light source 2002. The light-emitting device of the present invention has high luminous efficiency and has a long lifetime; therefore, a table lamp also has high luminous efficiency and a long lifetime.

Figure 9:
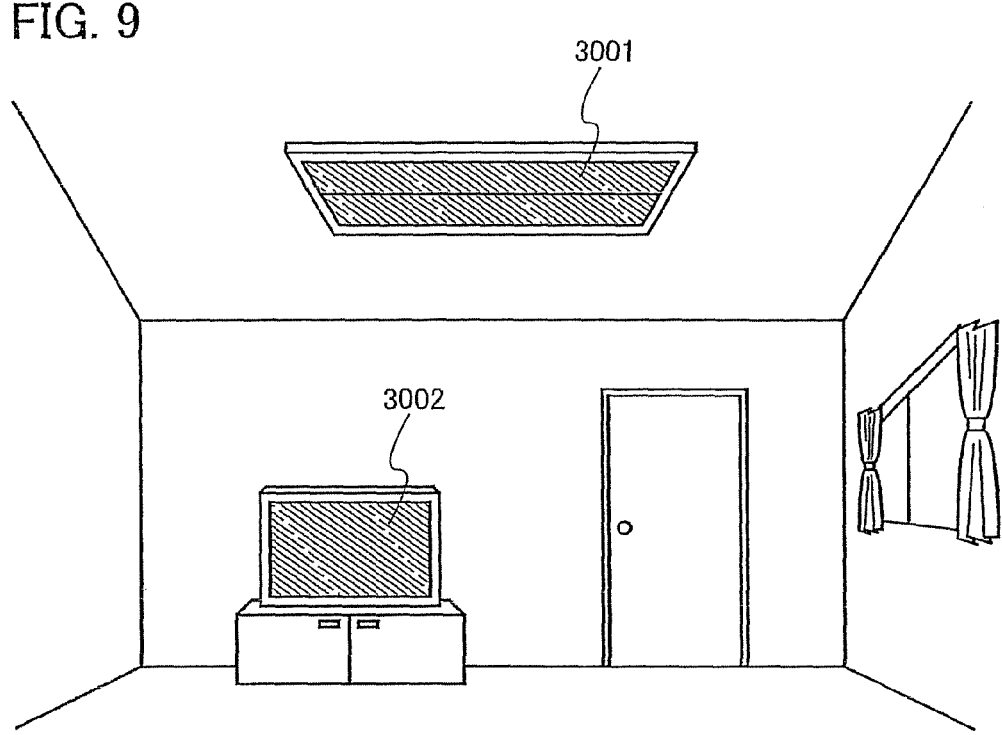
FIG. 9 describes a lighting device of the present invention.

FIG. 9 shows an example of a light-emitting device to which the present invention is applied. This Figure demonstrates an example for the application to an indoor lighting device 3001. Since the light-emitting device of the present invention can also have a large area, the light-emitting device of the present invention can be used as a lighting device having a large emission area. Further, the light-emitting device of the present invention has a thin shape and consumes low power; therefore, the light-emitting device of the present invention can be used as a lighting device having a thin shape and low-power consumption. A television device 3002 according to the present invention as explained in FIG. 6A is placed in a room in which the light-emitting device fabricated by the present invention is used as the indoor lighting device 3001, and public broadcasting and movies can be watched. In such a case, since both of the devices consume low power, a powerful image can be watched in a bright room without concern about electricity charges.

Embodiment 1

In this embodiment, a synthetic method of 9,10-diphenyl-2-[N-(4-diphenylaminophenyl)-N-phenylamino]anthracene (abbreviation: 2DPAPA), which is the anthracene derivative of the present invention represented by Structural Formula (101), will be specifically described.

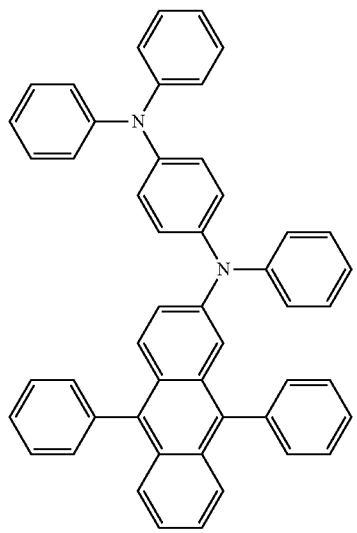

(101)

[Step 1] Synthesis of 2-bromo-9,10-diphenylanthracene (i) Synthesis of 2-bromo-9,10-anthraquinone A synthetic scheme of 2-bromo-9,10-anthraquinone is shown in (C-1).

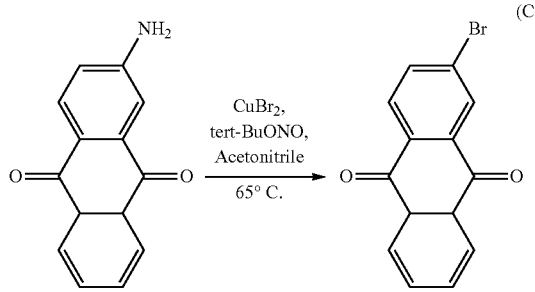

(C-1)

46 g (206 mmol) of copper bromide (II) and 500 mL of acetonitrile were put into a 1 L three-neck flask, and was added 17.3 g (168 mmol) of tert-butyl nitrite into the suspension, which was followed by heating at 65° C. Thereafter, 25 g (111.0 mmol) of 2-amino-9,10-anthraquinone was added into the mixture, and then the mixture was stirred for 6 hours at the same temperature. After the reaction, the reaction mixture was poured into 3M-hydrochloric acid and stirred for 3 hours. Then the precipitate was filtered and washed with water and then with ethanol. The precipitate was dissolved in toluene, and the resulting solution was filtered through Florisil, celite, and then alumina. The filtrate was concentrated, and the residue was recrystallized with chloroform and hexane, giving 18.6 g of 2-bromo-9,10-anthraquinone as a cream-colored solid in 58% yield.

(ii) Synthesis of 2-bromo-9,10-diphenyl-9,10-dihydroanthracene-9,10-diol

A synthetic scheme of 2-bromo-9,10-diphenyl-9,10-dihydroanthracene-9,10-diol is shown in (C-2).

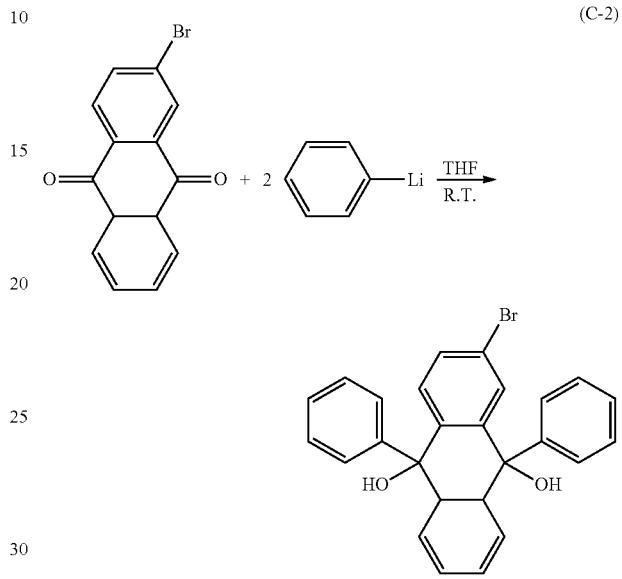

(C-2)

4.90 g (16.95 mmol) of 2-bromo-9,10-anthraquinone was put into a 300 mL three-neck flask, and the atmosphere of the flask was substituted with nitrogen. Into the flask was added 100 mL of tetrahydrofuran (THF), and 17.76 mL (37.29 mmol) of a dibutyl ether-solution of phenyllithium was dropwised, which was followed by stirring for about 12 hours at room temperature. After the reaction, the solution was washed with water, and the aqueous layer was extracted with ethyl acetate. The organic layer was dried over magnesium sulfate, filtered and concentrated to give 2-bromo-9,10-diphenyl-9,10-dihydroanthracene-9,10-diol as the target compound.

(iii) Synthesis of 2-bromo-9,10-diphenylanthracene

A synthetic scheme of 2-bromo-9,10-diphenylanthracene is shown in (C-3).

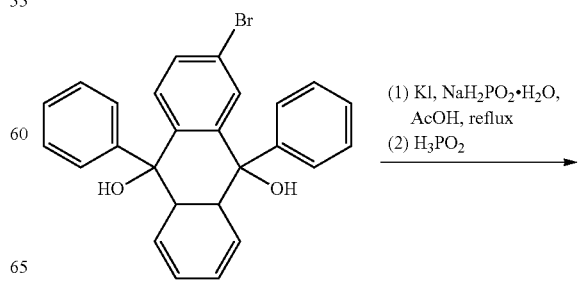

(C-3)

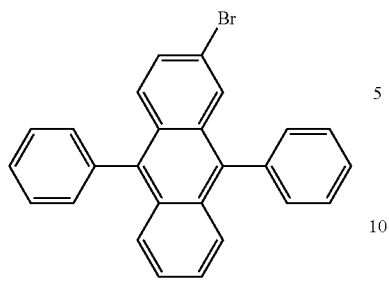

7.55 g (16.95 mmol) of the obtained 2-bromo-9,10-diphenyl-9,10-dihydroanthracene-9,10-diol, 5.06 g (30.51 mmol) of potassium iodide, 9.70 g (91.52 mmol) of sodium phosphinate monohydrate, and 50 mL of glacial acetic acid were put into a 500 mL three-neck flask, and the mixture was heated at 120° C. for 2 hours. Thereafter, 30 mL of 50% phosphinic acid was added to the mixture, and the mixture was stirred for 1 hour at 120° C. After the reaction, the mixture was washed with water, and the aqueous layer was extracted with ethyl acetate. The organic layer was dried over magnesium sulfate, filtered, and concentrated. The residue was dissolved in toluene, and the solution was filtered through celite, and then alumina. The filtrate was concentrated, and the residue was recrystallized with chloroform and hexane, giving 5.1 g of 2-bromo-9,10-diphenylanthracene as a light yellow solid in 74% yield.

[Step 2] Synthetic Method of 2DPAPA

A synthetic scheme of 2DPAPA is shown in (C-4).

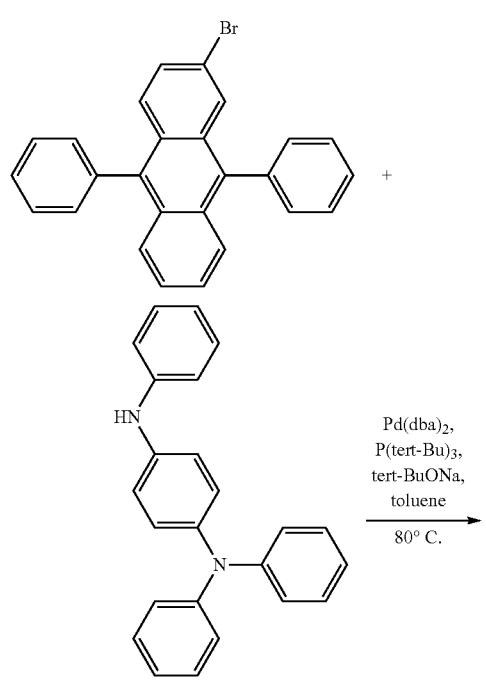

(C-4)

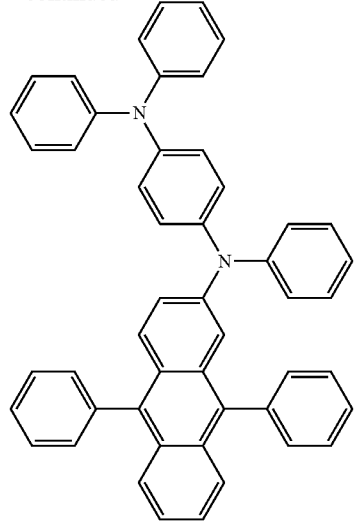

1.8 g (4.40 mmol) of 2-bromo-9,10-diphenylanthracene synthesized in Step 1 of Embodiment 1, 1.78 g (5.28 mmol) of N,N,N'-triphenyl-1,4-phenylenediamine (DPA), 0.126 g (0.220 mmol) of bis(dibenzylideneacetone)palladium (0), and 2.11 g (21.99 mmol) of sodium tert-butoxide were put into a 100 ml three-neck flask, and the atmosphere in the flask was substituted with nitrogen. Further, 30 mL of toluene and 0.44 g (0.220 mmol) of tri(tert-butyl)phosphine (a 10% hexane solution) were added to the flask, and the solution was heated at 80° C. for 6 hours. After the reaction, the solution was washed with water, and the aqueous layer was extracted with ethyl acetate. The organic layer was dried over magnesium sulfate, filtered and concentrated, and the residue was dissolved in toluene, which was followed by filtration through celite, Florisil, and then alumina. The filtrate was concentrated, and then the residue was recrystallized with chloroform, methanol, and hexane, resulting in 2.24 g of the target compound as a yellow solid in 77% yield. By a nuclear magnetic resonance measurement (NMR), it was confirmed that this compound was 9,10-diphenyl-2-[N-(4-diphenylaminophenyl)-N-phenylamino]anthracene (abbreviation: 2DPAPA).

Figure 11A:
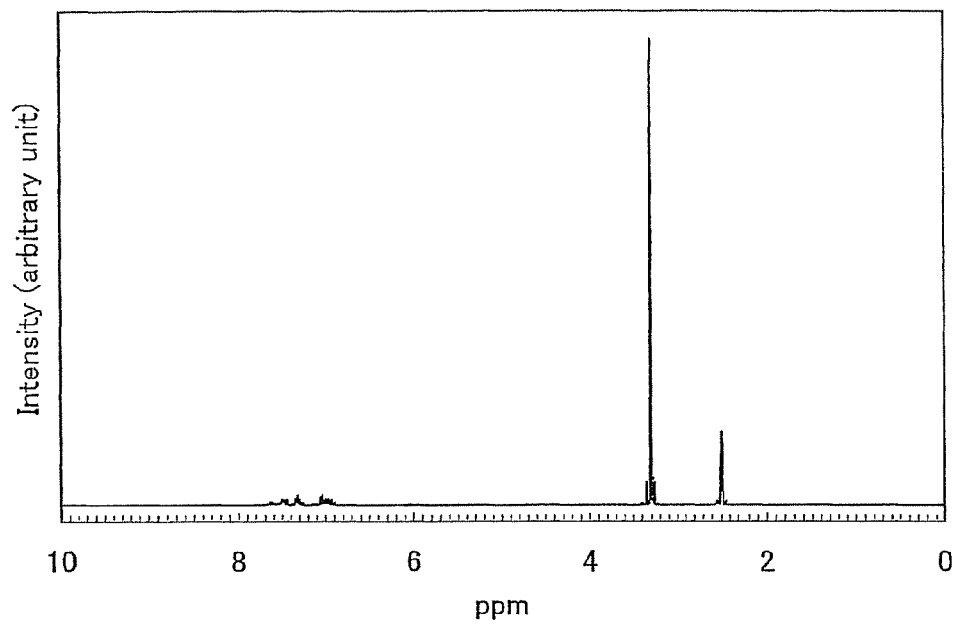
FIGS. 11A and 11B each show the $^1$H NMR chart of 9,10-diphenyl-2-[N-(4-diphenylaminophenyl)-N-phenylamino]anthracene (abbreviation: 2DPAPA)
Figure 11B:
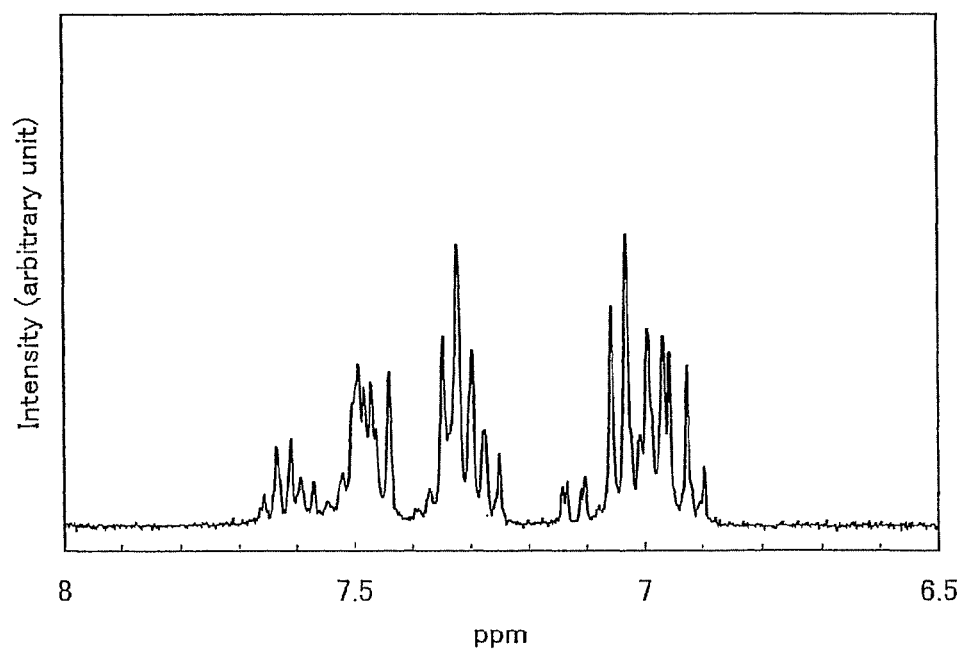

$^1$H NMR data of 2DPAPA is shown below. $^1$H NMR (DMSO-$d_6$, 300 MHz): δ=6.90-7.14 (m, 15H), 7.25-7.37 (m, 10H), 7.44-7.52 (m, 8H), 7.57-7.66 (m, 3H). The $^1$H NMR chart is shown in FIGS. 11A and 11B. Note that the range of 6.5 ppm to 8.0 ppm in FIG. 11A is expanded and shown in FIG. 11B.

The decomposition temperature ($T_d$) of 2DPAPA, measured with a thermogravimetric/differential thermal analyzer (type TG/DTA 320, manufactured by Seiko Instruments Inc.), was found to be 395.9° C., meaning high thermal stability of this compound.

Figure 12:
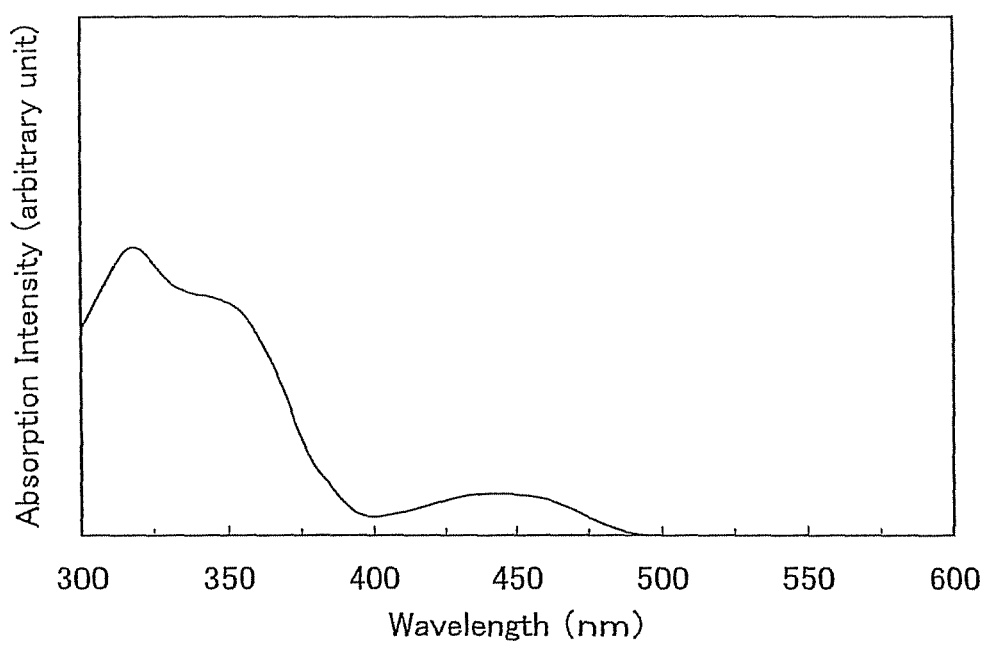
FIG. 12 shows the absorption spectrum of a toluene solution of 9,10-diphenyl-2-[N-(4-diphenylaminophenyl)-N-phenylamino]anthracene (abbreviation: 2DPAPA)
Figure 13:
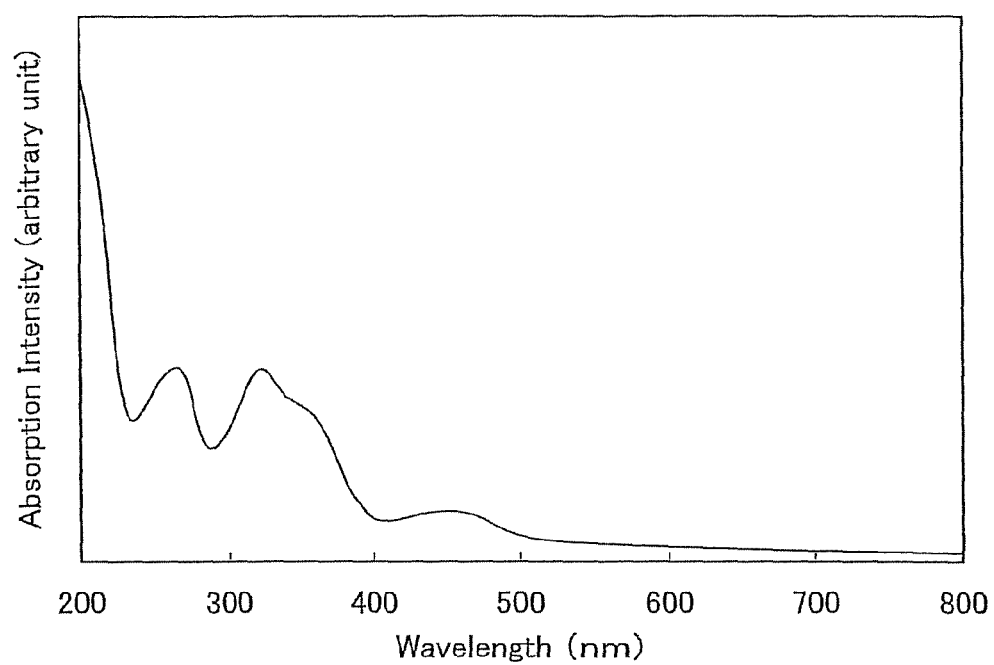
FIG. 13 shows the absorption spectrum of a thin film of 9,10-diphenyl-2-[N-(4-diphenylaminophenyl)-N-phenylamino]anthracene (abbreviation: 2DPAPA)
Figure 14:
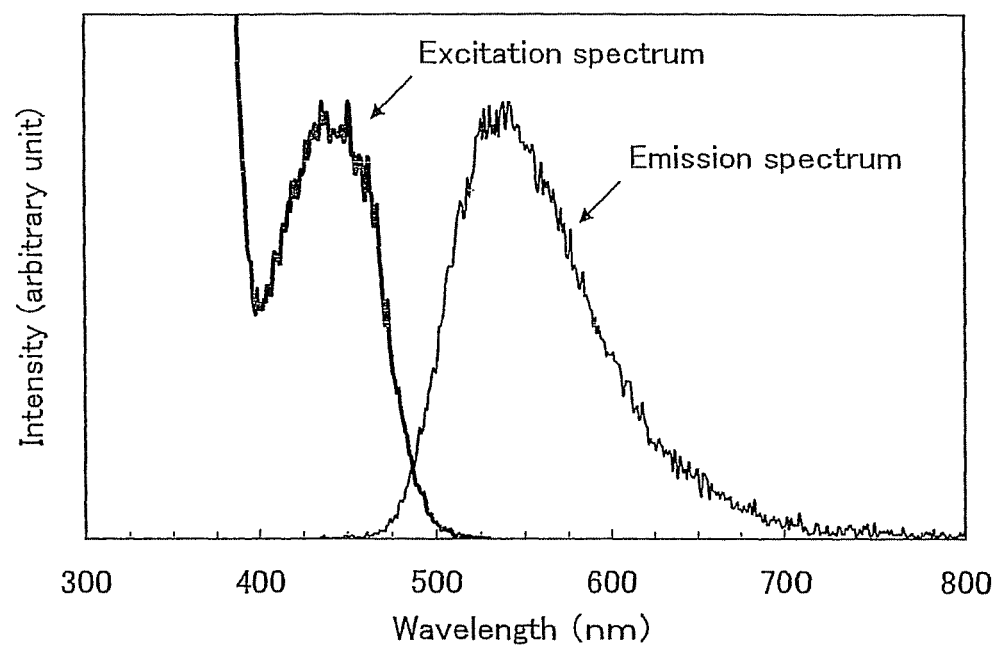
FIG. 14 shows the excitation spectrum and emission spectrum of a toluene solution of 9,10-diphenyl-2-[N-(4-diphenylaminophenyl)-N-phenylamino]anthracene (abbreviation: 2DPAPA)
Figure 15:
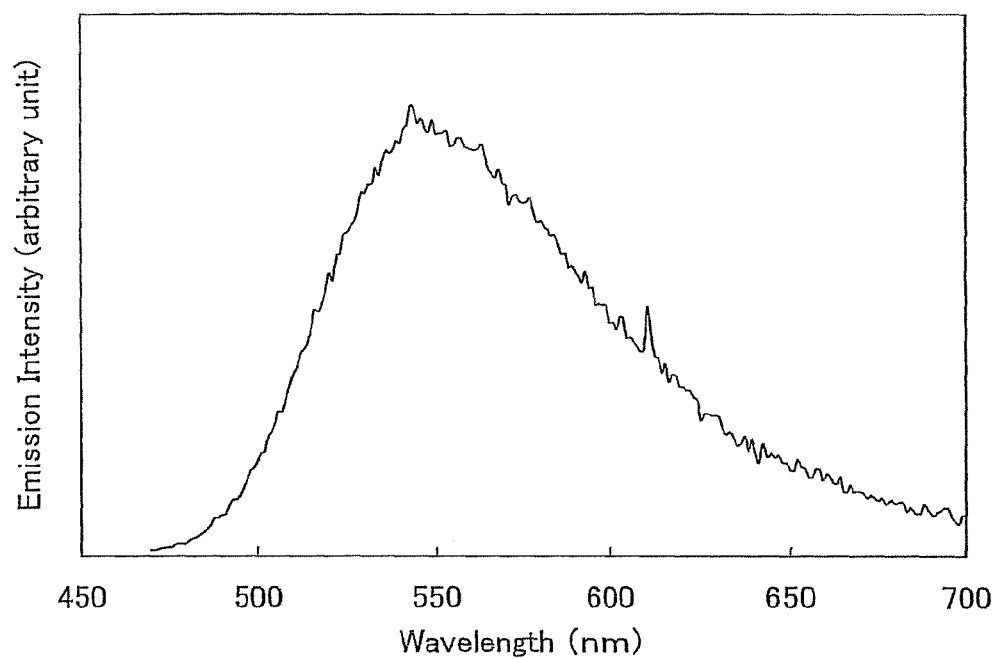
FIG. 15 shows the emission spectrum of a thin film of 9,10-diphenyl-2-[N-(4-diphenylaminophenyl)-N-phenylamino]anthracene (abbreviation: 2DPAPA)

The absorption spectrum of a toluene solution of 2DPAPA is shown in FIG. 12. In addition, an absorption spectrum of a thin film of 2DPAPA is shown in FIG. 13. An ultraviolet-visible spectrophotometer (type V550, manufactured by Japan Spectroscopy Corporation) was used for measurement. The spectrum of the solution was measured in a quartz cell. The sample of the thin film was fabricated by vapor deposition of 2DPAPA over a quartz substrate. The absorption spectra of the solution and the thin film are shown in FIGS. 12 and 13, respectively, which were obtained by subtracting the spectrum of the quartz substrate from the corresponding raw spectra. In each of FIGS. 12 and 13, a horizontal axis shows wavelength (nm) and a vertical axis shows absorption intensity (an arbitrary unit). In the case of the toluene solution, absorption was observed at around 442 nm, and in the case of the thin film, absorption was observed at around 452 nm. Further, an emission spectrum of the toluene solution (excitation wavelength of 430 nm) of 2DPAPA is shown in FIG. 14, and an emission spectrum of the thin film (excitation wavelength of 452 nm) of 2DPAPA is shown in FIG. 15. In each of FIGS. 14 and 15, a horizontal axis shows wavelength (nm) and a vertical axis shows emission intensity (an arbitrary unit). In the case of the toluene solution, the maximum emission wavelength was 539 nm (excitation wavelength of 430 nm), and in the case of the thin film, the maximum emission wavelength was 543 nm (excitation wavelength of 452 nm).

The HOMO level of 2DPAPA in a thin film state which was measured by a photoelectron spectrometer (AC-2, manufactured by Riken Keiki Co., Ltd.) under air was −5.28 eV. By the absorption edge obtained from a Tauc plot of the absorption spectrum of the thin film shown in FIG. 13, the optical energy gap was estimated to be 2.46 eV, which means that LUMO level of 2DPAPA is −2.82 eV.

Embodiment 2

In this embodiment, a synthetic method of 9,10-diphenyl-2-[N-phenyl-N-(9-phenyl-9H-carbazol-3-yl)amino]anthracene (abbreviation: 2PCAPA), which is the anthracene derivative of the present invention represented by Structural Formula (201), is specifically described.

(201)

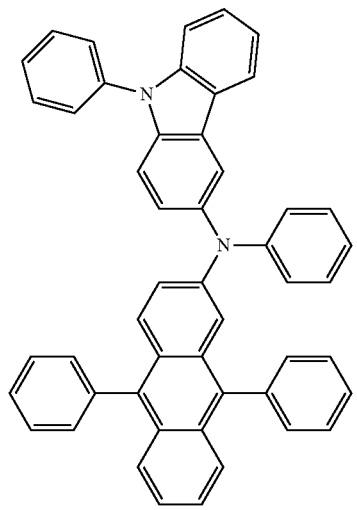

[Step: 1] Synthesis of N-phenyl-(9-phenyl-9H-carbazole-3-yl)amine (abbreviation: PCA)

(i) Synthesis of 3-bromo-9-phenylcarbazole

A synthetic scheme of 3-bromo-9-phenylcarbazole is shown in (C-5).

(C-5)

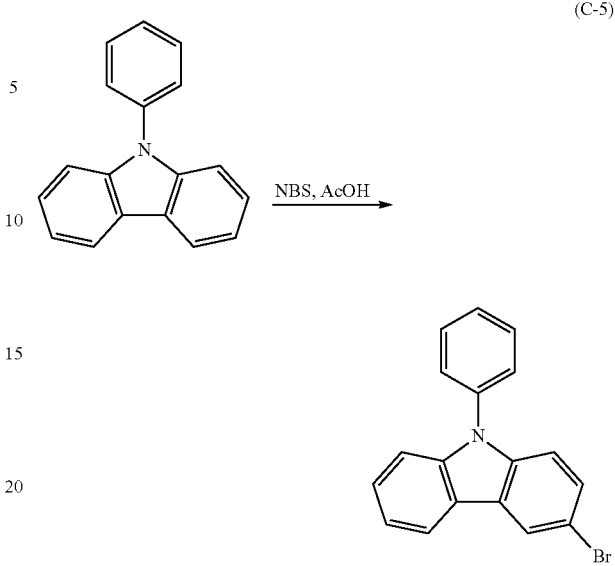

24.3 g (100 mmol) of 9-phenylcarbazole was put into a 2 L Meyer flask, and dissolved in 600 mL of glacial acetic acid. Then, 17.8 g (100 mmol) of N-bromosuccinimide was slowly added, and the solution was stirred for about 12 hours at room temperature. This solution was dropped into 1 L of ice water while stirring. A white solid precipitated was collected by suction filtration, and then washed with water three times. This solid was dissolved in 150 mL of diethyl ether, and the solution was washed with a saturated aqueous solution of sodium bicarbonate and then with water. The organic layer was dried over magnesium sulfate, filtered, and concentrated, and then the residue was dissolved in ca. 50 mL of ethanol. The precipitate formed as a white solid was collected by suction filtration and dried, giving 28.4 g (88% yield) of 3-bromo-9-phenylcarbazole as white powder.

(ii) Synthesis of N-phenyl-(9-phenyl-9H-carbazol-3-yl)amine (abbreviation: PCA)

A synthetic scheme of N-phenyl-(9-phenyl-9H-carbazol-3-yl)amine (abbreviation: PCA) is shown in (C-6).

(C-6)

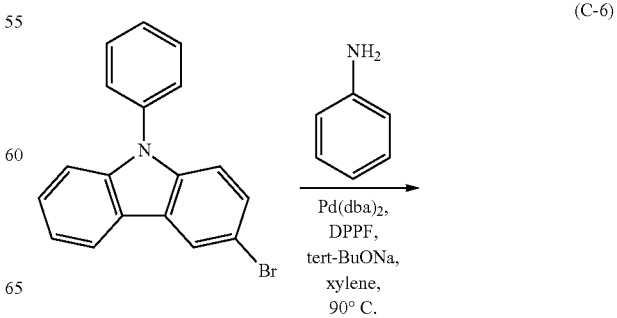

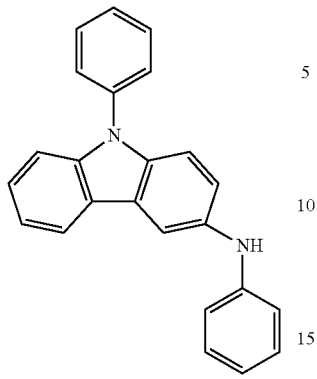

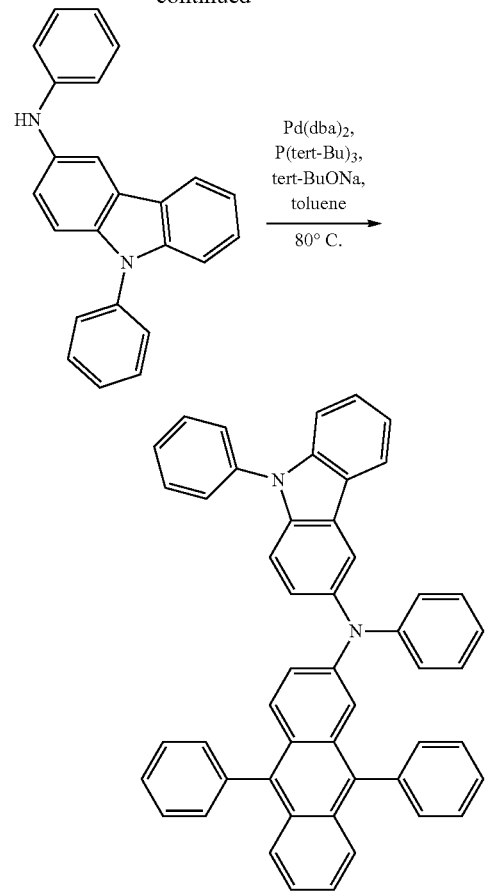

Into a 500 mL three-neck flask were added 19 g (60 mmol) of 3-bromo-9-phenylcarbazole, 340 mg (0.6 mmol) of bis(dibenzylideneacetone)palladium (0), 1.6 g (3.0 mmol) of 1,1-bis(diphenylphosphino)ferrocene, and 13 g (180 mmol) of sodium tert-butoxide, and the atmosphere in the flask was substituted with nitrogen. Thereafter, 110 mL of dehydrated xylene and 7.0 g (75 mmol) of aniline were added to the mixture. This mixture was heated and stirred for 7.5 hours at 90° C. After the reaction was completed, about 500 mL of hot toluene was added to the solution, and this solution was filtered through Florisil, alumina, and celite. The obtained filtrate was concentrated, and hexane and ethyl acetate were added to the residue, which was followed by irradiation with ultrasound. A solid precipitated was collected by suction filtration and dried to give 15 g (75% yield) of N-phenyl-(9-phenyl-9H-carbazol-3-yl)amine (abbreviation: PCA) as cream colored powder. By a nuclear magnetic resonance measurement (NMR), it was confirmed that this compound was N-phenyl-(9-phenyl-9H-carbazol-3-yl)amine (abbreviation: PCA).

Figure 16A:
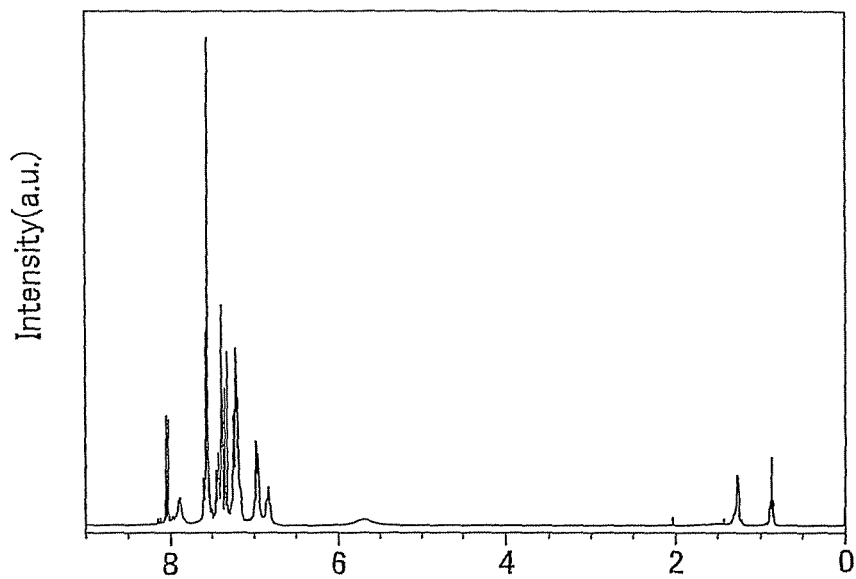
FIGS. 16A and 16B each show the $^1$H NMR chart of N-phenyl-(9-phenyl-9H-carbazol-3-yl)amine (abbreviation: PCA)
Figure 16B:
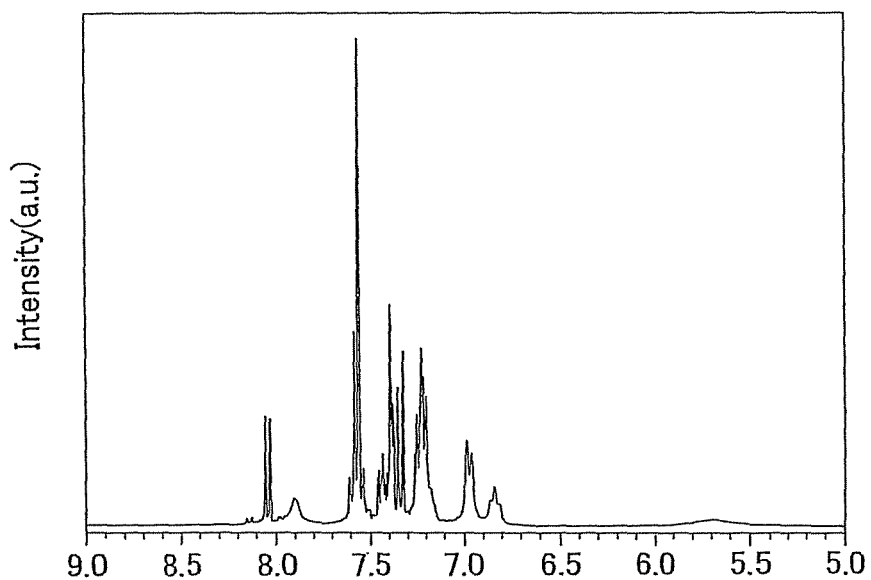

$^1$H NMR data of this compound is shown below. $^1$H NMR (300 MHz, CDCl$_3$): δ=6.84 (t, J=6.9 Hz, 1H), 6.97 (d, J=7.8 Hz, 2H), 7.20-7.61 (m, 13H), 7.90 (s, 1H), 8.04 (d, J=7.8 Hz, 1H). The $^1$H NMR chart is shown in FIGS. 16A and 16B. Note that the range of 5.0 ppm to 9.0 ppm in FIG. 16A is expanded and shown in FIG. 16B.

[Step 2] Synthetic Method of 2PCAPA

A synthetic scheme of 2PCAPA is shown in (C-7).

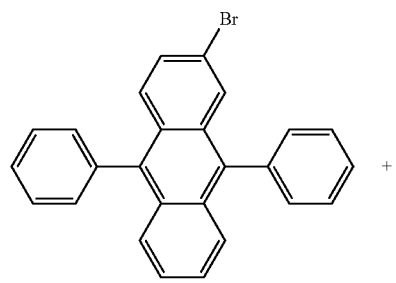

(C-7)

1.8 g (4.40 mmol) of 2-bromo-9,10-diphenylanthracene synthesized in Step 1 of Embodiment 1, 1.76 g (5.28 mmol) of N-phenyl-(9-phenyl-9H-carbazol-3-yl)amine (abbreviation: PCA), 0.126 g (0.220 mmol) of bis(dibenzylideneacetone)palladium (0), and 2.11 g (21.99 mmol) of sodium tert-butoxide were put into a 100 mL three-neck flask, and the atmosphere in the flask was substituted with nitrogen. 30 mL of toluene and 0.44 g (0.220 mmol) of tri(tert-butyl)phosphine (10% hexane solution) were added to the flask, and the mixture was heated at 80° C. with stirring for 6 hours. After the reaction, the solution was washed with water, and the aqueous layer was extracted with ethyl acetate. The organic layer was dried over magnesium sulfate. After filtration and concentration of the organic layer, the residue was dissolved in toluene, and the solution was filtered through celite, Florisil, and then alumina. The filtrate was concentrated, and the residue was recrystallized with chloroform, methanol, and hexane, obtaining 2.33 g of the target compound as a yellow solid in 80% yield. By the nuclear magnetic resonance analysis (NMR), it was confirmed that this compound was 9,10-diphenyl-2-[N-phenyl-N-(9-phenyl-9H-carbazol-3-yl)amino]anthracene (abbreviation: 2PCAPA).

Figure 17A:
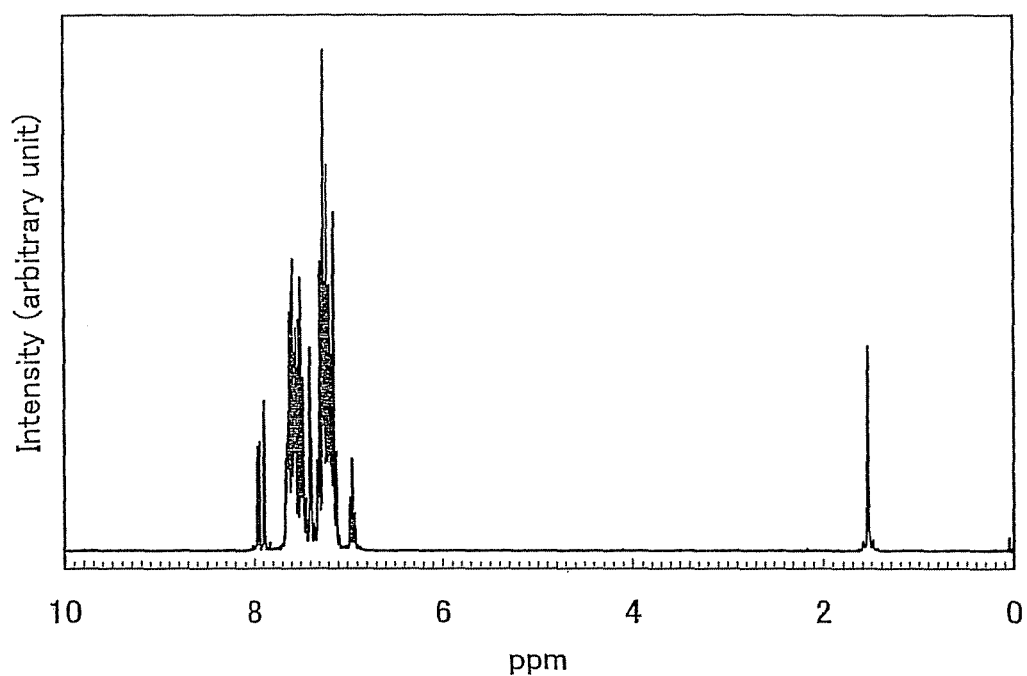
FIGS. 17A and 17B each show the $^1$H NMR chart of 9,10-diphenyl-2-[N-phenyl-N-(9-phenyl-9H-carbazol-3-yl)amino]anthracene (abbreviation: 2PCAPA)
Figure 17B:
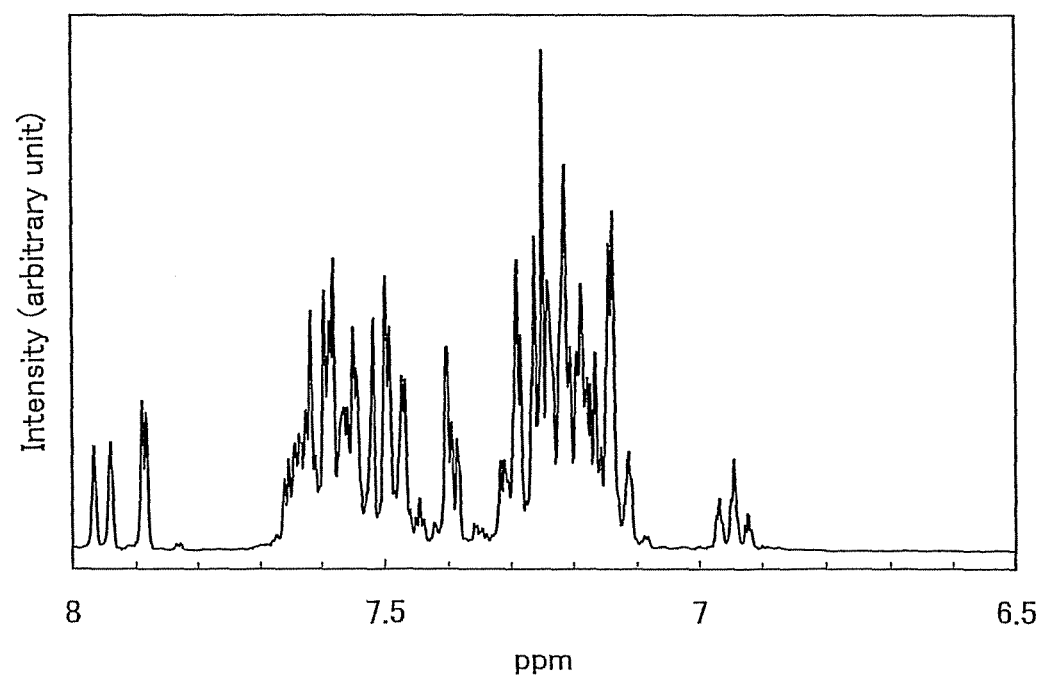

$^1$H NMR data of this compound is shown below. $^1$H NMR (CDCl$_3$, 300 MHz): δ=6.92-6.97 (m, 1H), 7.11-7.32 (m, 16H), 7.39-7.66 (m, 15H), 7.88-7.97 (m, 2H). Also, the $^1$H NMR chart is shown in FIGS. 17A and 17B. Note that the range of 6.5 ppm to 8.0 ppm in FIG. 17A is expanded and shown in FIG. 17B.

The decomposition temperature (T$_d$) of 2PCAPA, measured with a thermogravimetric/differential thermal analyzer (type TG/DTA 320, manufactured by Seiko Instruments Inc.), was found to be 410.1° C., meaning high thermal stability of this compound.

Figure 18:
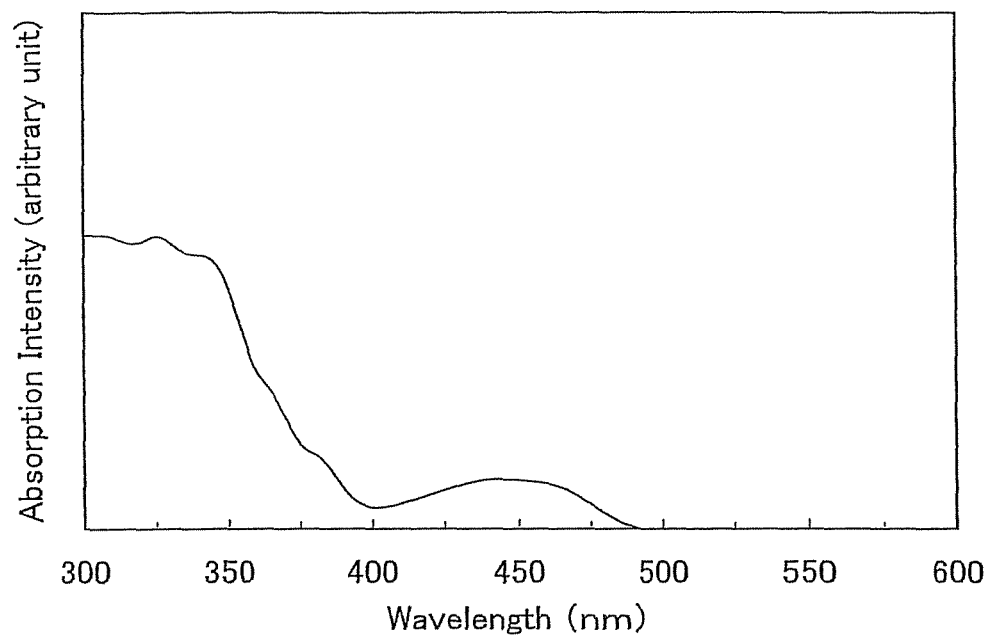
FIG. 18 shows the absorption spectrum of a toluene solution of 9,10-diphenyl-2-[N-phenyl-N-(9-phenyl-9H-carbazol-3-yl)amino]anthracene (abbreviation: 2PCAPA)
Figure 19:
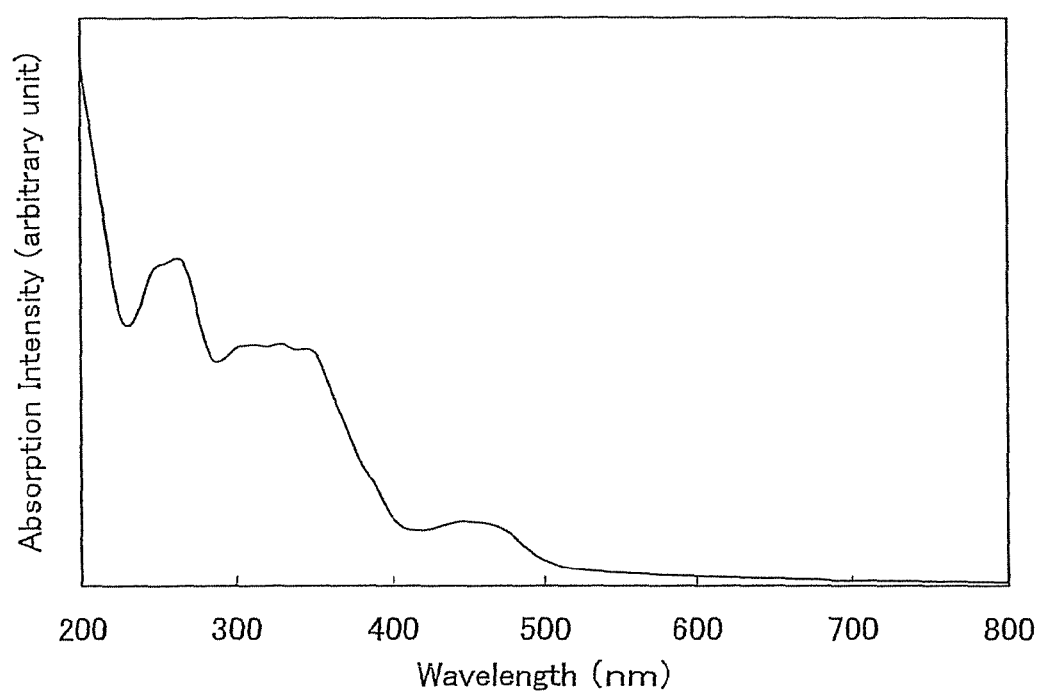
FIG. 19 shows the absorption spectrum of a thin film of 9,10-diphenyl-2-[N-phenyl-N-(9-phenyl-9i-carbazol-3-yl)amino]anthracene (abbreviation: 2PCAPA)
Figure 20:
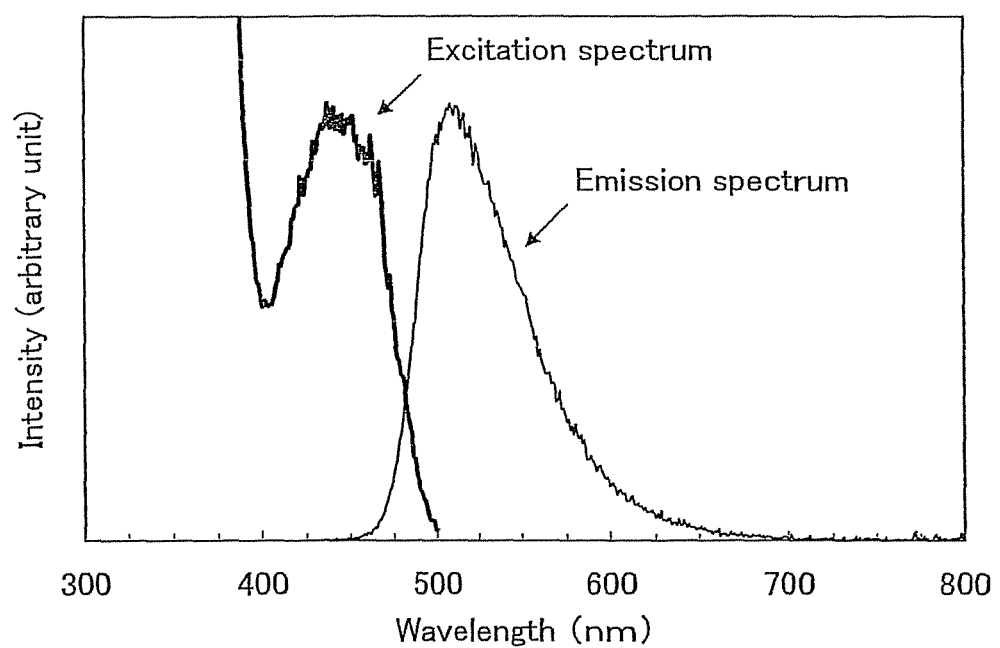
FIG. 20 shows the excitation spectrum and emission spectrum of a toluene solution of 9,10-diphenyl-2-[N-phenyl-N-(9-phenyl-9H-carbazol-3-yl)amino]anthracene (abbreviation: 2PCAPA)
Figure 21:
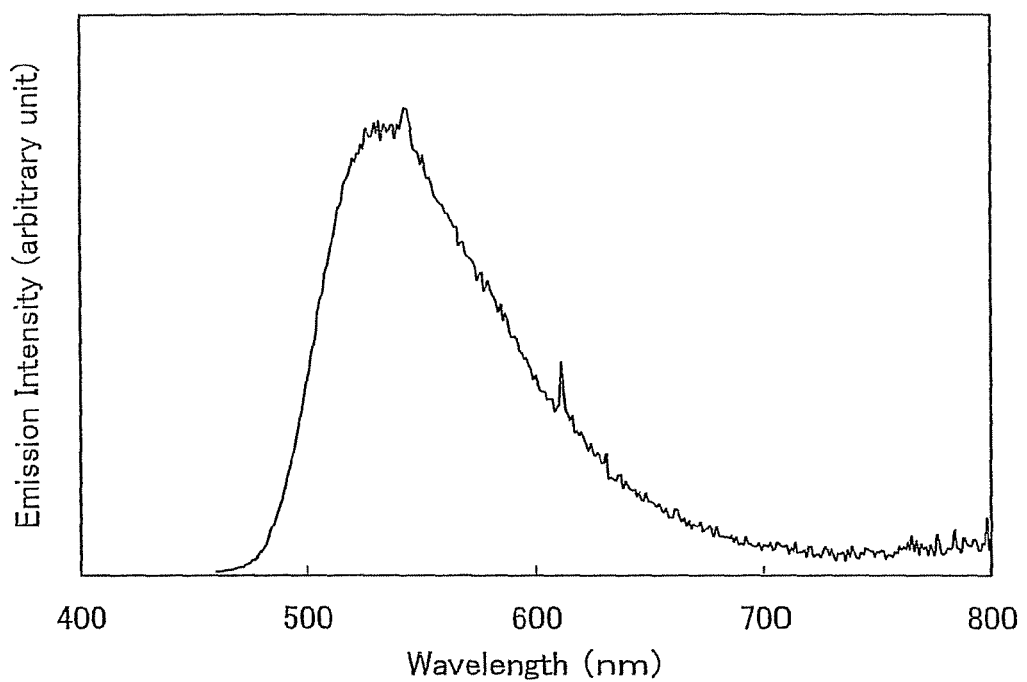
FIG. 21 shows the emission spectrum of a thin film of 9,10-diphenyl-2-[N-phenyl-N-(9-phenyl-9H-carbazol-3-yl)amino]anthracene (abbreviation: 2PCAPA)

The absorption spectrum of a toluene solution of 2PCAPA is shown in FIG. 18. In addition, an absorption spectrum of a thin film of 2PCAPA is shown in FIG. 19. An ultraviolet-visible spectrophotometer (type V550, manufactured by Japan Spectroscopy Corporation) was used for measurement. The spectrum of the solution was measured in a quartz cell. The sample of the thin film was fabricated by vapor deposition of 2PCAPA over a quartz substrate. The absorption spectra of the solution and the thin film are shown in FIGS. 18 and 19, respectively, which were obtained by subtracting the spectrum of the quartz substrate from the corresponding raw spectra. In each of FIGS. 18 and 19, a horizontal axis shows wavelength (nm) and a vertical axis shows absorption intensity (an arbitrary unit). In the case of the toluene solution, absorption was observed at around 442 nm, and in the case of the thin film, absorption was observed at around 448 nm. Further, an emission spectrum of the toluene solution (excitation wavelength of 430 nm) of 2PCAPA is shown in FIG. 20, and an emission spectrum of the thin film (excitation wavelength of 448 nm) of 2PCAPA is shown in FIG. 21. In each of FIGS. 20 and 21, a horizontal axis shows wavelength (nm) and a vertical axis shows emission intensity (an arbitrary unit). In the case of the toluene solution, the maximum light emission wavelength was 508 mu (excitation wavelength of 430 nm), and in the case of the thin film, the maximum emission wavelength was 537 nm (excitation wavelength of 448 nm).

The HOMO level of 2PCAPA in a thin film state which was measured by a photoelectron spectrometer (AC-2, manufactured by Riken Keiki Co., Ltd.) under air was −5.26 eV. By the absorption edge obtained from a Tauc plot of the absorption spectrum of the thin film shown in FIG. 19, the optical energy gap was estimated to be 2.47 eV, which means that LUMO level of 2PCAPA is −2.79 eV.

An oxidation-reduction characteristic of 2PCAPA was explored by a cyclic voltammetry (CV) measurement. For the measurement, an electrochemical analyzer (ALS model 600A, manufactured by BAS Inc.) was used.

As for a solution used in the CV measurement, dehydrated N,N-dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), a supporting electrolyte, was dissolved in DMF at the concentration of 100 mmol/L to prepare the electrolysis solution. The sample solution was prepared by dissolving the sample in the electrolysis solution at a concentration of 1 mmol/L. A platinum electrode (a PTE platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

An oxidation characteristic of 2PCAPA was evaluated in the following manner. The potential of the working electrode with respect to a reference electrode was swept from −0.23 V to 0.60 V, which was followed by sweeping the potential from 0.60 V to −0.23 V. This cycle was set as one cycle, and 100 cycles were performed. Also, a reduction characteristic of 2PCAPA was evaluated in the following manner. The potential of the working electrode with respect to the reference electrode was swept from −0.41 V to −2.50 V, which was followed by sweeping the potential from −2.50 V to −0.41 V. This cycle was set as one cycle, and 100 cycles were performed. Sweeping speed of the CV measurement was set to be 0.1V/s.

Figure 22:
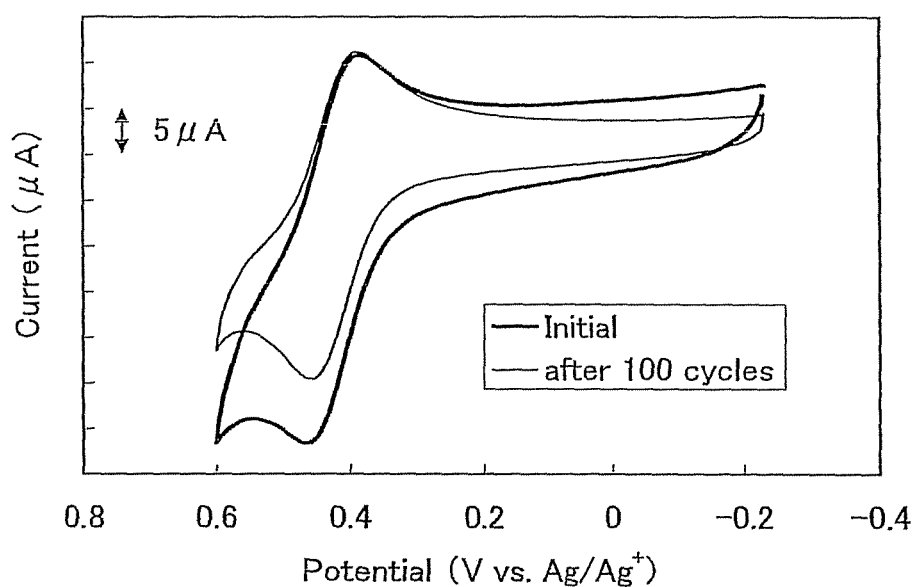
FIG. 22 shows the result of a CV measurement of 9,10-diphenyl-2-[N-phenyl-N-(9-phenyl-9H-carbazol-3-yl)amino]anthracene (abbreviation: 2PCAPA)
Figure 23:
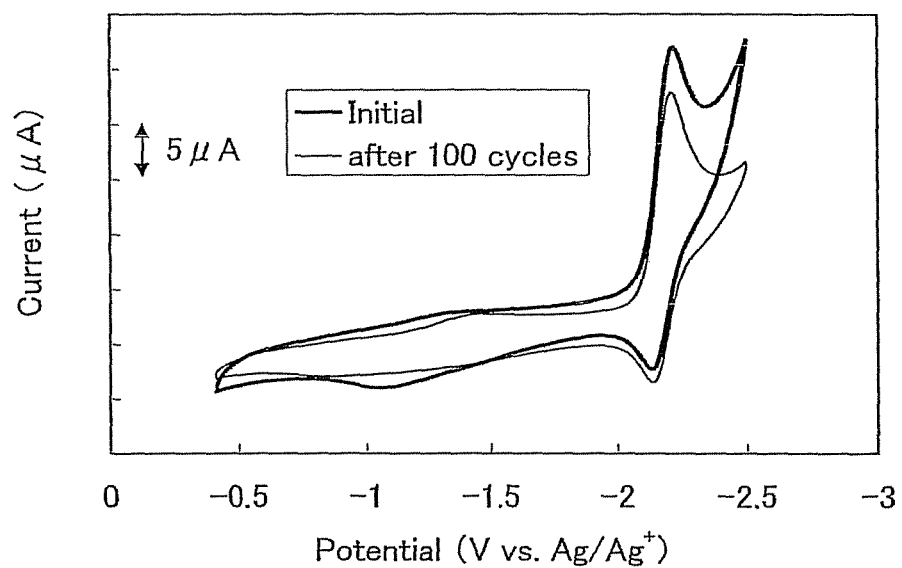
FIG. 23 shows the result of a CV measurement of 9,10-diphenyl-2-[N-phenyl-N-(9-phenyl-9H-carbazol-3-yl)amino]anthracene (abbreviation: 2PCAPA)

The CV measurement result of an oxidation side of 2PCAPA and the CV measurement result of a reduction side of 2PCAPA are shown in FIGS. 22 and 23, respectively. In each of FIGS. 22 and 23, a horizontal axis shows a potential (V) of the working electrode with respect to the reference electrode, and a vertical axis shows a current value (µA) that flowed between the working electrode and the counter electrode. From FIG. 22, a current exhibiting oxidation was observed around −0.47 V (vs. Ag/Ag$^+$). From FIG. 23, a current exhibiting reduction was observed around −2.22 V (vs. Ag/Ag$^+$).

In spite of the fact that 100 cycles of sweeping were repeated, a peak position and a peak intensity at the CV curve scarcely changed in the oxidation and reduction, which reveals that the anthracene derivative of the present invention is extremely stable against repetition of the oxidation and reduction.

Embodiment 3

In this embodiment, a synthetic method of 9,10-di(2-biphenylyl)-2-[N-(4-diphenylaminophenyl)-N-phenylamino]anthracene (abbreviation: 2DPABPhA), which is the anthracene derivative of the present invention represented by Structural Formula (115), is specifically described.

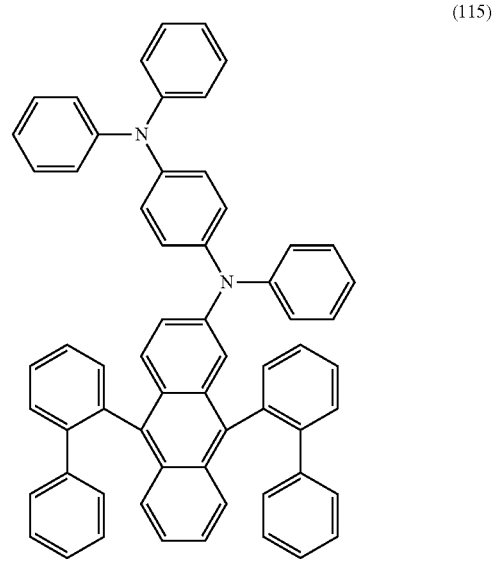 [SMILES: c1ccc(-c2ccccc2-c2c3ccccc3c(-c3ccccc3-c3ccccc3)c3cc(N(c4ccccc4)c4ccc(N(c5ccccc5)c5ccccc5)cc4)ccc23)cc1]

(115)

[Step 1] Synthesis of 9,10-di(2-biphenylyl)-2-bromoanthracene

A synthetic scheme of 9,10-di(2-biphenylyl)-2-bromoanthracene is shown in (C-8) to (C-10).

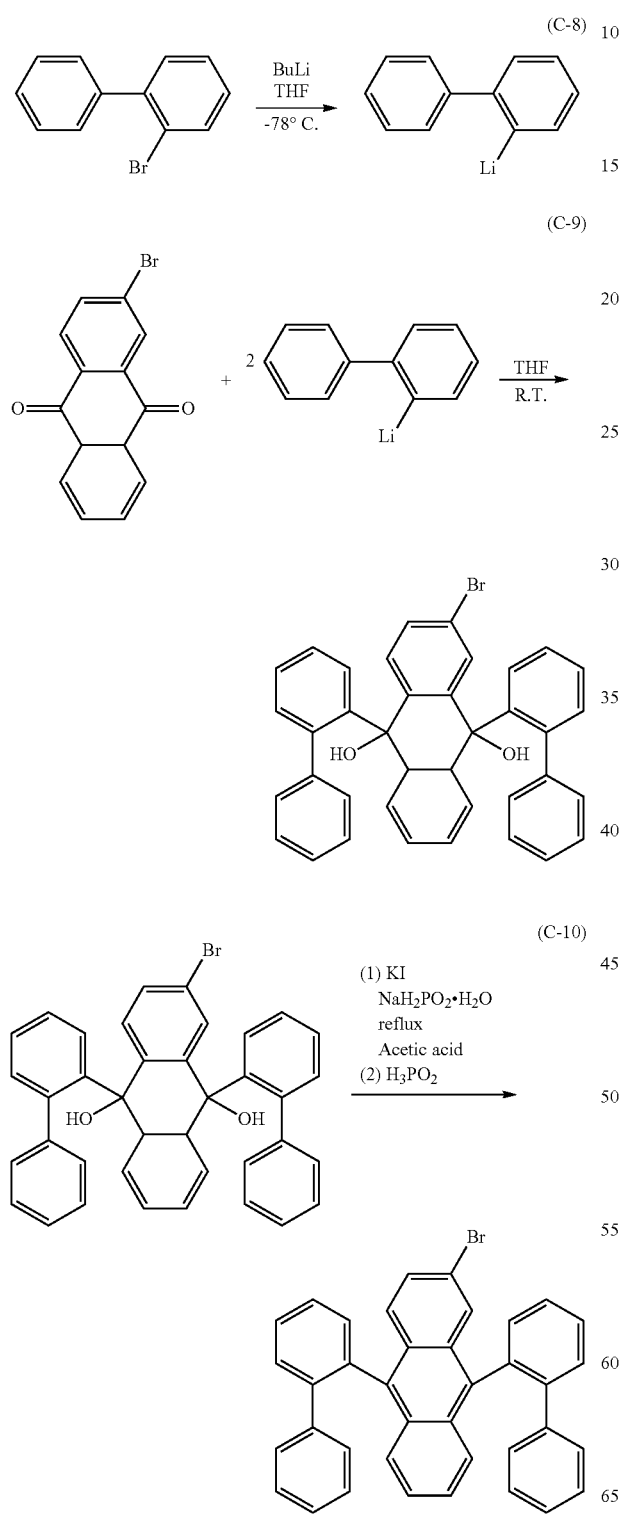

22.84 g (98.00 mmol) of 2-bromobiphenyl was put into a 500 mL three-neck flask, and the atmosphere of the flask was substituted with nitrogen. Into the flask was added 100 mL of tetrahydrofuran (THF), followed by dropwising 68.66 mL (107.80 mmol) of n-butyllithium (1.57 mol/L hexane solution) at −78° C. After stirring for 5 hours, 160 mL of THF containing 8.5 g (29.40 mmol) of 2-bromo-9,10-anthraquinone was dropwised to this solution under nitrogen, and the solution was stirred for about 12 hours while the reaction temperature was allowed to gradually increase to room temperature. After the reaction, into the solution was added water, and the precipitate formed was filtered, giving 9,10-di(2-biphenylyl)-2-bromo-9,10-dihydroanthracene-9,10-diol as a cream colored solid.

18.32 g (30.66 mmol) of the obtained 9,10-di(2-biphenylyl)-2-bromo-9,10-dihydroanthracene-9,10-diol, 9.16 g (55.19 mmol) of potassium iodide, 17.55 g (165.56 mmol) of sodium phosphinate monohydrate, and 150 mL of glacial acetic acid were put into a three-neck flask, and the mixture was stirred for 5 hours at 120° C. Thereafter, 100 mL of 50% phosphinic acid was added to the mixture, followed by stirring for 1 hour at 120° C. After the reaction, the solution was washed with water, and the precipitate was filtered, recrystallized with chloroform and hexane, obtaining 11.4 g of 9,10-di(2-biphenylyl)-2-bromoanthracene as a light yellow solid in 66% yield.

[Step 2] Synthetic Method of 2DPABPhA

A synthetic scheme of 2DPABPhA is shown in (C-11).

-continued

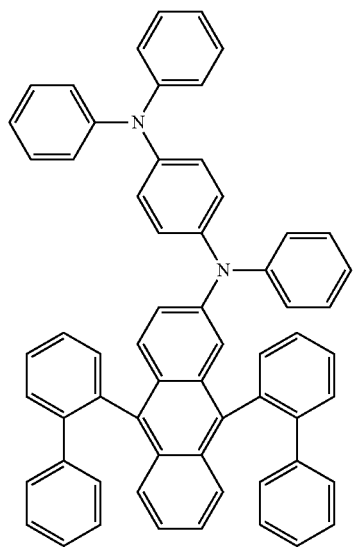

2.0 g (3.56 mmol) of 9,10-di(2-biphenylyl)-2-bromoanthracene synthesized in Step 1 of Embodiment 3, 1.44 g (4.27 mmol) of N,N,N'-triphenyl-1,4-phenylenediamine (DPA), 0.102 g (0.178 mmol) of bis(dibenzylideneacetone)palladium (0), and 1.71 g (17.81 mmol) of sodium tert-butoxide were put into a 100 mL three-neck flask, and the atmosphere in the flask was substituted with nitrogen. 30 mL of toluene and 0.36 g (0.178 mmol) of tri(tert-butyl)phosphine (10% hexane solution) were added to the flask, and the solution was heated at 80° C. with stirring for 7 hours. After the reaction, the solution was washed with water, and the aqueous layer was extracted with ethyl acetate. The organic layer was dried over magnesium sulfate, filtered and concentrated, and the residue was dissolved in toluene. This toluene solution was filtered through celite, Florisil, and then alumina. The filtrate was concentrated, and the residue was recrystallized with chloroform and methanol, giving 2.5 g of the target compound as a yellow solid in 87% yield. By the nuclear magnetic resonance measurement (NMR), it was confirmed that this compound was 9,10-di(2-biphenylyl)-2-[N-(4-diphenylaminophenyl)-N-phenylamino]anthracene (abbreviation: 2DPABPhA).

Figure 24A:
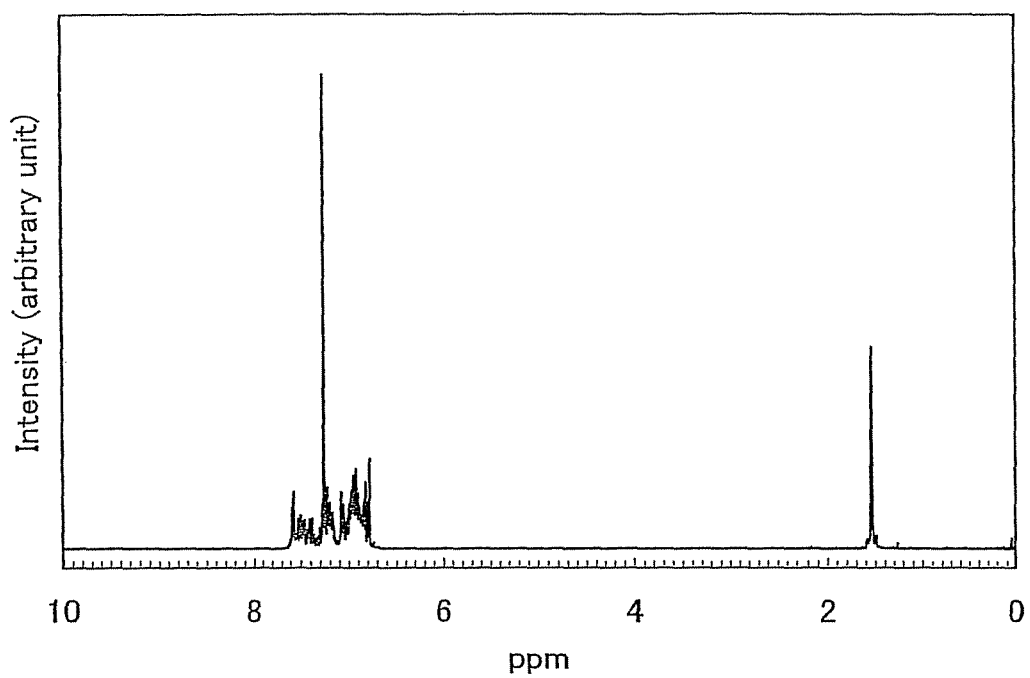
FIGS. 24A and 24B each show the $^1$H NMR chart of 9,10-di(2-biphenylyl)-2-[N-(4-diphenylaminophenyl)-N-phenylamino]anthracene (abbreviation: 2DPABPhA)
Figure 24B:
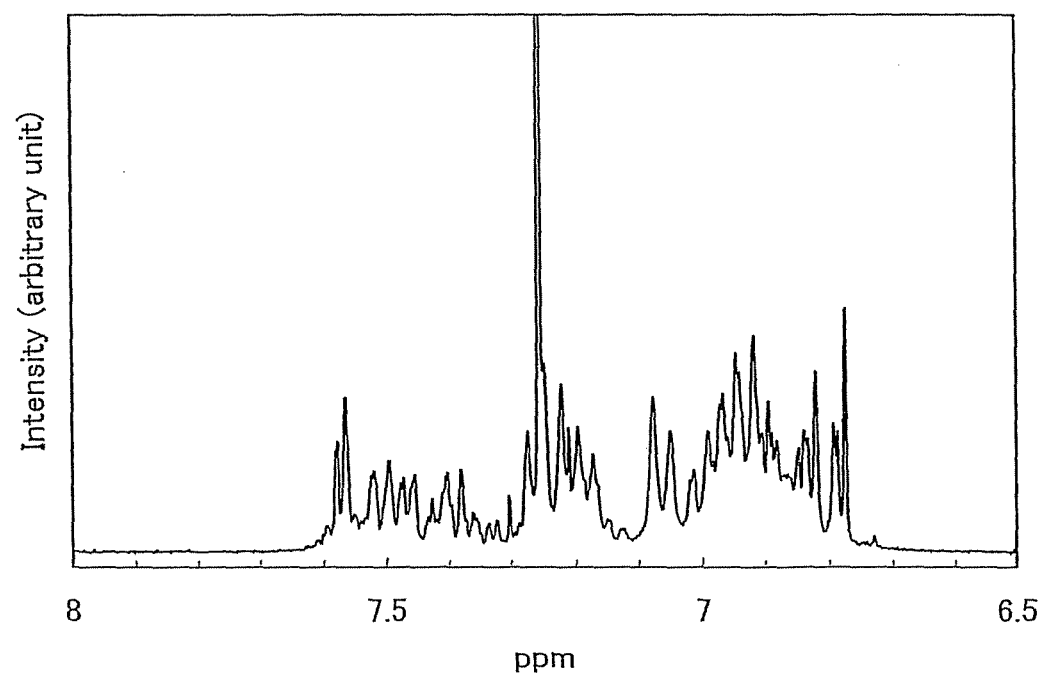

The $^1$H NMR data of this compound is shown below. $^1$H-NMR (CDCl$_3$, 300 MHz): δ=6.78-7.08 (m, 24H), 7.12-7.30 (m, 10H), 7.32-7.59 (m, 10H). The $^1$H NMR chart is shown in each of FIGS. 24A and 24B. Note that the range of 6.5 ppm to 8.0 ppm in FIG. 24A is expanded and shown in FIG. 24B.

The decomposition temperature ($T_d$) of 2DPABPhA, measured with a thermogravimetric/differential thermal analyzer (type TG/DTA 320, manufactured by Seiko Instruments Inc.), was found to be 419.8° C., meaning high thermal stability of this compound.

Figure 25:
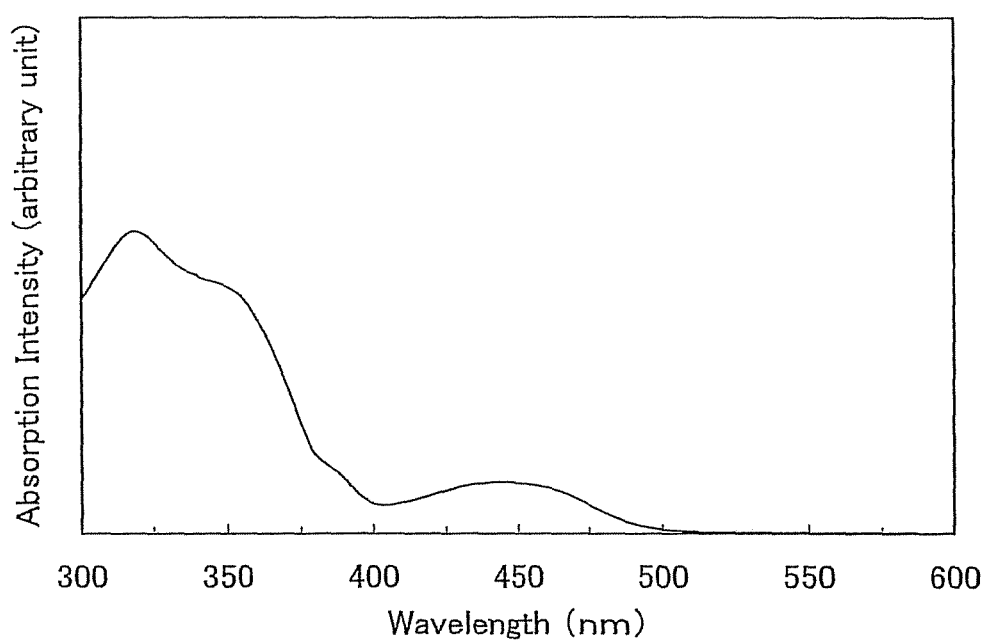
FIG. 25 shows the absorption spectrum of a toluene solution of 9,10-di(2-biphenylyl)-2-[N-(4-diphenylaminophenyl)-N-phenylamino]anthracene (abbreviation: 2DPABPhA)
Figure 26:
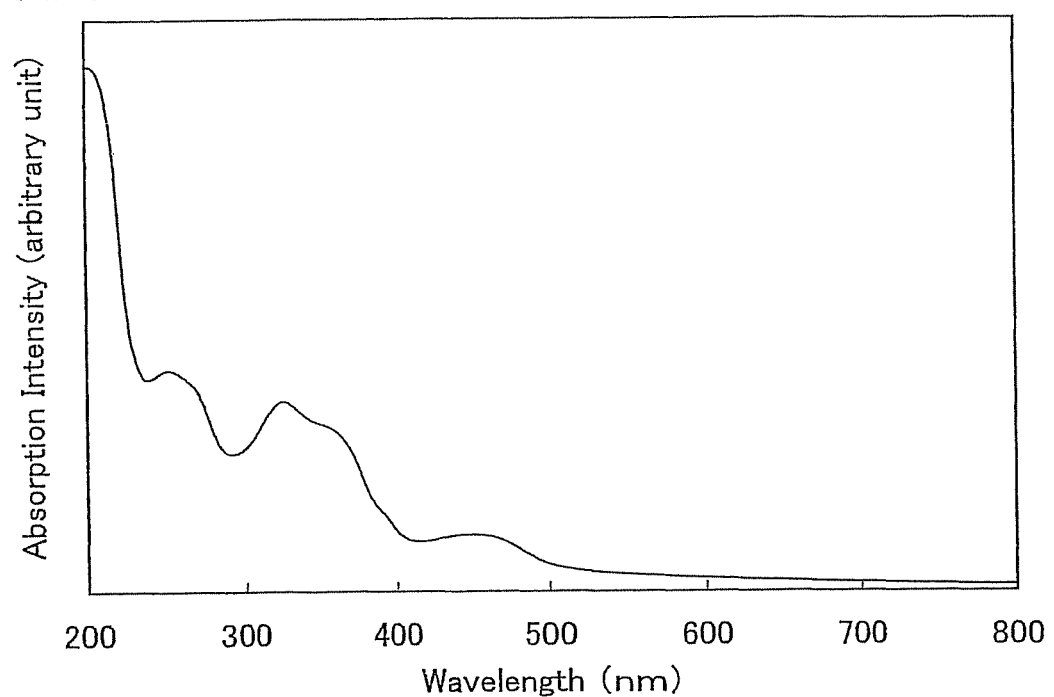
FIG. 26 shows the absorption spectrum of a thin film of 9,10-di(2-biphenylyl)-2-[N-(4-diphenylaminophenyl)-N-phenylamino]anthracene (abbreviation: 2DPABPhA)
Figure 27:
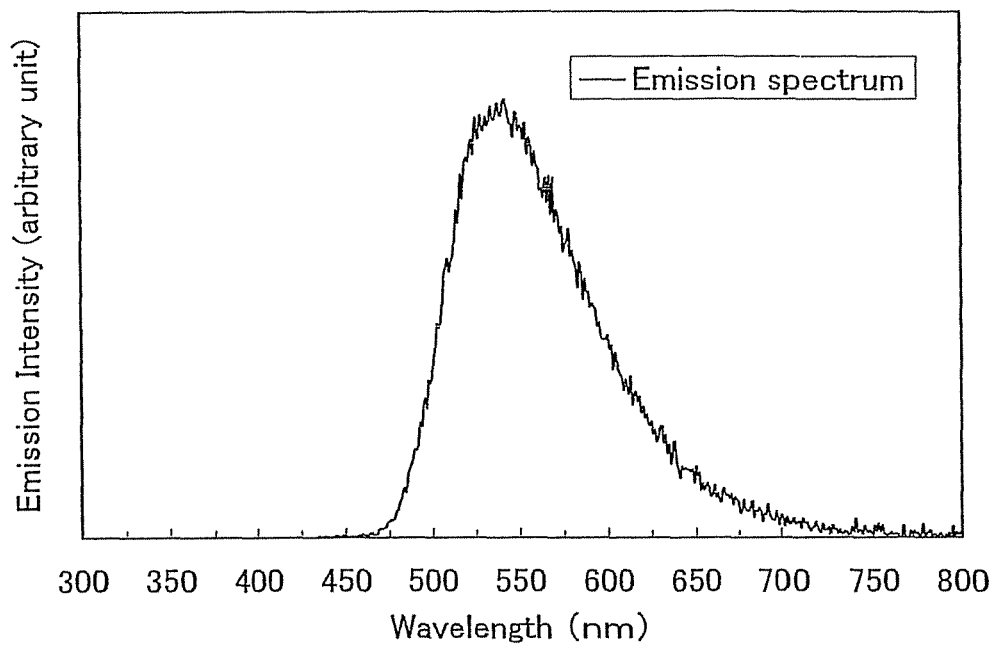
FIG. 27 shows the emission spectrum of a toluene solution of 9,10-di(2-biphenylyl)-2-[N-(4-diphenylaminophenyl)-N-phenylamino]anthracene (abbreviation: 2DPABPhA)
Figure 28:
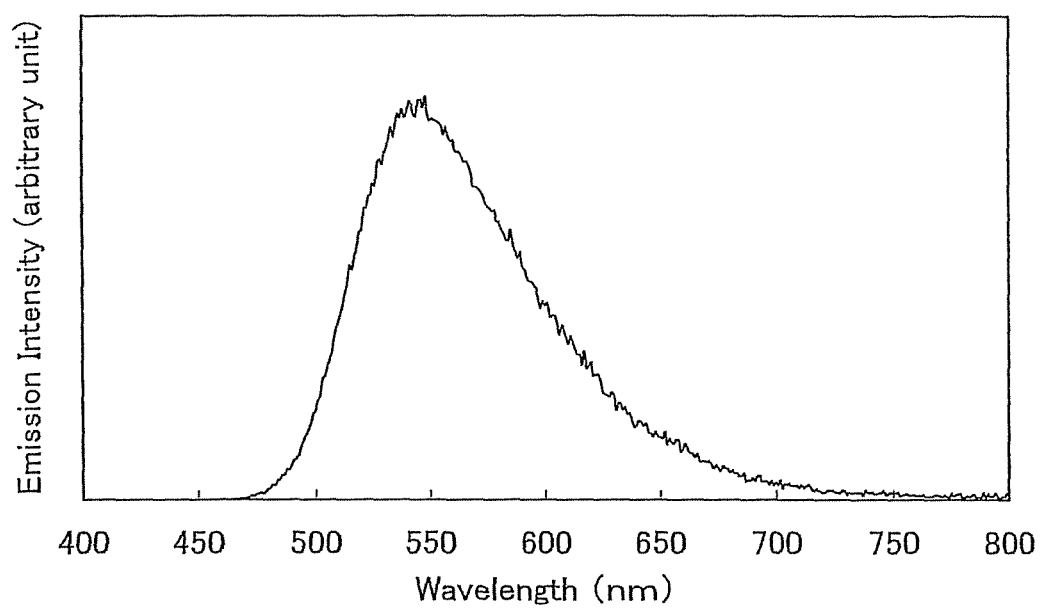
FIG. 28 shows the emission spectrum of a thin film of 9,10-di(2-biphenylyl)-2-[N-(4-diphenylaminophenyl)-N-phenylamino]anthracene (abbreviation: 2DPABPhA)

The absorption spectrum of a toluene solution of 2DPABPhA is shown in FIG. 25. In addition, an absorption spectrum of a thin film of 2DPABPhA is shown in FIG. 26. An ultraviolet-visible spectrophotometer (type V550, manufactured by Japan Spectroscopy Corporation) was used for measurement. The spectrum of the solution was measured in a quartz cell. The sample of the thin film was fabricated by vapor deposition of 2DPABPhA over a quartz substrate. The absorption spectra of the solution and the thin film are shown in FIGS. 25 and 26, respectively, which were obtained by subtracting the spectrum of the quartz substrate from the corresponding raw spectra. In each of FIGS. 25 and 26, a horizontal axis shows wavelength (nm) and a vertical axis shows absorption intensity (an arbitrary unit). In the case of the toluene solution, absorption was observed at around 446 nm, and in the case of the thin film, absorption was observed at around 449 nm. Further, an emission spectrum of the toluene solution (excitation wavelength of 430 nm) of 2DPABPhA is shown in FIG. 27, and an emission spectrum of the thin film (excitation wavelength of 430 nm) of 2DPABPhA is shown in FIG. 28. In each of FIGS. 27 and 28, a horizontal axis shows wavelength (nm) and a vertical axis shows emission intensity (an arbitrary unit). In the case of the toluene solution, the maximum emission wavelength was 542 nm (excitation wavelength of 430 nm), and in the case of the thin film, the maximum emission wavelength was 548 nm (excitation wavelength of 449 nm).

The HOMO level of 2DPABPhA in a thin film state which was measured by a photoelectron spectrometer (AC-2, manufactured by Riken Keiki Co., Ltd.) under air was −5.28 eV. By the absorption edge obtained from a Tauc plot of the absorption spectrum of the thin film shown in FIG. 26, the optical energy gap was estimated to be 2.47 eV, which means that LUMO level of 2DPABPhA is −2.81 eV.

Embodiment 4

In this embodiment, a synthetic method of 9,10-di(2-biphenylyl)-2-[N-phenyl-N-(9-phenyl-9H-carbazol-3-yl)amino]anthracene (abbreviation: 2PCABPhA), which is the anthracene derivative of the present invention represented by Structural Formula (215), is specifically described.

(215)

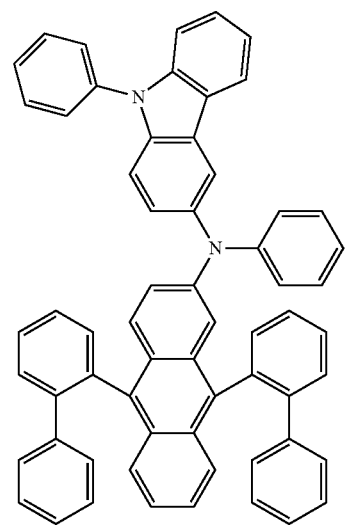

[Step 1] Synthetic Method of 2PCABPhA

A synthetic scheme of 2PCABPhA is shown in (C-12).

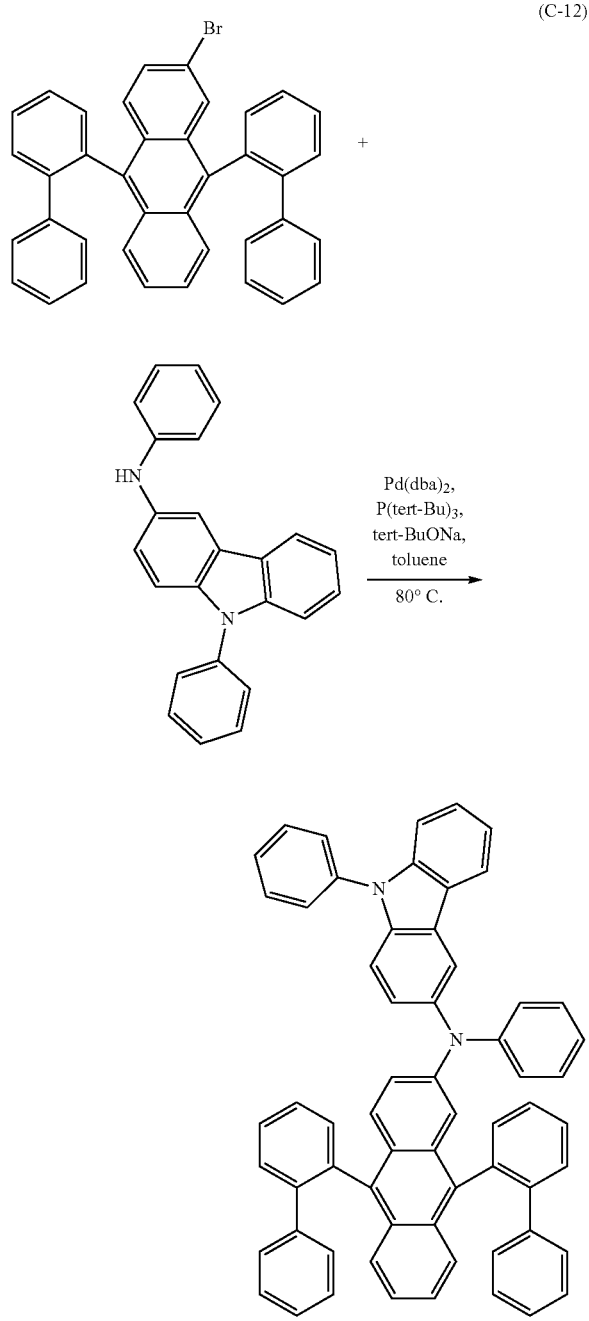

2.8 g (5.0 mmol) of 9,10-di(2-biphenylyl)-2-bromoanthracene synthesized in Step 1 of Embodiment 3, 1.67 g (5.0 mmol) of N-phenyl-(9-phenyl-9H-carbazol-3-yl)amine (abbreviation: PCA) synthesized in Step 1 of Embodiment 2, 0.14 g (0.25 mmol) of bis(dibenzylideneacetone)palladium, and 2.4 g (25 mmol) of sodium tert-butoxide were put into a 100 mL three-neck flask, and the atmosphere in the flask was substituted with nitrogen. 20 mL of toluene and 1.5 g (0.75 mmol) of tri(tert-butyl)phosphine (10% hexane solution) were added to the flask, and the solution was stirred for 6 hours at 80° C. After the reaction, the solution was washed with water, and the aqueous layer was extracted with ethyl acetate. The organic layer was dried over magnesium sulfate, filtered, and concentrated, and the residue was dissolved in toluene. The solution was filtered through celite, Florisil, and then alumina. The filtrate was concentrated, and the residue was recrystallized with toluene and hexane, obtaining 3.4 g of a target compound as a yellow solid in 83% yield. By a nuclear magnetic resonance measurement (NMR), it was confirmed that this compound was 9,10-di(2-biphenylyl)-2-[N-phenyl-N-(9-phenyl-9H-carbazol-3-yl)amino]anthracene (abbreviation: 2PCABPhA).

Figure 29A:
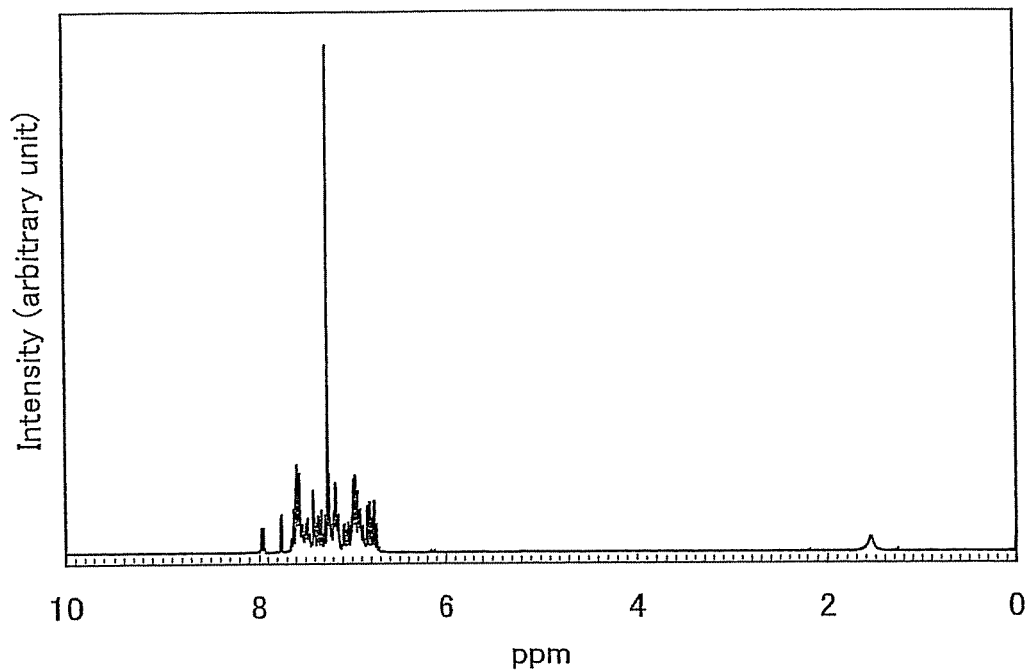
FIGS. 29A and 29B each show the $^1$H NMR chart of 9,10-di(2-biphenylyl)-2-[N-phenyl-N-(9-phenyl-9H-carbazol-3-yl)amino]anthracene (abbreviation: 2PCABPhA)
Figure 29B:
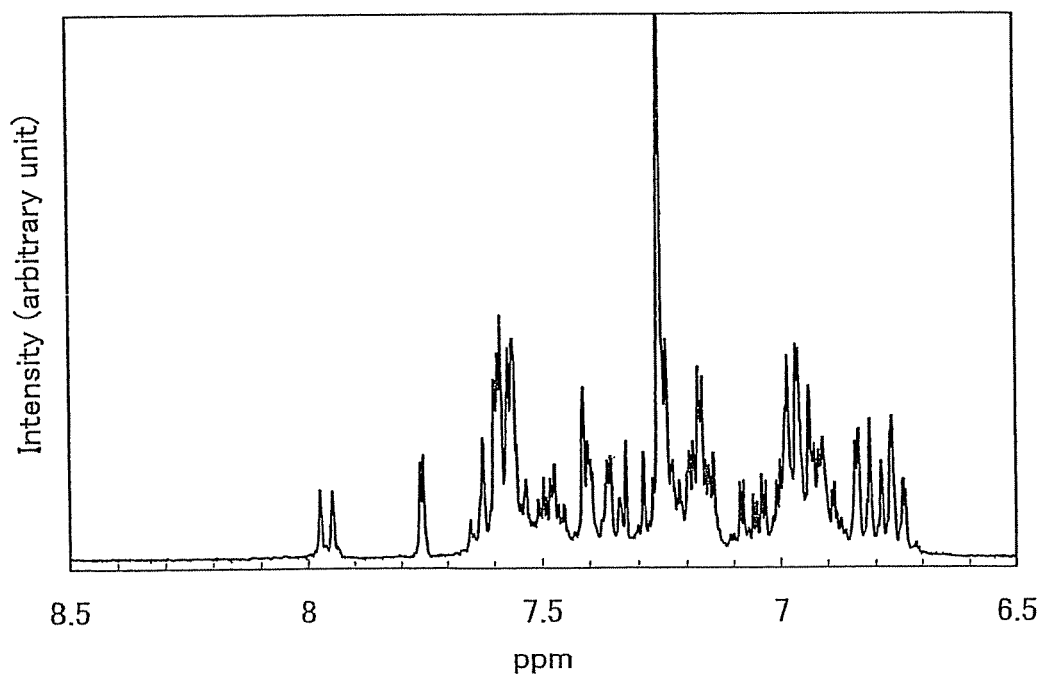

$^1$H NMR data of this compound is shown below. $^1$H-NMR (CDCl$_3$, 300 MHz): δ=6.74-7.09 (m, 16H), 7.14-7.29 (m, 8H), 7.32-7.62 (m, 16H), 7.75-7.97 (m, 2H). The $^1$H NMR chart is shown in each of FIGS. 29A and 29B. Note that the range of 6.5 ppm to 8.5 ppm in FIG. 29A is expanded and shown in FIG. 29B.

The decomposition temperature ($T_d$) of 2PCABPhA, measured with a thermogravimetric/differential thermal analyzer (type TG/DTA 320, manufactured by Seiko Instruments Inc.), was found to be 423.7° C., meaning high thermal stability of this compound.

Figure 30:
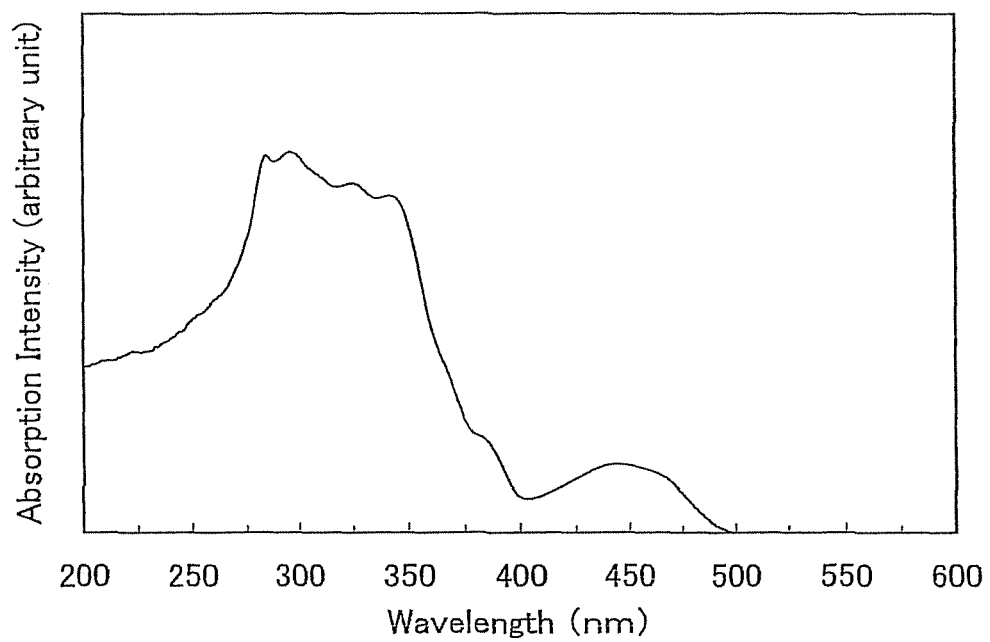
FIG. 30 shows the absorption spectrum of a toluene solution of 9,10-di(2-biphenylyl)-2-[N-phenyl-N-(9-phenyl-9H-carbazol-3-yl)amino]anthracene (abbreviation: 2PCABPhA)
Figure 31:
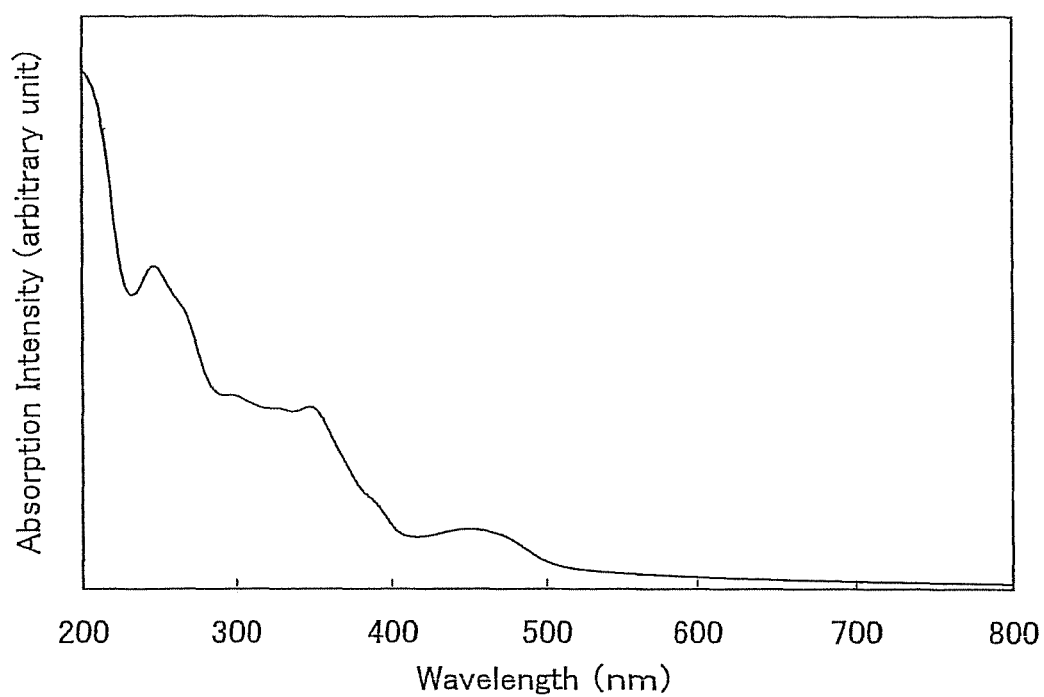
FIG. 31 shows the absorption spectrum of a thin film of 9,10-di(2-biphenylyl)-2-[N-phenyl-N-(9-phenyl-9H-carbazol-3-yl)amino]anthracene (abbreviation: 2PCABPhA)
Figure 32:
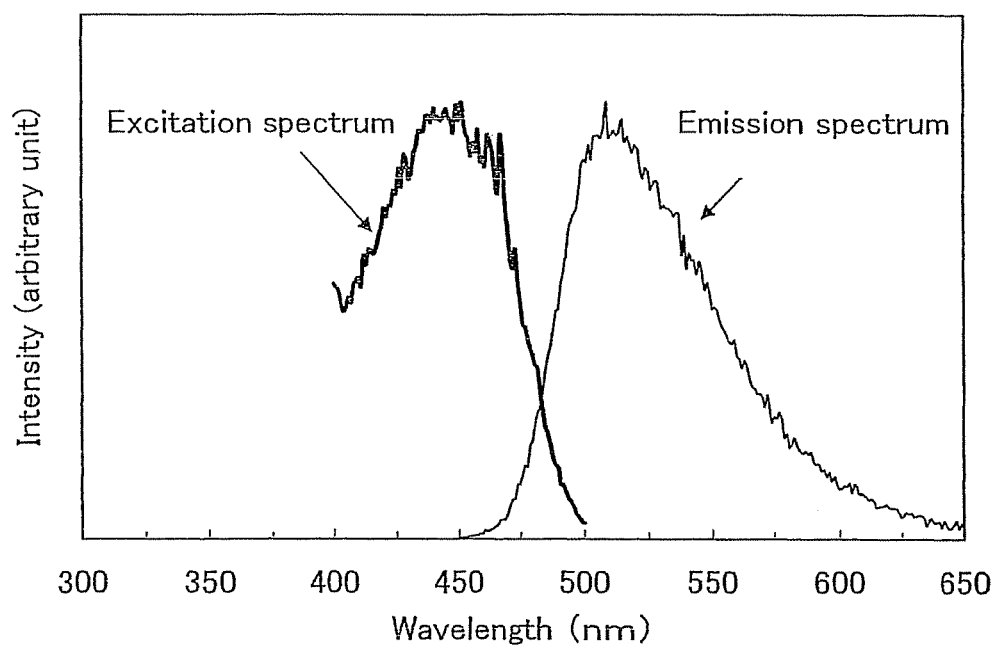
FIG. 32 shows the excitation spectrum and emission spectrum of a toluene solution of 9,10-di(2-biphenylyl)-2-[N-phenyl-N-(9-phenyl-9H-carbazol-3-yl)amino]anthracene (abbreviation: 2PCABPhA)
Figure 33:
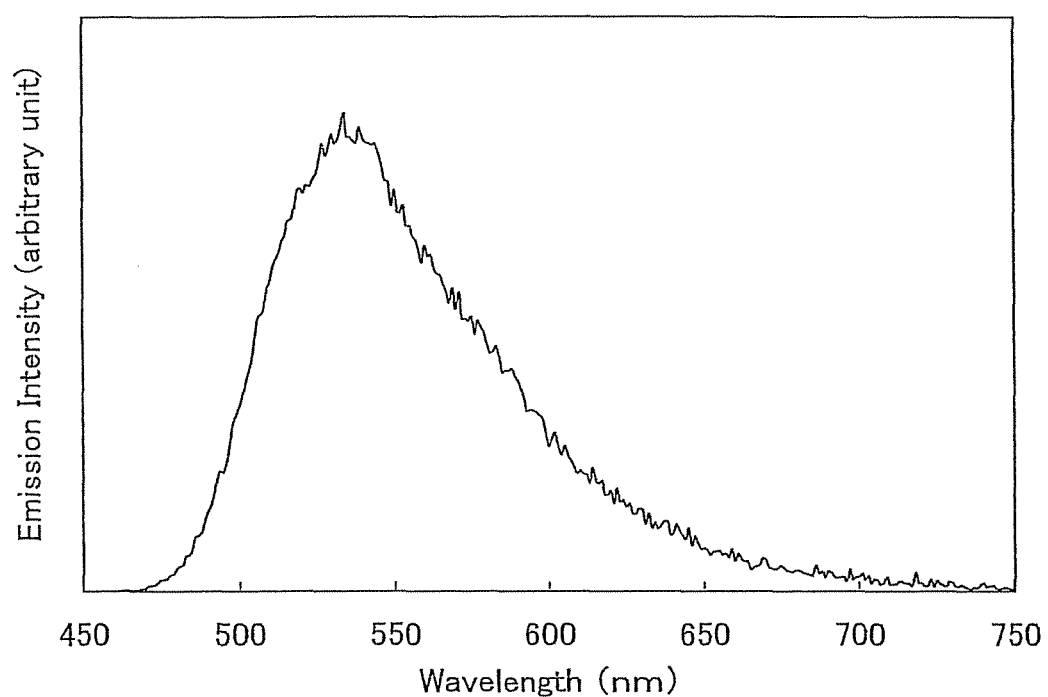
FIG. 33 shows the emission spectrum of a thin film of 9,10-di(2-biphenylyl)-2-[N-phenyl-N-(9-phenyl-9H-carbazol-3-yl)amino]anthracene (abbreviation: 2PCABPhA)

The absorption spectrum of a toluene solution of 2PCABPhA is shown in FIG. 30. In addition, an absorption spectrum of a thin film of 2PCABPhA is shown in FIG. 31. An ultraviolet-visible spectrophotometer (type V550, manufactured by Japan Spectroscopy Corporation) was used for measurement. The spectrum of the solution was measured in a quartz cell. The sample of the thin film was fabricated by vapor deposition of 2PCABPhA over a quartz substrate. The absorption spectra of the solution and the thin film are shown in FIGS. 30 and 31, respectively, which were obtained by subtracting the spectrum of the quartz substrate from the corresponding raw spectra. In each of FIGS. 30 and 31, a horizontal axis shows wavelength (nm) and a vertical axis shows absorption intensity (an arbitrary unit). In the case of the toluene solution, absorption was observed at around 440 nm, and in the case of the thin film, absorption was observed at around 449 nm. Further, an emission spectrum of the toluene solution (excitation wavelength of 430 nm) of 2PCABPhA is shown in FIG. 32, and an emission spectrum of the thin film (excitation wavelength of 449 nm) of 2PCABPhA is shown in FIG. 33. In each of FIGS. 32 and 33, a horizontal axis shows wavelength (nm) and a vertical axis shows emission intensity (an arbitrary unit). In the case of the toluene solution, the maximum emission wavelength was 509 nm (excitation wavelength of 430 nm), and in the case of the thin film, the maximum emission wavelength was 534 nm (excitation wavelength of 449 nm).

The HOMO level of 2PCABPhA in a thin film state which was measured by a photoelectron spectrometer (AC-2, manufactured by Riken Keiki Co., Ltd.) under air was −5.29 eV. By the absorption edge obtained from a Tauc plot of the absorption spectrum of the thin film shown in FIG. 31, the optical energy gap was estimated to be 2.46 eV, which means that LUMO level of 2DPAPA is −2.83 eV.

An oxidation-reduction characteristic of 2PCABPhA was explored by a cyclic voltammetry (CV) measurement. For the measurement, an electrochemical analyzer (ALS model 600A, manufactured by BAS Inc.) was used.

As for a solution used in the CV measurement, dehydrated N,N-dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), a supporting electrolyte, was dissolved in DMF at the concentration of 100 mmol/L to prepare the electrolysis solution. The sample solution was prepared by dissolving the sample in the electrolysis solution at a concentration of 1 mmol/L. A platinum electrode (a PIE platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

An oxidation characteristic of 2PCABPhA was evaluated in the following manner. The potential of the working electrode with respect to a reference electrode was swept from −0.23 V to 0.70 V, which was followed by sweeping the potential from 0.70 V to −0.23 V. This cycle was set as one cycle, and 100 cycles were performed. Also, a reduction characteristic of 2PCABPhA was evaluated in the following manner. The potential of the working electrode with respect to the reference electrode was swept from −0.36 V to −2.50 V, which was followed by sweeping the potential from −2.50 V to −0.36 V. This cycle was set as one cycle, and 100 cycles were performed. Sweeping speed of the CV measurement was set to be 0.1 V/s.

Figure 34:
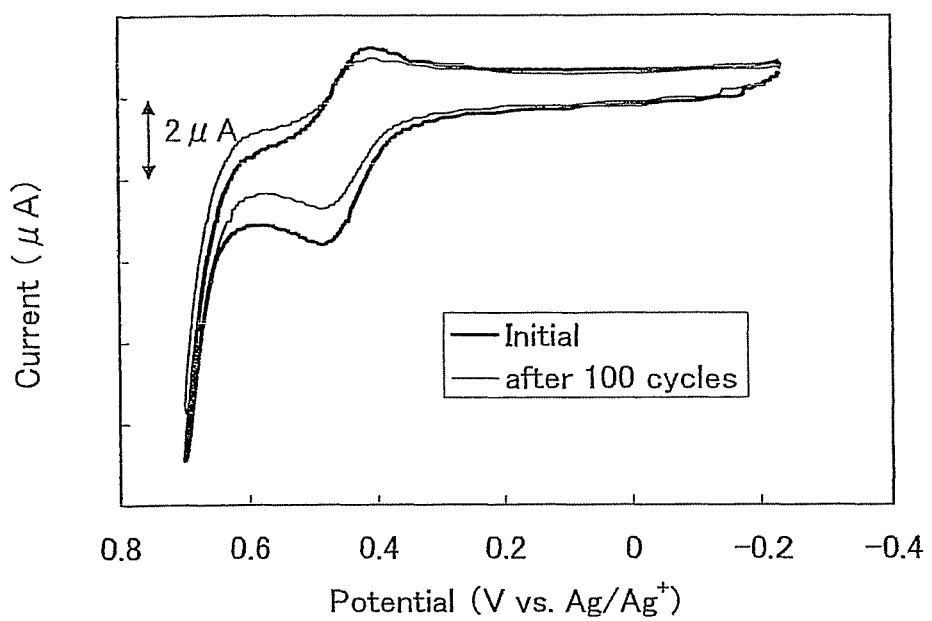
FIG. 34 shows the result of a CV measurement of 9,10-di(2-biphenylyl)-2-[N-phenyl-N-(9-phenyl-9H-carbazol-3-yl)amino]anthracene (abbreviation: 2PCABPhA)
Figure 35:
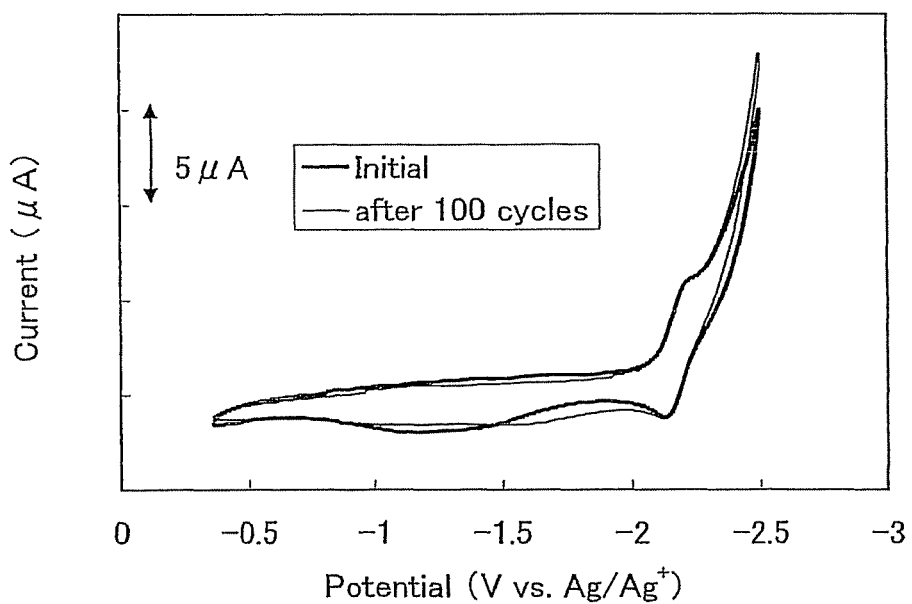
FIG. 35 shows the result of a CV measurement of 9,10-di(2-biphenylyl)-2-[N-phenyl-N-(9-phenyl-9H-carbazol-3-yl)amino]anthracene (abbreviation: 2PCABPhA)

The CV measurement result of an oxidation side of 2PCABPhA and the CV measurement result of a reduction side of 2PCABPhA are shown in FIGS. 34 and 35, respectively. In each of FIGS. 34 and 35, a horizontal axis shows a potential (V) of the working electrode with respect to the reference electrode, and a vertical axis shows a current value (μA) that flowed between the working electrode and the counter electrode. From FIG. 34, the current exhibiting oxidation was observed around 0.49 V (vs. Ag/Ag$^+$ electrode). From FIG. 35, the current exhibiting reduction was observed around −2.20 V (vs. Ag/Ag$^+$ electrode).

In spite of the fact that 100 cycles of sweeping were repeated, a peak position and a peak intensity at the CV curve scarcely changed in the oxidation and reduction, which reveals that the anthracene derivative of the present invention is extremely stable against repetition of the oxidation and reduction.

Embodiment 5

In this embodiment, a synthetic method of 9,10-di(2-biphenylyl)-2-{N-[4-(9H-carbazol-9-yl)phenyl]-N-phenylamino}anthracene (abbreviation: 2YGABPhA), which is the anthracene derivative of the present invention represented by Structural Formula (315), is specifically described.

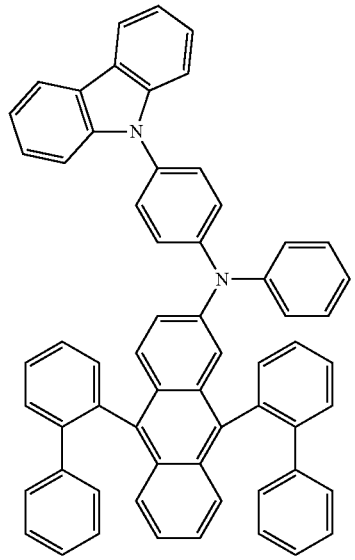

(315)

[Step 1] Synthesis of 4-(carbazol-9-yl)diphenylamine (abbreviation: YGA)

(i) Synthesis of N-(4-bromophenyl)carbazole

A synthetic scheme of N-(4-bromophenyl)carbazole is shown in (C-13).

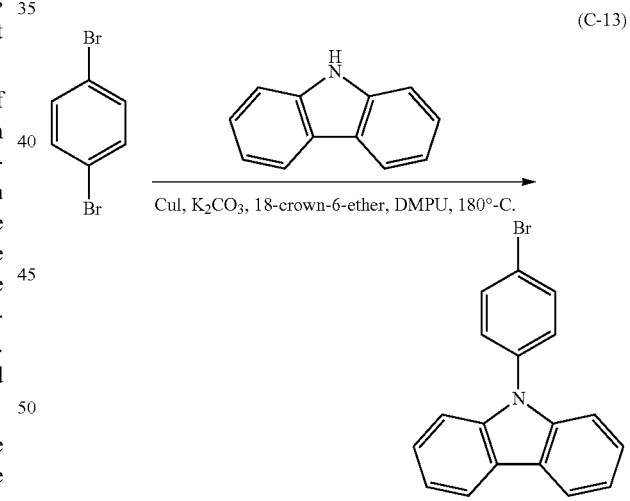

(C-13)

56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were put into a 300 mL three-neck flask, and the atmosphere of the flask was substituted with nitrogen. Thereafter, 8 mL of 1,3-dimethyl-3,4,5,6-tetrahydro-2(1H)-pyrimidinone (abbreviation: DMPU) was added, and then the mixture was stirred for 6 hours at 180° C. After the reaction mixture was cooled to room temperature, the precipitate was removed by suction filtration. The filtrate was washed with a diluted hydrochloric acid, a saturated sodium bicarbonate aqueous solution, and then brine, and dried with magnesium sulfate. After drying, the mixture was filtered, and the filtrate was concentrated to yield an oil which was purified by silica gel column chromatography (hexane:ethyl acetate=9:1). The resulting solid was recrystallized with chloroform and hexane, obtaining 20.7 g of N-(4-bromophenyl)carbazole as a light brown plate-like crystal in 35% yield. By the nuclear magnetic resonance measurement (NMR), it was confirmed that this compound was N-(4-bromophenyl)carbazole.

$^1$H NMR data of this compound is shown below. $^1$H NMR (300 MHz, CDCl$_3$): δ=8.14 (d, J=7.8 Hz, 2H), 7.73 (d, J=8.7 Hz, 2H), 7.46 (d, J=8.4 Hz, 2H), 7.42-7.26 (m, 6H).

(ii) Synthesis of 4-(carbazol-9-yl)diphenylamine (abbreviation: YGA)

A synthetic scheme of 4-(carbazol-9-yl)diphenylamine (abbreviation: YGA) is shown in (C-14).

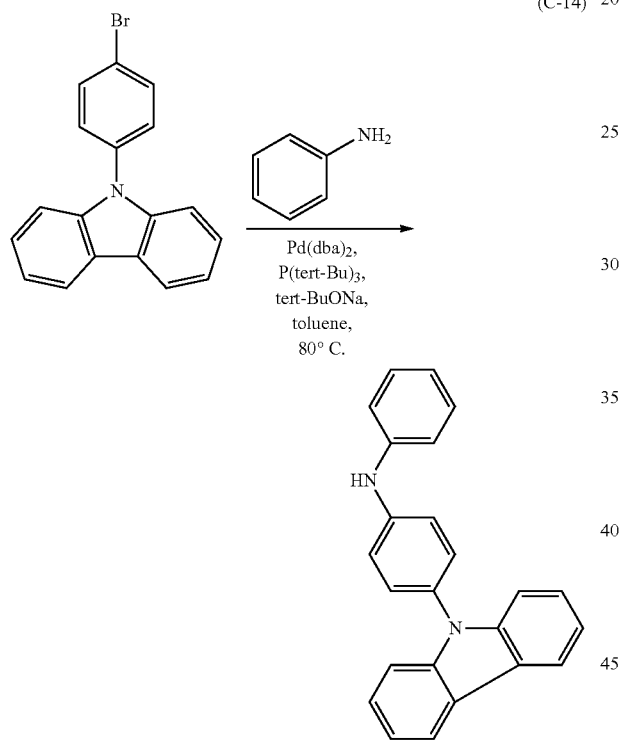

(C-14)

5.4 g (17.0 mmol) of N-(4-bromophenyl)carbazole obtained in the abovementioned step (i), 1.8 mL (20.0 mmol) of aniline, 100 mg (0.17 mmol) of bis(dibenzylideneacetone) palladium (0), and 3.9 g (40 mmol) of sodium tert-butoxide were put into a 200 mL three-neck flask, and the atmosphere of the flask was substituted with nitrogen. Thereafter, 0.1 mL of tri(tert-butyl)phosphine (10 wt % hexane solution) and 50 mL of toluene were added to the flask, and the solution was stirred for 6 hours at 80° C. The reaction mixture was filtered through Florisil, celite, and then alumina. The filtrate was washed with water, and then brine, and dried with magnesium sulfate. The mixture was filtered, and the filtrate was concentrated to give an oily substance which was purified by silica gel column chromatography (hexane:ethyl acetate=9:1), providing 4.1 g of 4-(carbazol-9-yl)diphenylamine (abbreviation: YGA) in 73% yield. It was confirmed by a nuclear magnetic resonance measurement (NMR) that this compound was 4-(carbazol-9-yl)diphenylamine (abbreviation: YGA).

Figure 36A:
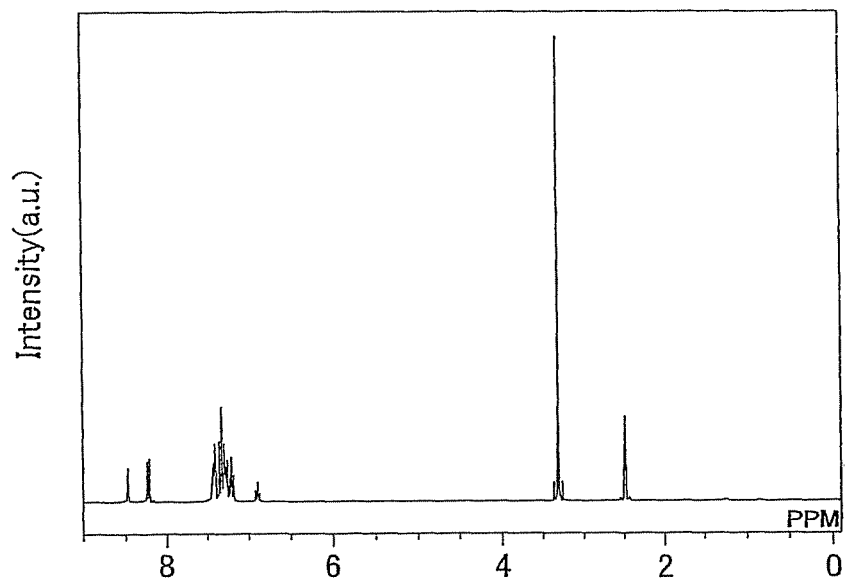
FIGS. 36A and 36B each show the $^1$H NMR chart of 4-(carbazol-9-yl)diphenylamine (abbreviation: YGA)
Figure 36B:
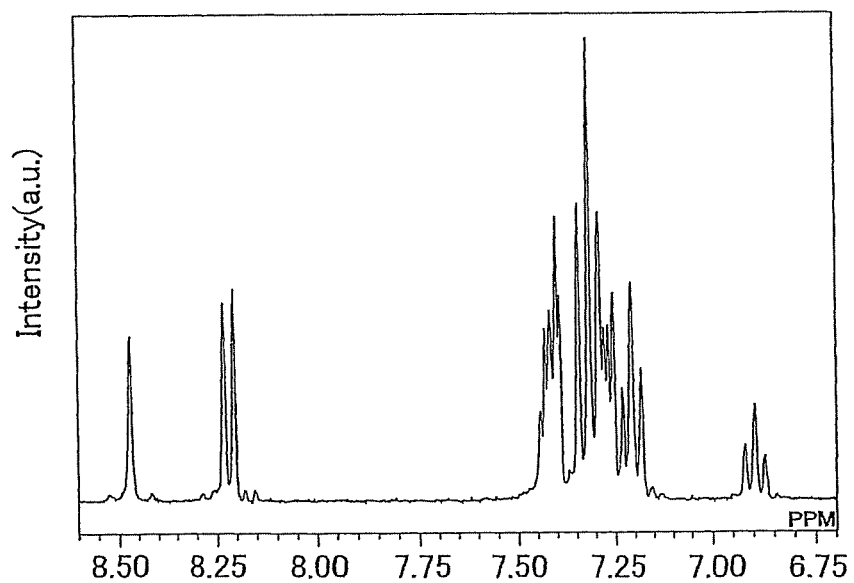

$^1$H NMR data of this compound is shown below. $^1$H NMR (300 MHz, DMSO-d$_6$): δ=8.47 (s, 1H), 8.22 (d, J=7.8 Hz, 2H), 7.44-7.16 (m; 14H), 6.92-6.87 (m, 1H). FIGS. 36A and 36B each show a $^1$H NMR chart. Note that the range of 6.5 ppm to 8.5 ppm in FIG. 36A is expanded and shown in FIG. 36B.

[Step 2] Synthetic Method of 2YGABPhA

A synthetic scheme of 2YGABPhA is shown in (C-15).

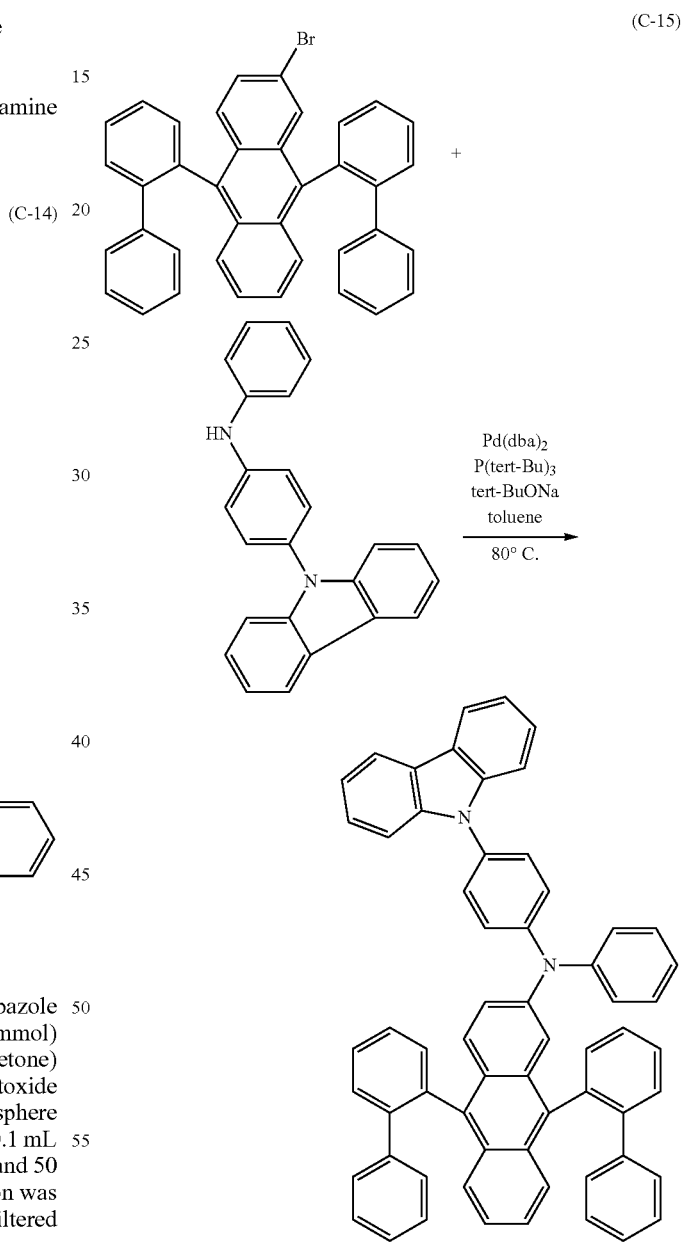

(C-15)

2.0 g (3.5 mmol) of 9,10-di(2-biphenylyl)-2-bromoanthracene synthesized in Step 1 of Embodiment 3, 597 mg (3.5 mmol) of 4-(carbazol-9-yl)diphenylamine (abbreviation: YGA) synthesized in Step 1 of Embodiment 5, and 2.0 g (21 mmol) of sodium tert-butoxide were put into a 100 mL three-neck flask, and the atmosphere of the flask was substituted with nitrogen. Thereafter, 30 mL of toluene and 0.1 mL of tri(tert-butyl)phosphine (10% hexane solution) were added to the flask, and the solution was degassed under reduced pressure. After degassing, 20 mg (0.035 mmol) of bis(dibenzylideneacetone)palladium (0) was added to the solution, and the solution was stirred for 3 hours at 80° C. After the reaction, the reaction solution was washed with water and brine in this order, and then the organic layer was dried with magnesium sulfate. After filtration, the filtrate was concentrated, and the obtained solid was purified by silica gel column chromatography (hexane: toluene=6:4). The resulting solid was recrystallized with dichloromethane-hexane, obtaining 2.0 g of the target compound as a yellow solid in 69% yield. It was confirmed by a nuclear magnetic resonance measurement (NMR) that this compound was 9,10-di(2-biphenylyl)-2-{N-[4-(9H-carbazol-9-yl)phenyl]-N-phenylamino}anthracene (abbreviation: 2YGABPhA).

Figure 37A:
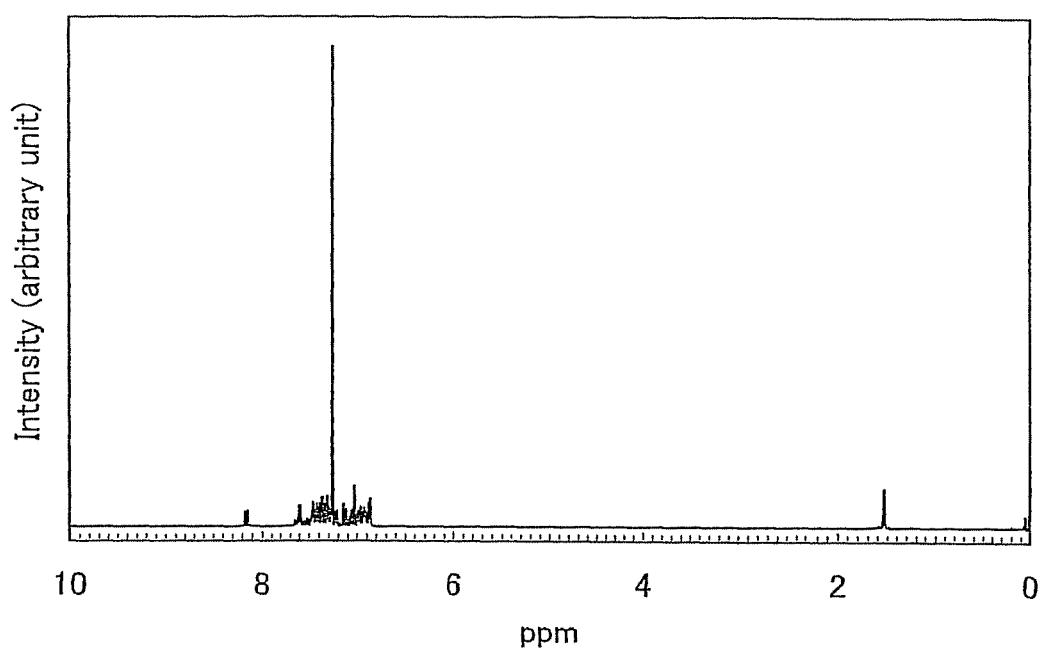
FIGS. 37A and 37B each show the $^1$H NMR chart of 9,10-di(2-biphenylyl)-2-{N-[4-(9H-carbazol-9-yl)phenyl]-N-phenylamino}anthracene (abbreviation: 2YGABPhA)
Figure 37B:
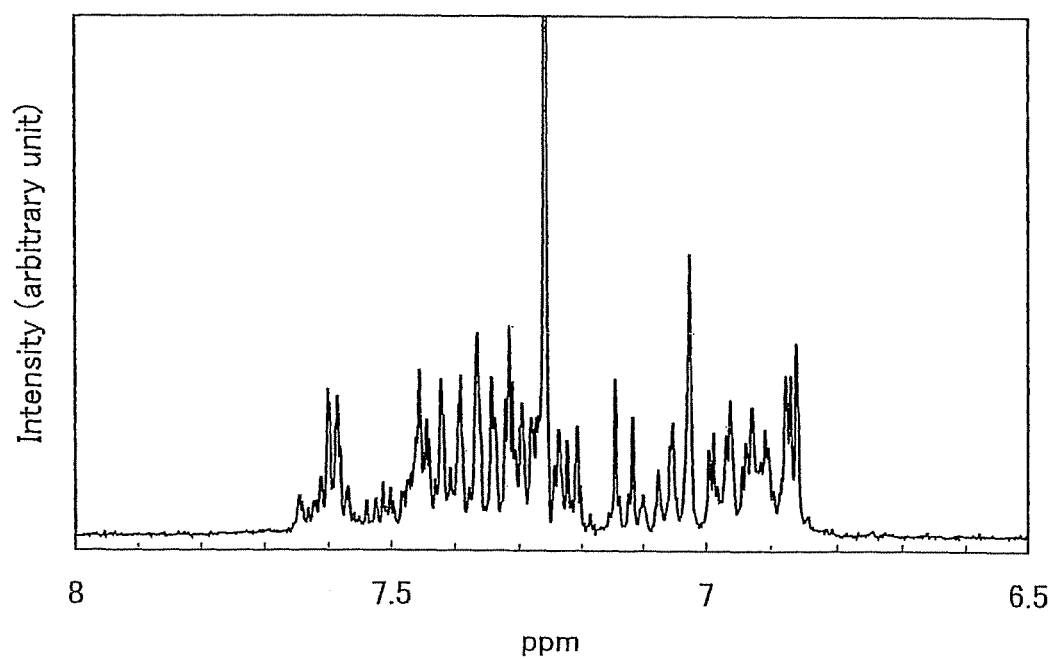

$^1$H NMR data of this compound is shown below. $^1$H NMR (300 MHz, CDCl$_3$): δ=6.86-7.08 (m, 14H), 7.13 (d, J=9.0 Hz, 2H), 7.21-7.24 (m, 3H), 7.26-7.64 (m, 19H), 8.15 (d, J=7.8 Hz, 2H). The $^1$H NMR chart is shown in each of FIGS. 37A and 37B. Note that the range of 6.5 ppm to 8.0 ppm in FIG. 37A is expanded and shown in FIG. 3713.

Figure 38:
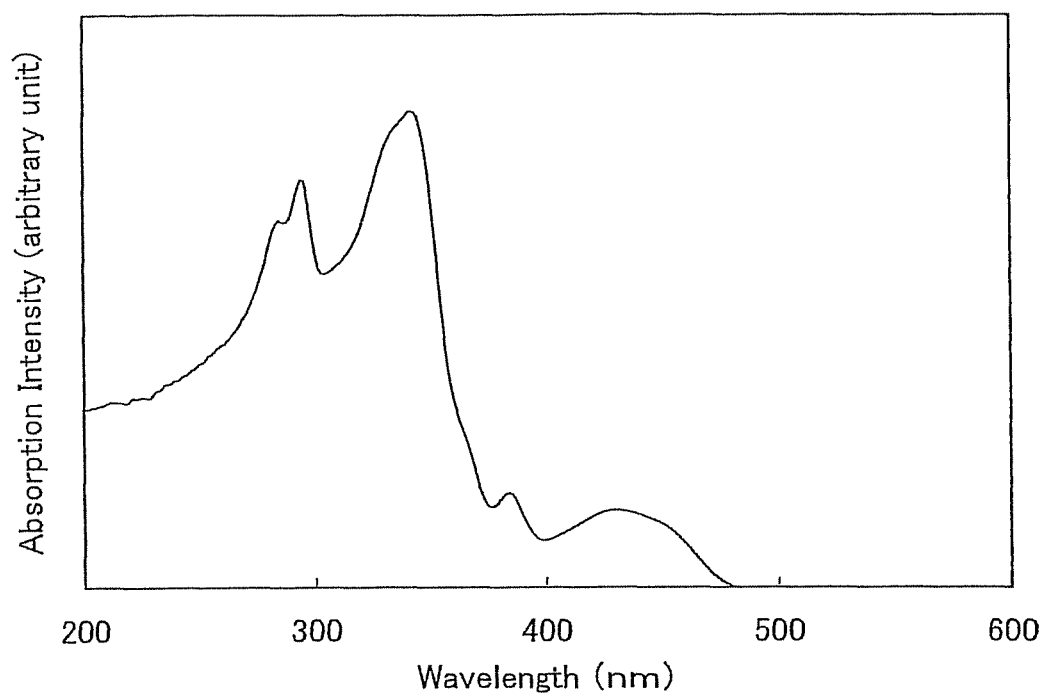
FIG. 38 shows the absorption spectrum of a toluene solution of 9,10-di(2-biphenylyl)-2-{N-[4-(9H-carbazol-9-yl)phenyl]-N-phenylamino}anthracene (abbreviation: 2YGABPhA)
Figure 39:
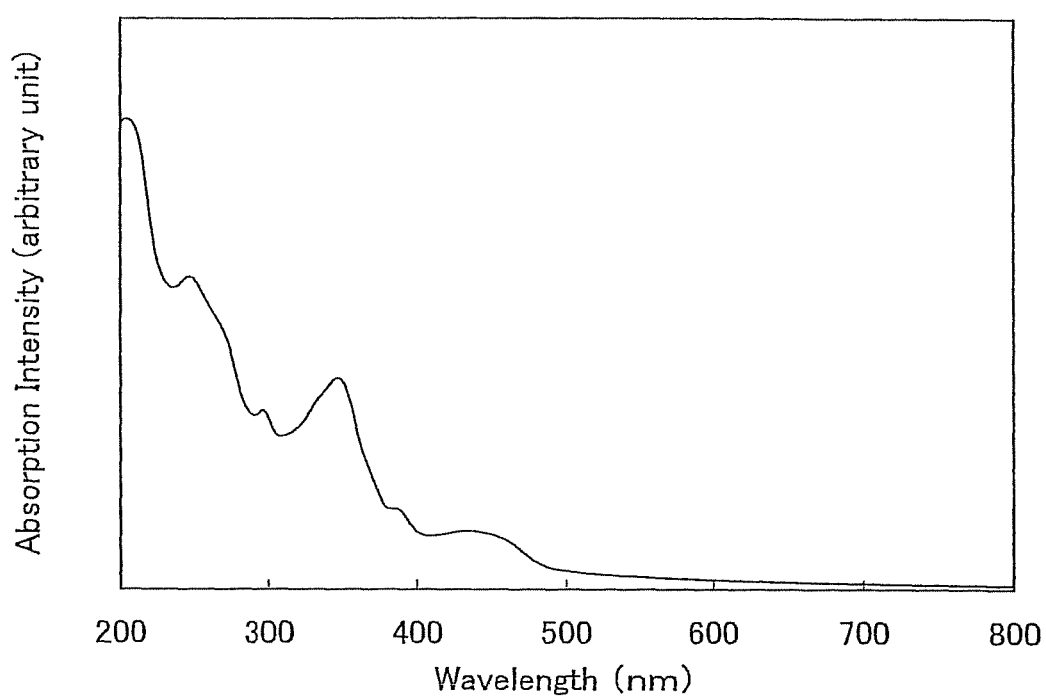
FIG. 39 shows the absorption spectrum of a thin film of 9,10-di(2-biphenylyl)-2-{N-[4-(9H-carbazol-9-yl)phenyl]-N-phenylamino}anthracene (abbreviation: 2YGABPhA)
Figure 40:
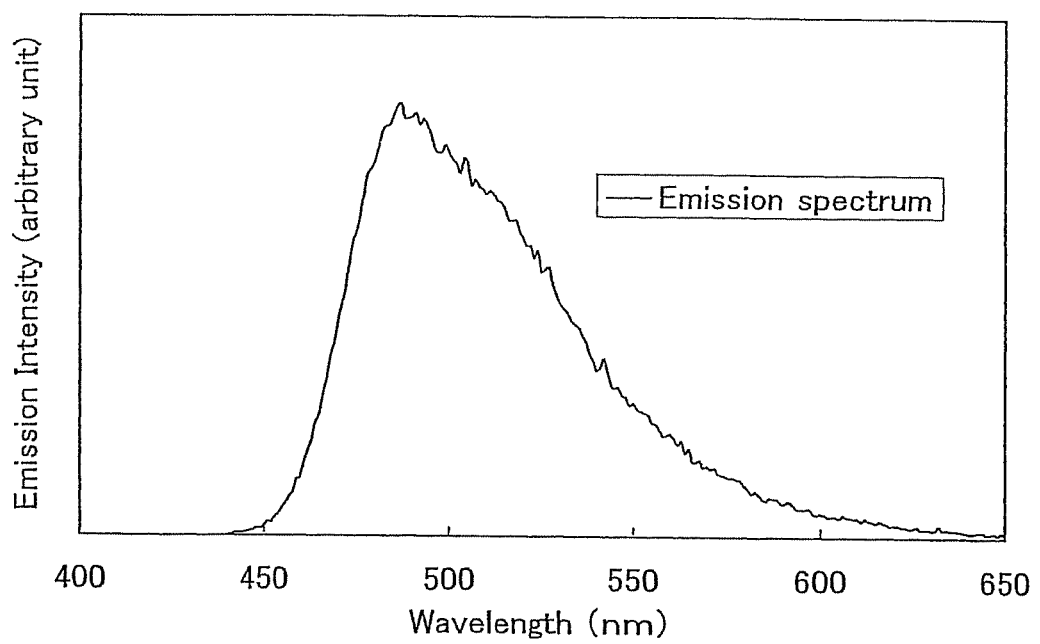
FIG. 40 shows the emission spectrum of a toluene solution of 9,10-di(2-biphenylyl)-2-{N-[4-(9H-carbazol-9-yl)phenyl]-N-phenylamino}anthracene (abbreviation: 2YGABPhA)
Figure 41:
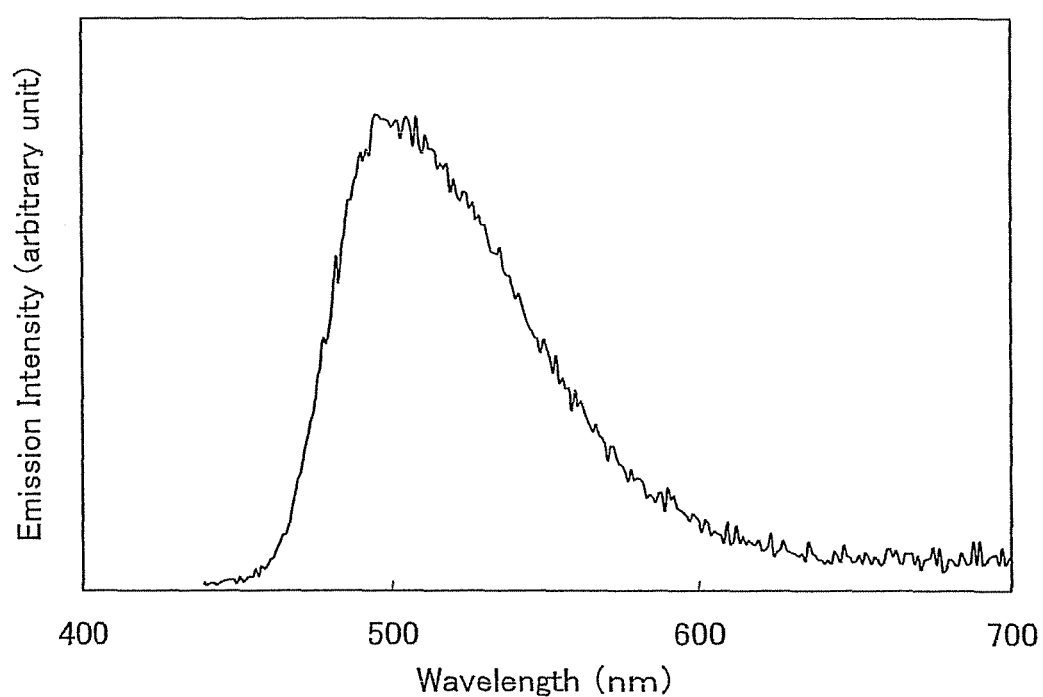
FIG. 41 shows the emission spectrum of a thin film of 9,10-di(2-biphenylyl)-2-{N-[4-(9H-carbazol-9-yl)phenyl]-N-phenylamino}anthracene (abbreviation: 2YGABPhA)

The absorption spectrum of a toluene solution of 2YGABPhA is shown in FIG. 38. In addition, an absorption spectrum of a thin film of 2YGABPhA is shown in FIG. 39. An ultraviolet-visible spectrophotometer (type V550, manufactured by Japan Spectroscopy Corporation) was used for measurement. The spectrum of the solution was measured in a quartz cell. The sample of the thin film was fabricated by vapor deposition of 2YGABPhA over a quartz substrate. The absorption spectra of the solution and the thin film are shown in FIGS. 38 and 39, respectively, which were obtained by subtracting the spectrum of the quartz substrate from the corresponding raw spectra. In each of FIGS. 38 and 39, a horizontal axis shows wavelength (nm) and a vertical axis shows absorption intensity (an arbitrary unit). In the case of the toluene solution, absorption was observed at around 430 nm, and in the case of the thin film, absorption was observed at around 435 am. Further, an emission spectrum of the toluene solution (excitation wavelength of 370 nm) of 2YGABPhA is shown in FIG. 40, and an emission spectrum of the thin film (excitation wavelength of 435 nm) of 2YGABPhA is shown in FIG. 41. In each of FIGS. 40 and 41, a horizontal axis shows wavelength (nm) and a vertical axis shows emission intensity (an arbitrary unit). In the case of the toluene solution, the maximum emission wavelength was 491 nm (excitation wavelength of 370 nm), and in the case of the thin film, the maximum emission wavelength was 495 nm (excitation wavelength of 435 nm).

The HOMO level of 2YGABPhA in a thin film state which was measured by a photoelectron spectrometer (AC-2, manufactured by Riken Keiki Co., Ltd.) under air was −5.36 eV. By the absorption edge obtained from a Tauc plot of the absorption spectrum of the thin film shown in FIG. 39, the optical energy gap was estimated to be 2.56 eV, which means that LUMO level of 2YGABPhA is −2.80 eV.

Embodiment 6

Figure 10:
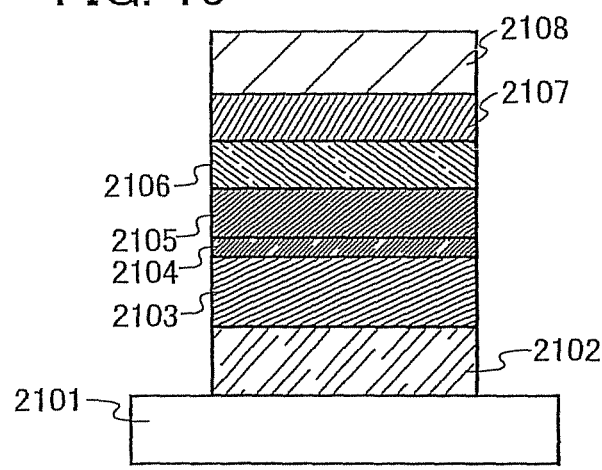
FIG. 10 describes a light-emitting element of an embodiment.

In this embodiment, a light-emitting element of the present invention is described with reference to FIG. 10. The chemical formulae of the materials used in this embodiment are shown below.

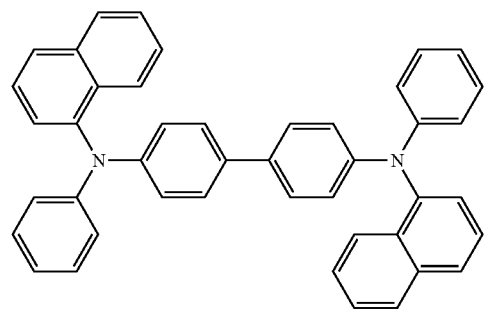

NPB

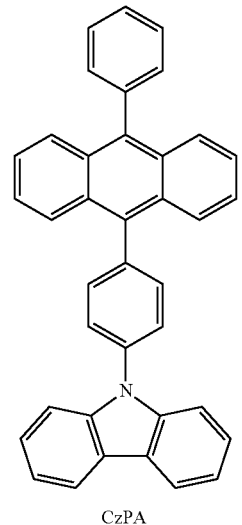

CzPA

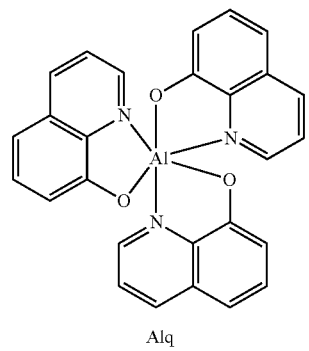

Alq

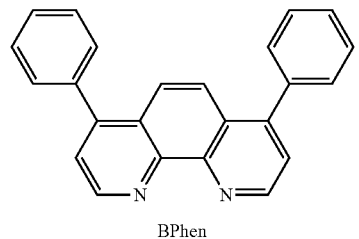

BPhen

The element structure of the light-emitting element manufactured in this embodiment is summarized in Table 1. In Table 1, the mixture ratios are all represented in weight ratios.

TABLE 1

The structure of the light-emitting elements 1-10

| No. | First electrode | Layer including composite material* | Hole transporting layer | Emission layer | Electron transporting layer | Electron injection layer | Second electrode |
|---|---|---|---|---|---|---|---|
| 1 | ITSO 110 nm | NPB:MoOx (4:1) 50 nm | NPB 10 nm | CzPA:2DPAPA (1:0.2) 40 nm | Alq 30 nm | LiF 1 nm | Al 20 nm |
| 2 | | | | CzPA:2DPAPA (1:0.2) 40 nm | BPhen 30 nm | | |
| 3 | | | | CzPA:2PCAPA (1:0.1) 40 nm | Alq 30 nm | | |
| 4 | | | | CzPA:2PCAPA (1:0.1) 40 nm | BPhen 30 nm | | |
| 5 | | | | CzPA:2DPABPhA (1:0.5) 40 nm | Alq 30 nm | | |
| 6 | | | | CzPA:2DPABPhA (1:0.5) 40 nm | BPhen 30 nm | | |
| 7 | | | | CzPA:2PCABPhA (1:0.5) 40 nm | Alq 30 nm | | |
| 8 | | | | CzPA:2PCABPhA (1:0.5) 40 nm | BPhen 30 nm | | |
| 9 | | | | CzPA:2YGABPhA 40 nm | Alq 30 nm | | |
| 10 | | | | CzPA:2YGABPhA 40 nm | BPhen 30 nm | | |

*The ratios shown in parentheses are weight ratios.

A fabrication method of the light-emitting element of this embodiment is described below.

First, a film of indium tin oxide containing silicon oxide (ITSO) was formed by sputtering over a glass substrate 2101 to form a first electrode 2102. Note that the film thickness of the first electrode was 110 nm, and an area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing the pressure of the vacuum evaporation apparatus to about $10^{-4}$ Pa, a layer 2103 containing a composite material, which was formed of an organic compound and an inorganic compound, was formed over the first electrode 2102 by co-evaporating 4,4'-bis[N-(1-napthyl)-N-phenylamino]biphenyl (abbreviation: NPB) and molybdenum oxide (VI). The film thickness of the layer 2103 was to be 50 nm, and the ratio of NPB and molybdenum oxide (VI) was adjusted to be 4:1 (=NPB:molybdenum oxide) in weight ratio. Note that the co-evaporation method is an evaporation method in which evaporation is carried out from a plurality of evaporation sources at the same time in one treatment chamber.

Subsequently, a film of 4,4'-bis[N-(1-napthyl)-N-phenylamino]biphenyl (abbreviation: NPB) was formed at a thickness of 10 nm over the layer 2103 containing the composite material by the evaporation method using the resistance heating system, thereby forming a hole transporting layer 2104.

Further, by co-evaporating 9-[4-(N-carbazolyl)]phenyl-10-phenylanthracene (abbreviation: CzPA) and an anthracene derivative of the present invention, a light-emitting layer 2105 with a thickness of 40 nm was formed over the hole transporting layer 2104. The weight ratio of CzPA and the anthracene derivative for each light-emitting element was adjusted to be the value shown in Table 1.

Thereafter, tris(8-quinolinolato)aluminum (abbreviation: Alq) was formed at a film thickness of 30 nm over the light-emitting layer 2105 in the cases of light-emitting elements 1, 3, 5, 7, and 9 by means of the evaporation method using the resistance heating system, resulting in the fabrication of an electron transporting layer 2106. In the cases of light-emitting elements 2, 4, 6, 8, and 10, a film of bathophenanthroline (abbreviation: BPhen) was formed with a thickness of 30 nm to form the electron transporting layer 2106.

Furthermore, a film of lithium fluoride (LiF) was formed at a thickness of 1 nm over the electron transporting layer 2106 to form an electron injecting layer 2107.

Finally, by forming a film of aluminum with a film thickness of 200 nm over the electron injecting layer 2107 by means of the evaporation method using the resistance heating system, a second electrode 2108 was formed. Accordingly, light-emitting elements 1 to 10 were fabricated.

Figure 42:
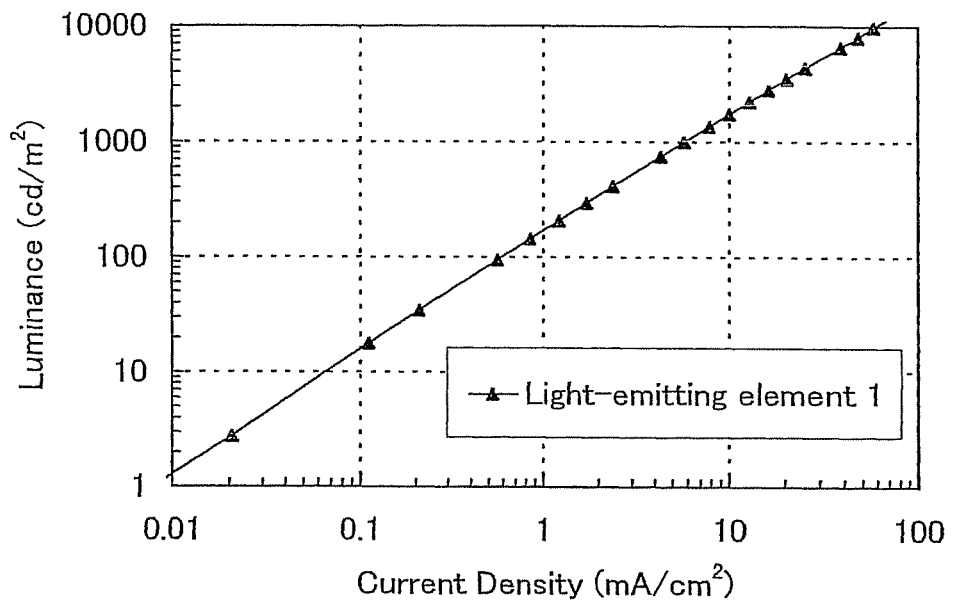
FIG. 42 shows the current density-luminance characteristic of light-emitting element 1.
Figure 43:
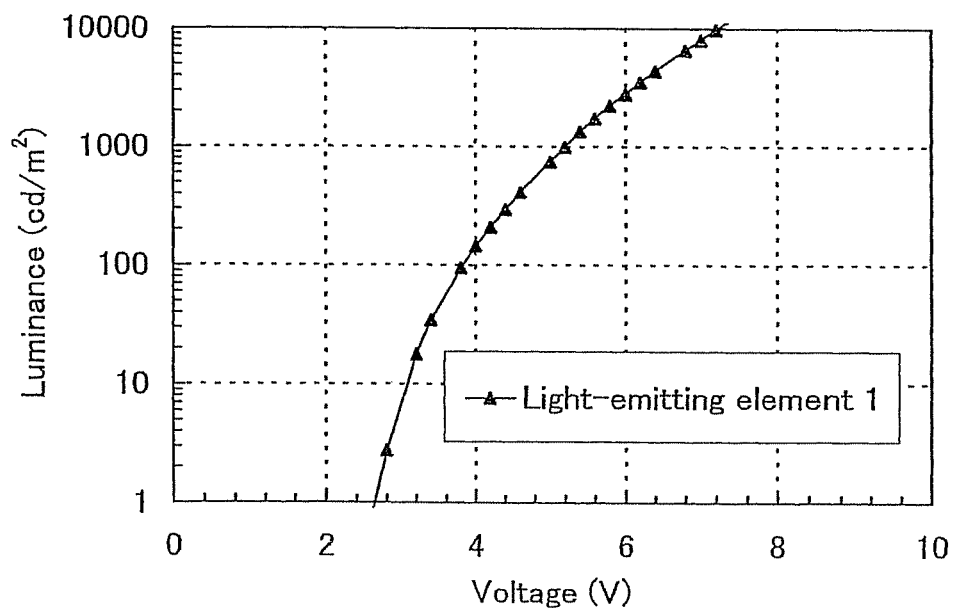
FIG. 43 shows the voltage-luminance characteristic of light-emitting element 1.
Figure 44:
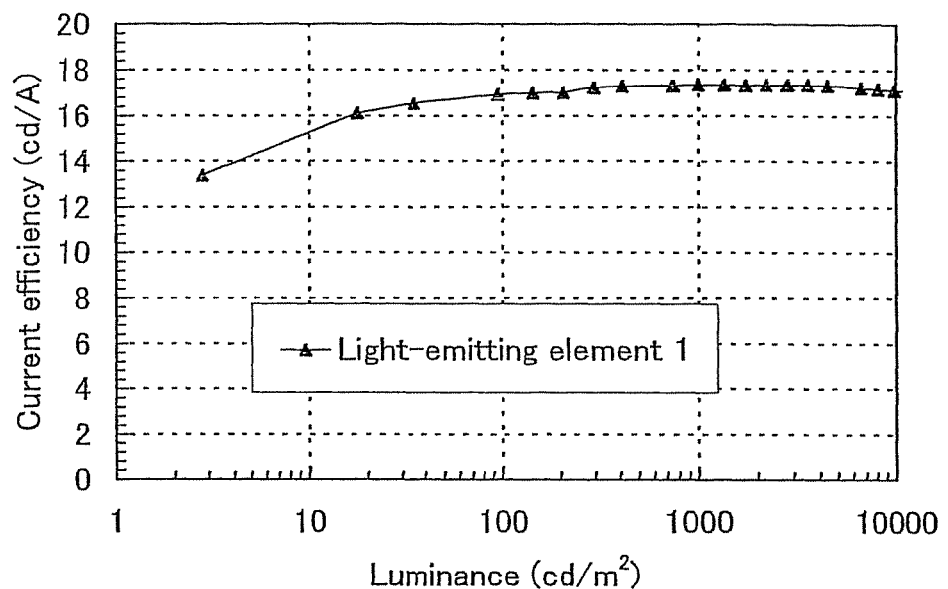
FIG. 44 shows the luminance-current efficiency characteristic of light-emitting element 1.
Figure 45:
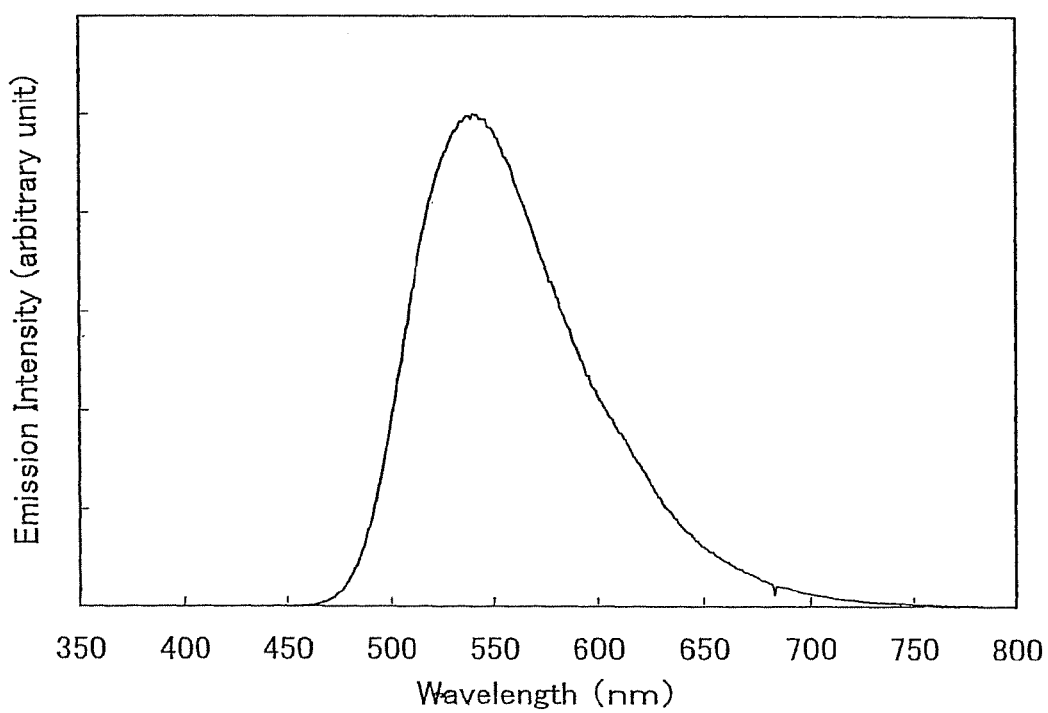
FIG. 45 shows the emission spectrum of light-emitting element 1.
Figure 46:
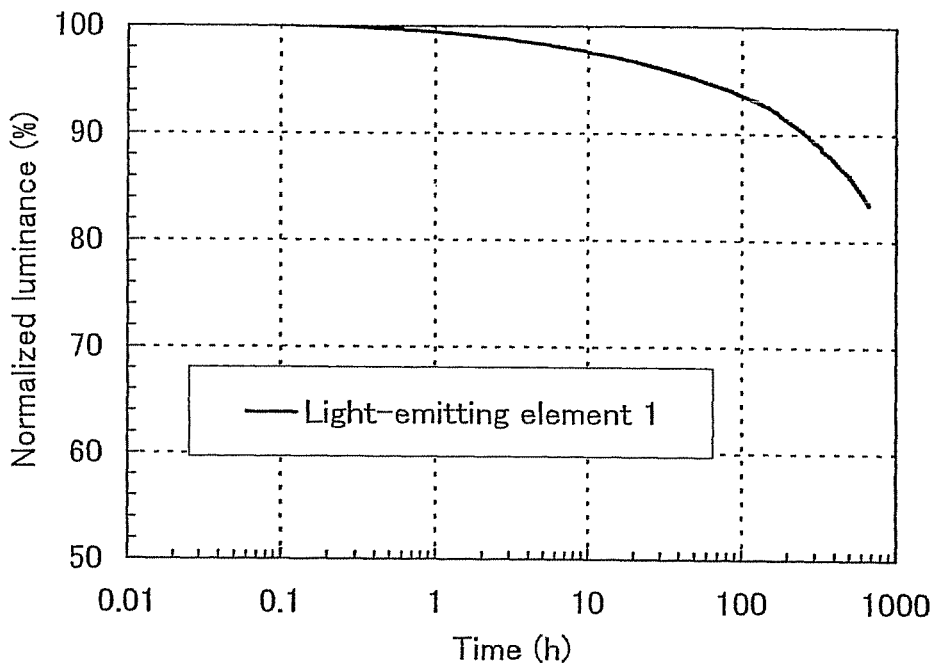
FIG. 46 shows time dependence of normalized luminance of light-emitting element 1.
Figure 47:
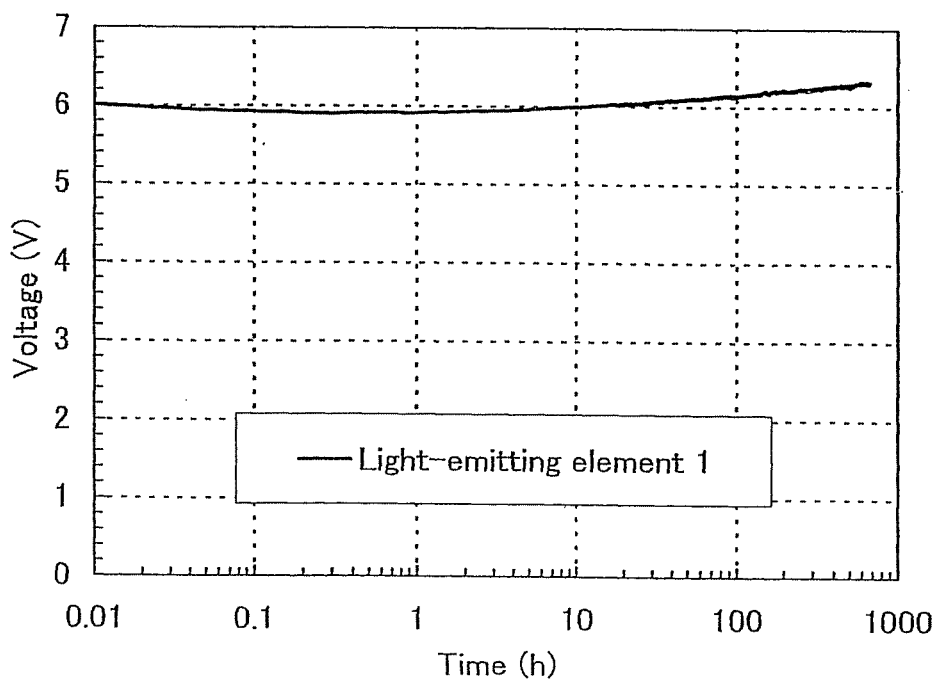
FIG. 47 shows time dependence of operation voltage of light-emitting element 1.

A current density-luminance characteristic, a voltage-luminance characteristic, and a luminance-current efficiency characteristic of the light-emitting element 1 are shown in FIGS. 42, 43, and 44, respectively. Also, the emission spectrum which was obtained at a current of 1 mA is illustrated in FIG. 45. Further, FIGS. 46 and 47 demonstrate time dependence of normalized luminance and time dependence of operation voltage, respectively, of the light-emitting element 1 when initial luminance was 3000 cd/m². A CIE chromaticity coordinate of the light-emitting element 1 at luminance of 3000 cd/m² was (x=0.36, y=0.60), and light emission was yellow green. Current efficiency at luminance of 3000 cd/m² was 17.4 cd/A, meaning that high current efficiency was exhibited. In addition, as shown in FIG. 45, maximum emission wavelength at a current of 1 mA was 540 nm. It can be concluded from FIG. 46 that the light-emitting element 1 has a long lifetime, since 84% of the initial luminance was maintained even after 600 hours.

Figure 48:
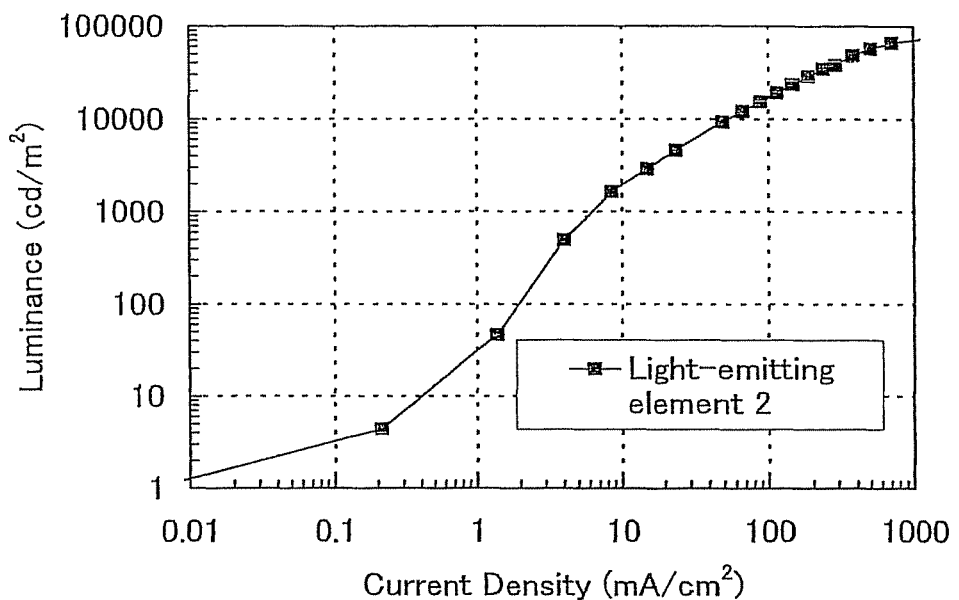
FIG. 48 shows the current density-luminance characteristic of light-emitting element 2.
Figure 49:
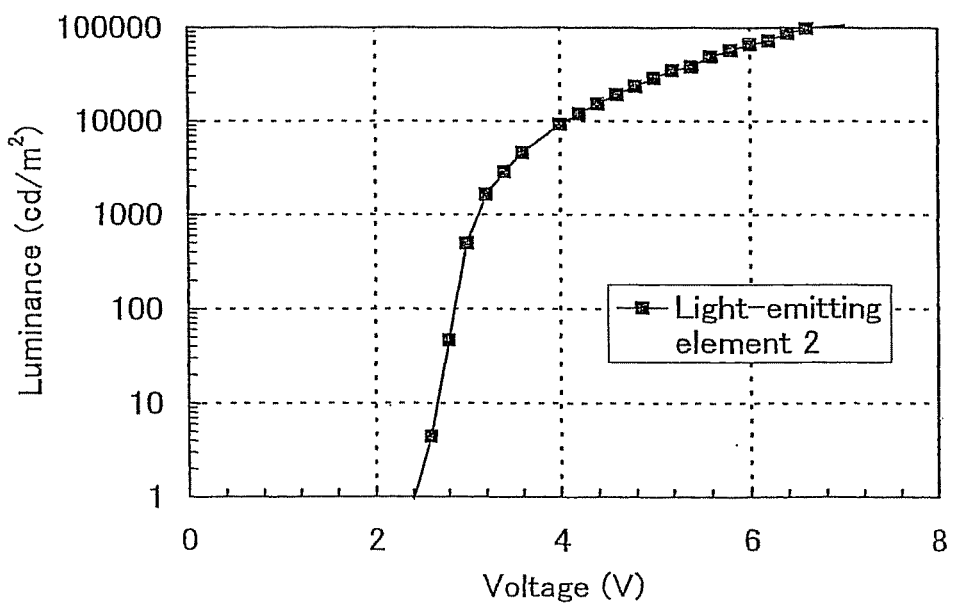
FIG. 49 shows the voltage-luminance characteristic of light-emitting element 2.
Figure 50:
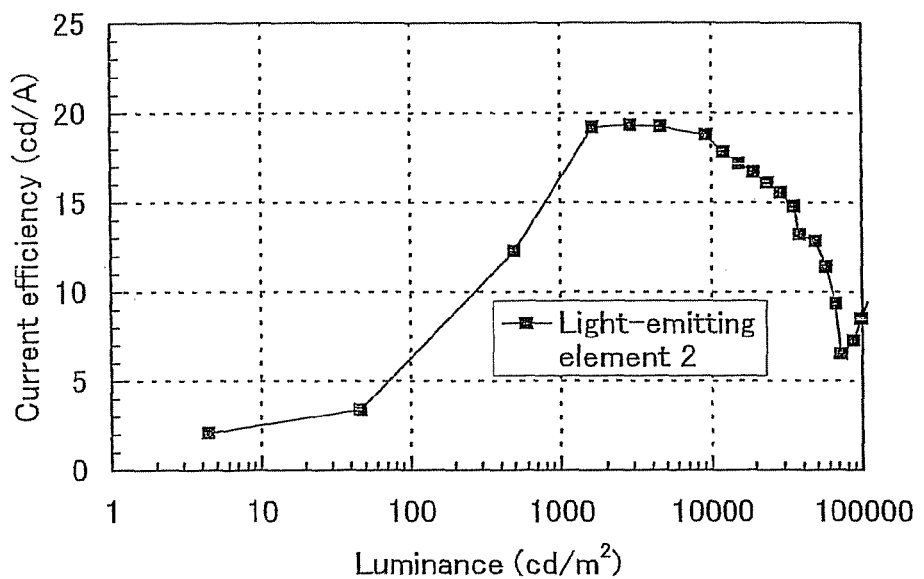
FIG. 50 shows the luminance-current efficiency characteristic of light-emitting element 2.
Figure 51:
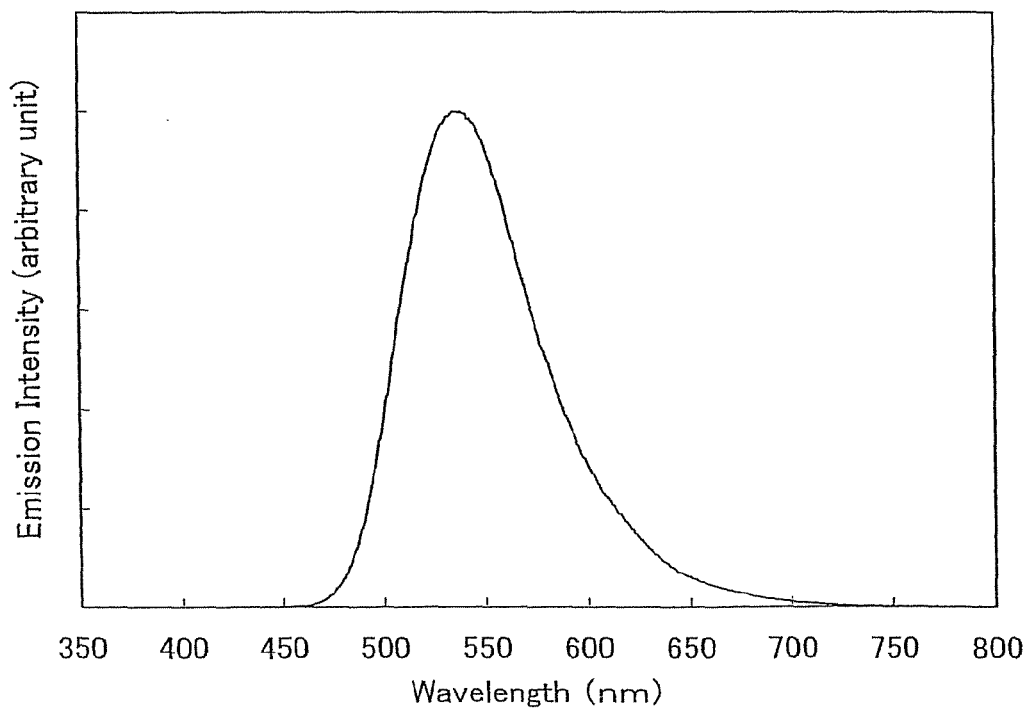
FIG. 51 shows the emission spectrum of light-emitting element 2.

A current density-luminance characteristic, a voltage-luminance characteristic, and a luminance-current efficiency characteristic of the light-emitting element 2 are shown in FIGS. 48, 49, and 50, respectively. Also, the emission spectrum which was obtained at a current of 1 mA is illustrated in FIG. 51. A CIE chromaticity coordinate of the light-emitting element 2 at luminance of 3000 cd/m² was (x=0.33, y=0.63), and light emission was green. Current efficiency at luminance of 3000 cd/m² was 19.3 cd/A, meaning that high current efficiency was exhibited. Power efficiency at luminance of 3000 cd/m² was 17.8 lm/W, indicating that the element 2 can be operated at low power consumption. In addition, as shown in FIG. 51, maximum emission wavelength at a current of 1 mA was 535 nm.

Figure 52:
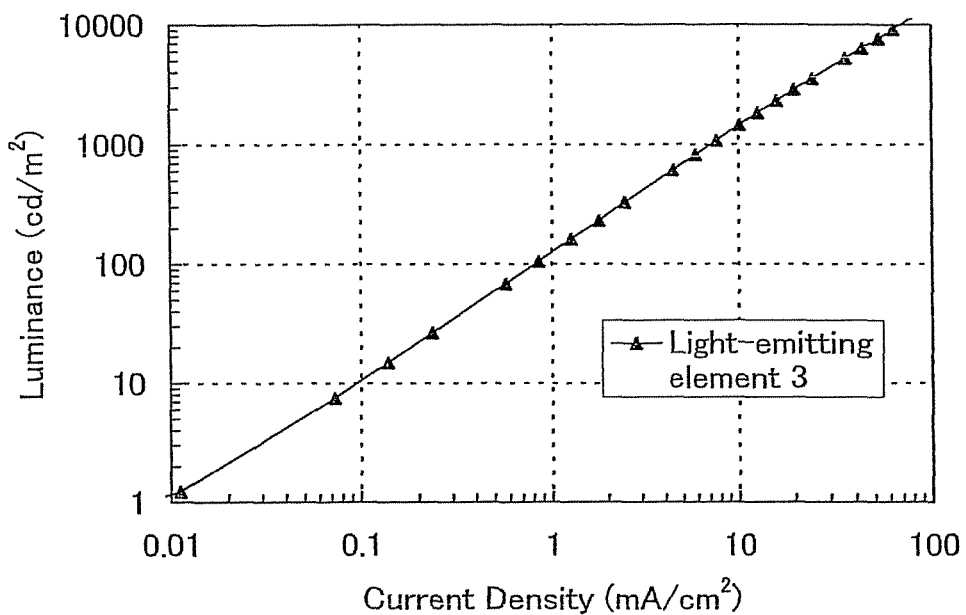
FIG. 52 shows the current density-luminance characteristic of light-emitting element 3.
Figure 53:
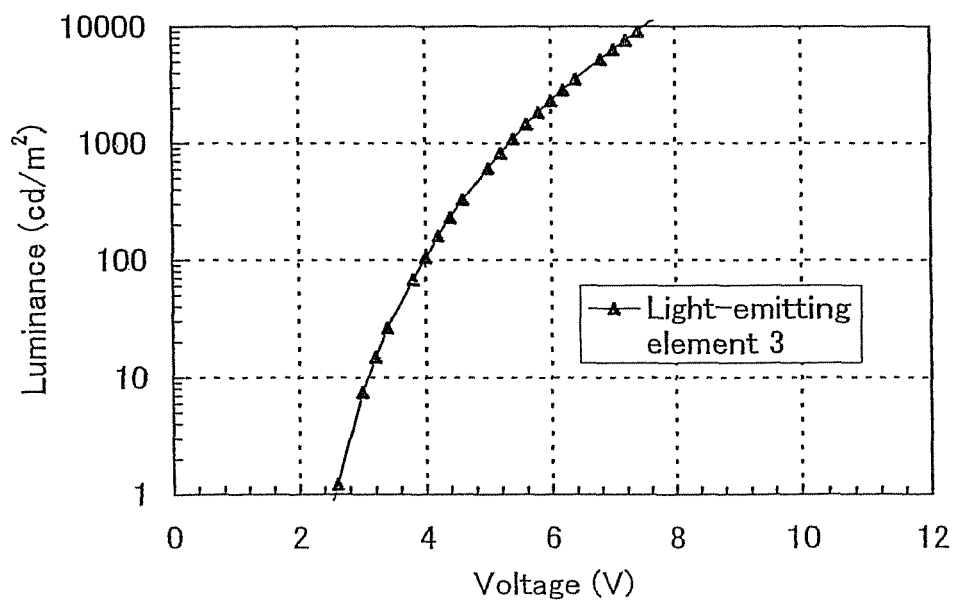
FIG. 53 shows the voltage-luminance characteristic of light-emitting element 3
Figure 54:
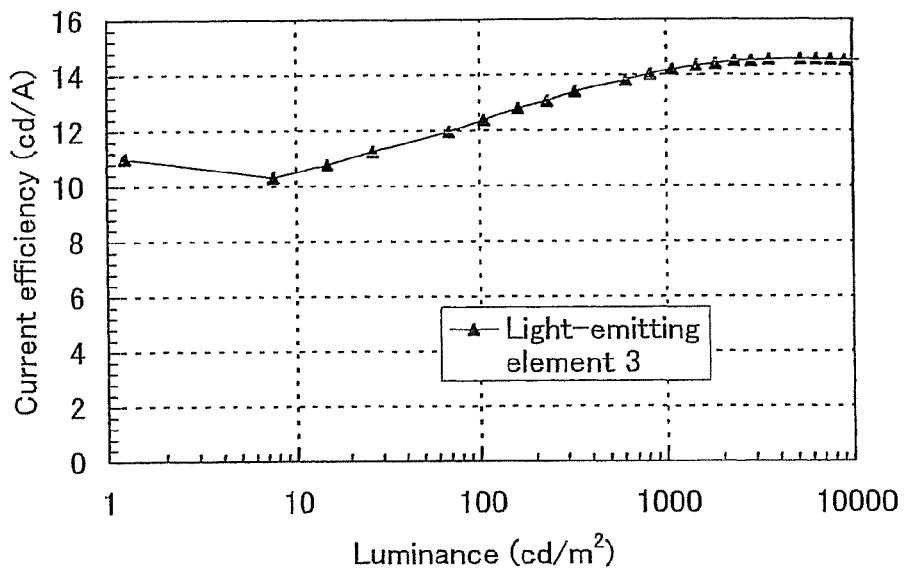
FIG. 54 shows the luminance-current efficiency characteristic of light-emitting element 3.
Figure 55:
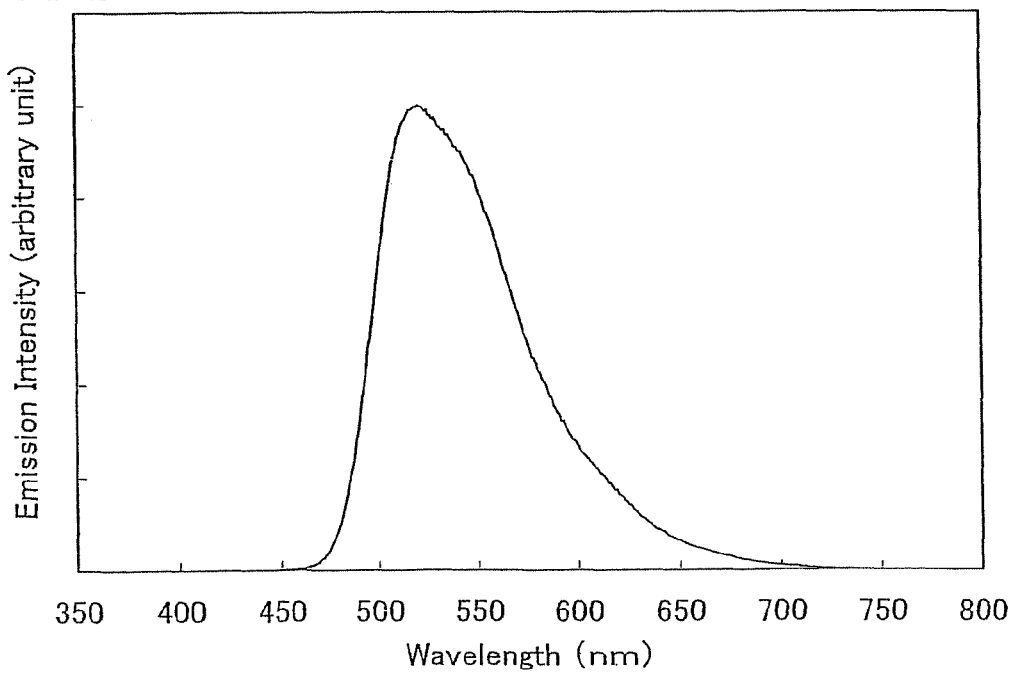
FIG. 55 shows the emission spectrum of light-emitting element 3.
Figure 56:
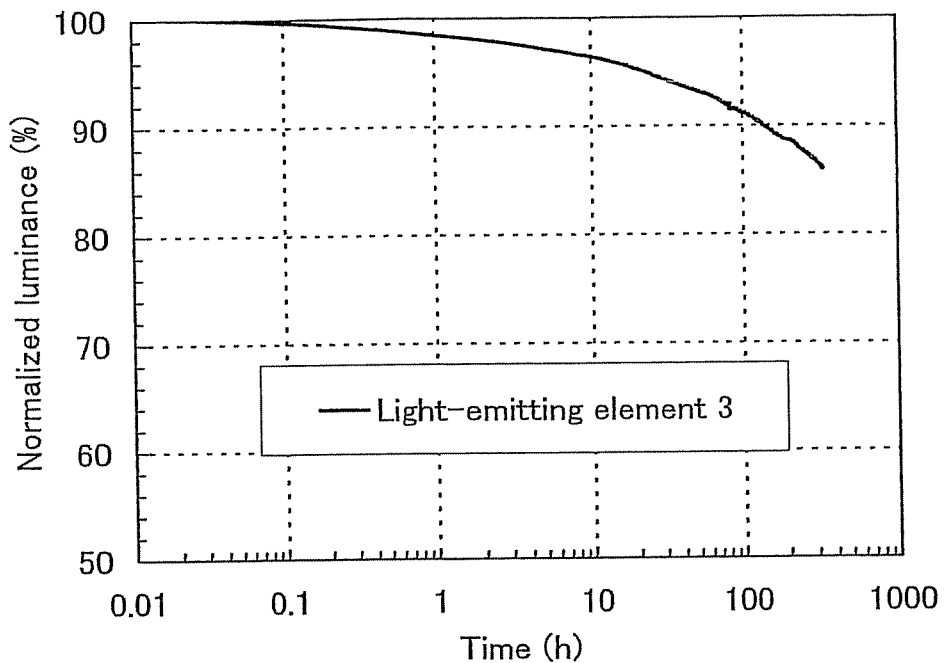
FIG. 56 shows time dependence of normalized luminance of light-emitting element 3.
Figure 57:
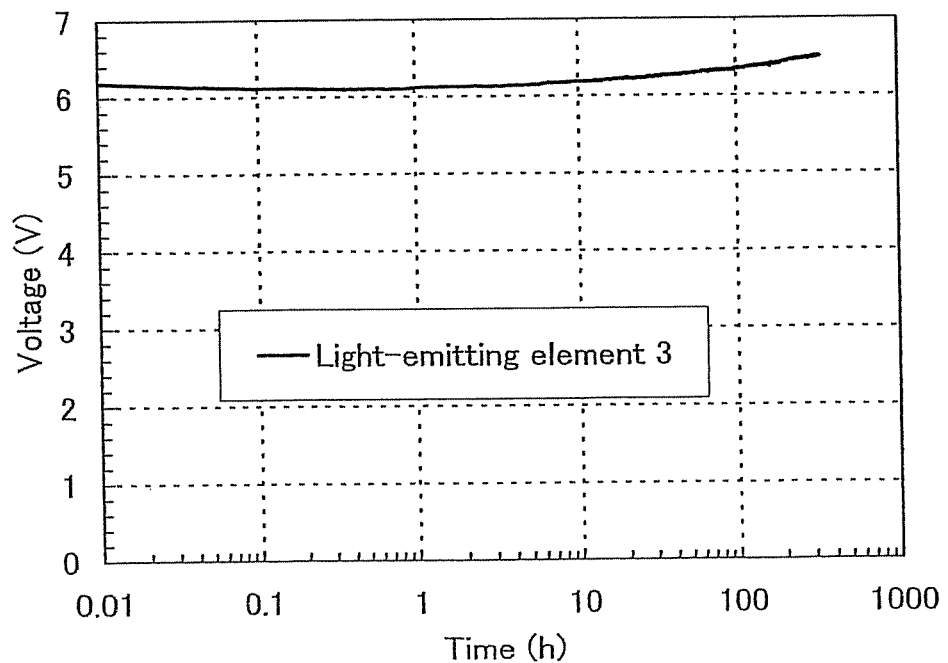
FIG. 57 shows time dependence of operation voltage of light-emitting element 3.

A current density-luminance characteristic, a voltage-luminance characteristic, and a luminance-current efficiency characteristic of the light-emitting element 3 are shown in FIGS. 52, 53, and 54, respectively. Also, the emission spectrum which was obtained at a current of 1 mA is illustrated in FIG. 55. Further, FIGS. 56 and 57 demonstrate time dependence of normalized luminance and time dependence of operation voltage, respectively, of the light-emitting element 3 when initial luminance was 3000 cd/m². A CIE chromaticity coordinate of the light-emitting element 3 at luminance of 3000 cd/m² was (x=0.31, y=0.63), and light emission was green. Current efficiency at luminance of 3000 cd/m² was 14.5 cd/A, meaning that high current efficiency was exhibited. In addition, as shown in FIG. 55, maximum emission wavelength at a current of 1 mA was 521 nm. It can be concluded from FIG. 56 that the light-emitting element 3 has a long lifetime, since 87% of the initial luminance was maintained even after 300 hours.

Figure 58:
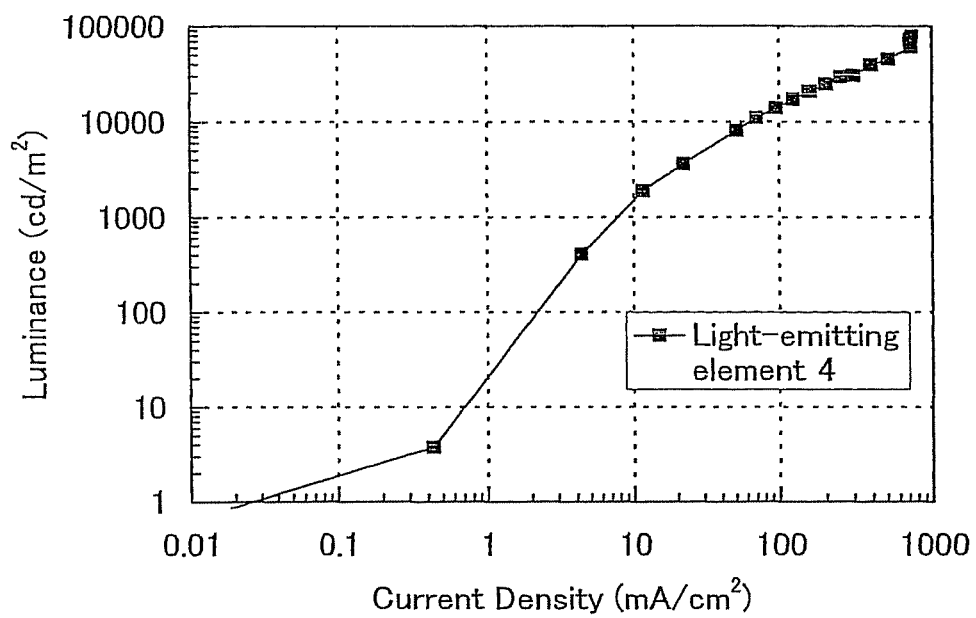
FIG. 58 shows the current density-luminance characteristic of light-emitting element 4.
Figure 59:
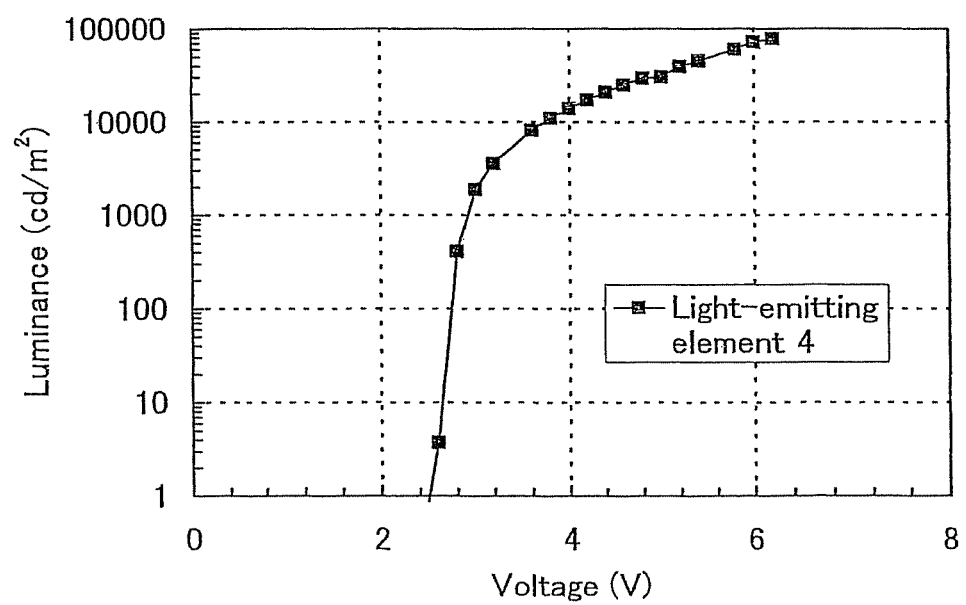
FIG. 59 shows the voltage-luminance characteristic of light-emitting element 4.
Figure 60:
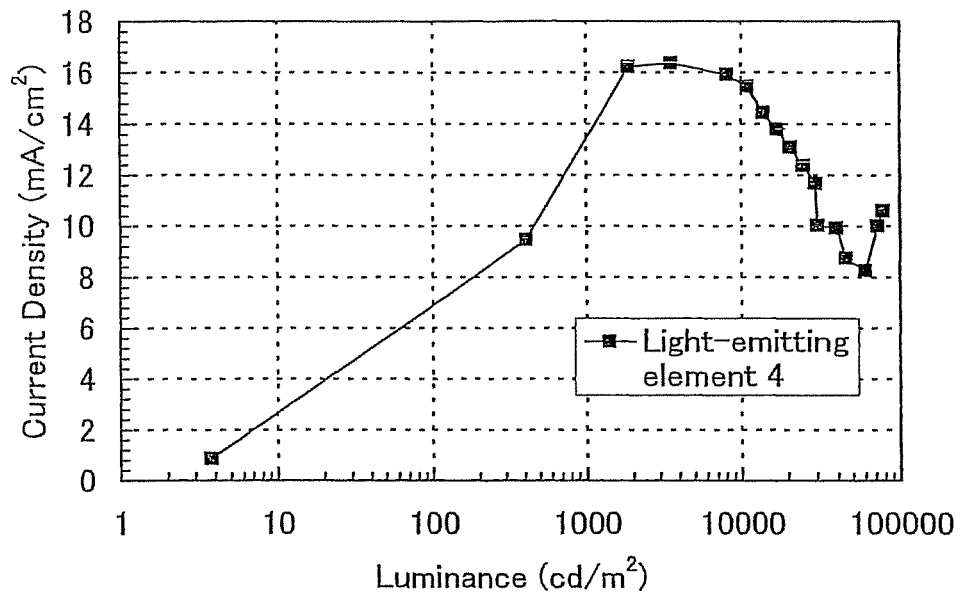
FIG. 60 shows the luminance-current efficiency characteristic of light-emitting element 4.
Figure 61:
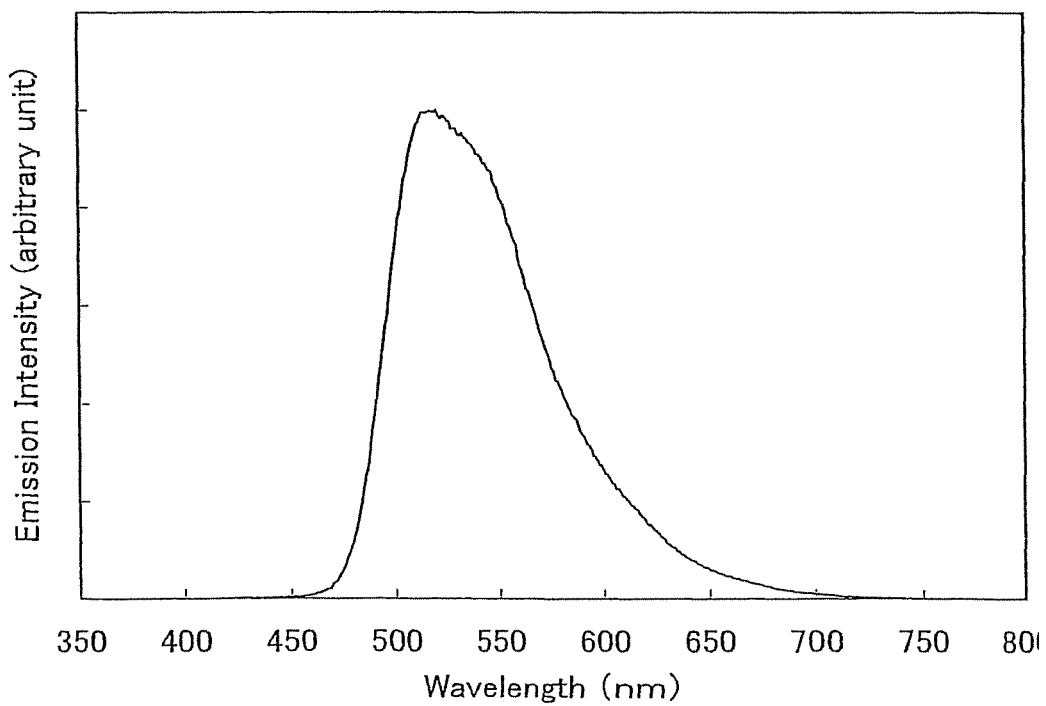
FIG. 61 shows the emission spectrum of light-emitting element 4.

A current density-luminance characteristic, a voltage-luminance characteristic, and a luminance-current efficiency characteristic of the light-emitting element 4 are shown in FIGS. 58, 59, and 60, respectively. Also, the emission spectrum which was obtained at a current of 1 mA is illustrated in FIG. 61. A CIE chromaticity coordinate of the light-emitting element 4 at luminance of 3000 cd/m² was (x=030, y=0.62), and light emission was green. Current efficiency at luminance of 3000 cd/m² was 16.3 cd/A, meaning that high current efficiency was exhibited. The power efficiency at luminance of 3000 cd/m² was 16.4 lm/W, indicating that the element. 4 can be operated at low power consumption. In addition, as shown in FIG. 61, maximum emission wavelength at a current of 1 mA was 520 nm.

Figure 62:
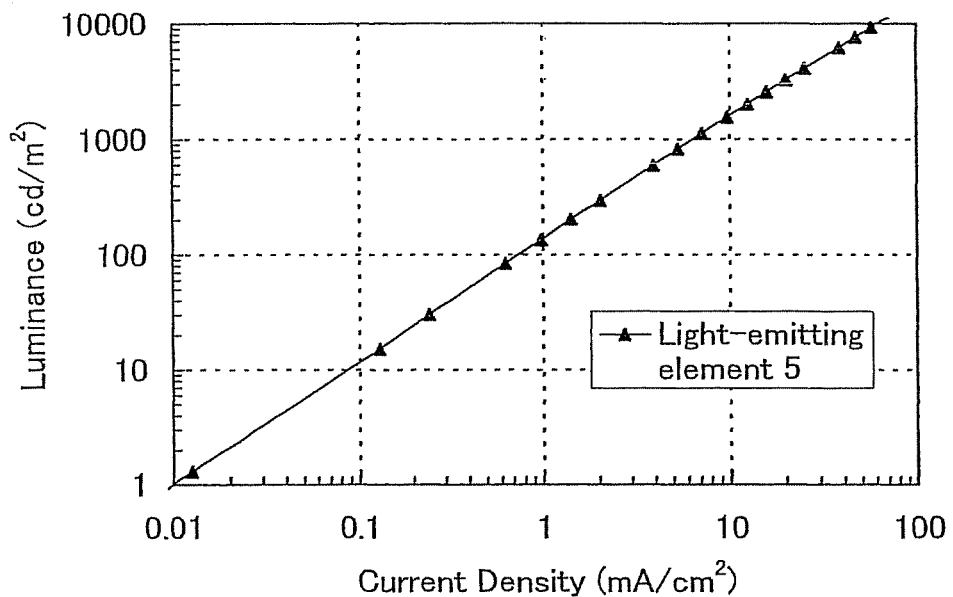
FIG. 62 shows the current density-luminance characteristic of light-emitting element 5.
Figure 63:
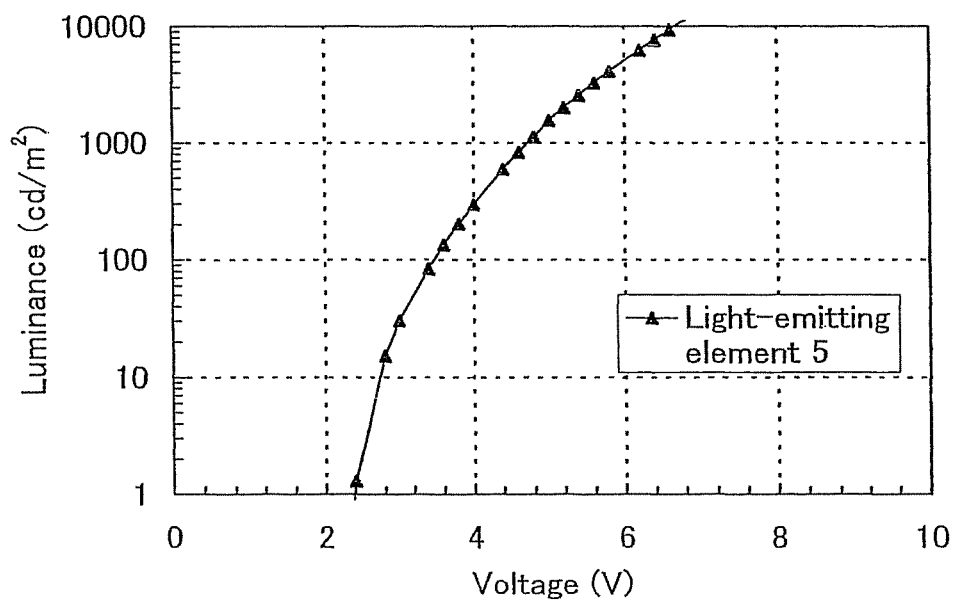
FIG. 63 shows the voltage-luminance characteristic of light-emitting element 5.
Figure 64:
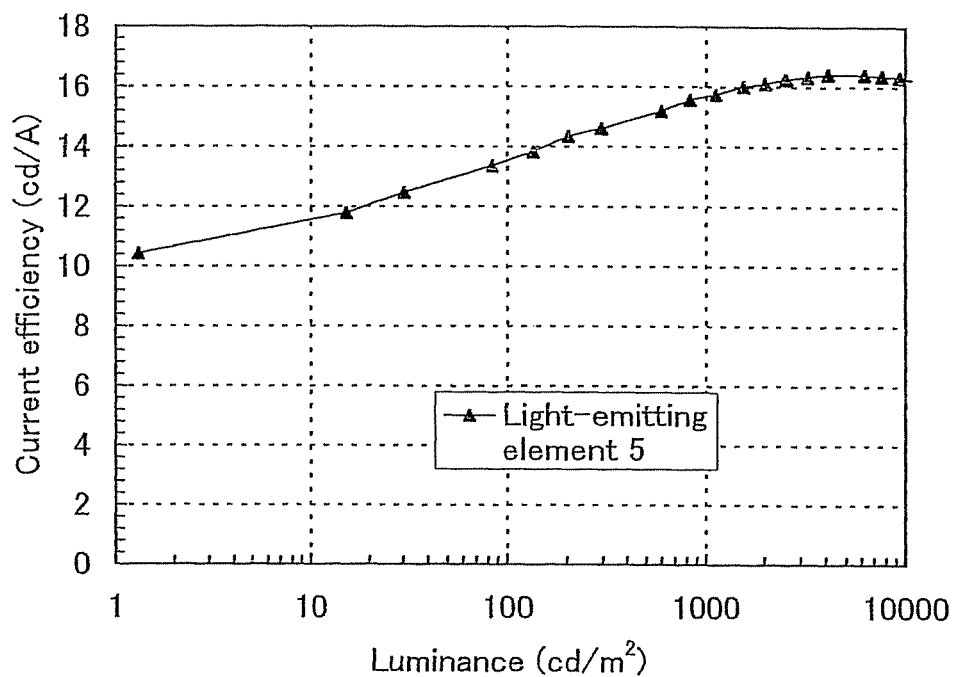
FIG. 64 shows the luminance-current efficiency characteristic of light-emitting element 5.
Figure 65:
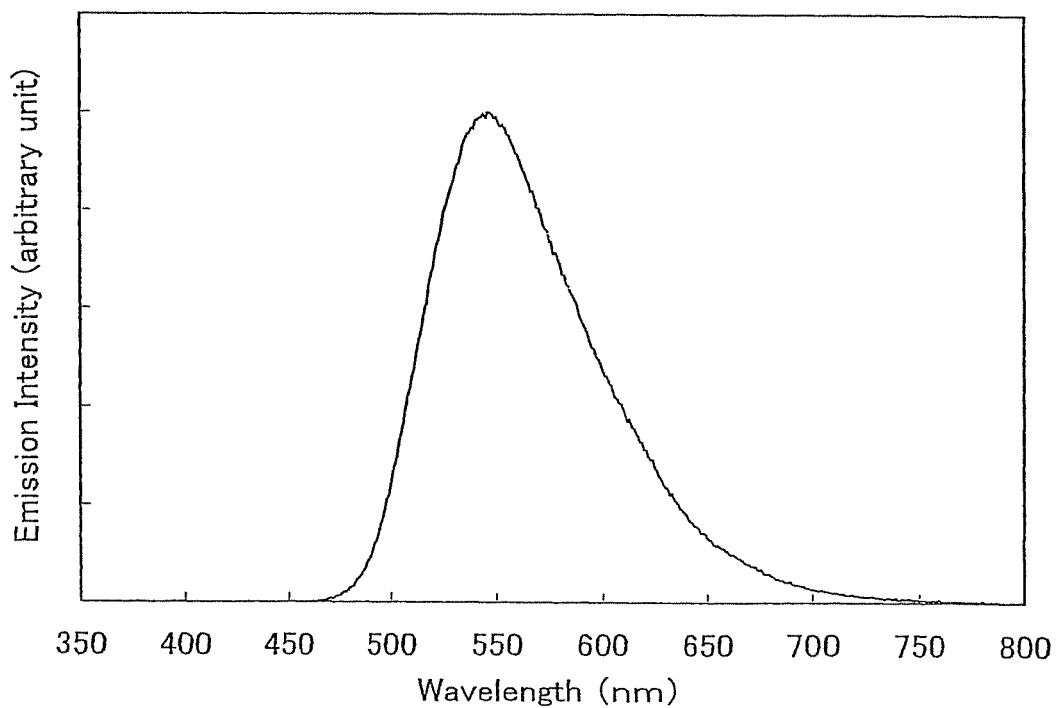
FIG. 65 shows the emission spectrum of light-emitting element 5.
Figure 66:
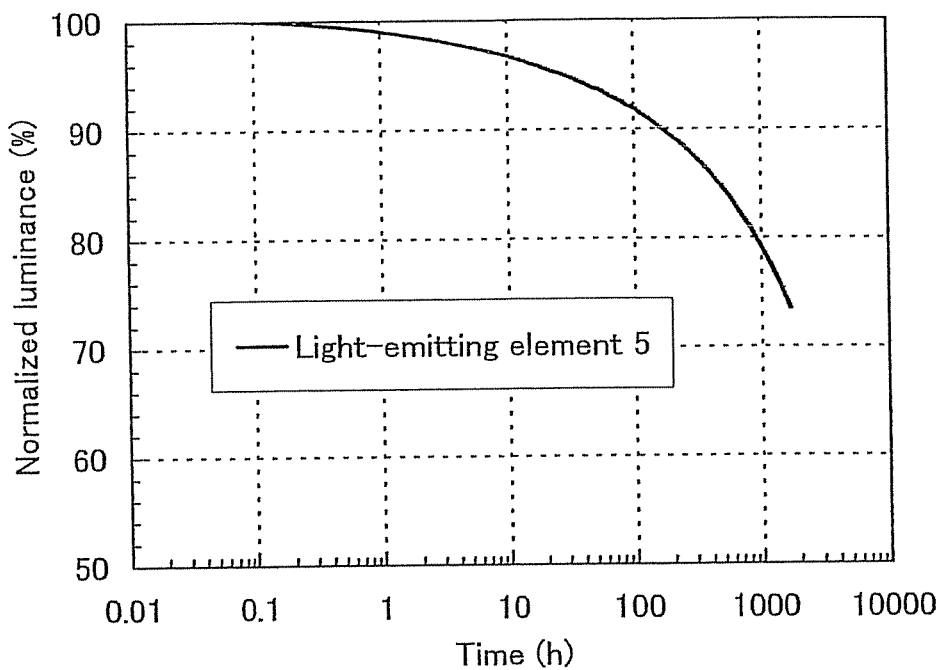
FIG. 66 shows time dependence of normalized luminance of light-emitting element 5.
Figure 67:
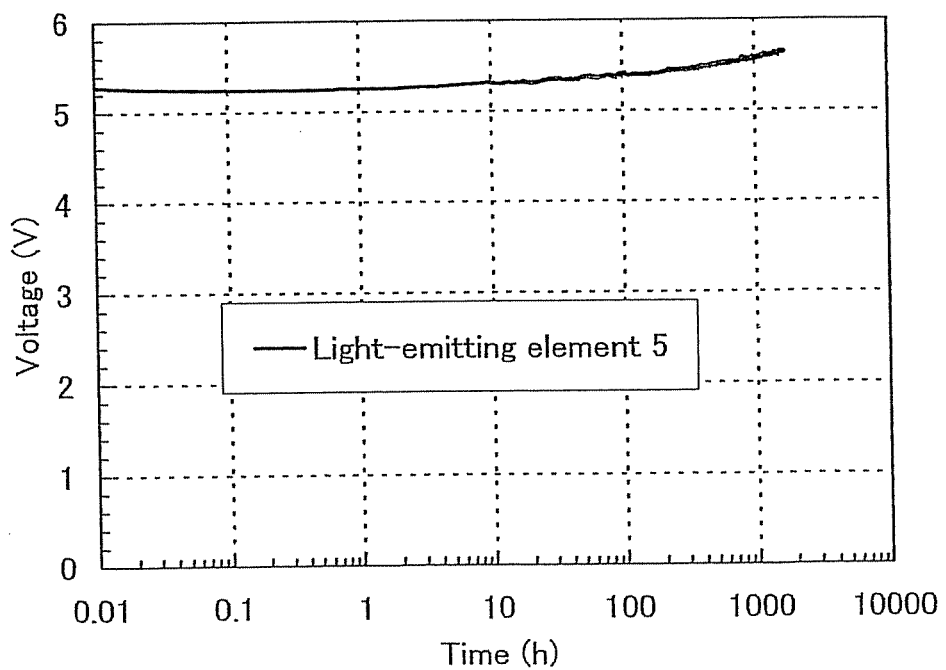
FIG. 67 shows time dependence of operation voltage of light-emitting element 5.

A current density-luminance characteristic, a voltage-luminance characteristic, and a luminance-current efficiency characteristic of the light-emitting element 5 are shown in FIGS. 62, 63, and 64, respectively. Also, the emission spectrum which was obtained at a current of 1 mA is illustrated in FIG. 65. Further, FIGS. 66 and 67 demonstrate time dependence of normalized luminance and time dependence of operation voltage, respectively, of the light-emitting element 5 when initial luminance was 3000 cd/m². A CIE chromaticity coordinate of the light-emitting element 5 at luminance of 3000 cd/m² was (x=0.39, y=0.59), and light emission was yellow green. Current efficiency at luminance of 3000 cd/m² was 16.3 cd/A, meaning that high current efficiency was exhibited. In addition, as shown in FIG. 65, maximum, emission wavelength at a current of 1 mA was 546 nm. It can be concluded from FIG. 66 that the light-emitting element 5 has a long lifetime, since 74% of the initial luminance was maintained even after 1600 hours.

Figure 68:
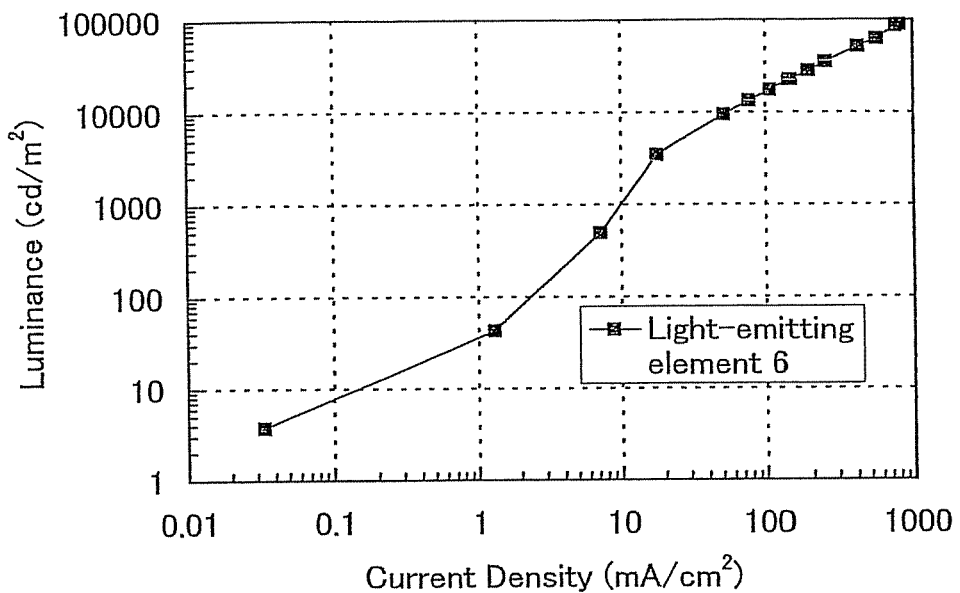
FIG. 68 shows the current density-luminance characteristic of light-emitting element 6.
Figure 69:
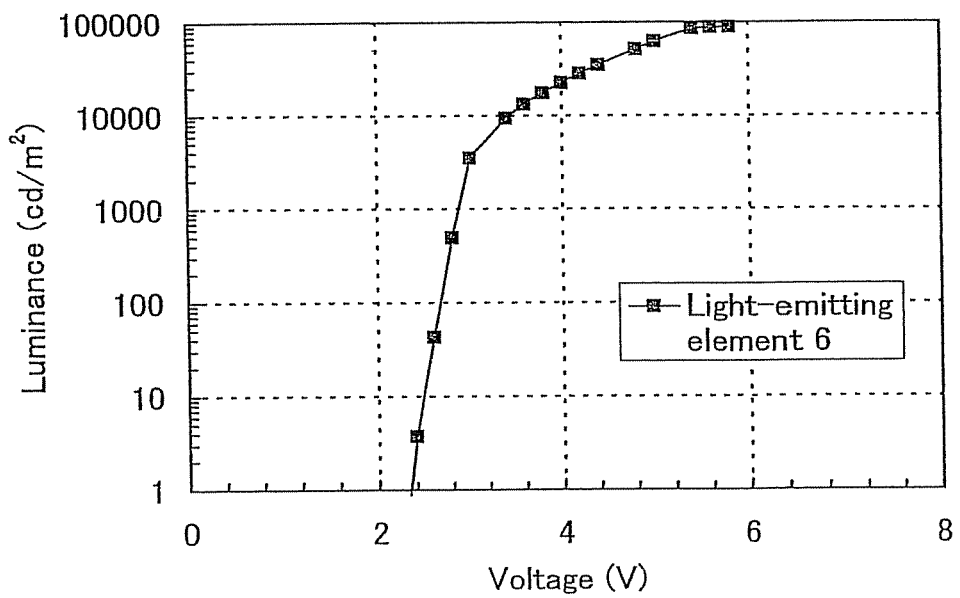
FIG. 69 shows the voltage-luminance characteristic of light-emitting element 6.
Figure 70:
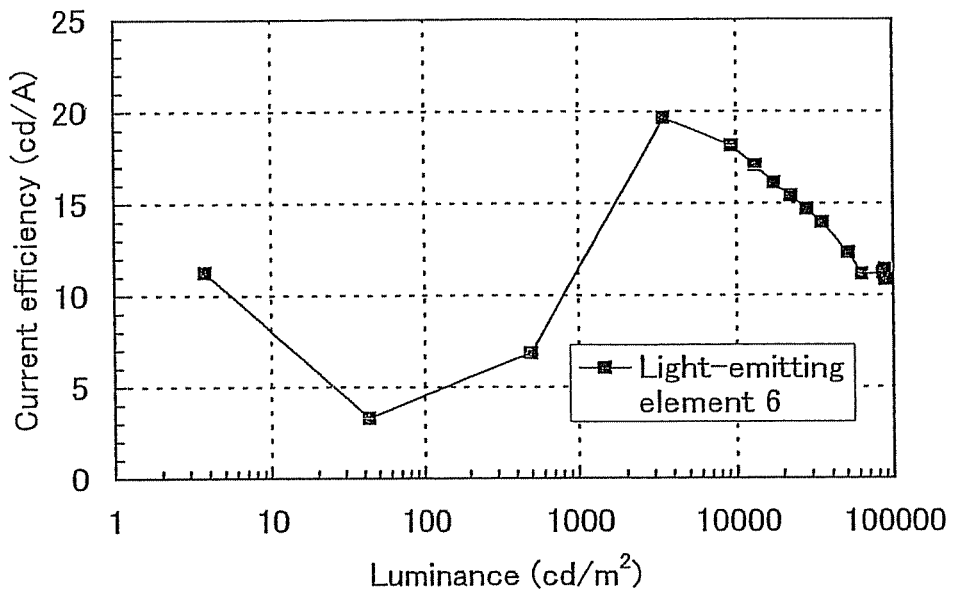
FIG. 70 shows the luminance-current efficiency characteristic of light-emitting element 6.
Figure 71:
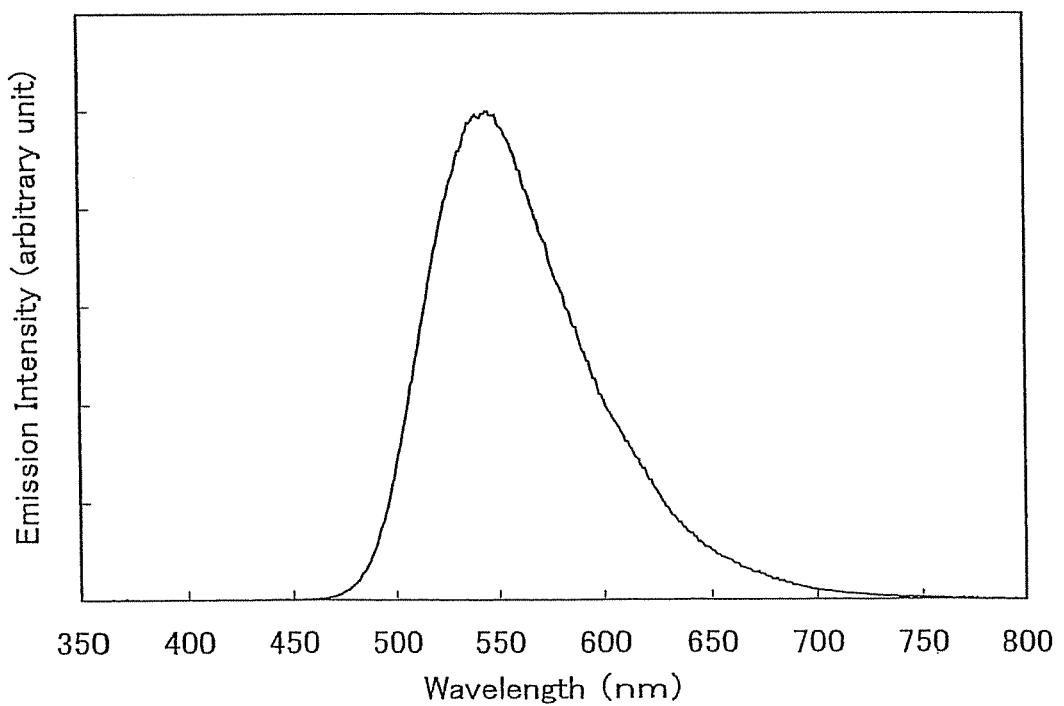
FIG. 71 shows the emission spectrum of light-emitting element 6.

A current density-luminance characteristic, a voltage-luminance characteristic, and a luminance-current efficiency characteristic of the light-emitting element 6 are shown in FIGS. 68, 69, and 70, respectively. Also, the emission spectrum which was obtained at a current of 1 mA is illustrated in FIG. 71, A CIE chromaticity coordinate of the light-emitting element 6 at luminance of 3000 cd/m² was (x=0.37, y=0.60), and light emission was yellow green. Current efficiency at luminance of 3000 cd/m² was 17.6 cd/A, meaning that high current efficiency was exhibited. The power efficiency at luminance of 3000 cd/m² was 18:6 lm/W, indicating that the element 6 can be operated at low power consumption. In addition, as shown in FIG. 71, maximum emission wavelength at a current of 1 mA was 545 nm.

Figure 72:
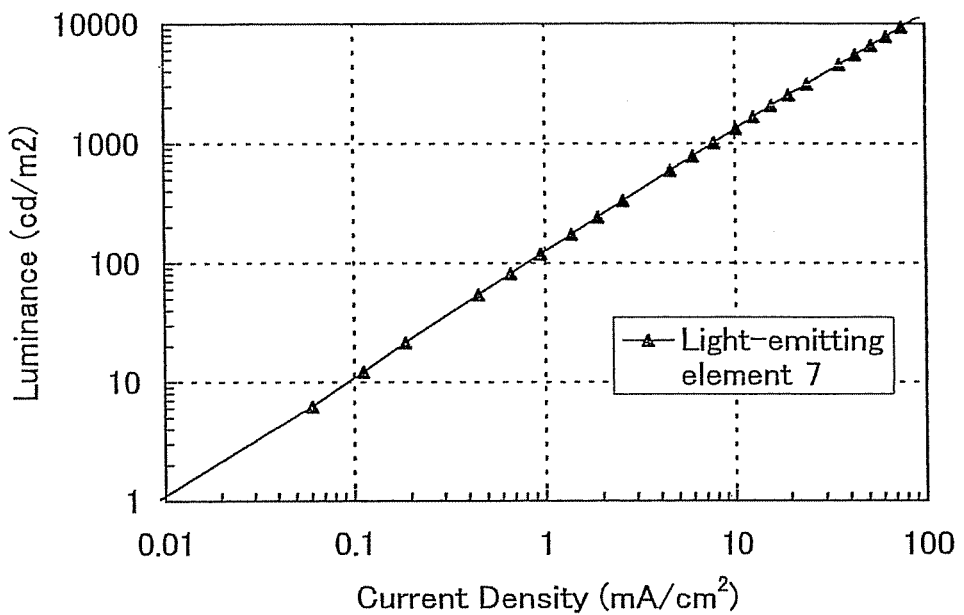
FIG. 72 shows the current density-luminance characteristic of light-emitting element 7.
Figure 73:
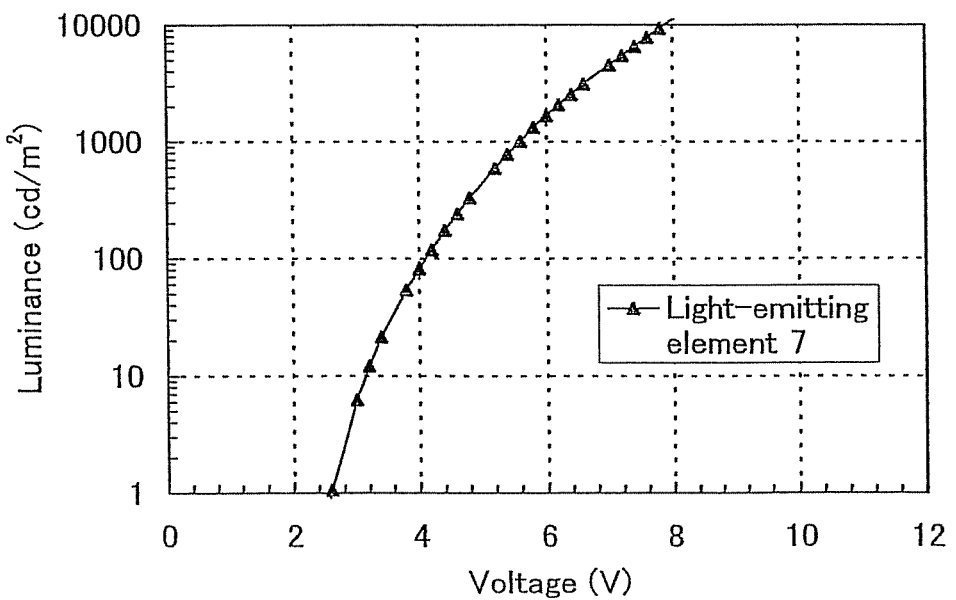
FIG. 73 shows the voltage-luminance characteristic of light-emitting element 7.
Figure 74:
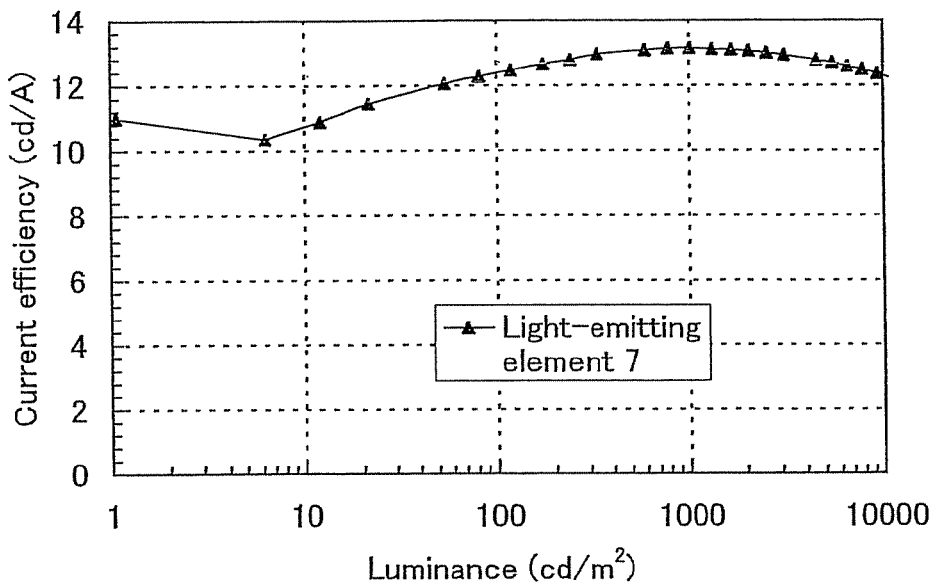
FIG. 74 shows the luminance-current efficiency characteristic of light-emitting element 7.
Figure 75:
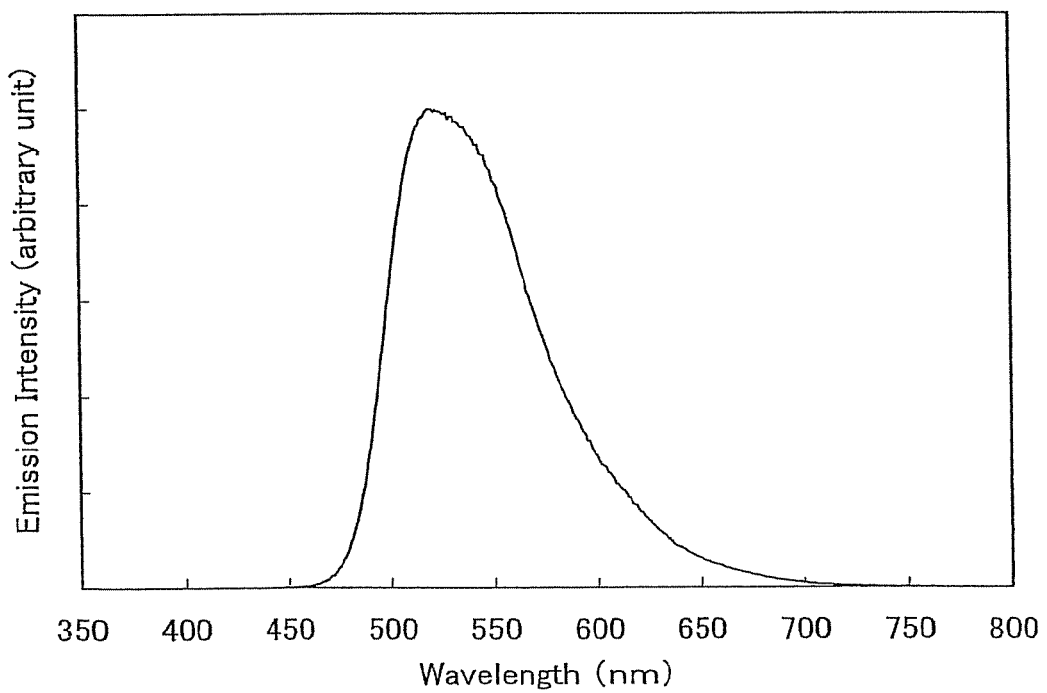
FIG. 75 shows the emission spectrum of light-emitting element 7.
Figure 76:
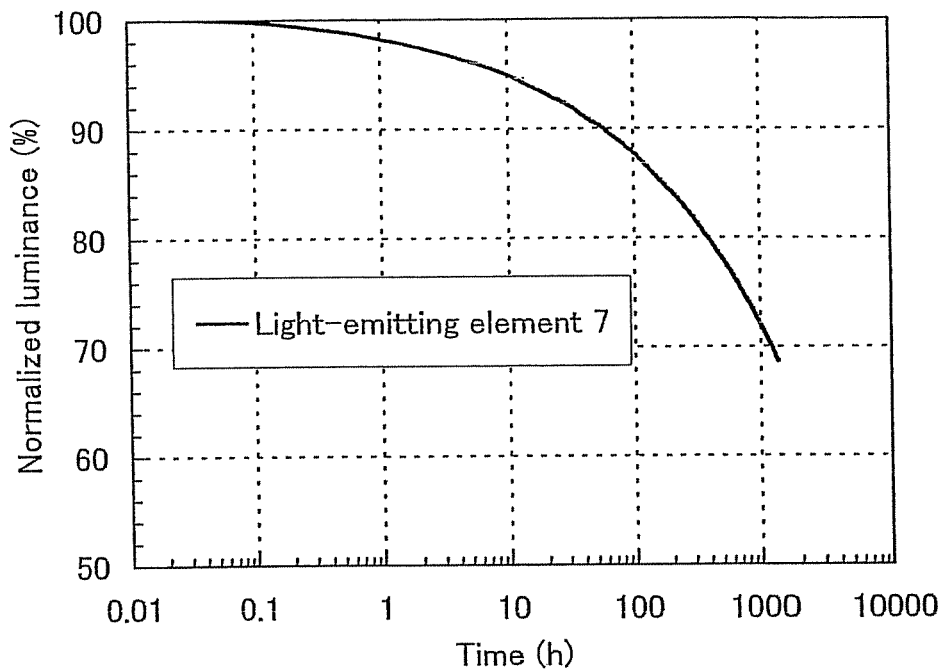
FIG. 76 shows time dependence of normalized luminance of light-emitting element 7.
Figure 77:
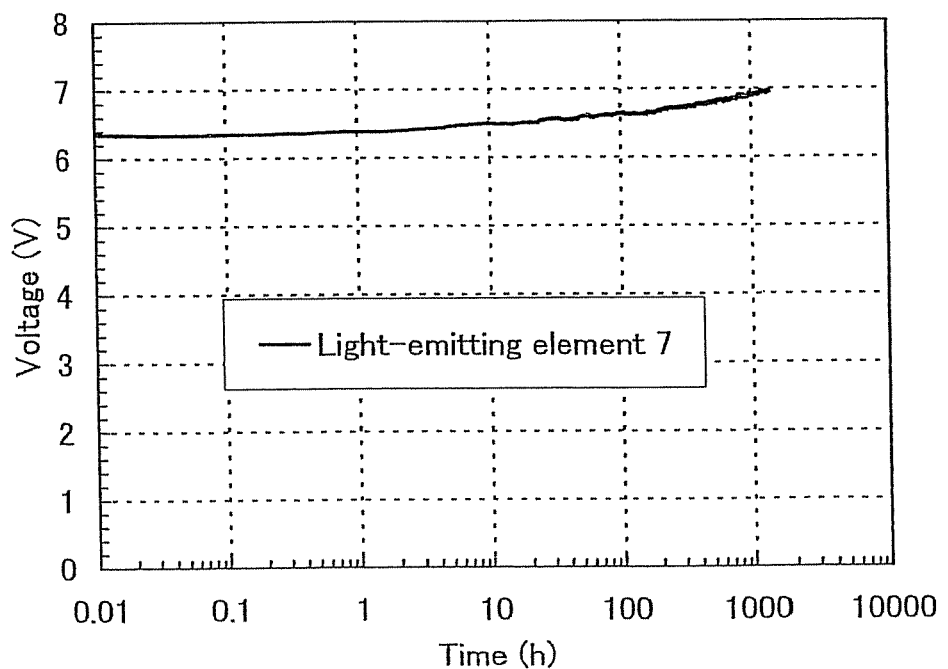
FIG. 77 shows time dependence of operation voltage of light-emitting element 7.

A current density-luminance characteristic, a voltage-luminance characteristic, and a luminance-current efficiency characteristic of the light-emitting element 7 are shown in FIGS. 72, 73, and 74, respectively. Also, the emission spectrum which was obtained at a current of 1 mA is illustrated in FIG. 75. Further, FIGS. 76 and 77 demonstrate time dependence of normalized luminance and time dependence of operation voltage, respectively, of the light-emitting element 7 when initial luminance was 3000 cd/m². A CIE chromaticity coordinate of the light-emitting element 7 at luminance of 3000 cd/m² was (x=0.31, y=0.63), and light emission was green. Current efficiency at luminance of 3000 cd/m² was 13.0 cd/A, meaning that high current efficiency was exhibited. In addition, as shown in FIG. 75, maximum emission wavelength at a current of 1 mA was 520 nm. It can be concluded from FIG. 76 that the light-emitting element 7 has a long lifetime, since 69% of the initial luminance was maintained even after 1300 hours.

Figure 78:
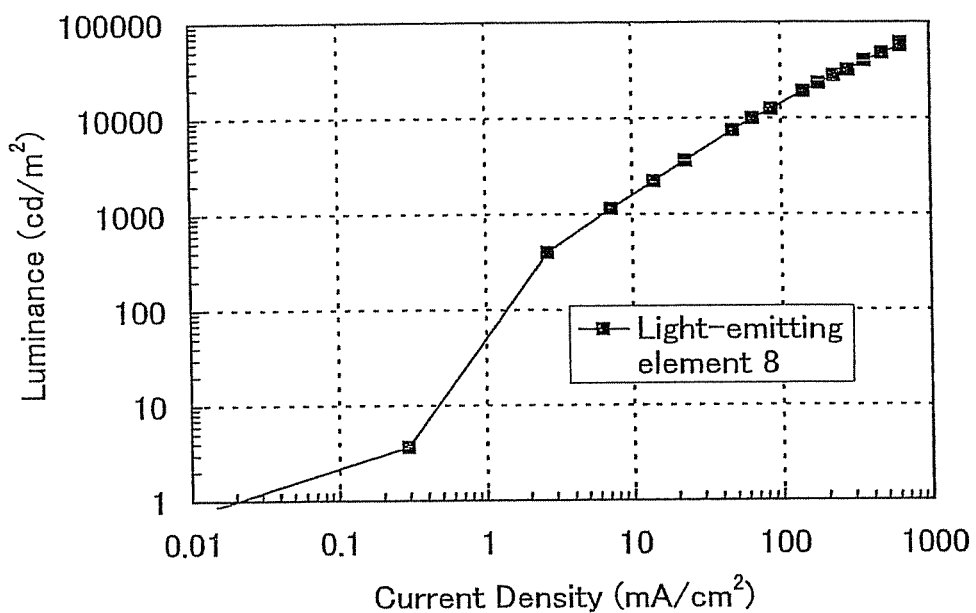
FIG. 78 shows the current density-luminance characteristic of light-emitting element 8.
Figure 79:
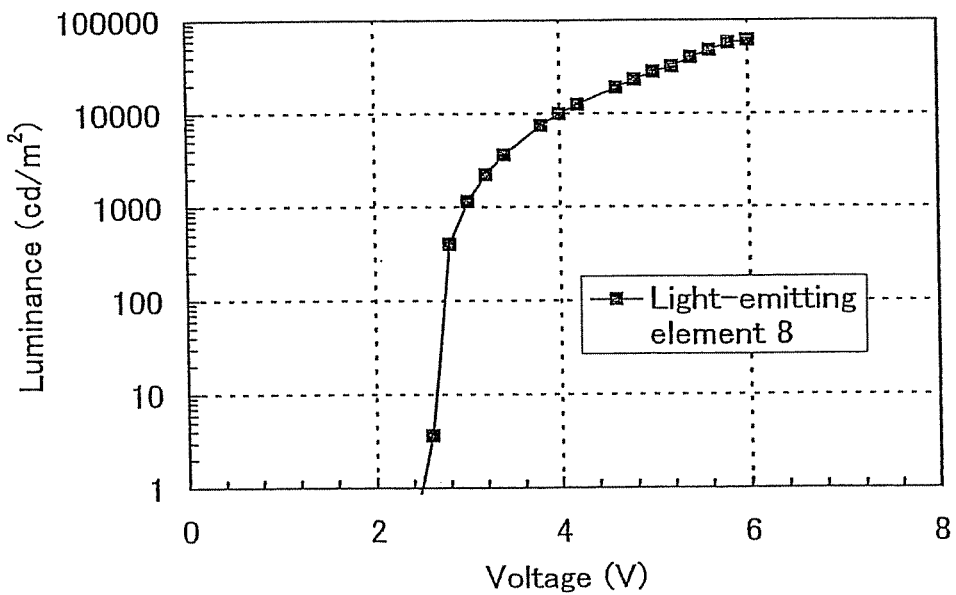
FIG. 79 shows the voltage-luminance characteristic of light-emitting element 8.
Figure 80:
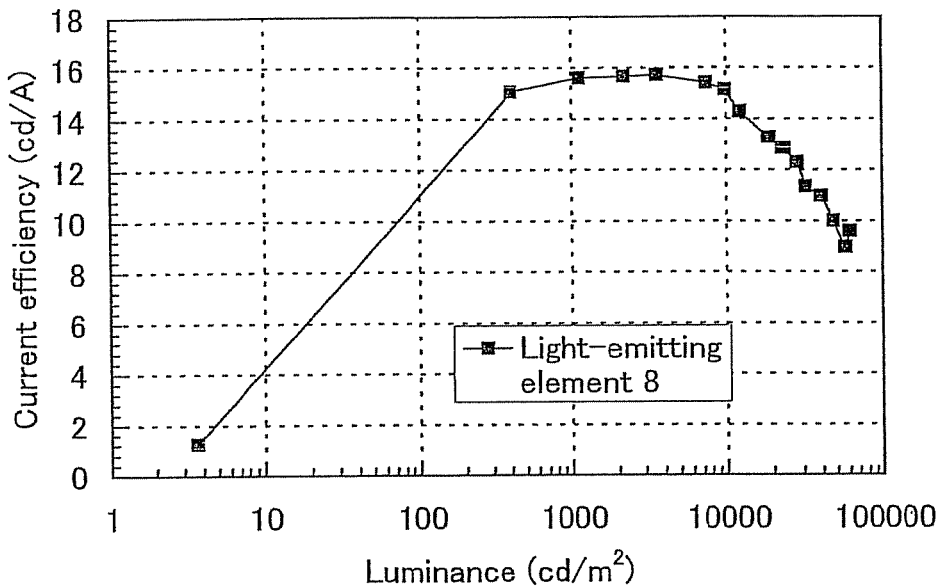
FIG. 80 shows the luminance-current efficiency characteristic of light-emitting element 8.
Figure 81:
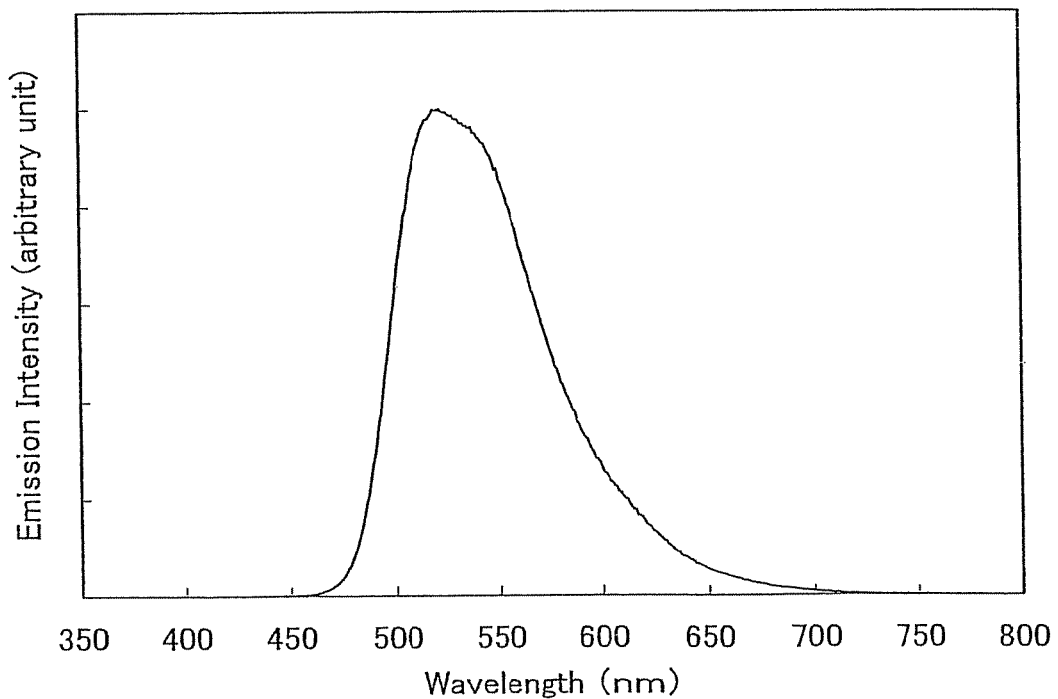
FIG. 81 shows the emission spectrum of light-emitting element 8.

A current density-luminance characteristic, a voltage-luminance characteristic, and a luminance-current efficiency characteristic of the light-emitting element 8 are shown in FIGS. 78, 79, and 80, respectively. Also, the emission spectrum which was obtained at a current of 1 mA is illustrated in FIG. 81. A CIE chromaticity coordinate of the light-emitting element 8 at luminance of 3000 cd/m² was (x=0.31, y=0.63), and light emission was green. Current efficiency at luminance of 3000 cd/m² was 15.74 cd/A, meaning that high current efficiency was exhibited. The power efficiency at luminance of 3000 cd/m² was 14.9 lm/W, indicating that the element 8 can be operated at low power consumption. In addition, as shown in FIG. 81, maximum emission wavelength at a current of 1 mA was 522 nm.

Figure 82:
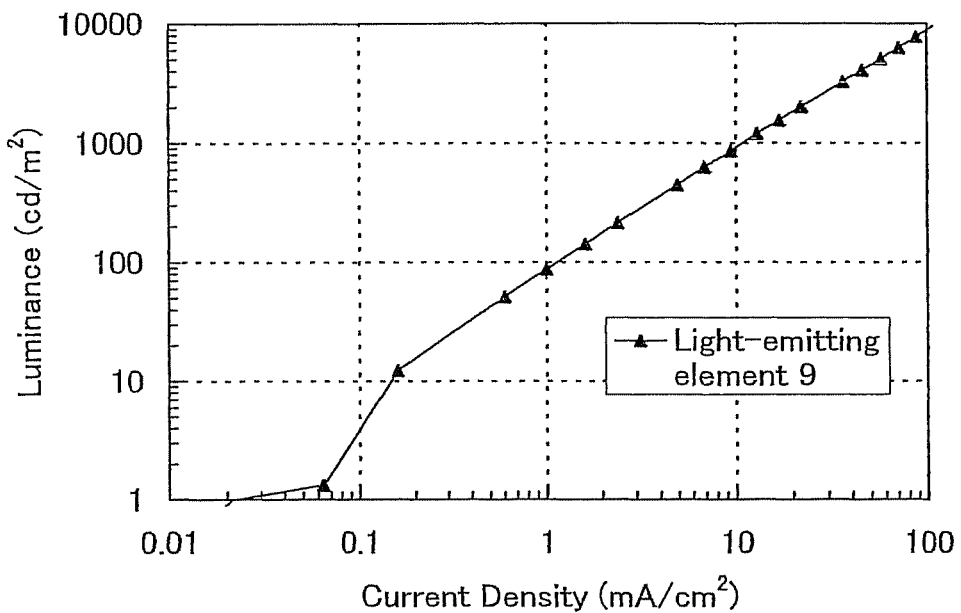
FIG. 82 shows the current density-luminance characteristic of light-emitting element 9.
Figure 83:
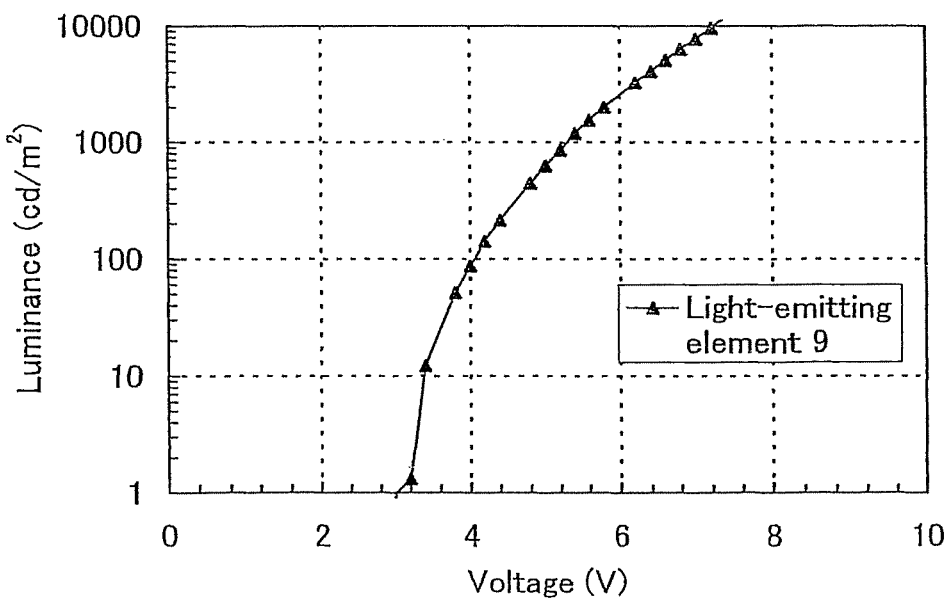
FIG. 83 shows the voltage-luminance characteristic of light-emitting element 9.
Figure 84:
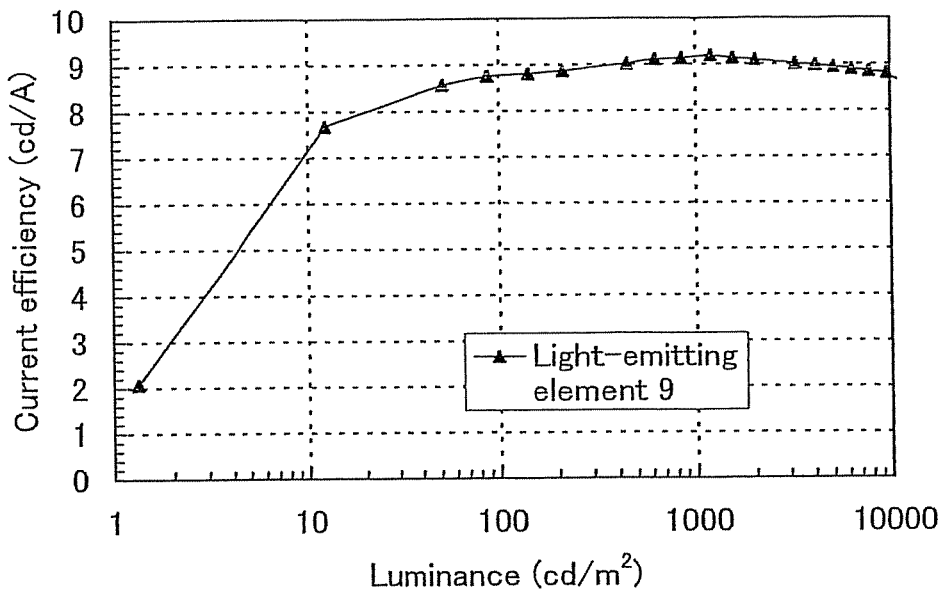
FIG. 84 shows the luminance-current efficiency characteristic of light-emitting element 9.
Figure 85:
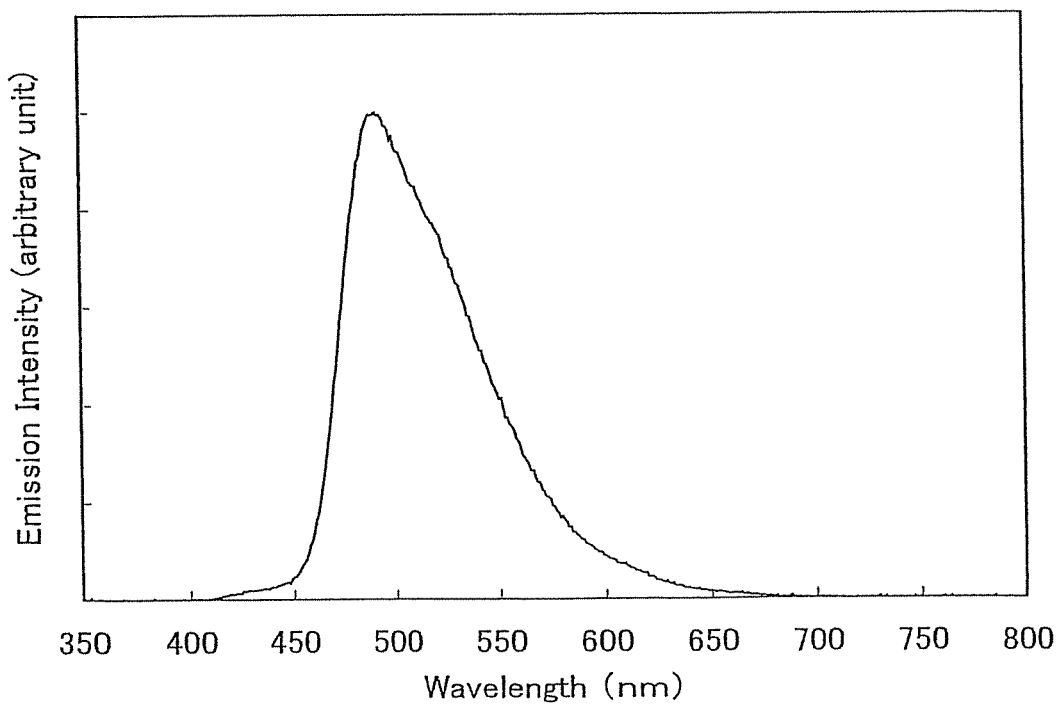
FIG. 85 shows the emission spectrum of light-emitting element 9.

A current density-luminance characteristic, a voltage-luminance characteristic, and a luminance-current efficiency characteristic of the light-emitting element 9 are shown in FIGS. 82, 83, and 84, respectively. Also, the emission spectrum which was obtained at a current of 1 mA is illustrated in FIG. 85. A CIE chromaticity coordinate of the light-emitting element 9 at luminance of 3000 cd/m² was (x=0.21, y=0.49), and light emission was blue green. Current efficiency at luminance of 3000 cd/m² was 8.9 cd/A, meaning that high current efficiency was exhibited. In addition, as shown in FIG. 85, maximum emission wavelength at a current of 1 mA was 491 nm.

Figure 86:
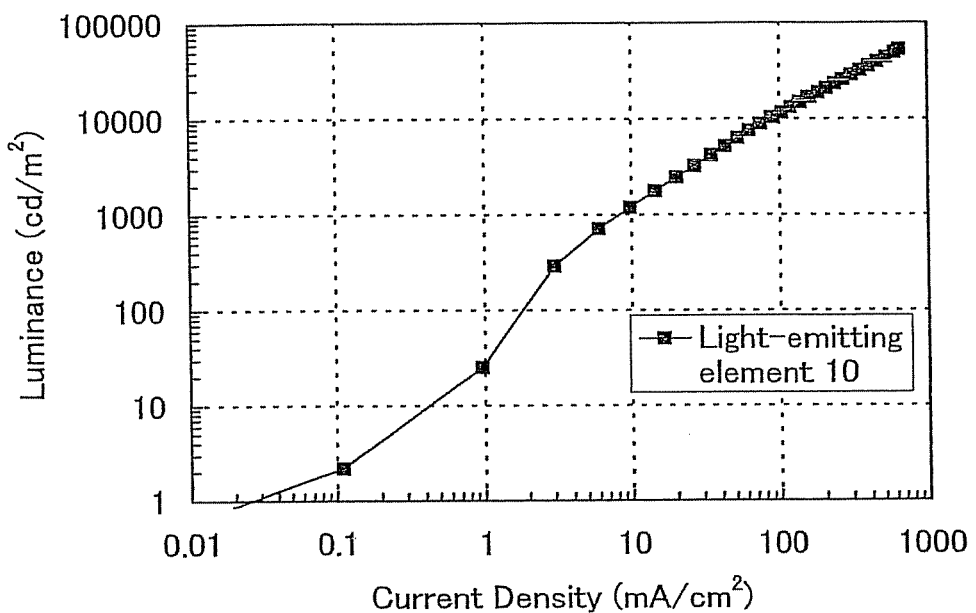
FIG. 86 shows the current density-luminance characteristic of light-emitting element 10.
Figure 87:
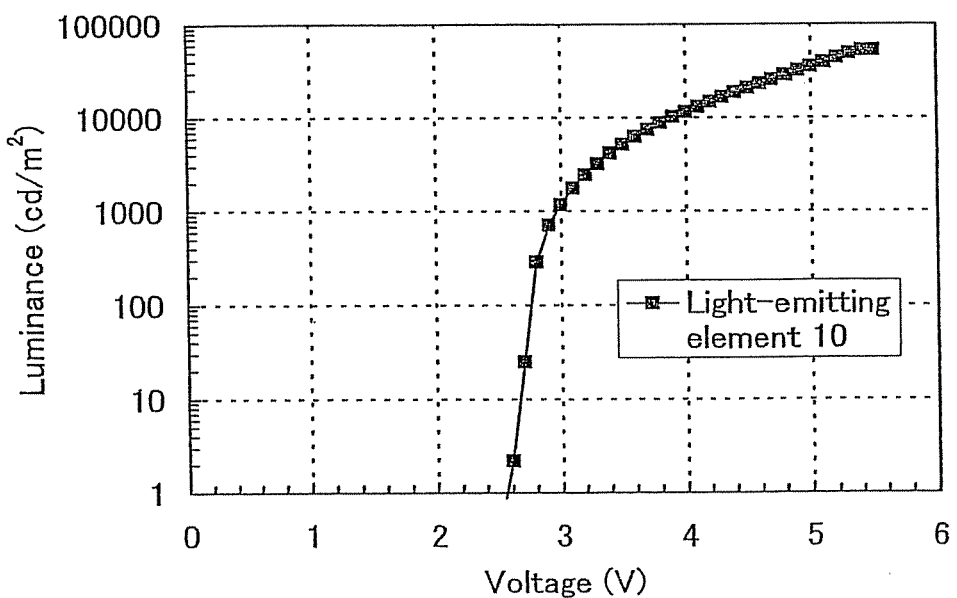
FIG. 87 shows the voltage-luminance characteristic of light-emitting element 10.
Figure 88:
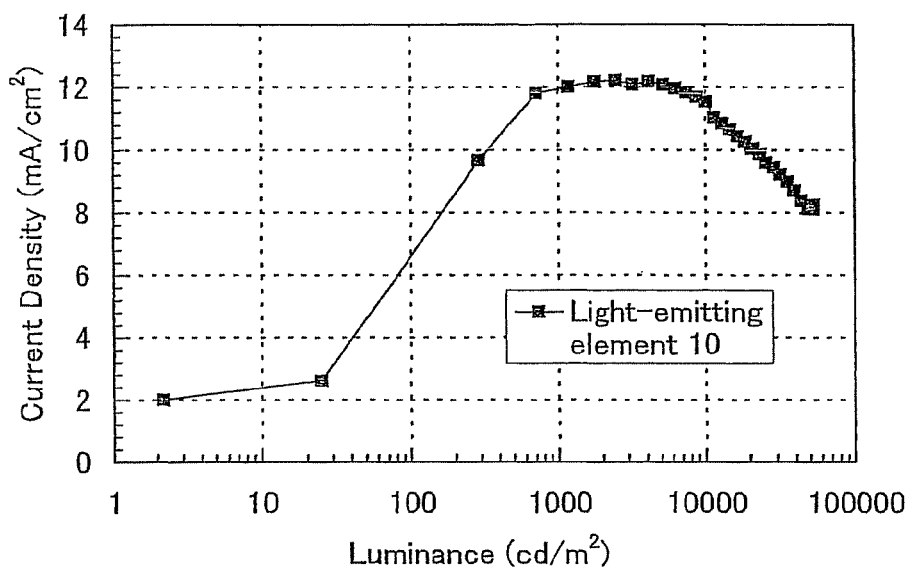
FIG. 88 shows the luminance-current efficiency characteristic of light-emitting element 10.
Figure 89:
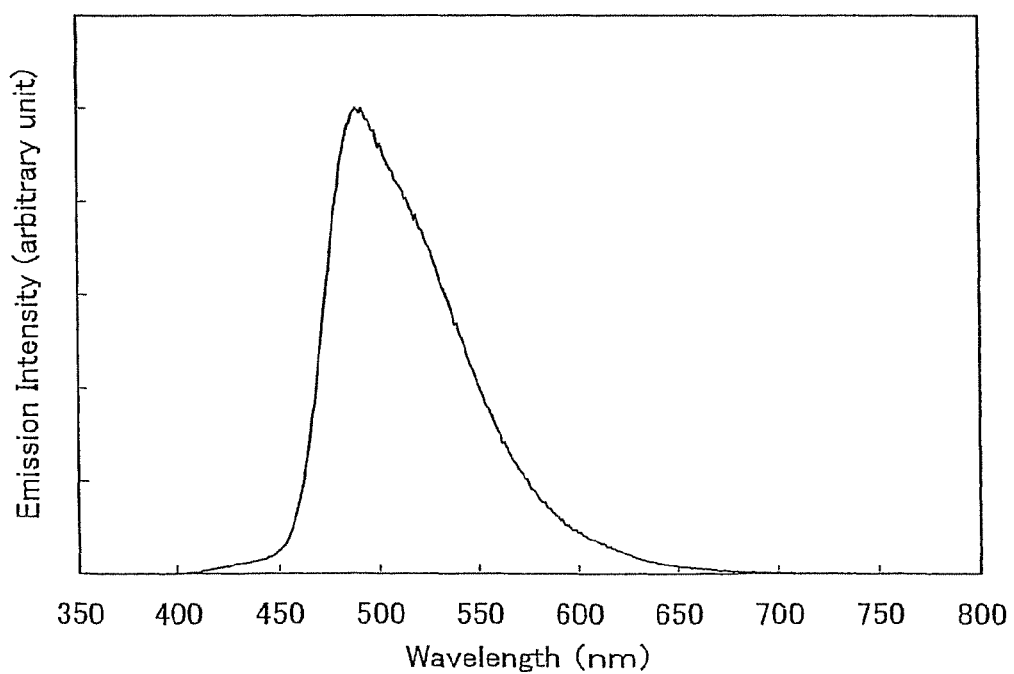
FIG. 89 shows the emission spectrum of light-emitting element 10.

A current density-luminance characteristic, a voltage-luminance characteristic, and a luminance-current efficiency characteristic of the light-emitting element 10 are shown in FIGS. 86, 87, and 88, respectively. Also, the emission spectrum which was obtained at a current of 1 mA is illustrated in FIG. 89. A CIE chromaticity coordinate of the light-emitting element 10 at luminance of 3000 cd/m² was (x=0.21, y=0.49), and light emission was blue green. Current efficiency at luminance of 3000 cd/m² was 12.1 cd/A, meaning that high current efficiency was exhibited. The power efficiency at luminance of 3000 cd/m² was 11.6 lm/W, indicating that the element 10 can be operated at low power consumption. In addition, as shown in FIG. 89, maximum emission wavelength at a current of 1 mA was 492 nm.

Embodiment 7

In this embodiment, a synthetic method of 2-[N-(1-naphthyl)-N-(9-phenylcarbazol-3-yl)-amino]-9,10-diphenylanthracene (abbreviation: 2PCNPA), which is the anthracene derivative of the present invention represented by Structural Formula (219), is specifically described.

(219)

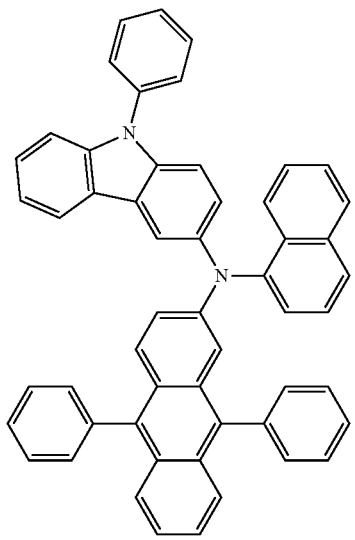

[Step 1] Synthesis of N-(1-naphthyl)-N-(9-phenyl-carbazol-3-yl)amine (abbreviation: PCN)

A synthetic scheme of N-(1-naphthyl)-N-(9-phenylcarbazol-3-yl)amine (abbreviation: PCN) is shown in (C-16).

(C-16)

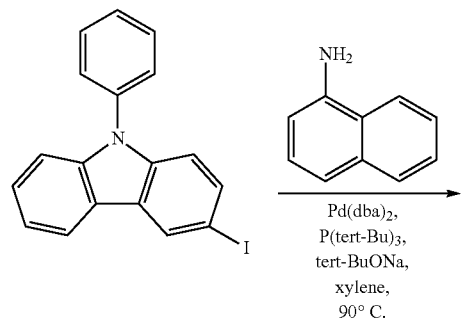

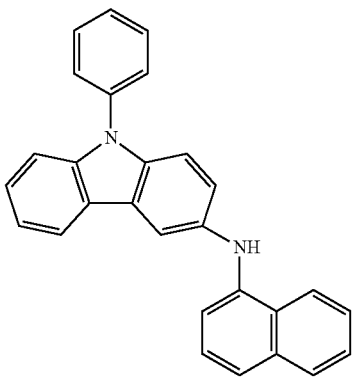

3.7 g (10 mmol) of 3-iodine-9-phenylcarbazole, 1.6 g (5 mmol) of 1-aminonaphthalene, 60 mg (0.1 mmol) of bis(dibenzylideneacetone)palladium (0), 0.2 mL (0.5 mmol) of tri(tert-butyl)phosphine (10 t % hexane solution), and 3.0 g (30 mmol) of sodium tert-butoxide were put into a 100 mL three-neck flask, and after nitrogen substitution was carried out in the flask, 12 mL of dehydrated xylene was added to the mixture. The reaction mixture was stirred for 7 hours at 90° C. under nitrogen. After the reaction was completed, about 200 mL of hot toluene was added to the reaction mixture, and the mixture was filtered through Florisil, alumina, and celite. The obtained filtrate was concentrated, and this concentrated solution was purified by silica gel column chromatography (eluting solvent was toluene:hexane=1:1). Recrystallization of the obtained solid with a mixed solvent of ethyl acetate and hexane gave 1.5 g of N-(1-naphthyl)-N-(9-phenylcarbazol-3-yl)amine as light brown powder in 79% yield. It was confirmed by a nuclear magnetic resonance measurement (NMR) that this compound was N-(1-naphthyl)-N-(9-phenylcarbazol-3-yl)amine (abbreviation: PCN).

¹H NMR data of this compound is shown below. ¹H NMR (300 MHz, DMSO-$d_6$): δ=7.13-7.71 (m, 15H), 7.85-7.88 (m, 1H), 8.03 (s, 1H), 8.15 (d, J=7.8 Hz, 1H), 8.24 (s, 1H), 8.36-8.39 (m, 1H).

[Step 2] Synthesis of 2PCNPA

A synthetic scheme of 2PCNPA is shown in (C-17).

(C-17)

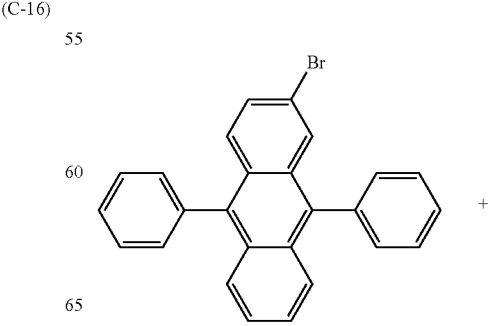

-continued

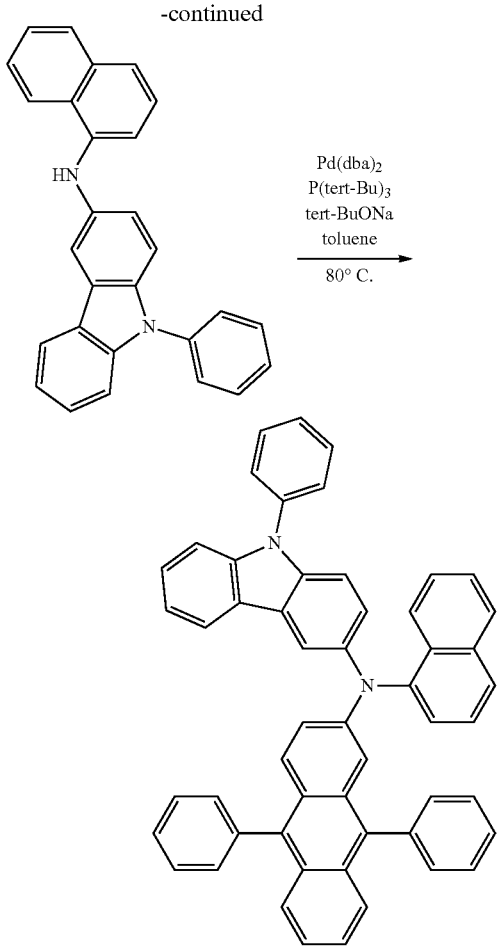

3.5 g (8.6 mmol) of 2-bromo-9,10-diphenylanthracene synthesized in Step 1 of Embodiment 1, 3.2 g (9.4 mmol) of N-(1-naphthyl)-N-(9-phenylcarbazol-3-yl)amine (abbreviation: PCN), 0.25 g (0.43 mmol) of bis(benzylideneacetone) palladium (0), and 2.1 g (21 mmol) of sodium tert-butoxide were put in a 200 mL three-neck flask, and the atmosphere of the flask was substituted with nitrogen. Thereafter, 50 mL of toluene and 0.86 g (0.43 mmol) of tri(tert-butyl)phosphine (10% hexane solution) were added to the mixture, and this reaction mixture was stirred for 5 hours at 80° C. After the reaction was completed, the reaction solution was washed with water, and the aqueous layer was extracted with ethyl acetate. The extracted solution was combined with the organic layer, and then dried with magnesium sulfate. After drying, this mixture was subjected to suction filtration, and the filtrate was concentrated. The obtained residue was purified by silica gel column chromatography (eluent:toluene). The obtained solid was recrystallized with a mixed solvent of chloroform and hexane, giving 2.6 g of 2-[N-(1-naphthyl)-N-(9-phenylcarbazol-3-yl)-amino]-9,10-diphenylanthracene (abbreviation: 2PCNPA) as yellow powder in 42% yield. It was confirmed by a nuclear magnetic resonance measurement (NMR) that this compound was 2-[N-(1-naphthyl)-N-(9-phenylcarbazol-3-yl)-amino]-9,10-diphenylanthracene (abbreviation: 2PCNPA).

Figure 90A:
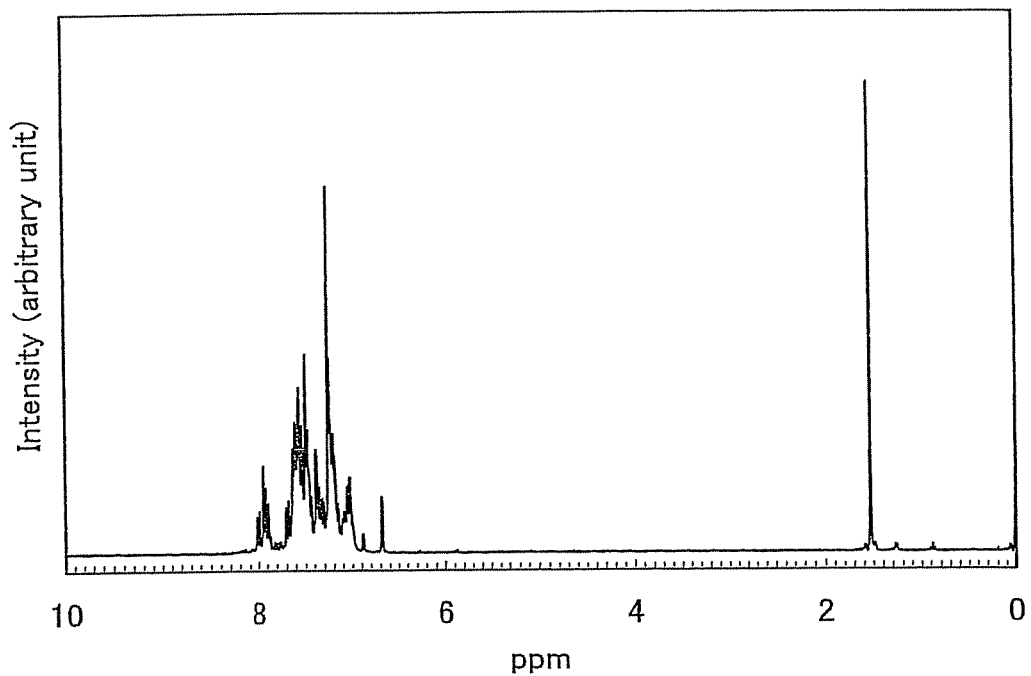
FIGS. 90A and 90B each show the $^1$H NMR chart of 2-[N-(1-naphthyl)-N-(9-phenylcarbazol-3-yl)-amino]-9,10-diphenylanthracene (abbreviation: 2PCNPA)
Figure 90B:
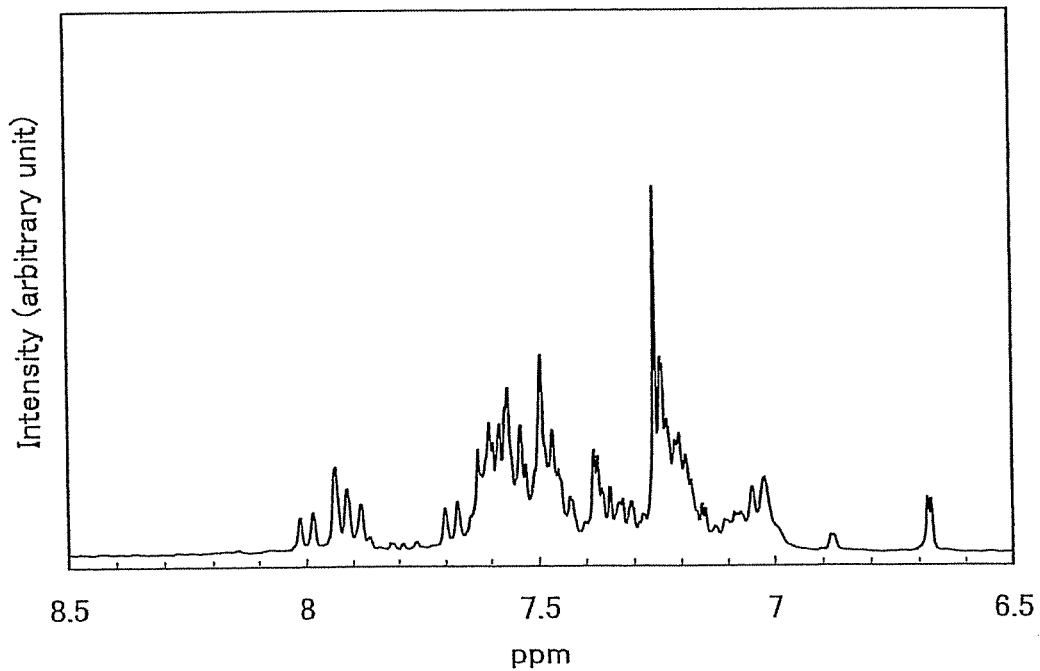

$^1$H NMR data of this compound is shown below. $^1$H NMR (CDCl$_3$, 300 MHz): δ=6.67-6.68 (m, 1H), 7.02-7.38 (m, 15H), 7.44-7.70 (m, 16H), 7.88-8.01 (m, 4H). The $^1$H NMR chart is shown in each of FIGS. 90A and 90B. Note that the range of 6.5 ppm to 8.5 ppm in FIG. 90A was expanded and shown in FIG. 90B.

Thermogravimetric/differential thermal analysis (TG-DTA) of 2PCNPA was carried out. In measuring, a high vacuum differential type differential thermal balance (type DTA2410SA, manufactured by Bruker AXS K.K.) was used. When measuring was carried out tinder reduced pressure of 10 Pa, it was found that the 5% weight-loss temperature was 289° C., which is indicative of high thermal stability of 2PCNPA.

Figure 91:
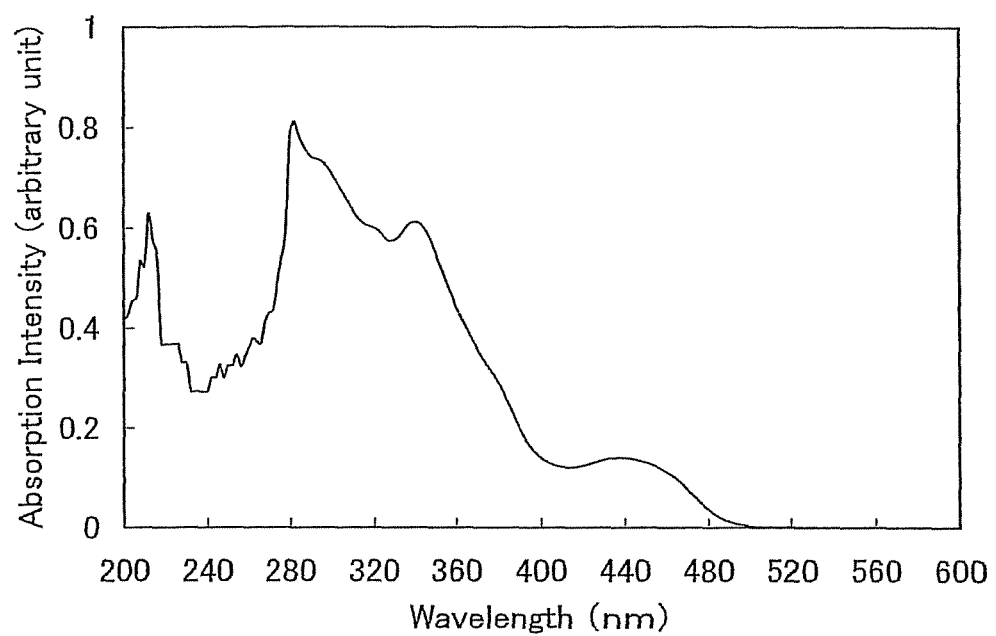
FIG. 91 shows the absorption spectrum of a toluene solution of 2-[N-(1-naphthyl)-N-(9-phenylcarbazol-3-yl)-amino]-9,10-diphenylanthracene (abbreviation: 2PCNPA)
Figure 92:
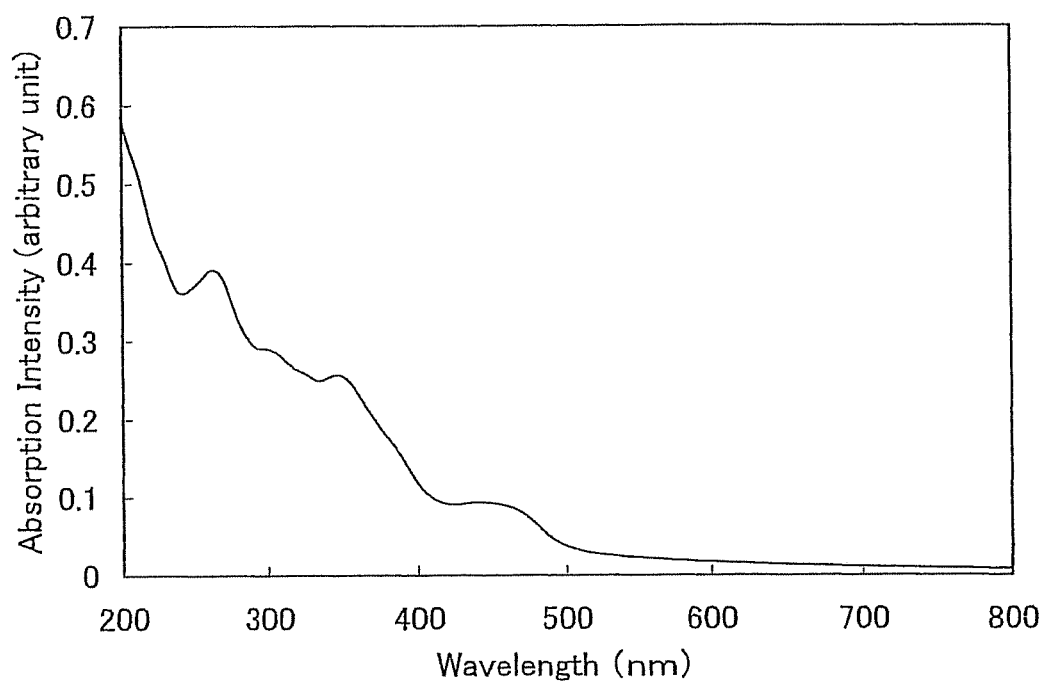
FIG. 92 shows the absorption spectrum of a thin film of 2-[N-(1-naphthyl)-N-(9-phenylcarbazol-3-yl)-amino]-9,10-diphenylanthracene (abbreviation: 2PCNPA)
Figure 93:
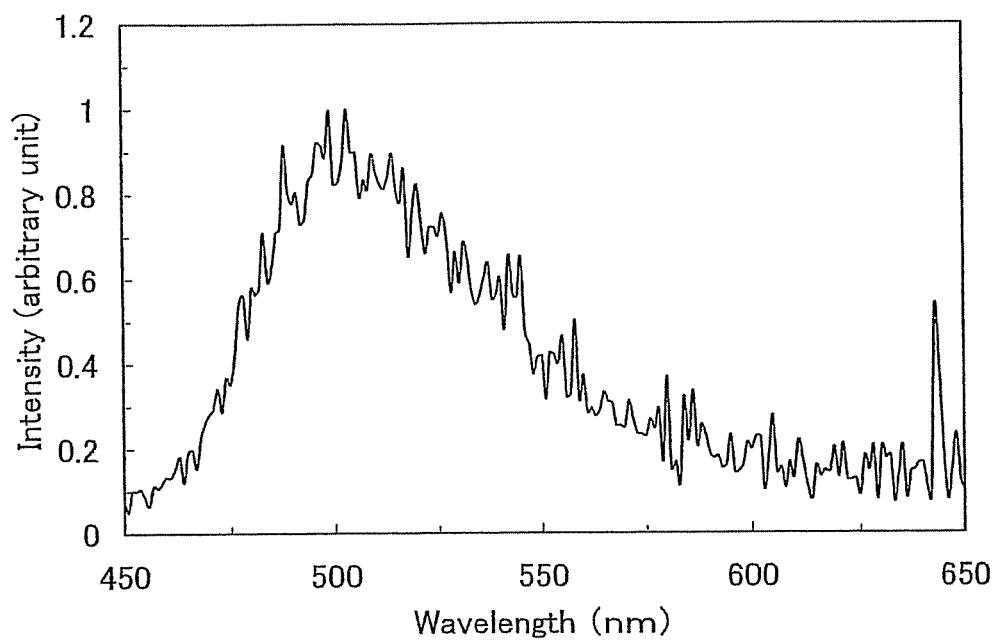
FIG. 93 shows the emission spectrum of a toluene solution of 2-[N-(1-naphthyl)-N-(9-phenylcarbazol-3-yl)-amino]-9,10-diphenylanthracene (abbreviation: 2PCNPA)
Figure 94:
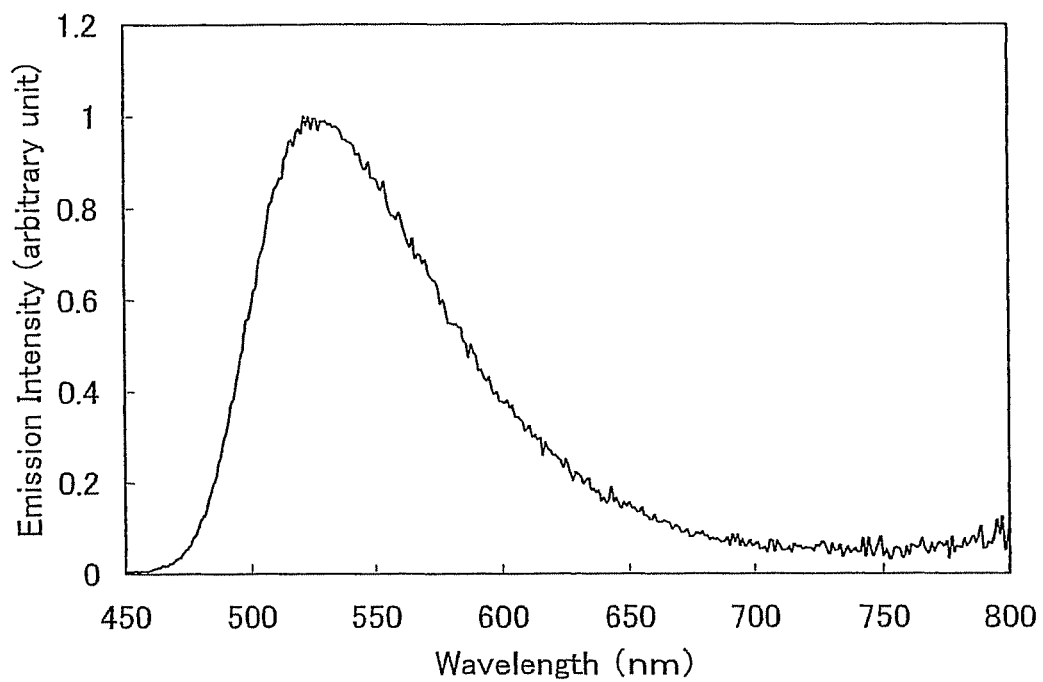
FIG. 94 shows the emission spectrum of a thin film of 2-[N-(1-naphthyl)-N-(9-phenylcarbazol-3-yl)-amino]-9,10-diphenylanthracene (abbreviation: 2PCNPA)

The absorption spectrum of a toluene solution of 2PCNPA is shown in FIG. 91. In addition, an absorption spectrum of a thin film of 2PCNPA is shown in FIG. 92. An ultraviolet-visible spectrophotometer (type V550, manufactured by Japan Spectroscopy Corporation) was used for measurement. The spectrum of the solution was measured in a quartz cell. The sample of the thin film was fabricated by vapor deposition of 2PCNPA over a quartz substrate. The absorption spectra of the solution and the thin film are shown in FIGS. 91 and 92, respectively, which were obtained by subtracting the spectrum of the quartz substrate from the corresponding raw spectra. In each of FIGS. 91 and 92, a horizontal axis shows wavelength (nm) and a vertical axis shows absorption intensity (an arbitrary unit). In the case of the toluene solution, absorption was observed at around 438 nm, and in the case of the thin film, absorption was observed at around 442 nm. Further, an emission spectrum of the toluene solution (excitation wavelength of 430 nm) of 2PCNPA is shown in FIG. 93, and an emission spectrum of the thin film (excitation wavelength of 442 nm) of 2PCNPA is shown in FIG. 94. In each of FIGS. 93 and 94, a horizontal axis shows wavelength (nm) and a vertical axis shows emission intensity (an arbitrary unit). In the case of the toluene solution, the maximum emission wavelength was 503 nm (excitation wavelength of 445 nm), and in the case of the thin film, the maximum emission wavelength was 522 nm (excitation wavelength of 430 nm).

The HOMO level of 2PCNPA in a thin film state which was measured by a photoelectron spectrometer (AC-2, manufactured by Riken Keiki Co., Ltd.) under air was −5.21 eV. By the absorption edge obtained from a Tauc plot of the absorption spectrum of the thin film shown in FIG. 92, the optical energy gap was estimated to be 2.48 eV, which means that LUMO level of 2PCNPA is −2.73 eV.

An oxidation-reduction characteristic of 2PCNPA was explored by a cyclic voltammetry (CV) measurement. For the measurement, an electrochemical analyzer (ALS model 600A, manufactured by BAS Inc.) was used.

As for a solution used in the CV measurement, dehydrated N,N-dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), a supporting electrolyte, was dissolved in DMF at the concentration of 100 mmol/L to prepare the electrolysis solution. The sample solution was prepared by dissolving the sample in the electrolysis solution at a concentration of 1 mmol/L. A platinum electrode (a PTE platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

An oxidation characteristic of 2PCNPA was evaluated in the following manner. The potential of the working electrode with respect to a reference electrode was swept from −0.40 V to 0.60 V, which was followed by sweeping the potential from 0.60 V to −0.40 V. This cycle was set as one cycle, and 100 cycles were performed. Also, a reduction characteristic of 2PCNPA was evaluated in the following manner. The potential of the working electrode with respect to the reference electrode was swept from −0.15 V to −2.55 V, which was followed by sweeping the potential from −2.55 V to −0.15 V. This cycle was set as one cycle, and 100 cycles were performed. Sweeping speed of the CV measurement was set to be 0.1 V/s.

Figure 95:
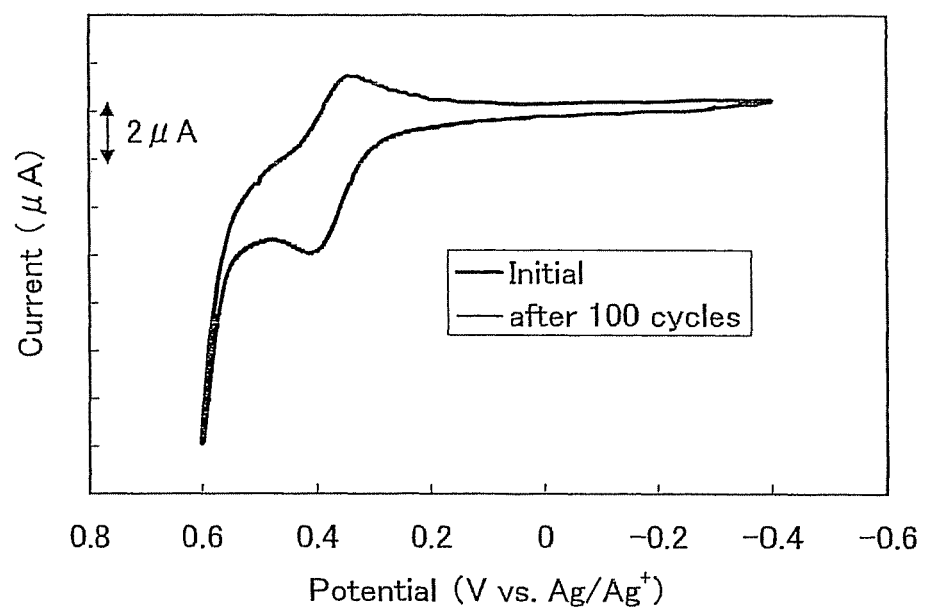
FIG. 95 shows the result of a CV measurement of 2-[N-(1-naphthyl)-N-(9-phenylcarbazol-3-yl)-amino]-9,10-diphenylanthracene (abbreviation: 2PCNPA)
Figure 96:
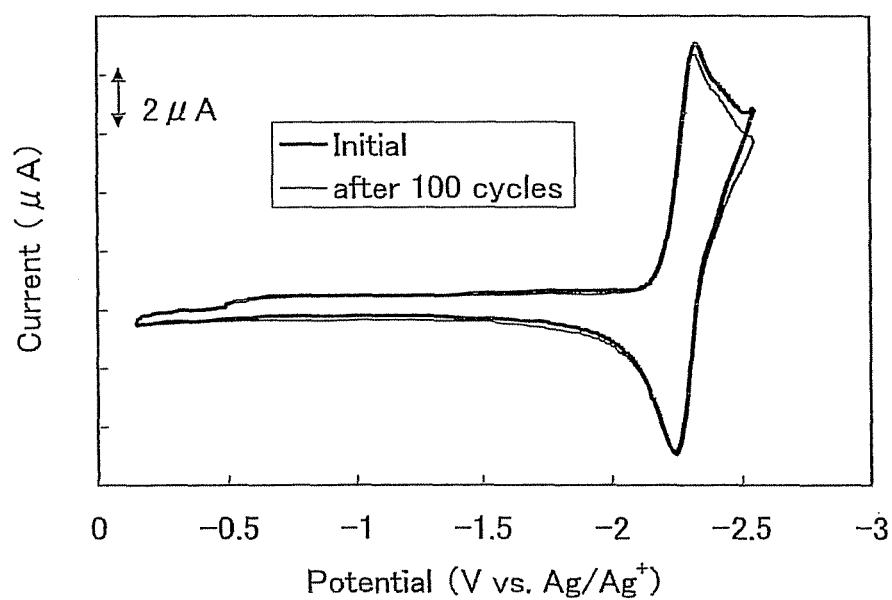
FIG. 96 shows the result of a CV measurement of 2-[N-(1-naphthyl)-N-(9-phenylcarbazol-3-yl)-amino]-9,10-diphenylanthracene (abbreviation: 2PCNPA)

The results of the CV measurement of the oxidation side and reduction side of 2PCNPA are shown in FIGS. 95 and 96, respectively. In each of FIGS. 95 and 96, a horizontal axis shows a voltage (V) of the working electrode with respect to the reference electrode, and a vertical axis shows a current value (μA) that flowed between the working electrode and the counter electrode. From FIG. 95, a current exhibiting oxidation was observed around 0.41 V (vs. Ag/Ag$^+$). Also, from FIG. 96, a current exhibiting reduction was observed around −2.33 V (vs. Ag/Ag$^+$).

In spite of the fact that 100 cycles of sweeping were repeated, a peak position and a peak intensity at the CV curve scarcely changed in the oxidation and reduction, which reveals that the anthracene derivative of the present invention is extremely stable against repetition of the oxidation and reduction.

Embodiment 8

In this embodiment, a synthetic method of 2-{N-(1-naphthyl)-N-[9-(1-naphthyl)carbazol-3-yl]amino}-9,10-diphenylanthracene (abbreviation: 2NCNPA), which is the anthracene derivative of the present invention represented by Structural Formula (220), is specifically described.

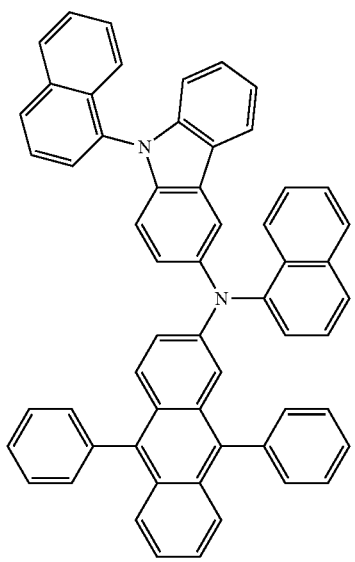

(220)

[Step 1] Synthesis of N,9-di(1-naphthyl)-9H-carbazole-3-amine (abbreviation: NCN)

(i) Synthesis of 9-(1-naphthyl)carbazole

A synthetic scheme of 9-(1-naphthyl)carbazole is shown in (C-18).

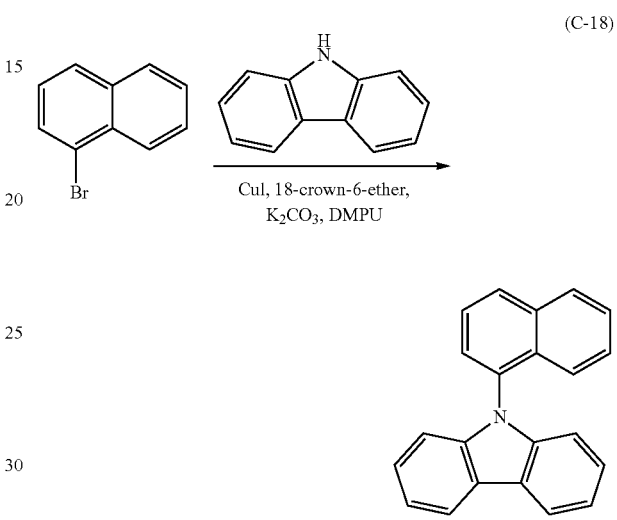

(C-18)

21 g (0.1 mol) of 1-bromonaphthalene, 17 g (0.1 mol) of carbazole, 950 mg (5 mmol) of copper iodide (I), 33 g (240 mmol) of potassium carbonate, and 660 mg (2.5 mmol) of 18-crown-6-ether were put into a 500 mL three-neck flask, and nitrogen substitution was carried out in the flask. To this mixture was added 80 mL of 1,3-dimethyl-3,4,5,6-tetrahydro-2(1H)-pyrimidinone (abbreviation: DMPU), which was followed by stirring for 6 hours at 170° C. under nitrogen. To this reaction mixture was further added 10 g (50 mmol) of 1-bromonaphthalene, 2.0 g (10 mmol) of copper iodide (I), and 2.6 g (10 mmol) of 18-crown-6-ether, and stirring was further conducted for 7.5 hours at 170° C. Furthermore, to this reaction mixture was added 10 g (50 mmol) of 1-bromonaphthalene, and additional stirring was carried out for 6 hours at 180° C. After the reaction was completed, to this reaction mixture was added about 200 mL of toluene and about 100 of 1 mol/L hydrochloric acid, and then the mixture was filtered through celite. The obtained filtrate was filtered through Florisil and celite. The obtained filtrate was separated into an organic layer and an aqueous layer, and after this organic layer was washed with 1 mol/L hydrochloric acid and then with water, the organic layer was dried over magnesium sulfate. This suspension was filtered through Florisil and celite. The filtrate was concentrated to give an oily substrate, and methanol was added to this oily substrate, followed by irradiation with ultrasound to precipitate a solid. The solid precipitated was collected by suction filtration, giving 22 g of 9-(1-naphthyl)carbazole as white powder (75% yield). The Rf values (SiO$_2$, eluent; hexane:ethyl acetate=10:1) of 9-(1- naphthyl)carbazole, 1-bromonaphthalene, and carbazole were 0.61, 0.74, and 0.24, respectively.

(ii) Synthesis of 3-bromo-9-(1-naphthyl)carbazole

A synthetic scheme of 3-bromo-9-(1-naphthyl)carbazole is shown in (C-19).

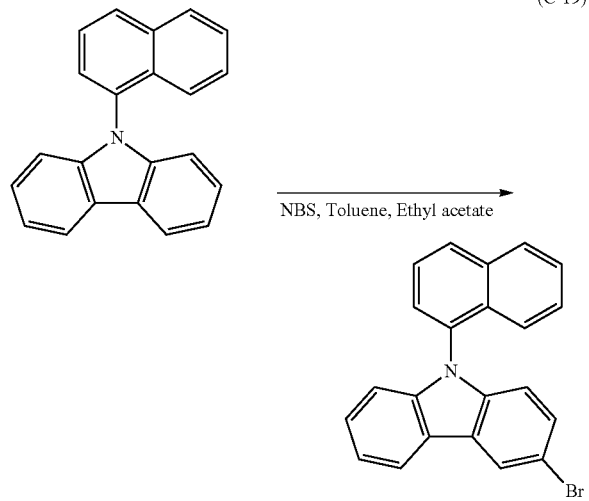

(C-19)

5.9 g (20 mmol) of 9-(1-naphthyl)carbazole was put into a 500 mL Meyer flask, and 50 mL of ethyl acetate and 50 mL of toluene were added thereto, and the reaction mixture was stirred. Then, 3.6 g (20 mmol) of N-bromosuccinimide was slowly added to the solution, and the solution was stirred for about 170 hours (one week) at room temperature. After this solution was washed with water, the organic layer was dried with magnesium sulfate. Filtration and concentration of the reaction mixture gave 7.4 g of 3-bromo-9-(1-naphthyl)carbazole as white powder (99% yield). The Rf values (SiO₂, eluent; hexane:ethyl acetate=2:1) of 3-bromo-9-(1-naphthyl)carbazole and 9-(1-naphthyl)carbazole were 0.43 and 0.35, respectively.

(iii) Synthesis of N,9-di(1-naphthyl)-9H-carbazole-3-amine (abbreviation: NCN)

A synthetic scheme of N,9-di(1-naphthyl)-9H-carbazole-3-amine (abbreviation NCN) is shown in (C-20).

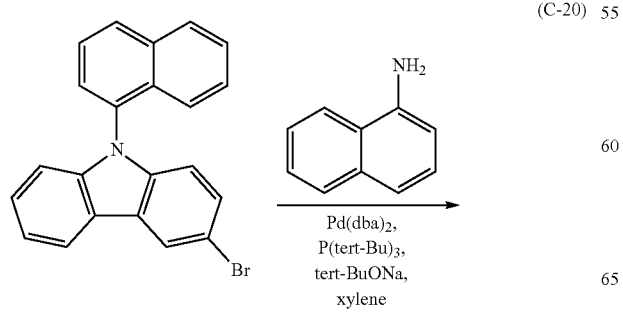

(C-20)

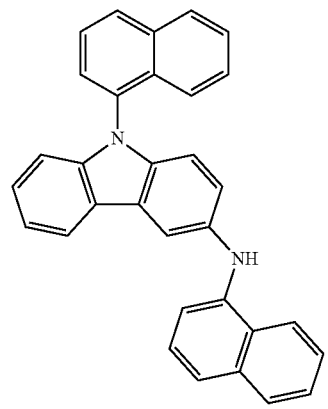

3.7 g (10 mmol) of 3-bromo-9-(1-naphthyl)carbazole, 1.7 g (12 mmol) of 1-naphthylamine, 58 mg (0.1 mmol) of bis(dibenzylideneacetone)palladium (0), 600 μL (0.3 mmol) of tri(tert-butyl)phosphine (10% hexane solution), and 1.5 g (15 mmol) of sodium tert-butoxide were put into a 100 mL three-neck flask, and nitrogen substitution was carried out in a flask. Thereafter, 20 mL of dehydrated xylene was added to this mixture. Then, this reaction mixture was heated and stirred for 7 hours at 110° C. under nitrogen. After the reaction was completed, about 400 mL of toluene was added to this reaction mixture, and the mixture was filtered through Florisil, alumina and then celite. After the obtained filtrate was washed with water, the organic layer was dried with magnesium sulfate. This suspension was filtered through Florisil, alumina, and then celite, and the obtained filtrate was concentrated. The resulting solid was purified by silica gel column chromatography (toluene:hexane=1:1) to give 2.2 g of light brown powder (51% yield). It was confirmed by a nuclear magnetic resonance measurement (NMR) that this light brown powder was N,9-di(1-naphthyl)-9H-carbazole-3-amine (abbreviation: NCN). Rf values (SiO₂, eluent; hexane:ethyl acetate=5:1) of N,9-di(1-naphthyl)-9H-carbazole-3-amine, 3-bromo-9-(1-naphthyl)carbazole, and 1-naphthylamine were 0.46, 0.68, and 0.22, respectively.

[Step 2] Synthesis of 2NCNPA

A synthetic scheme of 2NCNPA is shown in (C-21).

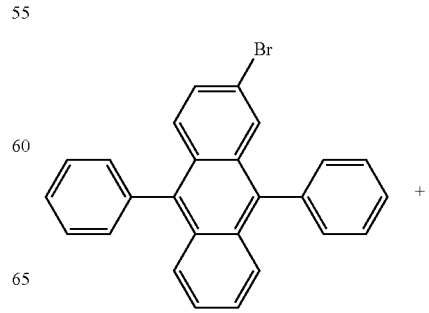

-continued

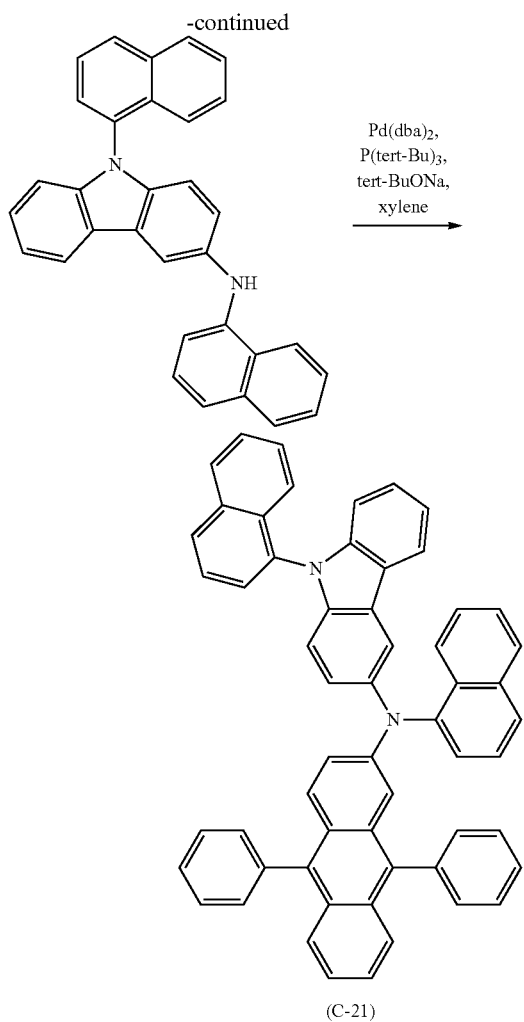

(C-21)

2.1 g (5.0 mmol) of 2-bromo-9,10-diphenylanthracene, 2.2 g (5.1 mmol) of NCN, 29 g (50 µmol) of bis(dibenzylideneacetone)palladium (0), 300 µL (0.2 mmol) of tri(tert-butyl)phosphine (10% hexane solution), and 1.0 g (10 mmol) of sodium tert-butoxide were put into a 100 mL three-neck flask, and nitrogen substitution was carried out in the flask. Thereafter, 20 mL of dehydrated xylene was added to this mixture. Then, this reaction mixture was heated and stirred for 4 hours at 110° C. under nitrogen. After the reaction was completed, about 300 mL of toluene was added to this reaction mixture, and this mixture was filtered through Florisil, alumina, and then celite. After the obtained filtrate was washed with water, the organic layer was dried with magnesium sulfate. This suspension was filtered through Florisil, alumina, and then celite, and the resulting filtrate was concentrated. The obtained solid was purified by silica gel column chromatography (toluene:hexane=1:1). To the oily residue obtained was added hexane, and the mixture was then irradiated with ultrasound to precipitate a solid. This solid was collected by suction filtration, giving 1.1 g of the target compound as yellow-green powder (29% yield). It was confirmed by a nuclear magnetic resonance measurement (NMR) that this yellow-green powder was 2-{N-(1-naphthyl)-N-[9-(1-naphthyl)carbazol-3-yl]amino}-9,10-diphenylanthracene (abbreviation: 2NCNPA).

Figure 97A:
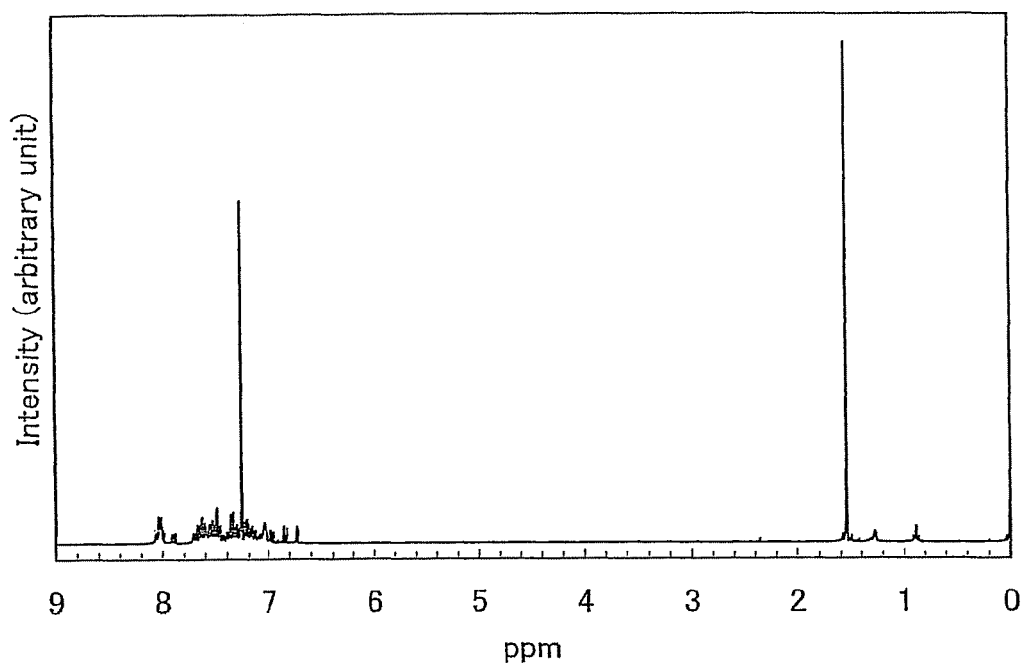
FIGS. 97A and 97B each show the $^1$H NMR chart of 2-{N-(1-naphthyl)-N-[9-(1-naphthyl)carbazol-3-yl]amino}-9,10-diphenylanthracene (abbreviation: 2NCNPA)
Figure 97B:
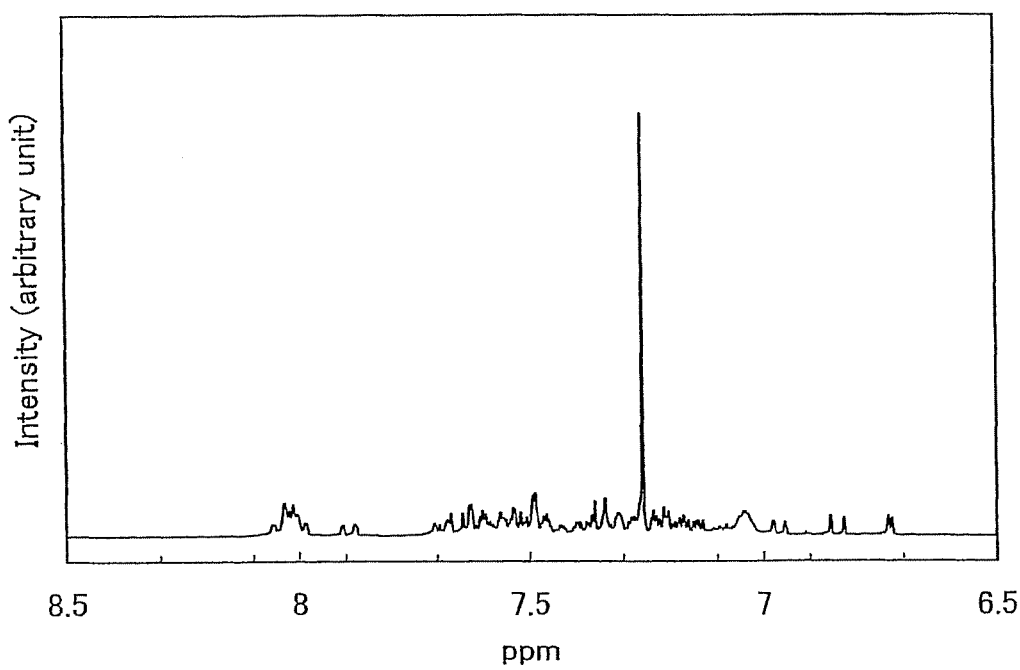

$^1$H NMR data of this compound is shown below. $^1$H NMR (300 MHz, CDCl$_3$): δ=6.73 (d, J=2.4 Hz, 1H), 6.84 (d, J=8.7 Hz, 1H), 6.96 (d, J=8.1 Hz, 1H), 7.04-7.70 (m, 29H), 7.89 (d, J=7.8 Hz, 1H), 7.99-8.06 (m, 5H). The $^1$H NMR chart is shown in each of FIGS. 97A and 97B. Note that the range of 6.5 ppm to 8.5 ppm in FIG. 97A is expanded and shown in FIG. 97B.

Figure 98:
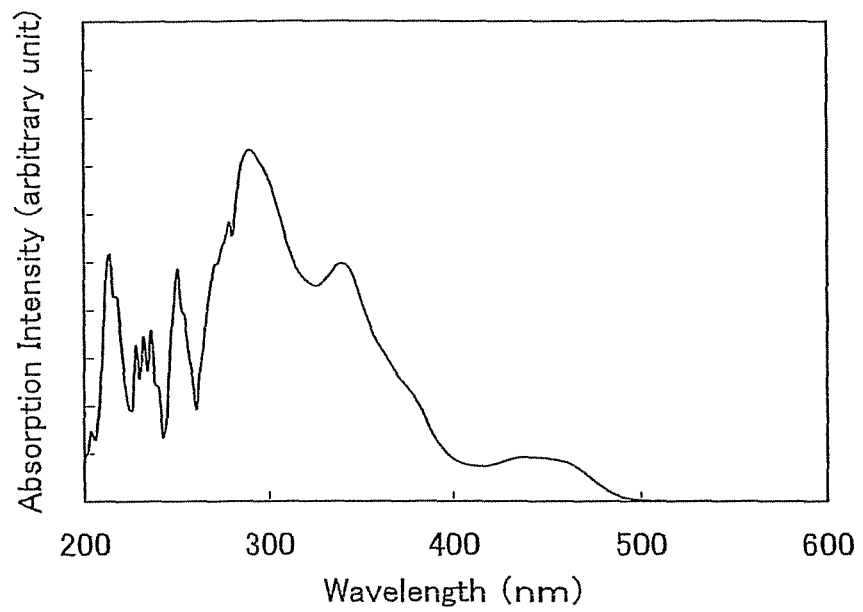
FIG. 98 shows the absorption spectrum of a toluene solution of 2-{N-(1-naphthyl)-N-[9-(1-naphthyl)carbazol-3-yl]amino}-9,10-diphenylanthracene (abbreviation: 2NCNPA)
Figure 99:
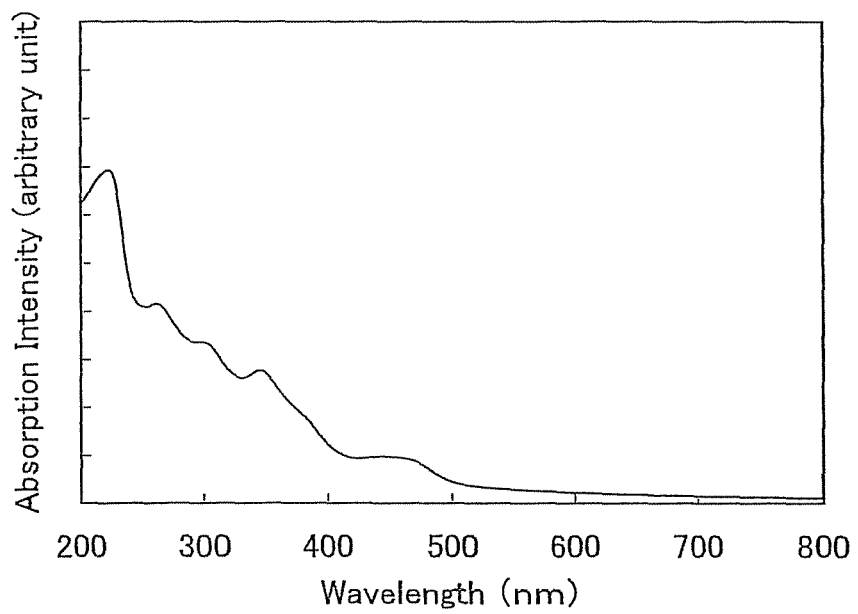
FIG. 99 shows the absorption spectrum of a thin film of 2-{N-(1-naphthyl)-N-[9-(1-naphthyl)carbazol-3-yl]amino}-9,10-diphenylanthracene (abbreviation: 2NCNPA)
Figure 100:
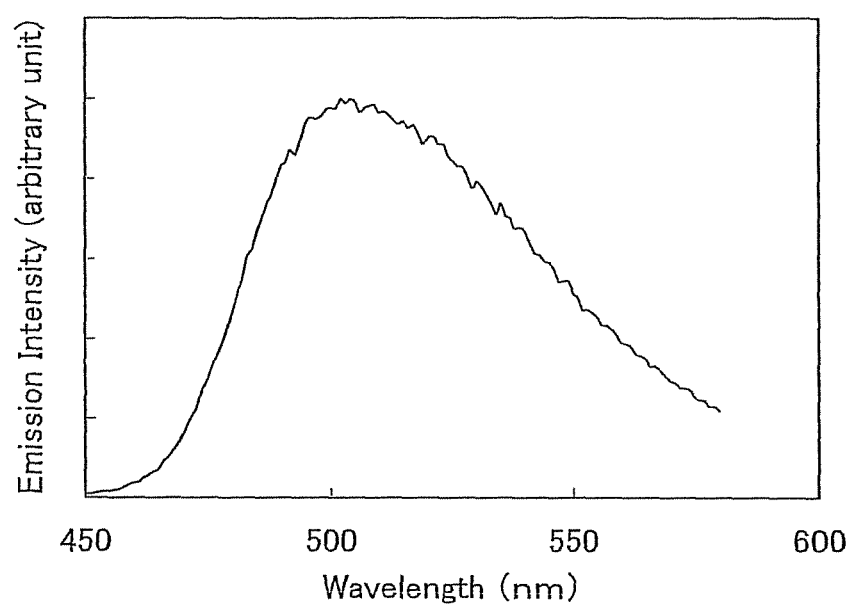
FIG. 100 shows the emission spectrum of a toluene solution of 2-{N-(1-naphthyl)-N-[9-(1-naphthyl)carbazol-3-yl]amino}-9,10-diphenylanthracene (abbreviation: 2NCNPA)
Figure 101:
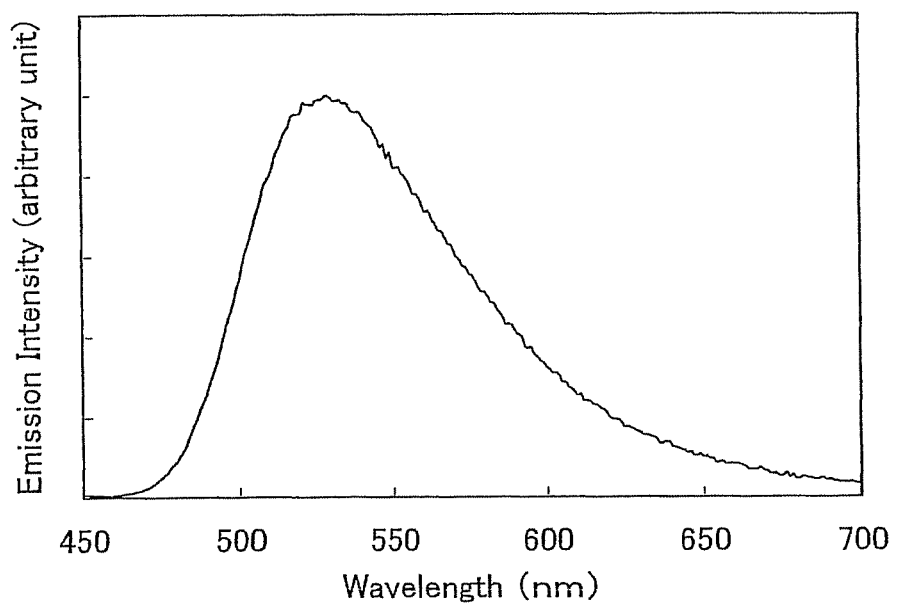
FIG. 101 shows the emission spectrum of a thin film of 2-{N-(1-naphthyl)-N-[9-(1-naphthyl)carbazol-3-yl]amino}-9,10-diphenylanthracene (abbreviation: 2NCNPA)

The absorption spectrum of a toluene solution of 2NCNPA is shown in FIG. 98. In addition, an absorption spectrum of a thin film of 2NCNPA is shown in FIG. 99. An ultraviolet-visible spectrophotometer (type V550, manufactured by Japan Spectroscopy Corporation) was used for measurement. The spectrum of the solution was measured in a quartz cell. The sample of the thin film was fabricated by vapor deposition of 2NCNPA over a quartz substrate. The absorption spectra of the solution and the thin film are shown in FIGS. 98 and 99, respectively, which were obtained by subtracting the spectrum of the quartz substrate from the corresponding raw spectra. In each of FIGS. 98 and 99, a horizontal axis shows wavelength (nm) and a vertical axis shows absorption intensity (an arbitrary unit). In the case of the toluene solution, absorption was observed at around 448 nm, and in the case of the thin film, absorption was observed at around 465 nm. Further, an emission spectrum of the toluene solution (excitation wavelength of 300 nm) of 2NCNPA is shown in FIG. 100, and an emission spectrum of the thin film (excitation wavelength of 446 nm) of 2NCNPA is shown in FIG. 101. In each of FIGS. 100 and 101, a horizontal axis shows wavelength (nm) and a vertical axis shows emission intensity (an arbitrary unit). In the case of the toluene solution, the maximum emission wavelength was 505 nm (excitation wavelength of 300 mu), and in the case of the thin film, the maximum emission wavelength was 529 nm (excitation wavelength of 446 nm).

The HOMO level of 2NCNPA in a thin film state which was measured by a photoelectron spectrometer (AC-2, manufactured by Riken Keiki Co., Ltd.) under air was −5.26 eV. By the absorption edge obtained from a Tauc plot of the absorption spectrum of the thin film shown in FIG. 99, the optical energy gap was estimated to be 2.47 eV, which means that LUMO level of 2NCNPA is −2.79 eV.

Thermogravimetric/differential thermal analysis (TG-DTA) of 2NCNPA was carried out. In measuring, a high vacuum differential type differential thermal balance (type DTA2410SA, manufactured by Bruker AXS K.K.) was used. When measuring was carried out under reduced pressure of 10 Pa, it was found that the 5% weight-loss temperature was 400° C., which is indicative of high thermal stability of 2NCNPA.

Further, a glass transition temperature was measured using a differential scanning calorimeter (DSC, manufactured by PerkinElmer, Inc., Pyris 1). First, a sample was heated to 300° C. at 40° C./min to melt the sample, and then cooled to room temperature at 10° C./min. Thereafter, the temperature was raised to 300° C. at 10° C./min. As a result, it was found that the glass transition temperature (T$_g$) of 2NCNPA was 174° C., which means that 2NCNPA has a high glass transition temperature.

An oxidation-reduction characteristic of 2NCNPA was explored by a cyclic voltammetry (CV) measurement. For the measurement, an electrochemical analyzer (ALS model 600A, manufactured by BAS Inc.) was used.

As for a solution used in the CV measurement, dehydrated N,N-dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), a supporting electrolyte, was dissolved in DMF at the concentration of 100 mmol/L to prepare the electrolysis solution. The sample solution was prepared by dissolving the sample in the electrolysis solution at a concentration of 1 mmol/L. A platinum electrode (a PTE, platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

An oxidation characteristic of 2NCNPA was evaluated in the following manner. The potential of the working electrode with respect to a reference electrode was swept from −0.07 V to 0.55 V, which was followed by sweeping the potential from 0.55 V to −0.07 V. This cycle was set as one cycle, and 100 cycles were performed. Also, a reduction characteristic of 2NCNPA was evaluated in the following manner. The potential of the working electrode with respect to the reference electrode was swept from −0.32 V to −2.45 V, which was followed by sweeping the potential from −2.45 V to −0.32 V. This cycle was set as one cycle, and 100 cycles were performed. Sweeping speed of the CV measurement was set to be 0.1 V/s.

Figure 110:
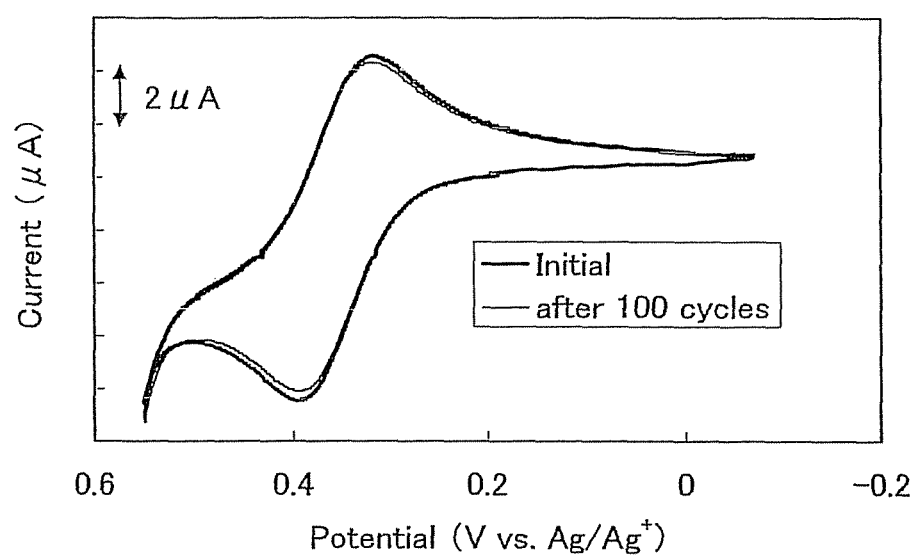
FIG. 110 shows the result of a CV measurement of 2-{N-(1-naphthyl)-N-[9-(1-naphthyl)carbazol-3-yl]amino}-9,10-diphenylanthracene (abbreviation: 2NCNPA)
Figure 111:
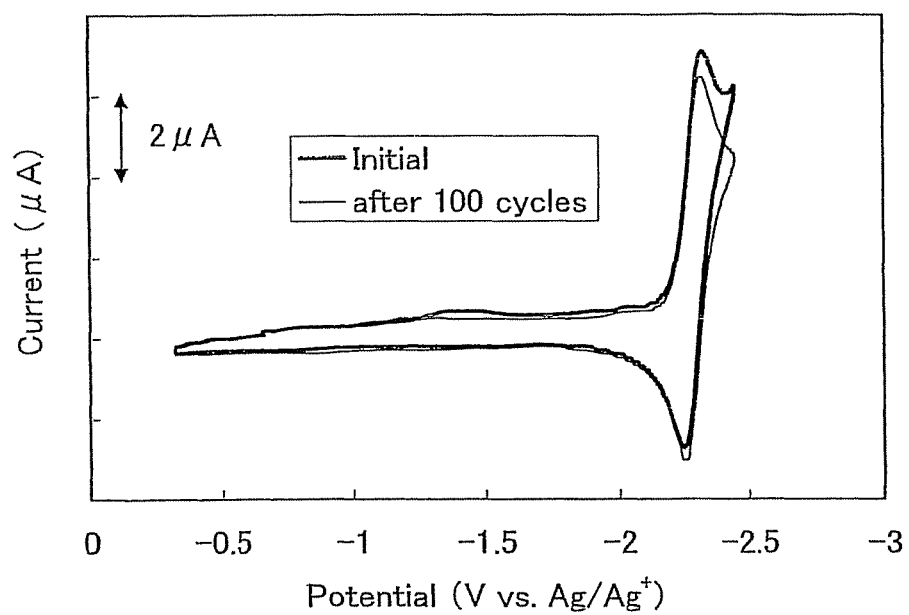
FIG. 111 shows the result of a CV measurement of 2-{N-(1-naphthyl)-N-[9-(1-naphthyl)carbazol-3-yl]amino}-9,10-diphenylanthracene (abbreviation: 2NCNPA)

The CV measurement result of the oxidation and reduction sides of 2NCNPA are shown in FIGS. 110 and 111, respectively. In each of FIGS. 110 and 111, a horizontal axis shows a voltage (V) of the working electrode with respect to the reference electrode, and a vertical axis shows a current value (μA) that flowed between the working electrode and the counter electrode. From FIG. 110, the current exhibiting oxidation was observed around 0.39 V (vs. Ag/Ag$^+$). Also, from FIG. 111, a current exhibiting reduction was observed around −2.32 V (vs. Ag/Ag$^+$).

In spite of the fact that 100 cycles of sweeping were repeated, a peak position and a peak intensity at the CV curve scarcely changed in the oxidation and reduction, which reveals that the anthracene derivative of the present invention is extremely stable against repetition of the oxidation and reduction.

Embodiment 9

In this embodiment, a light-emitting element of the present invention is described with reference to FIG. 10.

A manufacturing method of a light-emitting element of this embodiment is shown below.

First, a film of indium: tin oxide containing silicon oxide (ITSO) was formed by sputtering over the glass substrate 2101 to form the first electrode 2102. Note that the film thickness of the first electrode 2102 was 110 nm, and the area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing pressure of the vacuum evaporation apparatus to about 10$^{-4}$ Pa, the layer 2103 containing a composite material, which contains an organic compound and an inorganic compound, was formed over the first electrode 2102 by co-evaporating 4,4'-bis[N-(1-napthyl)-N-phenylamino]biphenyl (abbreviation: NPB) and molybdenum oxide (VI). The film thickness was to be 50 nm, and a ratio of NPB and molybdenum oxide (VI) was adjusted to be 4:1 (=NPB:molybdenum oxide) in weight ratio.

Subsequently, a film of 4,4'-bis[N-(1-napthyl)-N-phenylamino]biphenyl (abbreviation: NPB) was formed over the layer 2103 containing a composite material to have a thickness of 10 nm by the evaporation method using resistance heating system, thereby forming the hole transporting layer 2104.

Further, by co-evaporating 9-[4-(N-carbazolyl)]phenyl-10-phenylanthracene (abbreviation: CzPA) and 2-[N-(1-naphthyl)-N-(9-phenylcarbazol-3-yl)-amino]-9,10-diphenylanthracene (abbreviation: 2PCNPA), which is an anthracene derivative of the present invention represented by Structural Formula (219), the light-emitting layer 2105 with a thickness of 40 nm was formed over the hole transporting layer 2104. Here, a rate of evaporation was adjusted so that the weight ratio of CzPA and 2PCNPA was 1:0.05 (=CzPA:2PCNPA).

Thereafter, the electron transporting layer 2106 was formed over the light-emitting layer 2105 by forming a film of bathophenanthroline (abbreviation: BPhen) to have a film thickness of 30 nm by means of the evaporation using resistance heating system.

Further, the electron injecting layer 2107 was formed over the electron transporting layer 2106 by forming a film of lithium fluoride with a thickness of 1 nm.

Finally, by forming a film of aluminum as the second electrode 2108 with a film thickness of 200 nm over the electron injecting layer 2107 using the evaporation method by resistance heating system, a light-emitting element 11 was fabricated.

Figure 102:
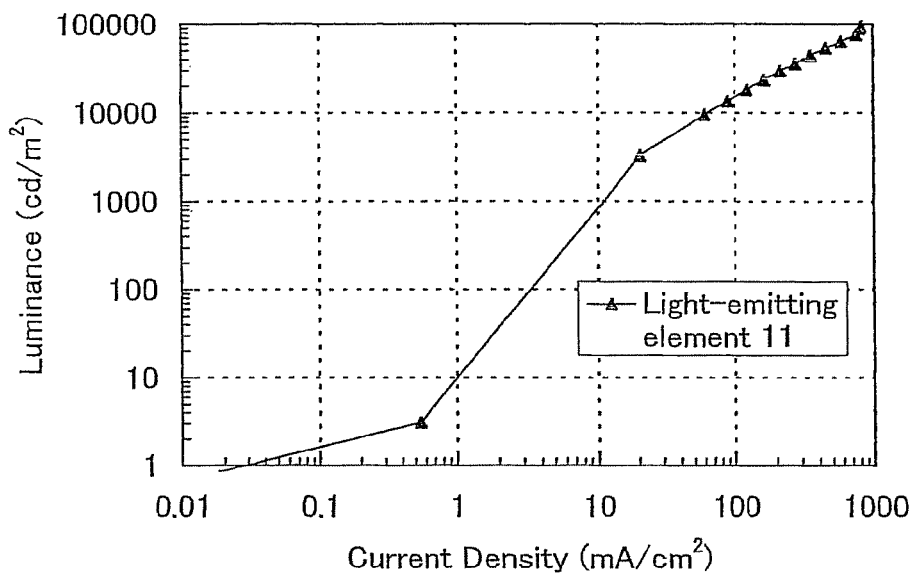
FIG. 102 shows the current density-luminance characteristic of light-emitting element 11.
Figure 103:
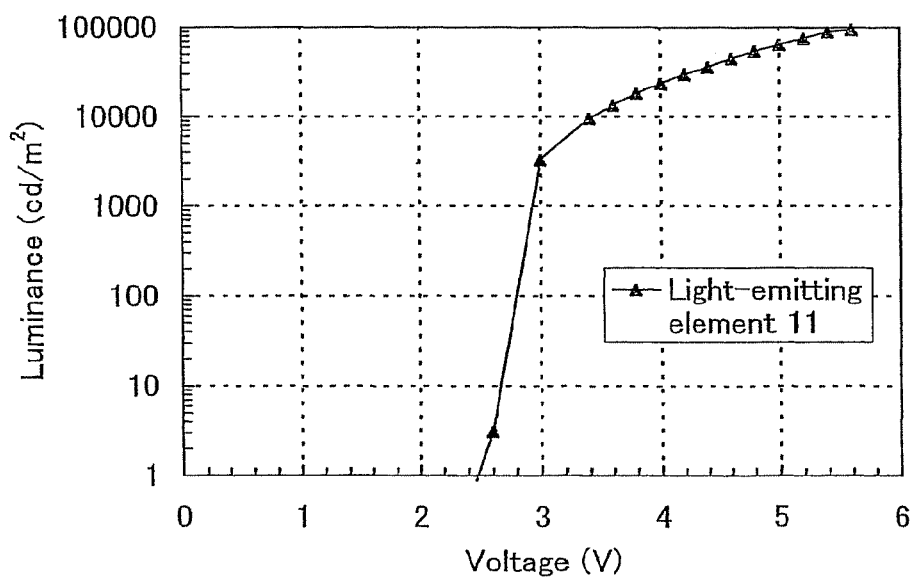
FIG. 103 shows the voltage-luminance characteristic of light-emitting element 11.
Figure 104:
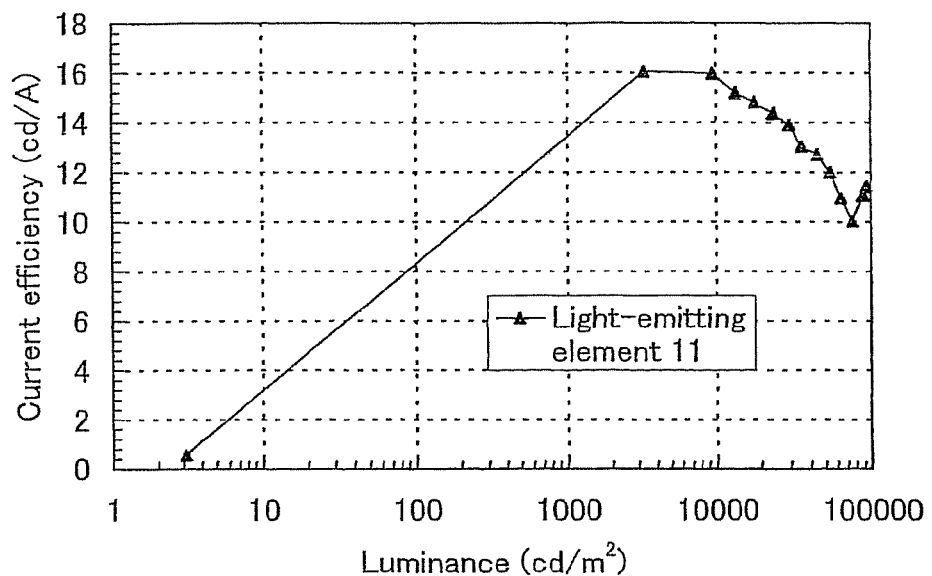
FIG. 104 shows the luminance-current efficiency characteristic of light-emitting element 11.
Figure 105:
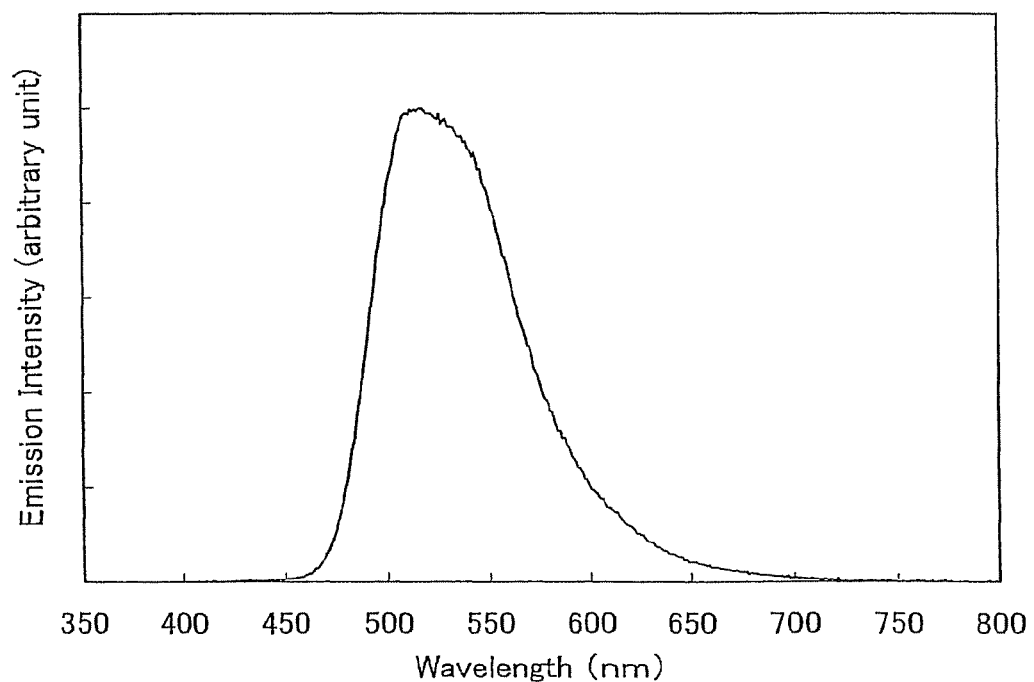
FIG. 105 shows the emission spectrum of light-emitting element 11.

A current density-luminance characteristic, a voltage-luminance characteristic, and a luminance-current efficiency characteristic of the light-emitting element 11 are shown in FIGS. 102, 103, and 104, respectively. Also, the emission spectrum which was obtained at a current of 1 mA is illustrated in FIG. 105. ACM chromaticity coordinate of the light-emitting element 11 at luminance of 3270 cd/m$^2$ was (x=027, y=0.62), and light emission was green. Current efficiency at luminance of 3270 cd/m$^2$ was 16.1 cd/A, meaning that high current efficiency was exhibited. In addition, as shown in FIG. 105, maximum emission wavelength at a current of 1 mA was 518 am.

Embodiment 10

In this embodiment, a light-emitting element of the present invention is described with reference to FIG. 10.

A fabrication method of a light-emitting element of this embodiment is shown below.

First, a film of indium tin oxide containing silicon oxide (ITSO) was formed by sputtering over the glass substrate 2101 to form the first electrode 2102. Note that the film thickness of the first electrode 2102 was 110 nm, and the area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing pressure of the vacuum evaporation apparatus to about 10$^{-4}$ Pa, the layer 2103 containing a composite material, which contains an organic compound and an inorganic compound, was formed over the first electrode 2102 by co-evaporating 4,4'-bis[N-(1-napthyl)-N-phenylamino]biphenyl (abbreviation: NPB) and molybdenum oxide (VI). The film thickness was to be 50 nm, and a ratio of NPB and molybdenum oxide (VI) was adjusted to be 4:1 (=NPB:molybdenum oxide) in weight ratio.

Subsequently, a film of 4,4'-bis[N-(1-napthyl)-N-phenylamino]biphenyl (abbreviation: NPB) was formed over the layer 2103 containing a composite material to have a thickness of 10 nm by the evaporation method using resistance heating system, thereby forming the hole transporting layer 2104.

Further, by co-evaporating 9-[4-(N-carbazolyl)]phenyl-10-phenylanthracene (abbreviation: CzPA) and 2-{N-(1-naphthyl)-N-[9-(1-naphthyl)carbazol-3-yl]amino}-9,10-diphenylanthracene (abbreviation: 2NCNPA), which is an anthracene derivative of the present invention represented by Structural Formula (220), the light-emitting layer 2105 with a thickness of 40 nm was formed over the hole transporting layer 2104. Here, a rate of evaporation was adjusted so that the weight ratio of CzPA and 2NCNPA was 1:0.01 (=CzPA: 2NCNPA).

Thereafter, the electron transporting layer 2106 was formed over the light-emitting layer 2105 by forming a film of bathophenanthroline (abbreviation: BPhen) to have a film thickness of 30 nm by means of the evaporation using resistance heating system.

Further, the electron injecting layer 2107 was formed over the electron transporting layer 2106 by forming a film of lithium fluoride with a thickness of 1 nm.

Finally, by forming a film of aluminum as the second electrode 2108 with a film thickness of 200 nm over the electron injecting layer 2107 using the evaporation method by resistance heating system, a light-emitting element 12 was fabricated.

Figure 106:
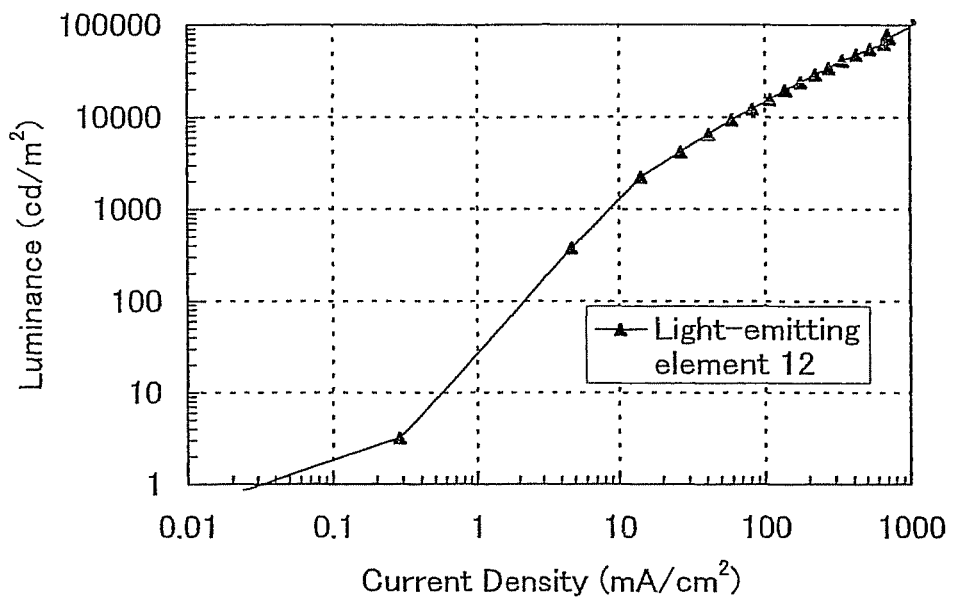
FIG. 106 shows the current density-luminance characteristic of light-emitting element 12.
Figure 107:
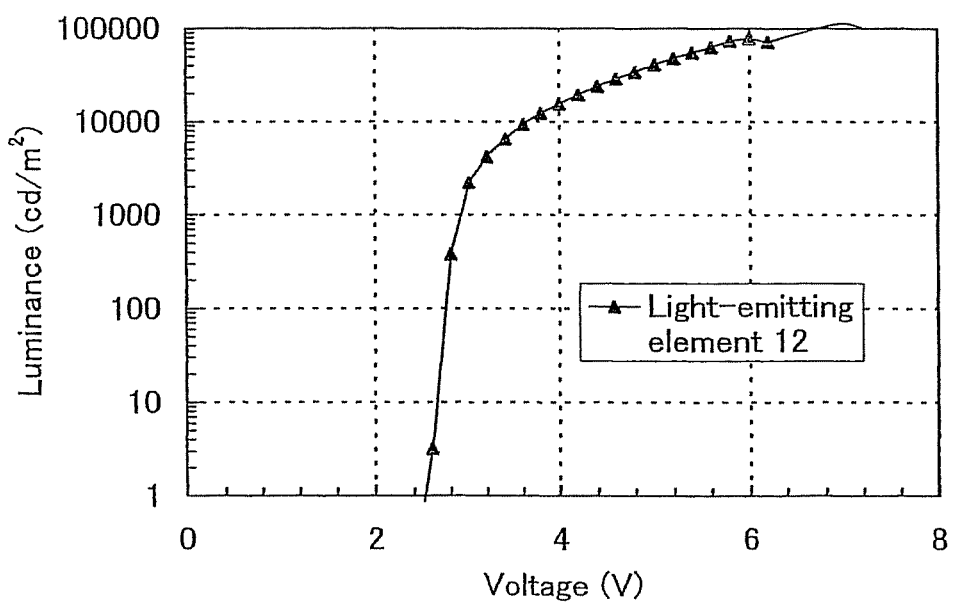
FIG. 107 shows the voltage-luminance characteristic of light-emitting element 12.
Figure 108:
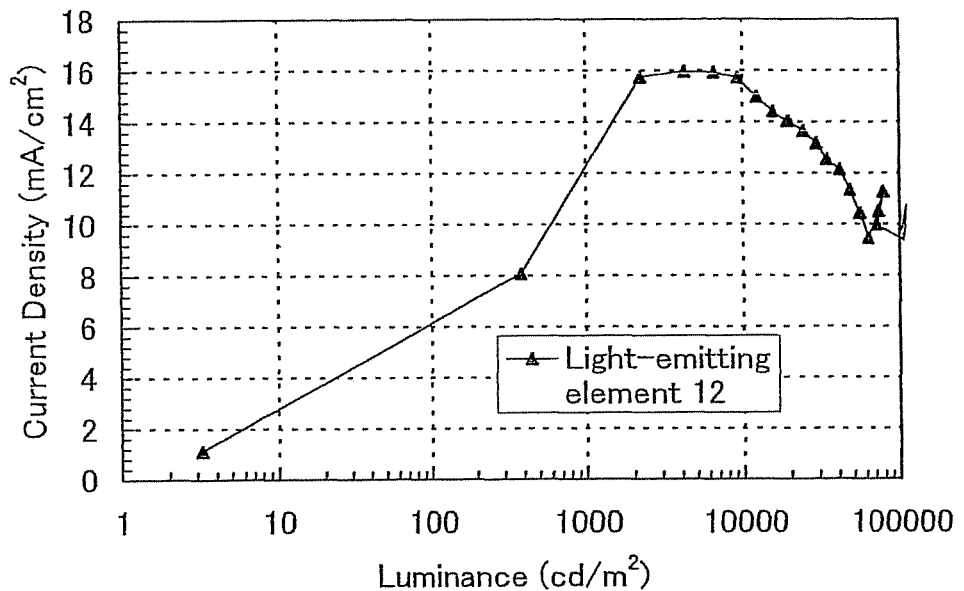
FIG. 108 shows the luminance-current efficiency characteristic of light-emitting element 12.
Figure 109:
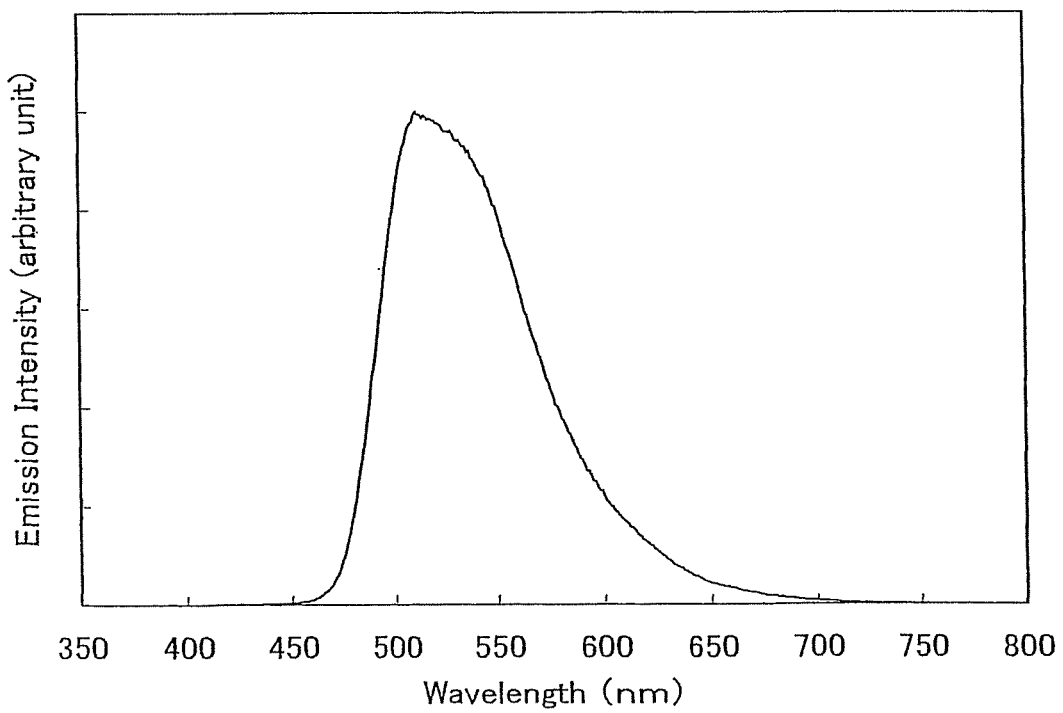
FIG. 109 shows the emission spectrum of a light-emitting element 12.

A current density-luminance characteristic, a voltage-luminance characteristic, and a luminance-current efficiency characteristic of the light-emitting element 12 are shown in FIGS. 106, 107, and 108, respectively. Also, the emission spectrum which was obtained at a current of 1 mA is illustrated in FIG. 109. ACM chromaticity coordinate of the light-emitting element 12 at luminance of 3090 cd/m$^2$ was (x=0.28, y=0.62), and light emission was green. Current efficiency at luminance of 3090 cd/m$^2$ was 14.0 cd/A, meaning that high current efficiency was exhibited. In addition, as shown in FIG. 109, maximum emission wavelength at a current of 1 mA was 511 nm.

Embodiment 11

In this embodiment, a synthetic method of 2-{N-[4-(carbazol-9-yl)phenyl]-N-phenylamino}-9,10-diphenylanthracene (abbreviation: 2YGAPA), which is the anthracene derivative of the present invention represented by Structural Formula (301), is specifically described.

(301)

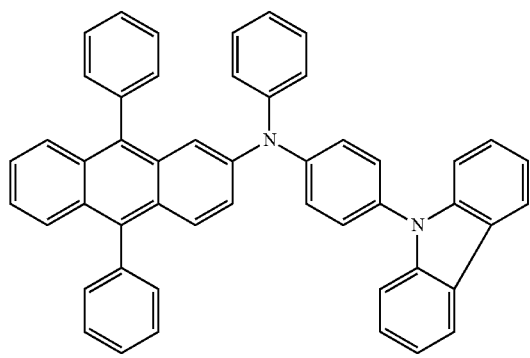

[Step 1] Synthetic Method of 2YGAPA

A synthetic method of 2YGAPA is shown in (C-22).

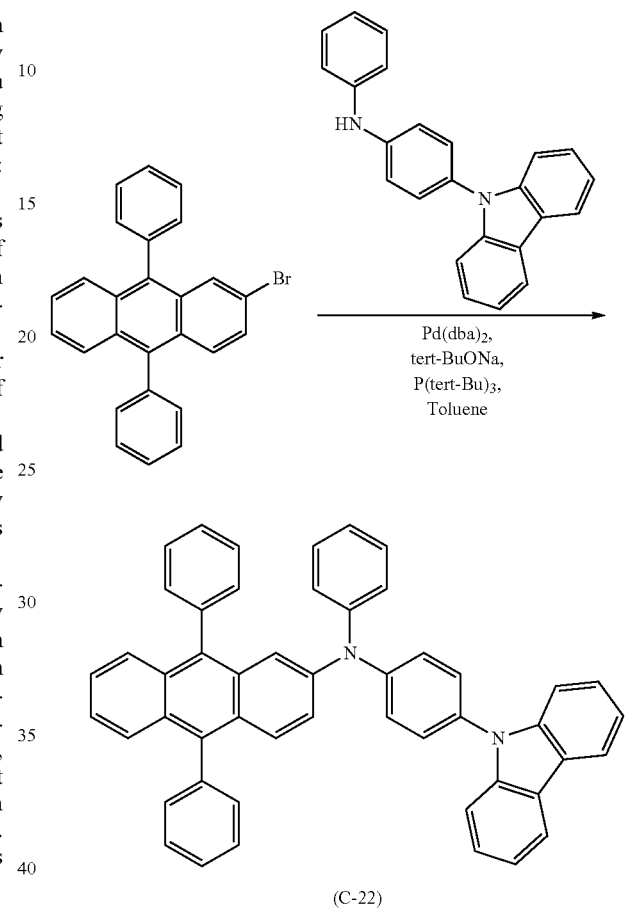

(C-22)

2.0 g (4.1 mmol) of 2-bromo-9,10-diphenylanthracene synthesized in Step 1 of Embodiment 1, 1.0 g (10 mmol) of sodium tert-butoxide, 1.4 g (4.1 mmol) of 4-(carbazol-9-yl)diphenylamine and 0.1 g (0.2 mmol) of bis(dibenzylideneacetone)palladium (0) were put into a 100 mL three-neck flask, and the inside of the flask was substituted with nitrogen. 30 mL of toluene and 0.1 mL of 10 wt % hexane solution of tri(tert-butyl)phosphine were added to this mixture. Then, this mixture was heated and stirred for 5 hours at 80° C. After the reaction, toluene was added to a reaction mixture, and this suspension was washed with a saturated sodium carbonate aqueous solution and then with brine. The aqueous layer and organic layer were separated, and the organic layer was subjected to suction filtration through Florisil, celite, and alumina, and the filtrate was obtained. The obtained filtrate was concentrated to give a solid. The obtained solid was recrystallized with a mixed solvent of chloroform and hexane, which provided 2.2 g of the target compound as a yellow solid in 81% yield. By the nuclear magnetic resonance measurement (NMR), it was confirmed that this compound was 2-{N-

[4-(carbazol-9-yl)phenyl]-N-phenylamino}-9,10-diphenylanthracene (abbreviation: 2YGAPA).

Figure 112A:
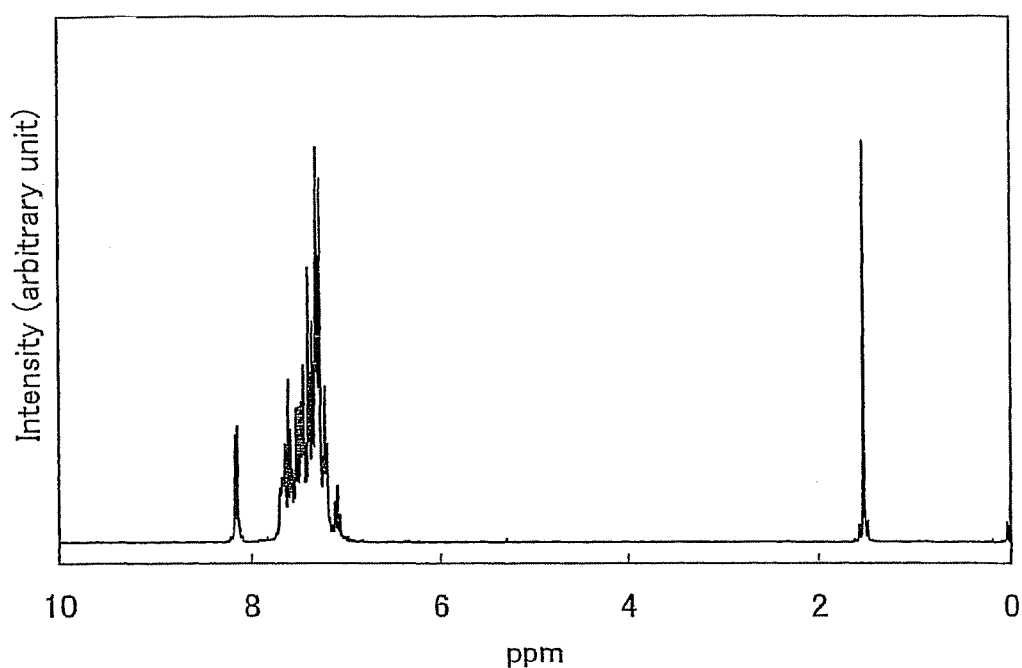
FIGS. 112A and 112B each show the $^1$H NMR chart of 2-{N-[4-(carbazol-9-yl)phenyl]-N-phenylamino}-9,10-diphenylanthracene (abbreviation: 2YGAPA)
Figure 112B:
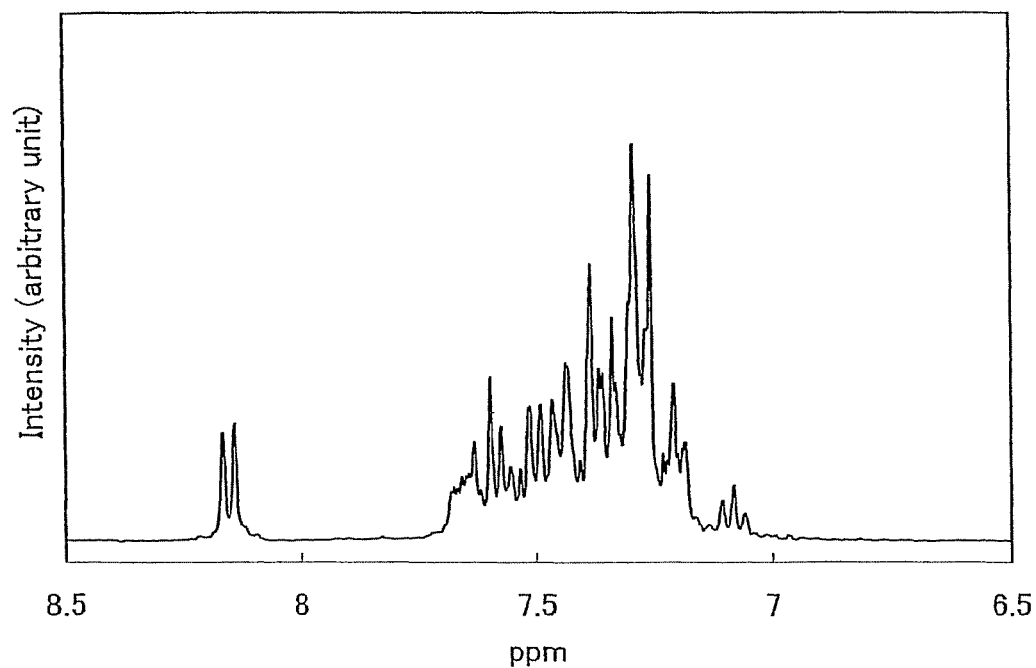

$^1$H NMR data of 2YGAPA is shown below. $^1$H NMR (300 MHz, CD Cl$_3$): δ=7.05-7.12 (m, 1H), 7.13-7.74 (m, 31H), 8.16 (d, J=6.8 Hz, 2H). The $^1$H NMR chart is shown in each of FIGS. 112A and 112B. Note that the range of 6.5 ppm to 8.5 ppm in FIG. 112A is expanded and shown in FIG. 112B.

Figure 113:
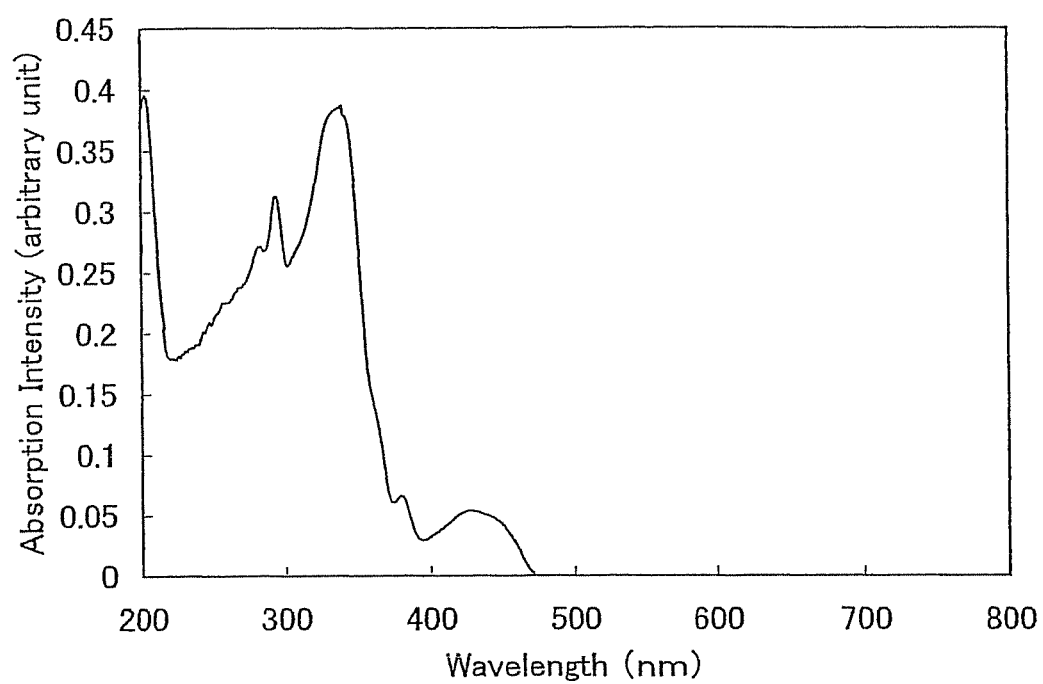
FIG. 113 shows the absorption spectrum of a toluene solution of 2-{N-[4-(carbazol-9-yl)phenyl]-N-phenylamino}-9,10-diphenylanthracene (abbreviation: 2YGAPA)
Figure 114:
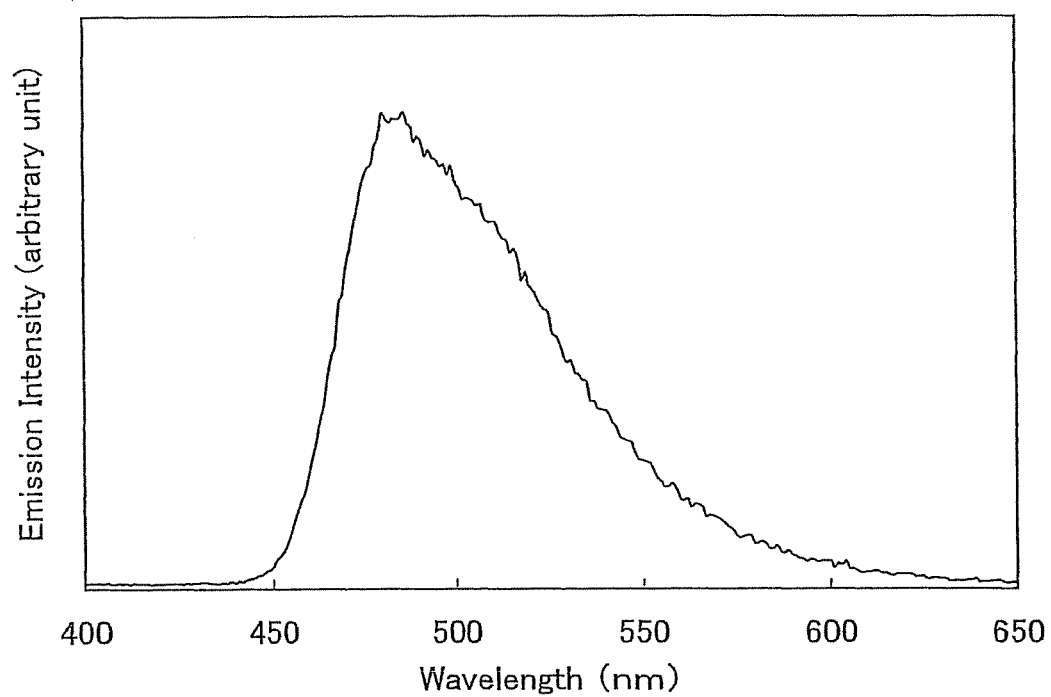
FIG. 114 shows the emission spectrum of a toluene solution of 2-{N-[4-(carbazol-9-yl)phenyl]-N-phenylamino}-9,10-diphenylanthracene (abbreviation: 2YGAPA)

The absorption spectrum of a toluene solution of 2YGAPA is shown in FIG. 113. An ultraviolet-visible spectrophotometer (type V550, manufactured by Japan Spectroscopy Corporation) was used for measurement. The absorption spectrum of the solution is shown in FIG. 113, which was obtained by subtracting the spectrum of the quartz substrate from the raw spectra of the sample solution charged in a quartz cell. In FIG. 113, a horizontal axis shows wavelength (nm) and a vertical axis shows absorption intensity (an arbitrary unit). In the case of the toluene solution, absorption was observed at around 428 nm. Further, an emission spectrum of the toluene solution (excitation wavelength of 430 nm) of 2YGAPA is shown in FIG. 114. In FIG. 114, a horizontal axis shows wavelength (nm) and a vertical axis shows emission intensity (an arbitrary unit). In the case of the toluene solution, the maximum emission wavelength was 486 nm (excitation wavelength of 430 mm).

The HOMO level of 2YGAPA in a thin film state, which was measured by a photoelectron spectrometer (AC-2, manufactured by Riken Keiki Co., Ltd.) under air, was −5.47 eV. By the absorption edge obtained from a Tauc plot of the absorption spectrum of the thin film, the optical energy gap was estimated to be 2.55 eV, which means that LUMO level of 2YGAPA is −2.92 eV.

Embodiment 12

In this embodiment, a synthetic method of 9,10-diphenyl-1-[N-(9-phenylcarbazol-3-yl)-N-phenylamino]anthracene (abbreviation: 1PCAPA), which is the anthracene derivative of the present invention represented by Structural Formula (202), is specifically described.

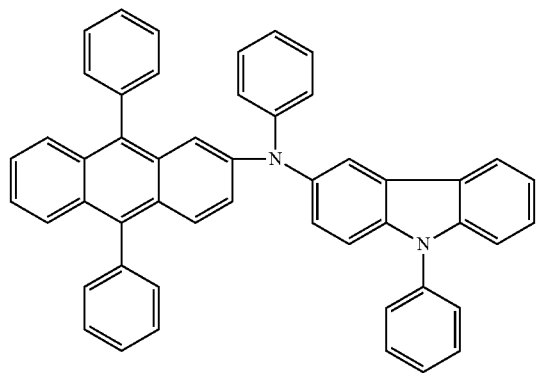

(202)

[Step 1] Synthesis of 1-bromo-9,10-diphenylanthracene (i) Synthesis of 1-bromo-9,10-anthraquinone A synthetic scheme of 1-bromo-9,10-anthraquinone is shown in (C-23).

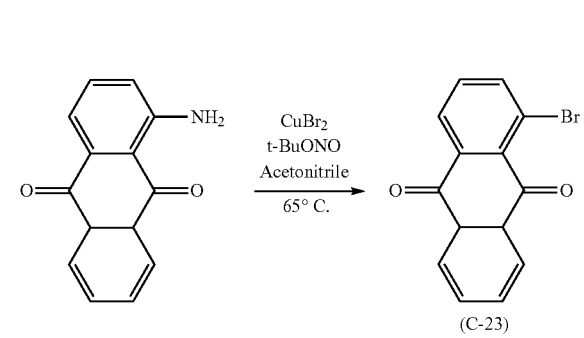

(C-23)

20.0 g (88.8 mmol) of 1-amino-9,10-anthraquinone, 36.7 g (164 mmol) of copper bromide (II), and 240 mL of acetonitrile were put into a 500 mL three-neck flask, and the atmosphere of the flask was substituted with nitrogen. Thereafter, 15.8 mL (133 mmol) of tert-butyl nitrite was added, and the mixture was stirred for 6 hours at 65° C. After the reaction was completed, the reaction mixture was poured into 1.3 L of 3 mol/L hydrochloric acid, which was followed by additional stirring for 3 hours at room temperature. A precipitate in the mixture was collected by suction filtration, and the precipitate was washed with water and then with ethanol. Then, the obtained solid was dissolved in a mixed solvent of toluene and chloroform, and the solution was subjected to suction filtration through Florisil, celite, and then alumina. The filtrate was concentrated, and the residue was purified by silica gel column chromatography (eluent: toluene). The obtained solid was recrystallized with a mixed solvent of chloroform and hexane, giving 9.37 g of 1-bromo-9,10-anthraquinone as yellow powder in 36% yield.

(ii) Synthesis of 1-bromo-9,10-diphenyl-9,10-dihydroanthracene-9,10-diol

A synthetic scheme of 1-bromo-9,10-diphenyl-9,10-dihydroanthracene-9,10-diol is shown in (C-24).

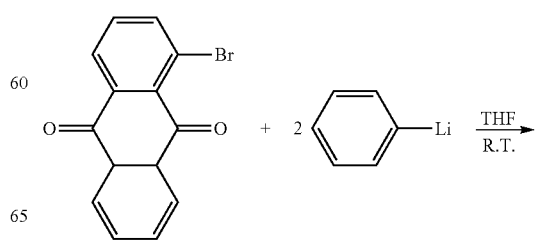

-continued

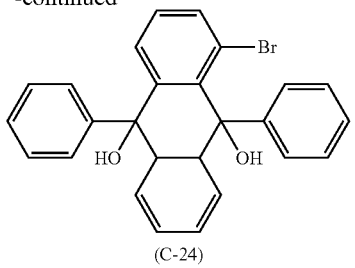

(C-24)

9.37 g (32.4 mmol) of 1-bromoanthraquinone was put into a 500 mL three neck-flask, and the atmosphere of the flask was substituted with nitrogen. 150 mL of tetrahydrofuran (abbreviation: THE) was added to the flask, and then 34.0 mL (71.3 mmol) of phenyllithium (2.1 mol/L dibutyl ether solution) was added in one portion. The solution was stirred for 24 hours at room temperature. After the reaction was completed, the reaction solution was washed with water, and the aqueous layer was extracted with ethyl acetate. The extracted part was combined with the organic layer, and then dried with magnesium sulfate. After drying, the mixture was subjected to suction filtration, and the filtrate was concentrated, resulting in 14.4 g of 1-bromo-9,10-diphenyl-9,10-dihydroanthracene-9,10-diol as a brown, oily compound in 100% yield.

(iii) Synthesis of 1-bromo-9,10-diphenylanthracene

A synthetic scheme of 1-bromo-9,10-diphenylanthracene is shown in (C-5).

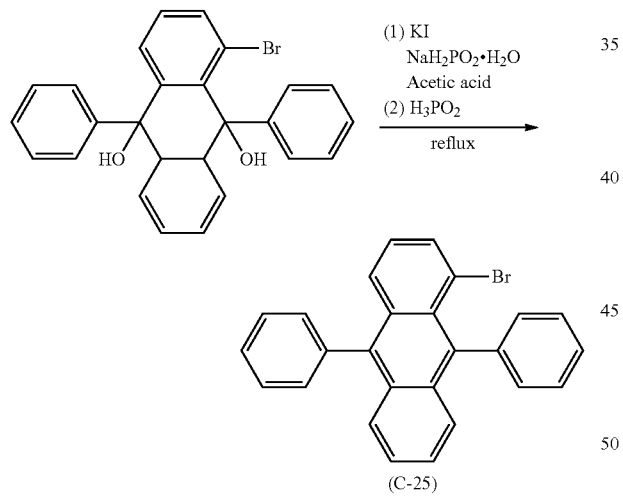

(C-25)

14.4 g (32.4 mmol) of 1-bromo-9,10-diphenyl-9,10-dihydroanthracene-9,10-diol, 9.68 g (58.3 mmol) of potassium iodide, 18.6 g (175 mmol) of sodium phosphinate monohydrate, and 100 mL of glacial acetic acid were put into a 500 mL three-neck flask, and the mixture was refluxed for 5 hours at 120° C. After the reaction was completed, 40 mL of a 50% phosphinic acid was added to the mixture, and stirring was kept for 18 hours at room temperature. After the reaction was completed, the reaction solution was washed with water, and the aqueous layer was extracted with ethyl acetate. The extracted part was combined with the organic layer, and then dried with magnesium sulfate. After drying, a mixture was subjected to suction filtration, and the filtrate was concentrated. The obtained residue was dissolved in toluene, and filtered through Florisil, celite, and then alumina, and the filtrate was concentrated. The obtained residue was purified by silica gel column chromatography (eluent; toluene:hexane=1:5). The resulting solid was washed with ethanol, providing 0.50 g of 1-bromo-9,10-diphenylanthracene as light yellow powder in 3.8% yield.

[Step 2] Synthetic Method of 1PCAPA

A synthetic scheme of 1PCAPA is shown in (C-26).

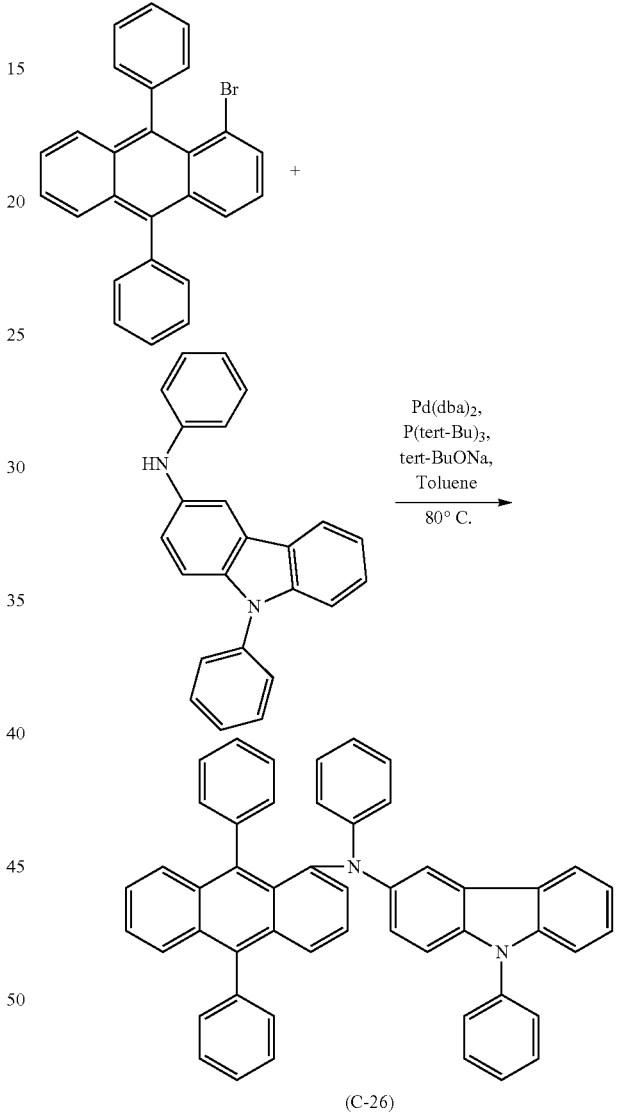

(C-26)

0.50 g (1.2 mmol) of 1-bromo-9,10-diphenylanthracene synthesized in Step 1 of Embodiment 12, 0.45 g (1.3 mmol) of N-phenyl-(9-phenyl-9H-carbazol-3-yl)amine (abbreviation: PCA), 0.035 g (0.061 mmol) of bis(dibenzylideneacetone) palladium (0), and 0.29 g (3.1 mmol) of sodium tert-butoxide were put into a 100 mL three-neck flask, and the atmosphere of the flask was substituted with nitrogen. Then, 10 mL of toluene and 0.12 g (0.061 mmol) of tri(tert-butyl)phosphine (10% hexane solution) were added to the flask, and the reaction mixture was stirred for 18 hours at 80° C. After the reaction was completed, the reaction mixture was diluted with toluene, and subjected to suction filtration through Florisil, celite, and then alumina, and then the filtrate was concentrated. The obtained residue was purified by silica gel column chromatography (eluent; hexane:toluene=3:2), and the obtained solid was recrystallized with chloroform and hexane, giving 0.08 g of the target compound as orange powder in 10% yield. It was confirmed by a nuclear magnetic resonance measurement (NMR) that this compound was 9,10-diphenyl-1-[N-(9-phenylcarbazol-3-yl)-N-phenylamino]anthracene (abbreviation: 1PCAPA).

Figure 115A:
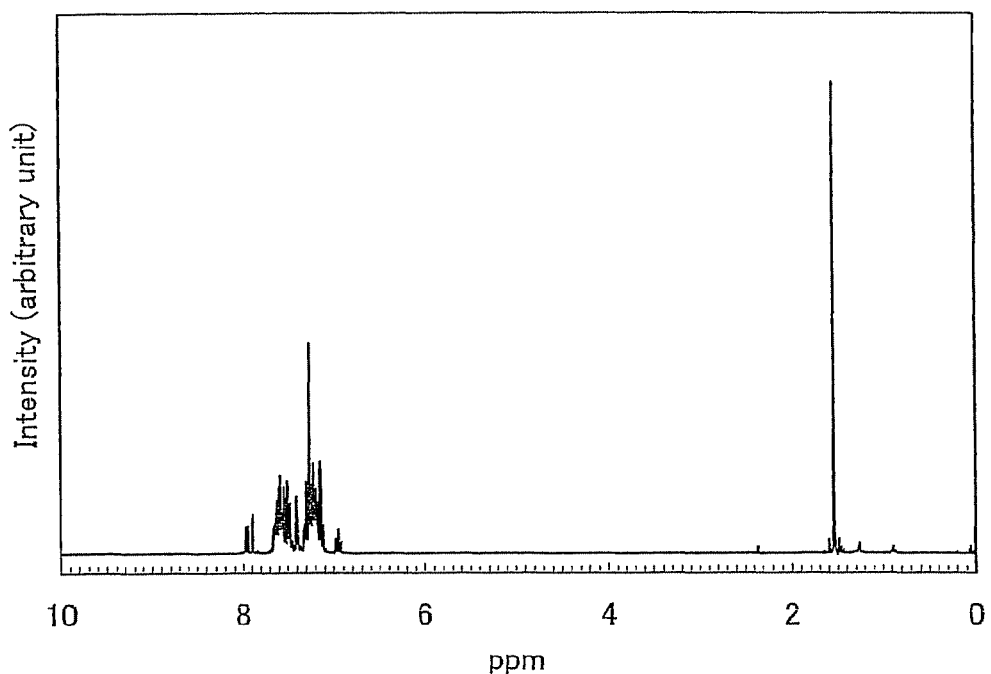
FIGS. 115A and 115B each show the $^1$H NMR chart of 9,10-diphenyl-1-[N-(9-phenylcarbazol-3-yl)-N-phenylamino]anthracene (abbreviation: 1PCAPA)
Figure 115B:
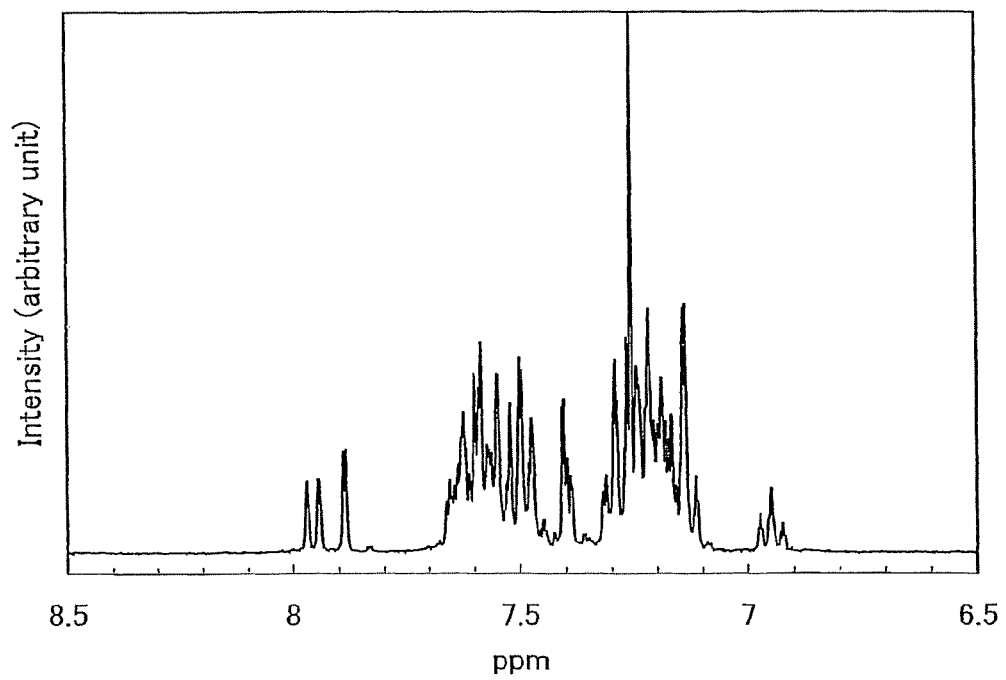

$^1$H NMR data of this compound is shown below. $^1$H NMR (300 MHz, CDCl$_3$): δ=6.93-6.97 (m, 1H), 7.12-7.32 (m, 16H), 7.39-7.41 (m, 2H), 7.47-7.66 (m, 13H), 7.88-7.97 (m, 2H). The $^1$H NMR chart is shown in each of FIGS. 115A and 115B. Note that the range of 6.5 ppm to 8.5 ppm in FIG. 115A is expanded and shown in FIG. 115B.

Figure 116:
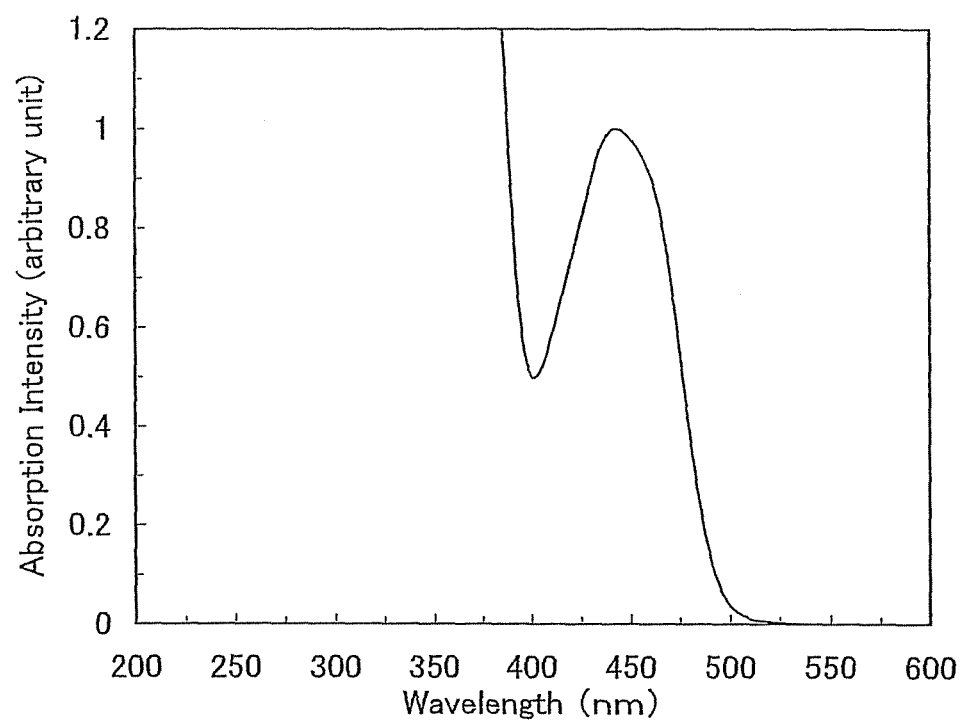
FIG. 116 shows the absorption spectrum of a toluene solution of 9,10-diphenyl-1-[N-(9-phenylcarbazol-3-yl)-N-phenylamino]anthracene (abbreviation: 1PCAPA)
Figure 117:
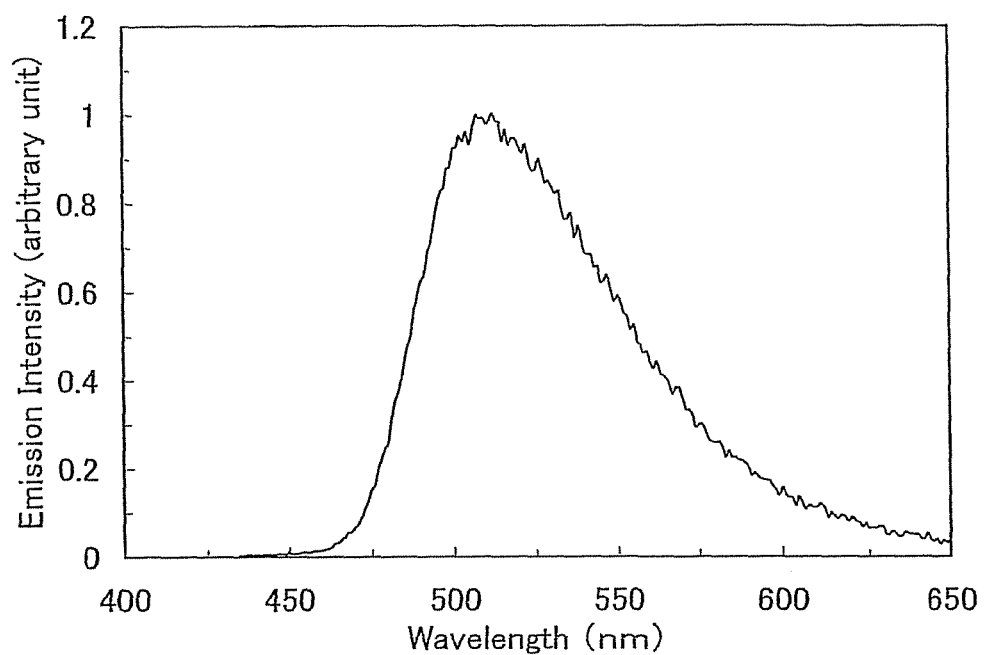
FIG. 117 shows the emission spectrum of a toluene solution of 9,10-diphenyl-1-[N-(9-phenylcarbazol-3-yl)-N-phenylamino]anthracene (abbreviation: 1PCAPA)

The absorption spectrum of a toluene solution of 1PCAPA is shown in FIG. 116. An ultraviolet-visible spectrophotometer (type V550, manufactured by Japan Spectroscopy Corporation) was used for measurement. The absorption spectrum of the solution is shown in FIG. 116, which was obtained by subtracting the spectrum of the quartz substrate from the raw spectra of the sample solution charged in a quartz cell. In FIG. 116, a horizontal axis shows wavelength (nm) and a vertical axis shows absorption intensity (an arbitrary unit). In the case of the toluene solution, absorption was observed at around 443 nm. Further, an emission spectrum of the toluene solution (excitation wavelength of 430 nm) of 1PCAPA is shown in FIG. 117. In FIG. 117, a horizontal axis shows wavelength (nm) and a vertical axis shows emission intensity (an arbitrary unit). In the case of the toluene solution, the maximum emission wavelength was 512 nm (excitation wavelength of 430 nm).

Embodiment 13

In this embodiment, a synthetic method of 9,10-bis(9,9-dimethylfluorene-2-yl)-2-[N-phenyl-N-(9-phenyl-9H-carbazol-3-yl)amino]anthracene (abbreviation: 2PCADFA), which is the anthracene derivative of the present invention represented by Structural Formula (207), is specifically described.

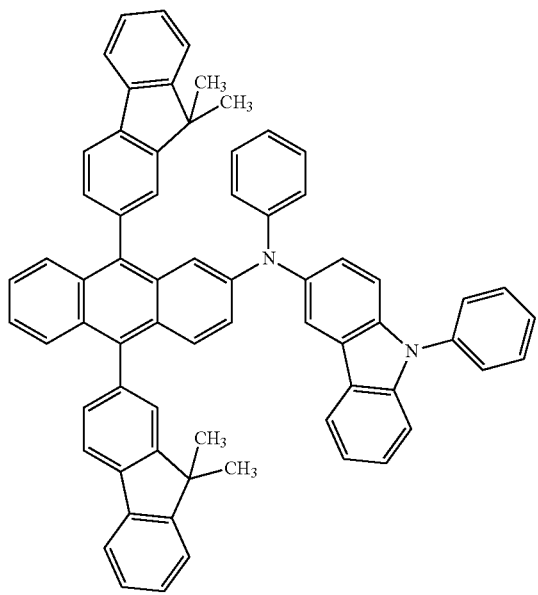

(207)

[Step 1] Synthesis of 2-bromo-9,9-dimethylfluorene (i) Synthesis of 2-bromo-9,9-dimethylfluorene A synthetic scheme of 2-bromo-9,9-dimethylfluorene is shown in (C-27).

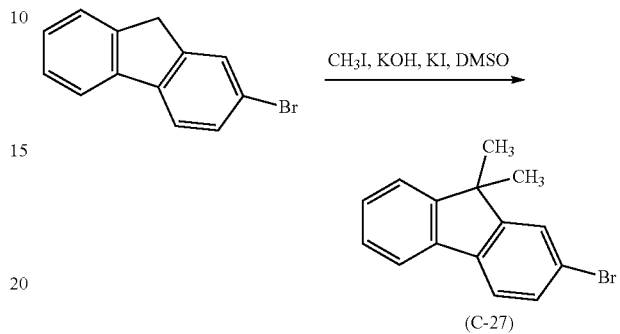

(C-27)

12.5 g (51 mmol) of 2-bromofluorene, 8.5 g (51 mmol) of potassium iodide, 14.3 g (0.50 mol) of potassium hydroxide, and 250 mL of dimethylsulfoxide were put into a 500 mL Erlenmeyer flask, and the mixture was stirred for 30 minutes. 10 mL of methyl iodide was slowly added to this mixture. This mixture was stirred for 48 hours at room temperature. After the reaction, 400 mL of chloroform was added to the reaction solution, and stirring was continued. This solution was washed with 1N hydrochloric acid, saturated sodium carbonate aqueous solution, and brine in this order. Then, magnesium sulfate was added to the organic layer to dry the layer. After drying, this mixture was subjected to suction filtration, and concentrated, and the residue was subjected to the purification by silica gel column chromatography. For the column chromatography, hexane was used as an eluent first, and then a mixed solvent of ethyl acetate:hexane=1:5 was used as a second eluent. The corresponding fraction was concentrated and dried, resulting in 12 g of a brown, oily compound in 97% yield.

(ii) Synthesis of 9,10-bis(9,9-dimethylfluorene-2-yl)-2-bromo-9,10-dihydroanthracene-9,10-diol A synthetic scheme of 9,10-bis(9,9-dimethylfluorene-2-yl)-2-bromo-9,10-dihydroanthracene-9,10-diol is shown in each of (C-28) and (C-29).

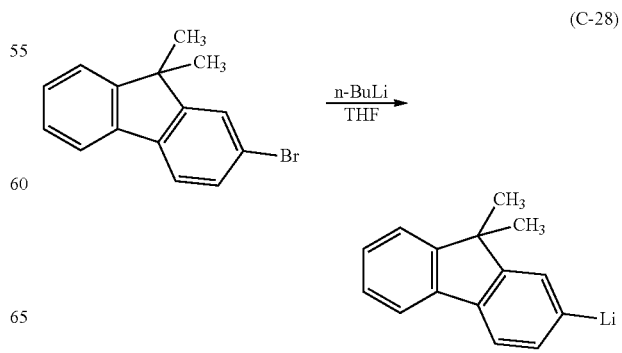

(C-28)

(iii) Synthesis of 9,10-bis(9,9-dimethylfluorene-2-yl)-2-bromoanthracene

A synthetic scheme of 9,10-bis(9,9-dimethylfluorene-2-yl)-2-bromoanthracene is shown in (C-30).

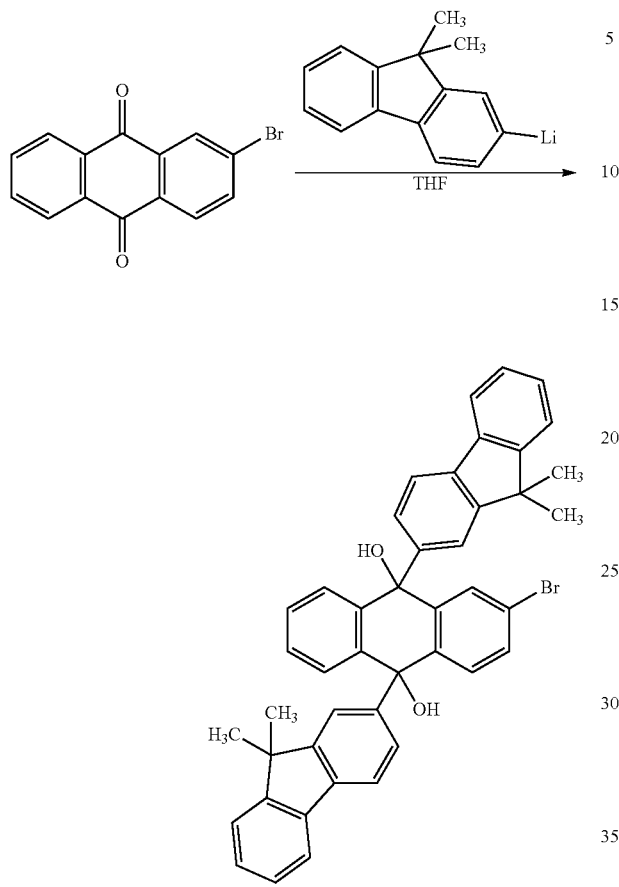

(C-29)

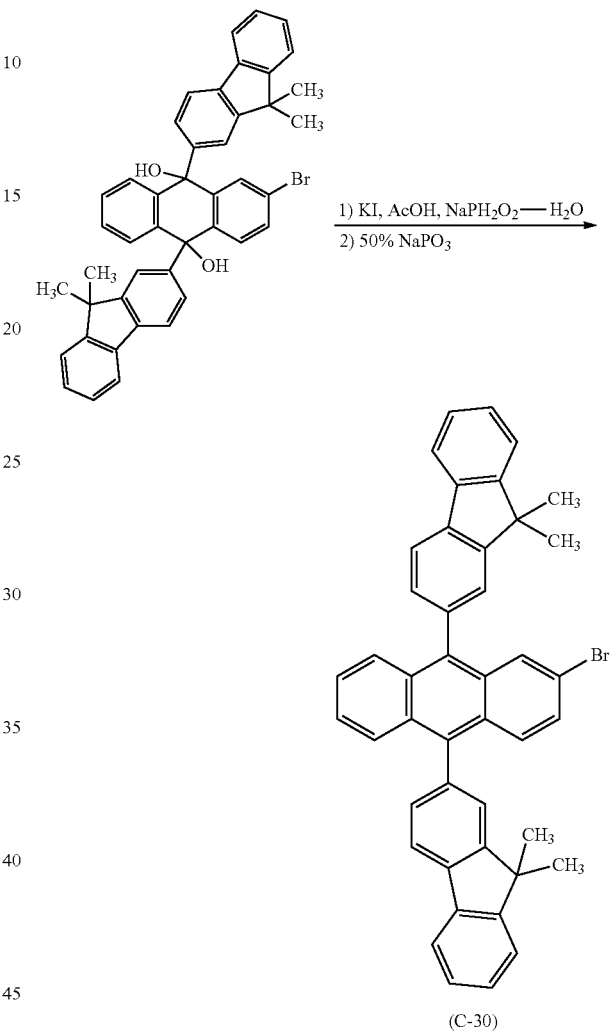

(C-30)

12 g (46 mmol) of 2-bromo-9,9-dimethylfluorene and 150 mL of tetrahydrofuran (abbreviation: THF) were put into a 500 mL three-neck flask, and the inside of the flask was substituted with nitrogen. This solution was stirred for 20 minutes at −78° C. Then, 35 mL of an 1.6 mol/L hexane solution of n-butyllithium was slowly dropwised into the solution, and stirring was conducted for 1.5 hours at −78° C. After the reaction, into the reaction mixture was added 5.4 g (19 mmol) of 2-bromo-9,10-anthraquinone dissolved in 100 mL of THF. The resulting solution was stirred for 18 hours at room temperature. After stirring, to this solution was added 1N hydrochloric acid, and the solution was stirred for 30 minutes. The reaction mixture was transferred to a separating funnel, and an aqueous layer was extracted with ethyl acetate. The extracted layer and the organic layer were combined and washed with a saturated sodium bicarbonate aqueous solution, and then with brine. After washing, magnesium sulfate was added to the organic layer to dry the organic layer. After drying, this mixture was subjected to suction filtration. The obtained filtrate was subjected to suction filtration through celite, Florisil and then alumna, and the filtrate obtained was concentrated to give the title compound as a brown, oily compound.

A solution of 46 mmol of 9,10-bis(9,9-dimethylfluorene-2-yl)-2-bromo-9,10-dihydroanthracene-9,10-diol, 24 g (0.23 mol) of sodium phosphinate monohydrate, and 15 g (91 mmol) of potassium iodide in 100 mL of glacial acetic acid was stirred for 4 hours at 120° C. After the reaction, 60 mL of a 50% phosphinic acid was added to the reaction mixture, and then stirring was kept for additional 2 hours at 120° C. Water was added to the mixture, and the mixture was stirred for 1 hour. After the mixture was filtered, the resulting solid was washed with water and dissolved in toluene, and the toluene-solution was washed with a saturated sodium bicarbonate aqueous solution and brine. Magnesium sulfate was added to this organic layer to dry the organic layer. This mixture was subjected to suction filtration, and the filtrate was filtered through celite, Florisil, and then alumina. The filtrate was concentrated, and the resulting solid was dissolved in a mixed solvent of chloroform and methanol, which was followed by irradiating ultrasound to yield 14 g of the title compound as a light yellow solid. Total yield of the steps of (ii) and (iii) was 47%.

[Step 2] Synthesis of 2PCADFA

A synthetic scheme of 2PCADFA is shown in (C-31).

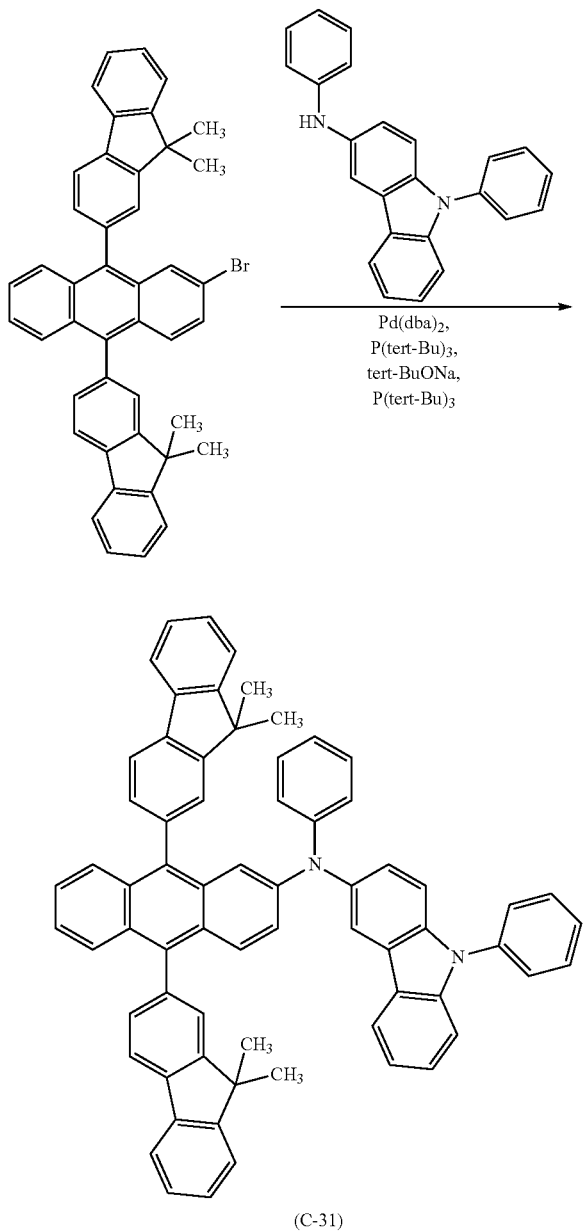

(C-31)

1.5 g (2.3 mmol) of 9,10-bis(9,9-dimethylfluorene-2-yl)-2-bromoanthracene, 1.0 g (10 mmol) of sodium tert-butoxide, 0.78 g (2.3 mmol) N-phenyl-(9-phenyl-9H-carbazol-3-yl) amine (abbreviation: PCA), and 0.08 g (0.16 mmol) of bis (dibenzylideneacetone)palladium (0) were put into a 100 mL three-neck flask, and the inside of the flask was substituted with nitrogen. 30 mL of toluene and 0.05 mL of a 10% hexane solution of tri(tert-butyl)phosphine were added to this mixture, and this mixture was heated and stirred for 5 hours at 80° C. After stirring, toluene was added to the reaction mixture, and this suspension was washed with a saturated sodium bicarbonate aqueous solution and brine. The organic layer was subjected to suction filtration through Florisil, celite, and then alumina, washed with water and then with brine, and dried over magnesium sulfate. This mixture was subjected to suction filtration to remove magnesium sulfate, and the obtained filtrate was concentrated. The resulting solid was purified by silica gel column chromatography (eluent; toluene:hexane=1:9, then toluene:hexane=1:5, and then toluene: hexane=1:2). The obtained solid was recrystallized with a mixed solvent of dichloromethane and hexane, giving 0.70 g yellow powder in 77% yield. It was confirmed by nuclear magnetic resonance measurement (NMR) that this compound was 9,10-bis(9,9-dimethylfluorene-2-yl)-2-[N-phenyl-N-(9-phenyl-9H-carbazol-3-yl)amino]anthracene (abbreviation: 2PCADFA).

Figure 118A:
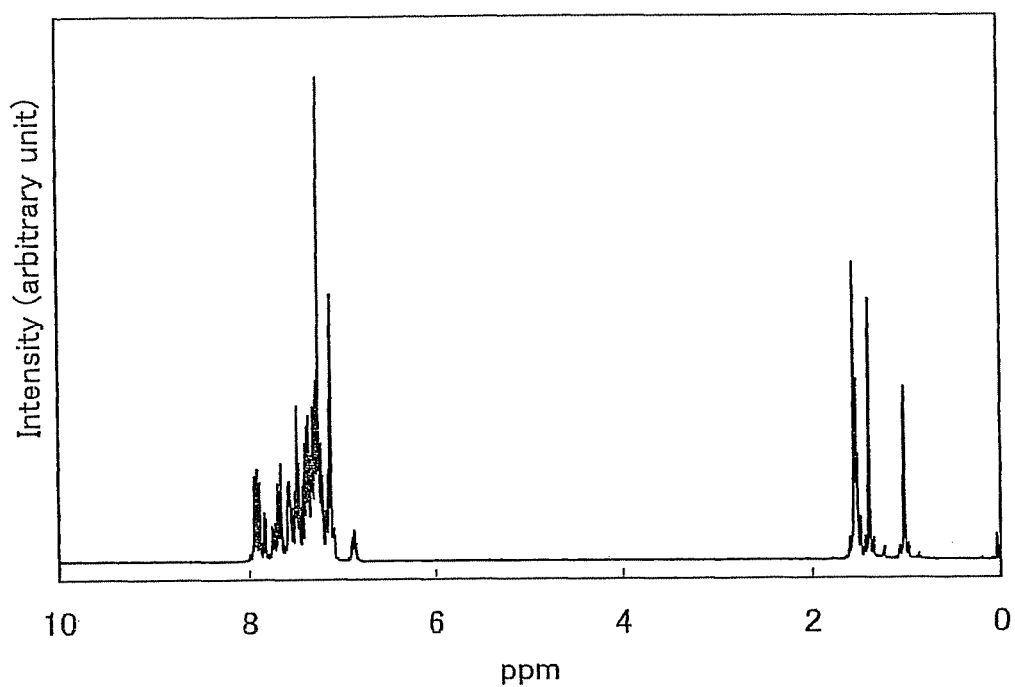
FIGS. 118A and 118B each show the $^1$H NMR chart of 9,10-bis(9,9-dimethylfluorene-2-yl)-2-[N-phenyl-N-(9-phenyl-9H-carbazol-3-yl)amino]anthracene (abbreviation: 2PCADFA)
Figure 118B:
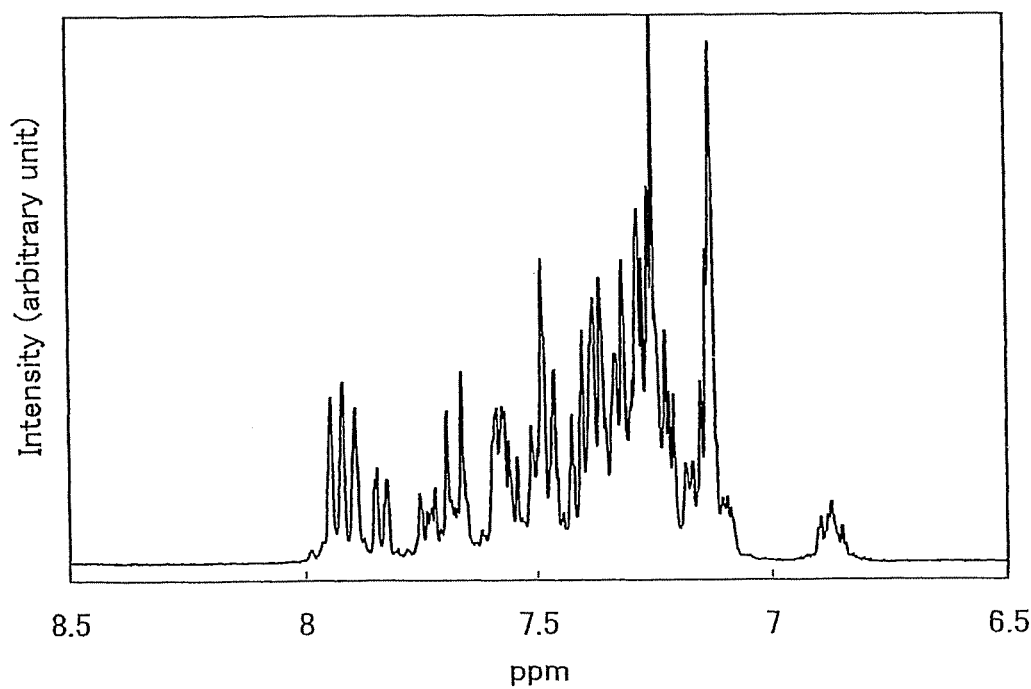

$^1$H NMR data of this compound is shown below. $^1$H NMR (300 MHz, CDCl$_3$): δ=1.04 (d, J=1.95, 3H), 1.41 (s, 3H), 1.54-1.59 (m, 6H), 6.83-6.90 (m, 1H), 7.09-7.24 (m, 10H), 7.25-7.64 (m, 20H), 7.63-7.70 (m, 2H), 7.70-7.75 (m, 1H), 7.82 (dd, J=2.0, 6.8 Hz, 1H), 7.88 (s, 1H), 7.92 (d, J=8.3 Hz, 2H). The $^1$H NMR chart is shown in each of FIGS. 118A and 118B. Note that the range of 6.5 ppm to 8.5 ppm in FIG. 118A is expanded and shown in FIG. 118B.

Sublimation purification of 0.70 g of the obtained yellow solid was carried out by a train sublimation method. The sublimation purification was carried out under reduced pressure of 7.0 Pa, with a flow rate of argon at 3 mL/min, at 352° C. for 15 hours. 0.62 g of the compound was recovered, which corresponds to the yield of 89%.

Figure 119:
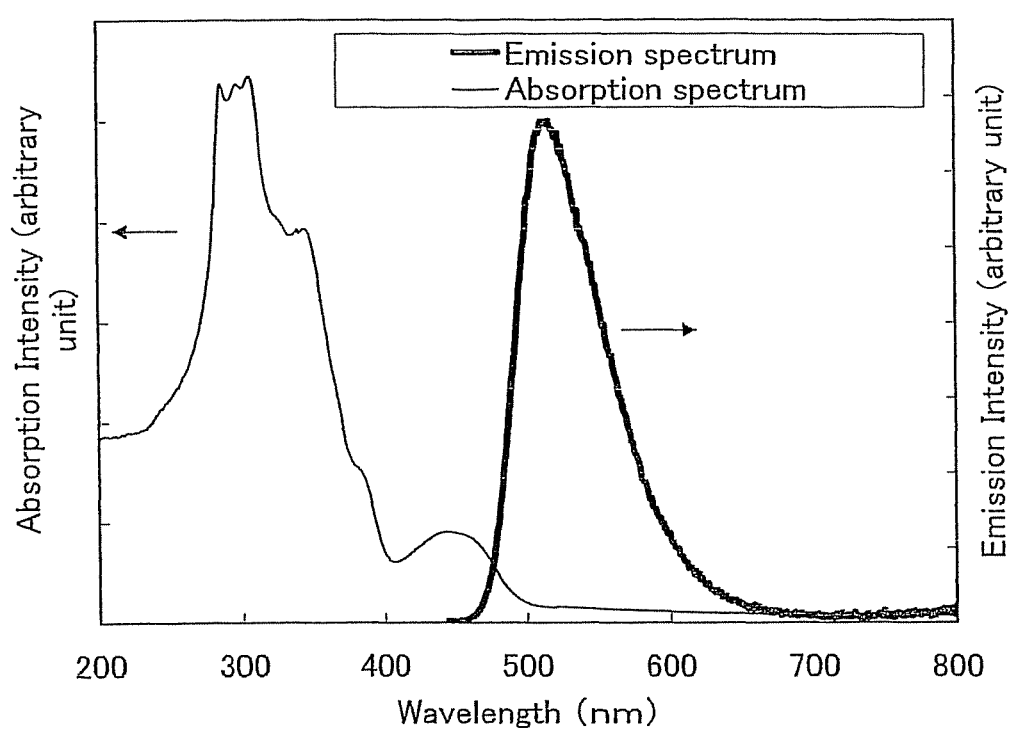
FIG. 119 shows the absorption spectrum and emission spectrum of a toluene solution of 9,10-bis(9,9-dimethylfluorene-2-yl)-2-[N-phenyl-N-(9-phenyl-9H-carbazol-3-yl)amino]anthracene (abbreviation: 2PCADFA)

The absorption spectrum of a toluene solution of 2PCADFA is shown in FIG. 119. An ultraviolet-visible spectrophotometer (type V550, manufactured by Japan Spectroscopy Corporation) was used for measurement. The absorption spectrum of the solution is shown in FIG. 119, which was obtained by subtracting the spectrum of the quartz substrate from the raw spectra of the sample solution charged in a quartz cell. In FIG. 119, a horizontal axis shows wavelength (nm) and a vertical axis shows absorption intensity (an arbitrary unit). In the case of the toluene solution, absorption was observed at around 442 nm. Further, an emission spectrum of the toluene solution (excitation wavelength of 430 nm) of 2PCADFA is shown in FIG. 119. In FIG. 119, a horizontal axis shows wavelength (nm) and a vertical axis shows emission intensity (an arbitrary unit). In the case of the toluene solution, the maximum light emission wavelength was 516 nm (excitation wavelength of 439 nm).

Embodiment 14

In this embodiment, a synthetic method of 9,10-diphenyl-2-[N-(4'-diphenylamino-1,1'-biphenyl-4-yl)-N-phenylamino]anthracene (abbreviation: 2DPBAPA), which is the anthracene derivative of the present invention represented by Structural Formula (119), is specifically described. Note that 2DPBAPA represented by Structural Formula (119) corresponds to the case where Ar$^1$ and Ar$^2$ in General Formula (5) are each Structural Formula (20-1), and A is Structural formula (31-18).

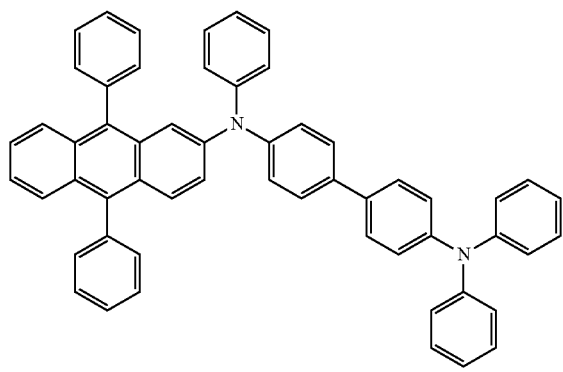

(119)

[Step 1] Synthesis of triphenylamine-4-boronic acid

A synthetic scheme of triphenylamine-4-boronic acid is shown in (C-32).

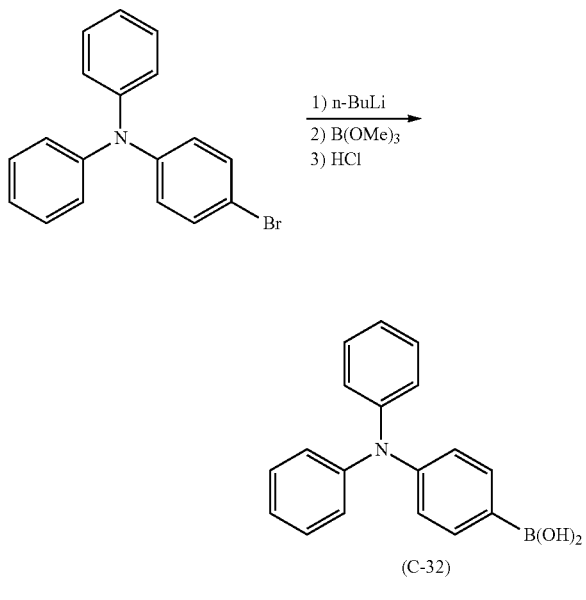

(C-32)

Under nitrogen, into a solution of 10 g (31 mmol) of 4-bromotriphenylamine in tetrahydrofuran (THF, 150 mL) was added 20 mL (32 mmol) of n-butyllithium (1.58 mol/L hexane solution) with a syringe at −80° C., which was followed by stirring for 1 h at the same temperature. After adding 3.8 mL (34 mmol) of trimethyl borate to this solution, stirring was kept allowing the temperature of the solution to gradually rise to room temperature for about 15 hours. About 150 mL of diluted hydrochloric acid (1.0 mol/L) was added to this solution, and the solution was stirred for 1 hour. The aqueous layer of this mixture was extracted with ethyl acetate, and the extracted solution and the organic layer were combined and washed with a saturated sodium bicarbonate aqueous solution. Thereafter, the organic layer was dried with magnesium sulfate, filtered, and concentrated to give a light brown, oily compound. This oily compound was dissolved in 20 mL of chloroform, and then about 50 ml of hexane was added to the solution. A white solid was precipitated after keeping 1 hour, which was followed by filtration, giving 5.2 g of the target compound as a white solid in 58% yield.

[Step 2] Synthesis of N,N',N'-triphenylbenzidine (abbreviation: DPAB)

A synthetic scheme of N,N',N'-triphenylbenzidine (abbreviation: DPAB) is shown in (C-33).

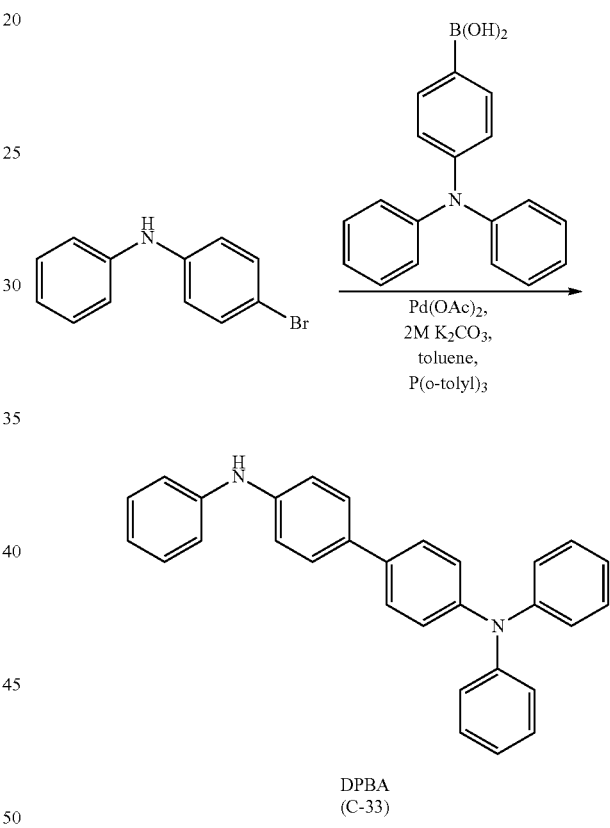

DPBA
(C-33)

4.3 g (17 mmol) of 4-bromodiphenylamine, 5 g (17 mmol) of triphenylamine-4-boronic acid, and 532 mg (1.8 mmol) of tri(o-tolyl)phosphine were put into a 500 mL three-neck flask, and the inside of the flask was substituted with nitrogen. Then, 60 mL of toluene, 40 mL of ethanol, and 14 mL of potassium carbonate aqueous solution (0.2 mol/L) were added to this mixture. After this mixture was degassed under reduced pressure while being stirred, 75 mg (0.35 mmol) of palladium acetate (II) was added. This mixture was refluxed for 10.5 hours at 100° C. The aqueous layer of this mixture was extracted with toluene. This extracted solution and the organic layer were combined, washed with brine, dried with magnesium sulfate, filtered, and concentrated, which resulted in a light brown, oily compound. This oily compound was dissolved in about 50 mL of toluene, and then subjected to suction filtration through celite, alumina, and Florisil. The filtrate was concentrated, and the residue was purified by silica gel column chromatography (eluent; hexane:toluene=4:6) to give a white solid which was then recrystallized with chloroform/hexane to afford 33 g of the target compound as a white solid in 49% yield.

[Step 3] Synthesis of 2DPBAPA

A synthetic scheme of 2DPBAPA is shown in (C-34).

1.5 g (3.6 mmol) of 2-bromo-9,10-diphenylanthracene, 1.5 g (3.6 mmol) of N,N',N'-triphenylbenzidine (abbreviation: DPAB), and 1.5 g (16 mmol) of sodium tert-butoxide were put into a 100 mL three-neck flask, and the inside of the flask was substituted with nitrogen. 20 mL of toluene and 0.10 mL of tri(tert-butyl)phosphine (10 wt % hexane solution) were added to this mixture. After this mixture was degassed under reduced pressure while being stirred, 41 mg (0.072 mmol) of bis(dibenzylideneacetone)palladium (0) was added. Then, the mixture was stirred for 3 hours at 100° C. After about 50 mL of toluene was added to the reaction mixture, this mixture was subjected to suction filtration through celite, Florisil, and alumina. The obtained filtrate was concentrated, yielding oily compound. About 10 mL of toluene was added to this oily compound, which was left for about 2 hours to afford a yellow solid as a precipitate. Suction filtration of this precipitate gave 2.5 g of the target compound as yellow powder in 91% yield. By a nuclear magnetic resonance measurement (NMR), it was confirmed that this compound was 9,10-diphenyl-2-[N(4'-diphenylamino-1,1'-biphenyl-4-yl)-N-phenylamino]anthracene (abbreviation: 2DPBAPA).

Figure 120A:
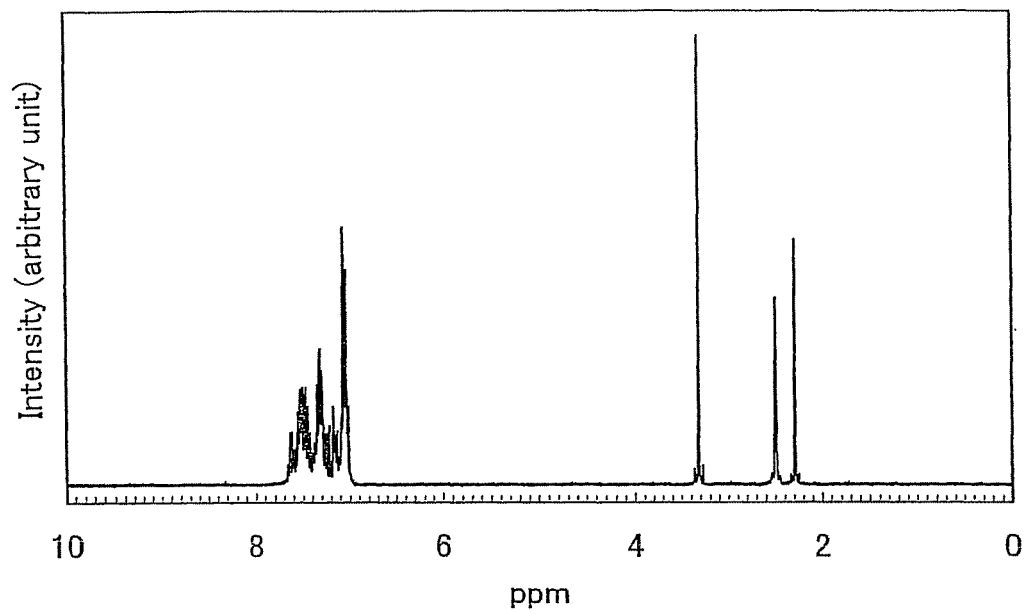
FIGS. 120A and 120B each show the $^1$H NMR chart of 9,10-diphenyl-2[N-(4'-diphenylamino-1,1'-biphenyl-4-yl)-N-phenylamino]anthracene (abbreviation: 2DPBAPA)
Figure 120B:
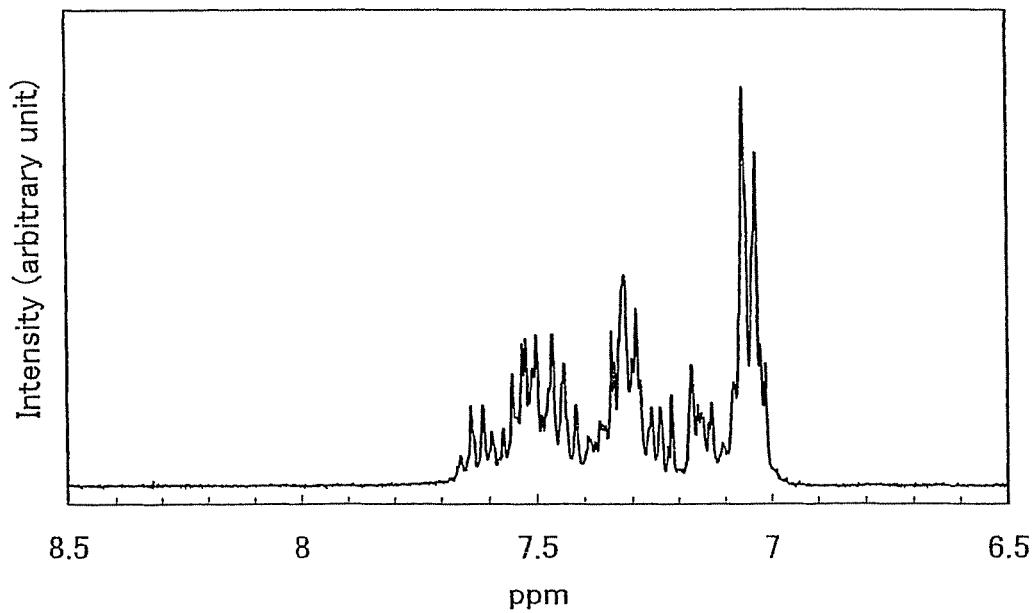

$^1$H NMR data of this compound is shown below. $^1$H NMR (300 MHz, DMSO-$d_6$): δ=7.01-7.08 (m, 11H), 7.13-7.17 (m, 5H), 7.22-7.89 (m, 12H), 7.42-7.66 (m, 12H). The $^1$H NMR chart is shown in each of FIGS. 120A and 120B. Note that the range of 6.5 ppm to 8.5 ppm in FIG. 120A is expanded and shown in FIG. 120B.

Figure 121:
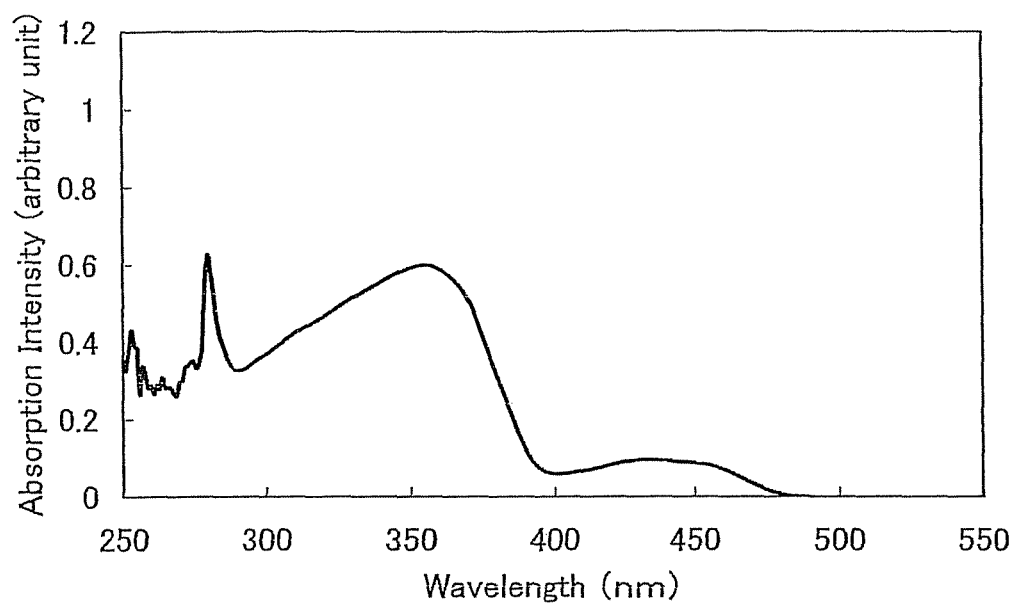
Figure 122:
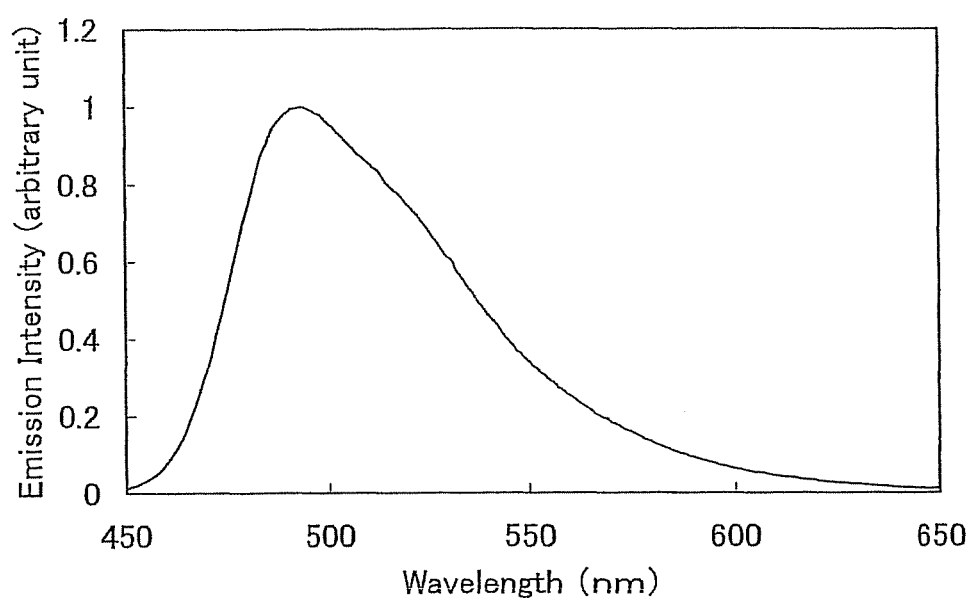

The absorption spectrum of a toluene solution of 2DPBAPA is shown in FIG. 121. An ultraviolet-visible spectrophotometer (type V550, manufactured by Japan Spectroscopy Corporation) was used for measurement. The absorption spectrum of the solution is shown in FIG. 121, which was obtained by subtracting the spectrum of the quartz substrate from the raw spectra of the sample solution charged in a quartz cell. In FIG. 121, a horizontal axis shows wavelength (am) and a vertical axis shows absorption intensity (an arbitrary unit). In the case of the toluene solution, absorption was observed at around 355 nm. Further, an emission spectrum of the toluene solution (excitation wavelength of 370 nm) of 2DPBAPA is shown in FIG. 122. In FIG. 122, a horizontal axis shows wavelength (nm) and a vertical axis shows emission intensity (an arbitrary unit). In the case of the toluene solution, the maximum emission wavelength was 493 nm (excitation wavelength of 370 nm).

Embodiment 15

In this embodiment, a synthetic method of 2-{N-[4'-(9H-carbazol-9-yl)-1,1'-biphenyl-4-yl]-N-phenylamino}-9,10-diphenylanthracene (abbreviation: 2YGBAPA), which is the anthracene derivative of the present invention represented by Structural Formula (319), is specifically described. Note that 2YGBAPA represented by Structural Formula (319) corresponds to the case where $Ar^1$ and $Ar^2$ in General Formula (5) are each Structural Formula (20-1), and A is Structural formula (33-10).

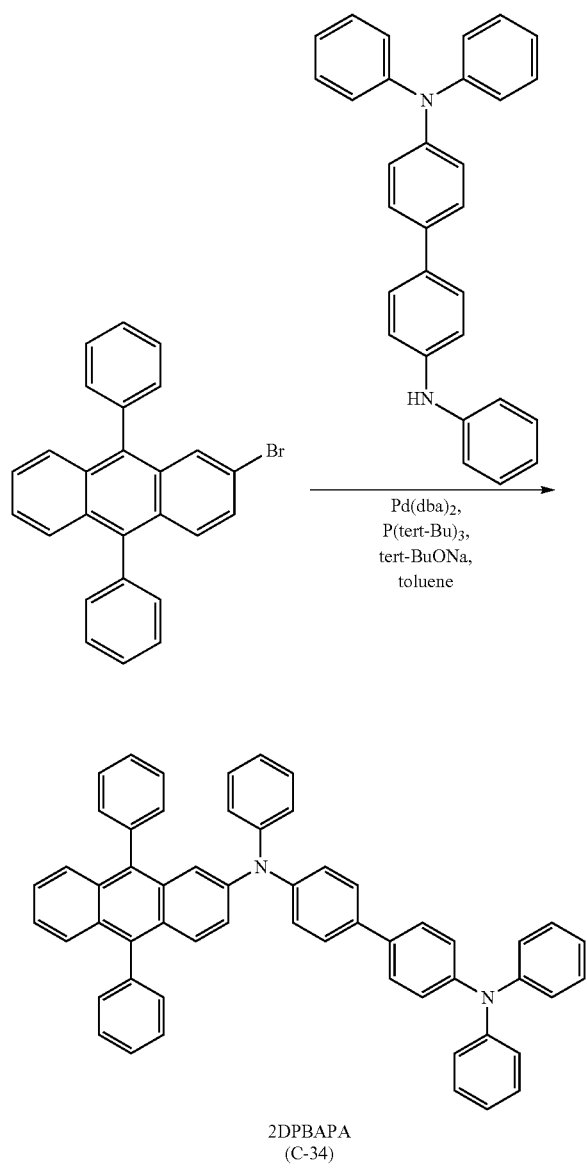

2DPBAPA
(C-34)

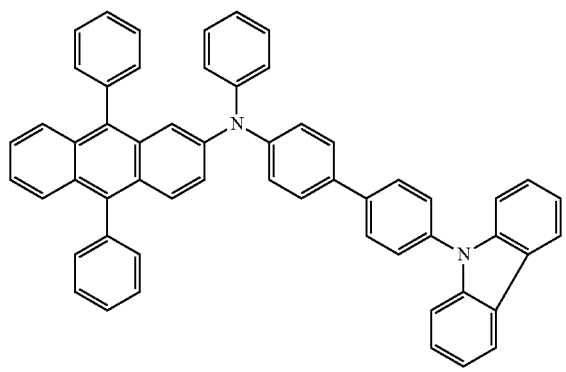

(319)

[Step 1] Synthesis of 9-phenylcarbazole-3-ylboronic acid

A synthetic scheme of 9-phenylcarbazole-3-ylboronic acid is shown in (C-35)

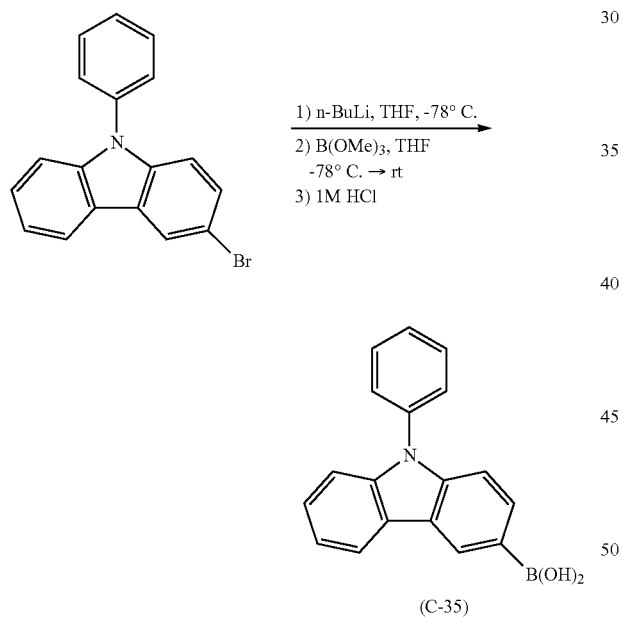

(C-35)

Into a solution of 19.6 g (60.7 mmol) of 3-bromo-9-phenylcarbazole, prepared in Step 1 of the Embodiment 2, in THF (100 mL) was added dropwise 66.8 mL (42.3 mmol) of an n-butyllithium hexane solution (1.58 mol/L) at −78° C. under nitrogen, which was followed by stirring for 3 hours at the same temperature. Thereafter, 13.5 mL (140 mmol) of trimethyl borate was added, and stirring was continued for 24 hours while gradually raising the reaction temperature to room temperature. 200 mL of 2.0 mmol/L hydrochloric acid was added to the solution, and additional stirring was conducted for 1 hour at room temperature. After the solution was extracted with ethyl acetate, the organic layer was washed with brine, dried with magnesium sulfate, filtered, and concentrated: The resulting solid was recrystallized with a mixed solvent of chloroform and hexane, giving 10.2 g of 9-phenylcarbazole-3-ylboronic acid as white powder in 58% yield.

[Step 2] Synthesis of 4-[4(9H-carbazol-9-yl)phenyl]diphenylamine (abbreviation: YGBA)

A synthetic scheme of 4-[4(9H-carbazol-9-yl)phenyl]diphenylamine (abbreviation: YGBA) is shown in (C-36).

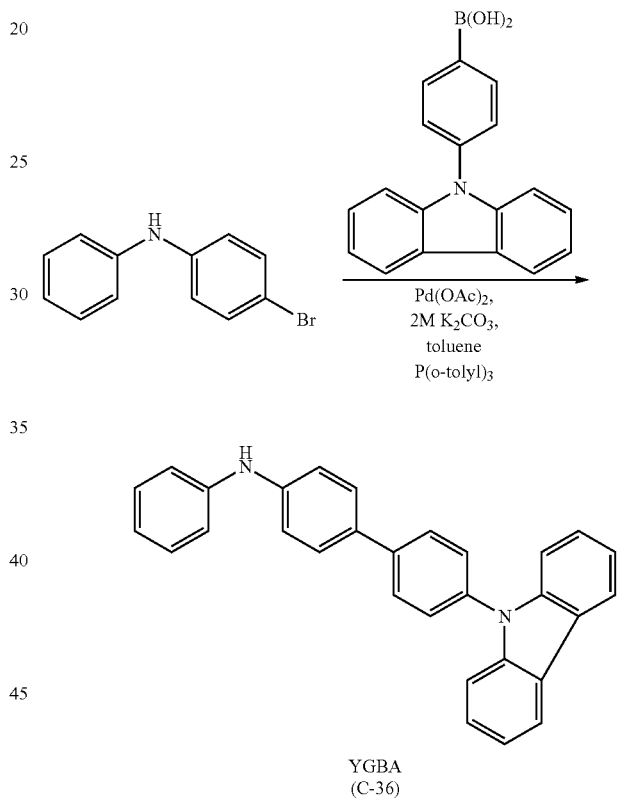

YGBA
(C-36)

2.2 g (8.8 mmol) of 4-bromodiphenylamine, 2.5 g (8.8 mmol) of triphenylamine-4-boronic acid, and 398 mg (1.3 mmol) of tri(o-tolyl)phosphine were put into a 200 mL three-neck flask, and the inside of the flask was substituted with nitrogen. 30 mL of toluene, 20 mL of ethanol, and 14 mL of potassium carbonate aqueous solution (0.2 mol/L) were added to this mixture. This mixture was degassed under reduced pressure while being stirred, and 59 mg (0.26 mmol) of palladium acetate (II) was added. This mixture was refluxed for 6.5 hours at 100° C. After this mixture was left to cool for about 15 hours, a light blackish-brown solid was precipitated. This solid was collected by suction filtration, and 2.5 g of the target compound was obtained as light blackish-brown solid in 70% yield.

[Step 3] Synthesis of 2YGBAPA

A synthetic scheme of 2YGBAPA is shown in (C-37).

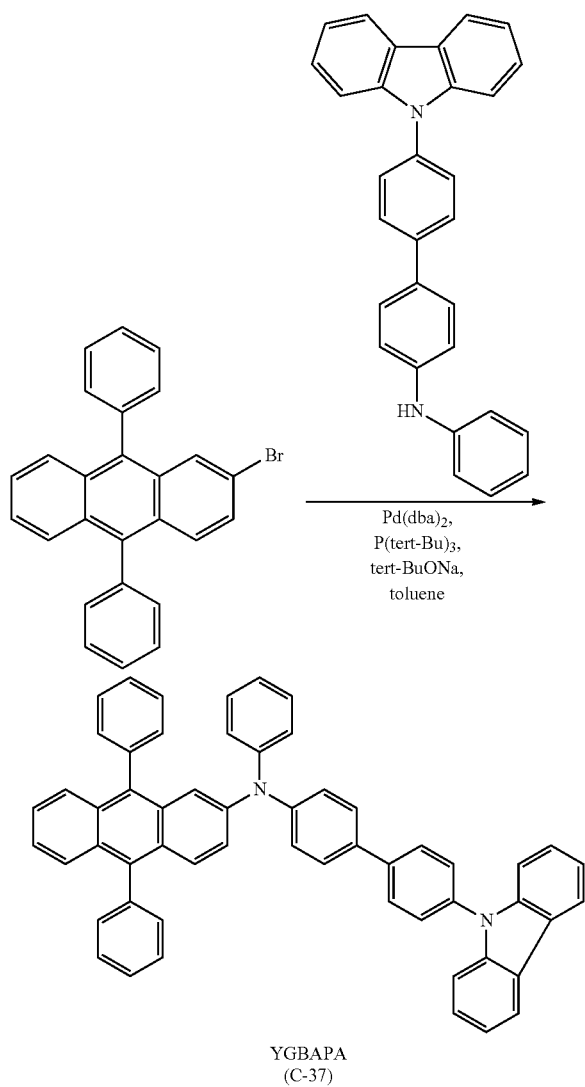

YGBAPA
(C-37)

1.2 g (3.0 mmol) of 2-bromo-9,10-diphenylanthracene, 1.2 g (3.0 mmol) of YGBA, and 1.5 g (16 mmol) of sodium tert-butoxide were put into a 100 mL three-neck flask, and the inside of the flask was charged with nitrogen. 15 mL of toluene and 0.20 mL of tri(tert-butyl)phosphine (10 wt % hexane solution) were added to this mixture. This mixture was degassed under reduced pressure while being stirred, and 86 mg (0.15 mmol) of bis(dibenzylideneacetone)palladium (0) was added. Thereafter, this mixture was stirred for 3 hours at 100° C. This mixture was subjected to suction filtration through celite, alumina, and Florisil. An oily compound obtained by concentrating the obtained filtrate was purified by silica gel column chromatography (eluent was hexane: toluene=7:3), and the resulting yellow solid was recrystallized with chloroform/methanol, giving 462 g of the target compound as a yellow solid in 21% yield. By a nuclear magnetic resonance measurement (NMR), it was confirmed that this compound was 2-{N-[4'-(9H-carbazol-9-yl)-1,1'-biphenyl-4-yl]-N-phenylamino}-9,10-diphenylanthracene (abbreviation: 2YGBAPA)

$^1$H NMR data of this compound is shown below. $^1$H NMR (300 MHz, DMSO-d$_6$): δ=7.08-7.14 (m, 5H), 7.20 (dd, J=2.4, 9.5 Hz, 1H), 7.28-7.61 (m, 22H), 7.64 (d, J=7.2 Hz, 2H), 7.70 (dd, J=2.4, 7.7 Hz, 4H), 7.91 (d, J=8.4 Hz, 2H), 8.26 (d, J=7.8 Hz, 2H). The $^1$H NMR chart is shown in each of FIGS. 123A and 123B. Note that the range of 6.5 ppm to 9.0 ppm in FIG. 123A is expanded and shown in FIG. 123B.

The absorption spectrum of a toluene solution of 2YGBAPA is shown in FIG. 124. An ultraviolet-visible spectrophotometer (type V550, manufactured by Japan Spectroscopy Corporation) was used for measurement. The absorption spectrum of the solution is shown in FIG. 124, which was obtained by subtracting the spectrum of the quartz substrate from the raw spectra of the sample solution located in a quartz cell. In FIG. 124, a horizontal axis shows wavelength (nm) and a vertical axis shows absorption intensity (an arbitrary unit). In the case of the toluene solution, absorption was observed at around 344 nm. Further, an emission spectrum of the toluene solution (excitation wavelength of 370 nm) of 2YGBAPA is shown in FIG. 125. In FIG. 125, a horizontal axis shows wavelength (nm) and a vertical axis shows emission intensity (an arbitrary unit). In the case of the toluene solution, the maximum light emission wavelength was 485 nm (excitation wavelength of 370 nm).

Embodiment 16

In this embodiment, a light-emitting element of the present invention is described with reference to FIG. 10.

A manufacturing method of a light-emitting element of this embodiment is described below.

First, a film of indium tin oxide containing silicon oxide (ITSO) was formed by sputtering over the glass substrate 2101 to form the first electrode 2102. Note that the film thickness of the first electrode 2102 was 110 nm, and the area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing pressure of the vacuum evaporation apparatus to about $10^{-4}$ Pa, the layer 2103 containing a composite material, which contains an organic compound and an inorganic compound, was formed over the first electrode 2102 by co-evaporating 4,4'-bis[N-(1-napthyl)-N-phenylamino]biphenyl (abbreviation: NPB) and molybdenum oxide (VI). The film thickness was to be 50 nm, and a ratio of NPB and molybdenum oxide (1/1) was adjusted to be 4:1 (=NPB:molybdenum oxide) in weight ratio.

Subsequently, a film of 4,4'-bis[N-(1-napthyl)-N-phenylamino]biphenyl (abbreviation: NPB) was formed over the layer 2103 containing a composite material to have a thickness of 10 nm by the evaporation method using resistance heating system, thereby forming the hole transporting layer 2104.

Further, by co-evaporating 9-[4-(N-carbazolyl)]phenyl-10-phenylanthracene (abbreviation: CzPA) and 2-{N-[4-(carbazol-9-yl)phenyl]-N-phenylamino}-9,10-diphenylanthracene (abbreviation: 2YGAPA), which is the anthracene derivative of the present invention represented by Structural Formula (301), the light-emitting layer 2105 with a thickness of 30 nm was formed over the hole transporting layer 2104. Here, a rate of evaporation was adjusted so that the weight ratio of CzPA and 2YGAPA was 1:0.05 (=CzPA: 2YGAPA).

Thereafter, the electron transporting layer 2106 was formed over the light-emitting layer 2105 by forming a film of tris(8-quinolinolato)aluminum (abbreviation: Alq) to have a film thickness of 10 nm by means of the evaporation using resistance heating system.

Further, the electron injecting layer 2107 was formed at a thickness of 20 nm over the electron transporting layer 2106 by co-evaporating tris(8-quinolinolato)aluminum (abbreviation: Alq) and lithium (Li). Here, the rate of evaporation was adjusted so that the weight ratio of Alq and Li was 1:0.01 (=Alq:Li).

Finally, by forming a film of aluminum as the second electrode 2108 with a film thickness of 200 nm over the electron injecting layer 2107 using the evaporation method by resistance heating system, a light-emitting element 12 was fabricated.

A current density-luminance characteristic, a voltage-luminance characteristic, and a luminance-current efficiency characteristic of the light-emitting element 13 are shown in FIGS. 126, 127, and 128, respectively. Also, the emission spectrum which was obtained at a current of 1 mA is illustrated in FIG. 129. Further, FIGS. 130 and 131 demonstrate time dependence of normalized luminance and time dependence of operation voltage, respectively, of the light-emitting element 13 when initial luminance was 1000 cd/m$^2$. A CIE chromaticity coordinate of the light-emitting element 13 at luminance of 1000 cd/m$^2$ was (x=0.21, y=0.51), and light emission was blue green. Current efficiency at luminance of 1000 cd/m$^2$ was 9.6 cd/A, meaning that high current efficiency was exhibited. In addition, as shown in FIG. 129, maximum emission wavelength at a current of 1 mA was 489 nm. It can be concluded from FIG. 130 that the light-emitting element 13 has a long lifetime, since 82% of the initial luminance was maintained even after 640 hours.

Embodiment 17

In this embodiment, a light-emitting element of the present invention is described with reference to FIG. 10.

Hereinafter, a manufacturing method of a light-emitting element of this embodiment is shown.

First, a film of indium tin oxide containing silicon oxide (ITSO) was formed by sputtering over the glass substrate 2101 to form the first electrode 2102. Note that the film thickness of the first electrode 2102 was 110 nm, and the area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing pressure of the vacuum evaporation apparatus to about 10$^{-4}$ Pa, the layer 2103 containing a composite material, which contains an organic compound and an inorganic compound, was formed over the first electrode 2102 by co-evaporating 4,4'-bis[N-(1-napthyl)-N-phenylamino]biphenyl (abbreviation: NPB) and molybdenum oxide (VI). The film thickness was to be 50 nm, and a ratio of NPB and molybdenum oxide (VI) was adjusted to be 4:1 (=NPB:molybdenum oxide) in weight ratio.

Subsequently, a film of 4,4'-bis[N-(1-napthyl)-N-phenylamino]biphenyl (abbreviation: NPB) was formed over the layer 2103 containing, a composite material to have a thickness of 10 nm by the evaporation method using resistance heating system, thereby forming the hole transporting layer 2104.

Further, by co-evaporating 9-[4-(N-carbazolyl)]phenyl-10-phenylanthracene (abbreviation: CzPA) and 9,10-diphenyl-1-[N-(9-phenylcarbazol-3-yl)-N-phenylamino]anthracene (abbreviation: 1PCAPA), which is the anthracene derivative of the present invention represented by Structural Formula (202), the light-emitting layer 2105 with a thickness of 40 nm was formed over the hole transporting layer 2104. Here, a rate of evaporation was adjusted so that the weight ratio of CzPA and 1PCAPA was 1:0.05 (=CzPA: 1PCAPA).

Thereafter, as to the light-emitting element 14, the electron transporting layer 2106 was formed over the light-emitting layer 2105 by fabricating a film of tris(8-quinolinolato)aluminum (abbreviation: Alq) with a film thickness of 30 nm by means of the evaporation method using resistance heating system. As to the light-emitting element 15, a film of bathophenanthroline (abbreviation: BPhen) was formed with a thickness of 30 nm to form the electron transporting layer 2106.

Furthermore, a film of lithium fluoride (LiF) was formed over the electron transporting layer 2106 to have a thickness of 1 nm, to form an electron injecting layer 2107.

Finally, by forming a film of aluminum as the second electrode 2108 with a film thickness of 200 nm over the electron injecting layer 2107 using the evaporation method by resistance heating system, light-emitting elements 14 and 15 were fabricated.

A current density-luminance characteristic, a voltage-luminance characteristic, and a luminance-current efficiency characteristic of the light-emitting element 14 are shown in FIGS. 132, 133, and 134, respectively. Also, the emission spectrum which was obtained at a current of 1 mA is illustrated in FIG. 135. Further, FIGS. 136 and 137 demonstrate time dependence of normalized luminance and time dependence of operation voltage, respectively, of the light-emitting element 14 when initial luminance was 3000 cd/m$^2$. A CIE chromaticity coordinate of the light-emitting element 14 at luminance of 3000 cd/m$^2$ was (x=0.31, y=0.61), and light emission was green. Current efficiency at luminance of 3000 cd/m$^2$ was 13.9 cd/A, meaning that high current efficiency was exhibited. In addition, as shown in FIG. 135, maximum emission wavelength at a current of 1 mA was 515 nm. It can be concluded from FIG. 136 that the light-emitting-element 14 has a long lifetime, since 74% of the initial luminance was maintained even after 500 hours.

A current density-luminance characteristic, a voltage-luminance characteristic, and a luminance-current efficiency characteristic of the light-emitting element 15 are shown in FIGS. 138, 139, and 140, respectively. Also, the emission spectrum which was obtained at a current of 1 mA is illustrated in FIG. 141. A CM chromaticity coordinate of the light-emitting element 15 at luminance of 3000 cd/m$^2$ was (x=0.32, y=0.59), and light emission was green. Current efficiency at luminance of 3000 cd/m$^2$ was 15.9 cd/A, meaning that high current efficiency was exhibited. Power efficiency at luminance of 3000 cd/m$^2$ was 16.7 lm/W, indicating that the element 15 can be operated at low power consumption. In addition, as shown in FIG. 141, maximum emission wavelength at a current of 1 mA was 515 nm.

This application is based on Japanese Patent Application serial no. 2006-127118 filed on Apr. 28, 2006 and Japanese Patent Application serial no. 2006-233244 filed on Aug. 30, 2006 in Japan Patent Office, the entire contents of which are hereby incorporated by reference.

EXPLANATION OF REFERENCE

101: substrate, 102: first electrode, 103: first layer, 104: second layer, 105: third layer, 106: fourth layer, 107: second electrode, 301: substrate, 302: first electrode, 303: first layer, 304: second layer, 305: third layer, 306: fourth layer, 307: second electrode, 501: first electrode, 502: second electrode, 511: first light-emitting unit, 512: second light-emitting unit, 513: charge generation layer, 601: source side driver circuit, 602: pixel portion, 603: gate side driver circuit, 604: sealing substrate, 605: sealing material, 607: space, 608: wiring, 609: FPC (flexible printed circuit), 610: element substrate, 611: switching TFT, 612: current control TFT, 613: first electrode, 614: insulator, 616: layer including light-emitting substance, 617: second electrode, 618: light-emitting element, 623: n-channel TFT, 624: p-channel TFT, 901: housing, 902: liquid crystal layer, 903: backlight, 904: housing, 905: driver IC, 906: terminal, 951: substrate, 952: electrode, 953: insulating layer, 954: partition layer, 955: layer including light-emitting substance, 956: electrode, 2001: housing, 2002: light source, 2101: glass substrate, 2102: first electrode, 2103: layer including composite material, 2104: hole transporting layer, 2105: light-emitting layer, 2106: electron transporting layer, 2107: electron injecting layer, 2108: second electrode, 3001: lighting device, 3002: television device, 9101: housing, 9102: supporting base, 9103: display portion, 9104: speaker portion, 9105: video input terminal, 9201: main body, 9202: housing, 9203: display portion, 9204: keyboard, 9205: external connection port, 9206: pointing device, 9401: main body, 9402: housing, 9403: display portion, 9404: audio input portion, 9405: audio output portion, 9406: operation key, 9407: external connection port, 9408: antenna, 9501: main body, 9502: display portion, 9503: housing, 9504: external connection port, 9505: a remote control receiving portion, 9506: image receiving portion, 9507: battery, 9508: audio input portion, 9509: operation key, 9510: eye piece portion

The invention claimed is:

1. A method for synthesizing a compound represented by the following formula:

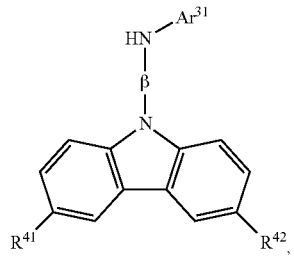

the method comprising conducting a reaction according to the following scheme:

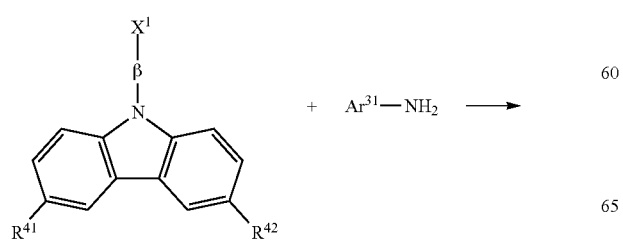

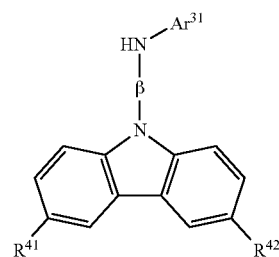

wherein:

$X^1$ represents halogen;

$Ar^{31}$ represents an aryl group having 6 to 25 carbon atoms;

$R^{41}$ and $R^{42}$ independently represent any of hydrogen, an alkyl group having 1 to 4 carbon atoms, and an aryl group having 6 to 25 carbon atoms; and $\beta$ represents an arylene group having 6 to 25 carbon atoms.

2. The method according to claim 1, wherein the aryl group is selected from the following substituents:

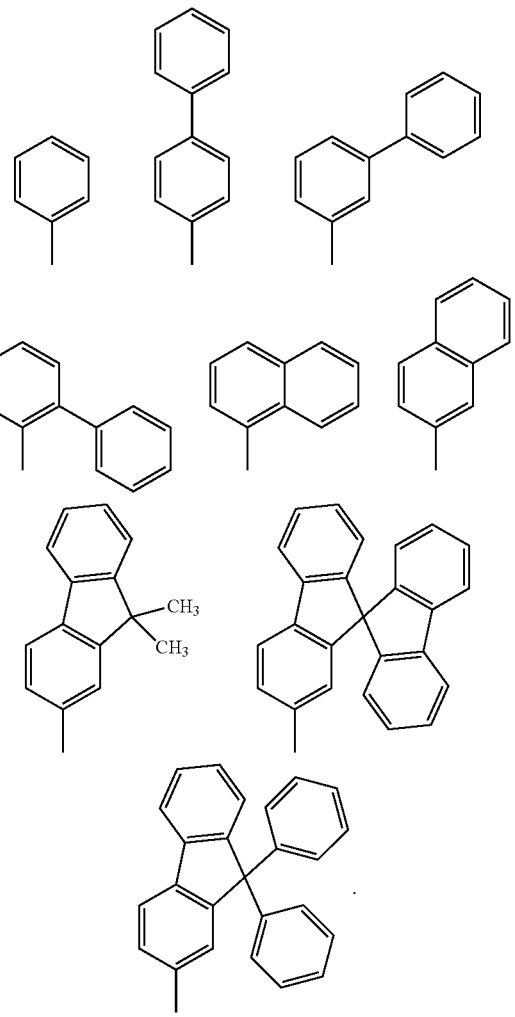

3. The method according to claim 1, wherein β is selected from the following structures:

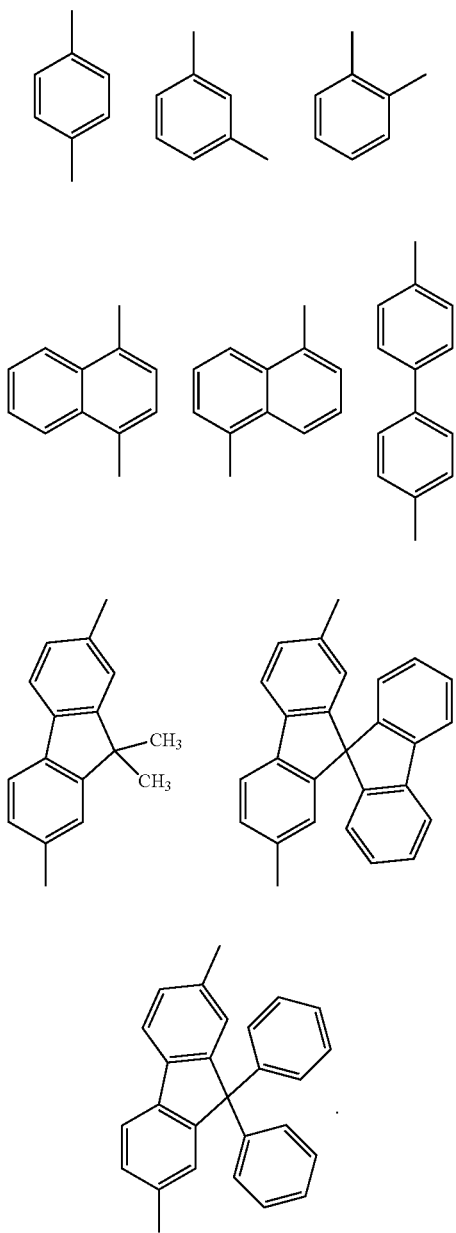

4. The method according to claim 1, wherein the reaction is conducted in the presence of a metal catalyst.

5. The method according to claim 4, wherein the metal catalyst includes palladium.

6. A method for synthesizing a compound, the method comprising:

preforming a reaction of the compound according to claim 1 with an aryl halide.

7. The method according to claim 6, wherein the aryl group is selected from the following substituents:

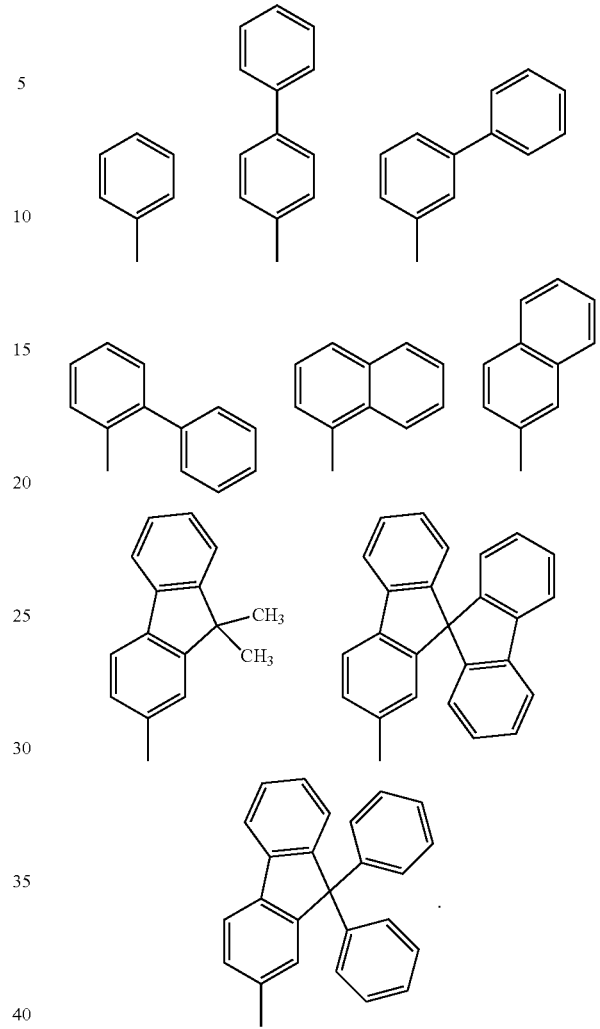

8. The method according to claim 6, wherein β is selected from the following structures:

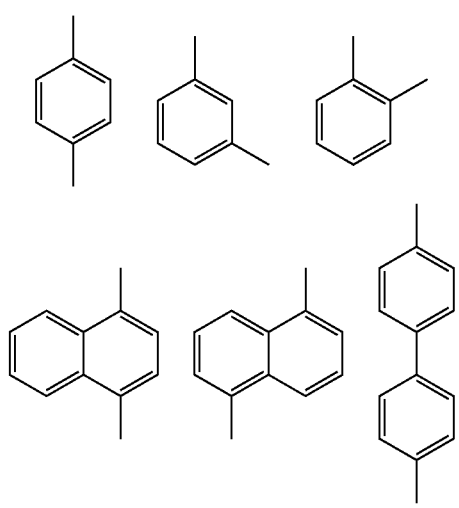

-continued
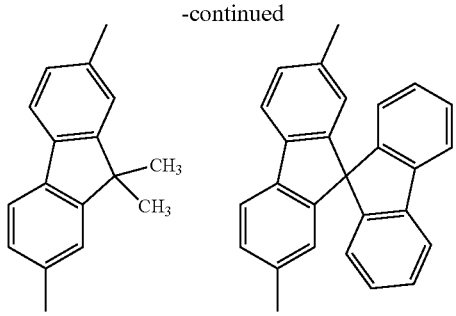
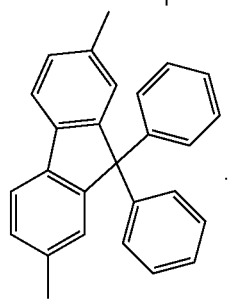
9. The method according to claim 6, wherein the reaction is conducted in the presence of a metal catalyst.
10. The method according to claim 9, wherein the metal catalyst includes palladium.
* * * * *